Figure 1:
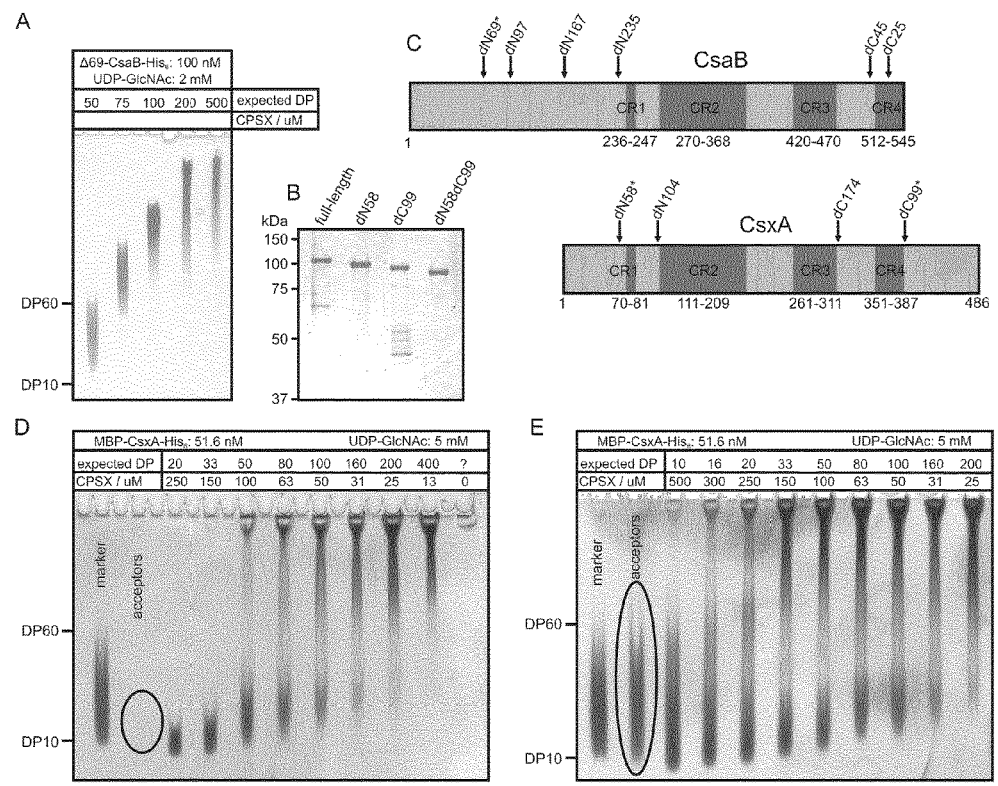

(12) United States Patent
Fiebig et al.

(10) Patent No.: US 10,407,703 B2
(45) Date of Patent: Sep. 10, 2019

(54) **MEANS AND METHODS FOR PRODUCING *NEISSERIA MENINGITIDIS* CAPSULAR POLYSACCHARIDES O groups A and X. Also provided herein are pharmaceuticals, in particular vaccines, comprising the synthetic capsular polysaccharides of Neisseria meningitidis which have a defined length. Furthermore, the invention provides for methods for the production of said vaccines.

24 Claims, 58 Drawing Sheets

Specification includes a Sequence Listing.

(51) Int. Cl.
C07K 14/22 (2006.01)
C08B 37/00 (2006.01)
C12P 19/04 (2006.01)
C12P 19/18 (2006.01)
A61K 39/095 (2006.01)

(52) U.S. Cl.
CPC ........ C08B 37/0009 (2013.01); C12N 9/1241 (2013.01); C12P 19/18 (2013.01); C12Y 207/07 (2013.01); A61K 2039/55544 (2013.01)

(58) Field of Classification Search
USPC ............... 435/101, 193, 252.3, 471, 69.1; 536/23.2; 424/249.1
See application file for complete search history.

(56) References Cited

FOREIGN PATENT DOCUMENTS

| WO | WO 2008/011201 | | 1/2008 | |
| WO | WO 2008011201 | * | 1/2008 | ............ C12N 1/20 |
| WO | WO 2011/023764 | * | 3/2011 | ............ A61K 39/095 |
| WO | WO 2011023764 | * | 3/2011 | ............ A61K 39/095 |
| WO | WO 2013/174832 | | 11/2013 | |

OTHER PUBLICATIONS

Griffiss et al., "Safety and immunogenicity of group Y and group W135 meningococcal capsular polysaccharide vaccines in adults," *Infection and Immunity*, 34(3):725-732, 1981.

Nato et al., "Production of polyclonal and monoclonal antibodies against group A, B, and C capsular polysaccharides of *Neisseria meningitidis* and preparation of latex reagents," *Journal of Clinical Microbiology*, 29(7):1447-1452, 1991.

PCT International Search Report and Written Opinion issued in International Application No. PCT/EP2015/058399, dated Oct. 12, 2015.

Costantino, P., et al., "The design of semi-synthetic and synthetic glycoconjugate vaccines", Expert Opin. Drug Discov., XP008163752, 6(10):1045-1066, (Jun. 10, 2011).

European Office Action for European Application No. 15 720 621.0-1118, 12 pages, dated Sep. 11, 2018.

Fiebig, T., et al., "Functional expression of the capsule polymerase of *Neisseria meningitidis* serogroup X: A new perspective for vaccine development", Glycobiology, vol. 24(2), pp. 150-158 (Nov. 20, 2013).

Xie, O., et al., "Characterization of size, structure and purity of serogroup X Neisseria meningitidis polysaccharide, and development of an assy for quantification of human antibodies", Elsevier, www.elsevier.com/locate/vaccine, XP002705005, Vaccine 30, pp. 5812-5823 (Jul. 24, 2012).

Xie, O., et al., "Emergence of serogroup X meningococcal disease in Africa: Need for a vaccine", Elsevier, www.elsevier.com/locate/vaccine, Vaccine 31, pp. 2852-2861 (Apr. 24, 2013).

* cited by examiner

E

4-MU-Sia (4-MU-DP1)

4-MU-Sia-Gal (4-MU-DP2)

4-MU-Sia-Gal-Sia (4-MU-DP3)

a non-O-acetylated

O-acetylated

B

D

HNMR of CPSA (OAc) and CPSA (deOAc) from NVD in comparison with CPSAiv from Bag 2 Tube 4 (deOAc), 5 and 6 (OAc)

A: ΔC99-CP-X     B: ΔN58ΔC99-CP-X

MEANS AND METHODS FOR PRODUCING *NEISSERIA MENINGITIDIS* CAPSULAR POLYSACCHARIDES OF LOW DISPERSITY

This application is a national phase application under 35 U.S.C. § 371 of International Application No. PCT/EP2015/058399, filed Apr. 17, 2015, which claims benefit of U.S. Provisional Application No. 61/980,819, filed Apr. 17, 2014, the entire contents of each of which are hereby incorporated by reference.

The present invention relates to in vitro methods for producing *Neisseria meningitidis* capsular polysaccharides which have a defined length. The present invention also relates to compositions comprising at least one capsule polymerase, at least one donor carbohydrate and at least one acceptor carbohydrate, wherein the ratio of donor carbohydrate to acceptor carbohydrate is a ratio from 10:1 to 400:1. Moreover, the present invention provides truncated versions of the capsule polymerases of *Neisseria meningitidis* serogroups A and X. Also provided herein are pharmaceuticals, in particular vaccines, comprising the synthetic capsular polysaccharides of *Neisseria meningitidis* which have a defined length. Furthermore, the invention provides for methods for the production of said vaccines.

Bacterial *meningitidis* is a serious threat to global health. It is estimated that each year bacterial *meningitidis* accounts for 170,000 deaths worldwide (WHO, http://www.who.int/nuvi/meningitidis/en/). Despite the availability of potent antimicrobial agents, case-fatality rates are high (10-40%) and survivors frequently suffer from sequelae such as neurologic disability or limb loss and deafness (Van Deuren et al., Clin Micriobiol Rev 2000; 13(1): 144-166; Kaper et al., Nat Rev Microbiol 2004, 2(2): 123-140). *Neisseria meningitidis* (Nm) is one of the most important causative agents of bacterial *meningitidis* because of its potential to spread in epidemic waves (Kaper et al., Nat Rev Microbiol 2004, 2(2): 123-140; Rosenstein et al., N Eng J Med 2001, 344(18): 1378-1388). Crucial virulence determinants of disease causing Nm species are their extracellular polysaccharide capsules that are essential for meningococcal survival in human serum (Vogel et al., Infect Immun 1997, 65(10): 4022-4029). Based on antigenic variation of these polysaccharides at least twelve different serogroups of Nm have been identified (A, B, C, E29, H, I, K, L, W-135, X, Y and Z), but only six (A, B, C, W-135, Y and X) account for virtually all cases of disease; see also Frosch, M., VOGEL, U. (2006) "Structure and genetics of the meningococcal capsule." In Handbook of Meningococcal Disease. Frosch, M., Maiden, M. C. J. (eds). Weinheim: Wiley-VCH.

Serogroup A (NmA) and C (NmC) are the main causes of meningococcal *meningitidis* in sub-Saharan Africa, while serogroups B (NmB) and C are the major disease causing isolates in industrialized countries. However, serogroups W-135 (NmW-135) and Y (NmY) are becoming increasingly prevalent. For NmW-135, this is most explicitly evidenced by the 2002 epidemic in Burkina Faso with over 13,000 cases and more than 1,400 deaths (Connolly et al., Lancet 2004, 364(9449): 1974-1983; WHO, Epidemic and Pandemic Alert and Response (EPR) 2008). In contrast, NmY is gaining importance in the United States where its prevalence increased from 2% during 1989-1991 to 37% during 1997-2002 (Pollard et al., J Paediatr Child Health 2001, 37(5): S20-S27). However, also the previously only sporadically found serogroup X (NmX) appeared with high incidence in Niger and caused outbreaks in Kenya and Uganda (Biosier et al., Clin Infect Dis 2007, 44(5): 657-663; Lewis, WHO Health Action in Crisis 1, 6 2006).

The serogroups A, B, C, 29E, H, I, K, L, W-135, X, Y and Z are well known in the art and are described, e.g., in Frosch, M., VOGEL, U. (2006) loc. cit. The capsular polysaccharides (CPS) of all serogroups are negatively charged linear polymers. Serogroup B and C are encapsuled in homoplymeric CPS composed of sialic acid (Neu5Ac) moieties that are linked by either $\alpha$-2→8 glycosidic linkages in serogroup B or by $\alpha$-2→9 linkages in serogroup C (Bhattacharjee et al., J Biol Chem 1975, 250(5): 1926-1932). Serogroup W-135 and Y both are heteropolymers. They are composed of either galactose/Neu5Ac repeating units [→6)-$\alpha$-D-Glcp-(1→4)-$\alpha$-Neu5Ac-(2→)]$_n$ in serogroup W-135 or glucose/Neu5Ac repeating units [→6)-$\alpha$-D-Galp-(1→4)-$\alpha$-Neu5Ac-(2→)]$_n$ in serogroup Y (Bhattacharjee et al., Can J Biochem 1976, 54(1): 1-8). The CPS of NmA and NmX do not contain Neu5Ac moieties, but are instead built from N-Acetylmannosamine 1-phosphate [→6)-$\alpha$-D-ManpNAc-(1→OPO$_3$→)]$_n$ or N-Acetyl-glucosamine 1-phosphate [→6)-$\alpha$-D-GlcpNAc-(1→OPO$_3$→)]$_n$ repeating units, respectively (Bundle et al., Carbohydr Res 1973, 26(1): 268-270; Bundle et al., J Biol Chem 1974, 249(15): 4797-4801); Bundle et al., J Biol Chem 1974, 249(7): 2275-2281; Jennings et al., J Infect Dis 1977, 136 Suppl: S78-S83).

The CPS of disease causing Nm are attractive vaccine candidates and polysaccharide or polysaccharide-conjugate vaccines are available for serogroups A, C, Y, and W-135 (Broker et al., Minerva Med 2007, 98(5):575-589). Recently, also vaccines for serogroup X have been described (Micoli, P. Proc Natl Acad Sci USA. (2013) 110: 19077-82).

Key enzymes in the CPS biosynthesis are membrane associated capsule polymerases. Candidate genes have been identified for all six disease causing serogroups (Frosch et al., Proc Natl Acad Sci USA 1989, 86(5): 1669-1673; Claus et al., Mol Gen Genet 1997, 257(1): 28-34; Tzeng et al., Infect Immun 2003, 71(2): 6712-6720). However, our knowledge of enzymology or structure-function relations of those important enzymes is still very limited.

Until now, polysaccharide production for neisserial vaccines still requires fermentation of *Neisseria meningitidis* with subsequent multistep purification of the polysaccharides from the culture medium. In these conventional vaccine production processes, the obtained capsule polysaccharides are mostly long polymers. However, for vaccine production, the oligosaccharides ranging in size between degree of polymerization (DP) DP10 to DP60 are needed. Therefore, after purification of the capsule polysaccharides from the culture medium, the obtained polysaccharides have to be fragmented and the fragments have to be characterized and sorted by length. Foremost the biohazard associated with mass production of pathogenic *Neisseria* stains, but also the technological platforms needed to produce homogenous oligosaccharide fractions for vaccine production and their functionalization for coupling to carrier proteins (e.g. an inactive form of Diphteria-toxin or tetanus toxoid), make the conventional vaccine production processes cost intensive and time consuming. Moreover, due to the complexity of the vaccine production chain it can hardly be carried out in developing countries where most of the Nm infections occur. In addition, these conventional vaccine production processes are at risk for contaminations by neisserial toxins, media components or chemicals required for subsequent purification procedures.

Thus, the technical problem underlying the present invention is the provision of means and methods which lead to a more convenient production process of vaccines against *Neisseria meningitidis*.

The technical problem has been overcome by the methods of the present invention for producing capsular polysaccharides of *Neisseria meningitidis* in vitro which have a defined length and carry functional groups at the reducing end for carrier protein coupling as will be detailed below. In particular, the herein provided means and methods lead to a vaccine production process which is less expensive and less time consuming as compared to the processes of the prior art. Furthermore, these convenient processes as provided herein can also be carried out in the developing world. Accordingly, the technical problem is solved by the provision of the embodiments as defined in the claims.

Accordingly, the present invention relates to an in vitro method for producing *Neisseria meningitidis* capsular polysaccharides which have a defined length, said method comprising the steps:
(a) incubating at least one capsule polymerase with at least one donor carbohydrate and at least one acceptor carbohydrate; wherein the ratio of donor carbohydrate to acceptor carbohydrate is a ratio from 10:1 to 400:1; and
(b) isolating the resulting capsular polysaccharides,
wherein the capsule polymerase is the capsule polymerase of *Neisseria meningitidis* serogroup A or a truncated version of the capsule polymerase of *Neisseria meningitidis* serogroup X.

The present invention solves the above identified technical problem since, as documented herein below and in the appended Examples, it was surprisingly found that capsule polysaccharides of *Neisseria meningitidis* (Nm) serogroups A and X which have a uniform and defined length can be produced in vitro.

The inventive means and methods have the advantageous property that the biohazard in association with large scale Nm cultures and the significant coasts for purifying capsular polysaccharides which have the desired length can be avoided. Moreover, the inventive methods provide the perspective that vaccine production chains can be established also in areas that are lacking advanced infrastructural conditions. In particular, the present invention provides for a pyrogen-free, enzyme catalyzed in vitro synthesis production of capsular polysaccharides which have a defined length.

More specifically, the inventors of the present invention surprisingly identified that the capsular polymerase (CP) of Nm serogroup A (CP-A) can be regulated by the ratio of donor to acceptor saccharides. More specifically, in context of the present invention it has been found that this capsular polymerase can be regulated via the donor-acceptor ratio such that it produces capsular polysaccharides with a uniform and defined length. This finding is of high relevance as for vaccine production, neisserial capsular polysaccharides with a uniform and defined length are required. In addition, regulation of the capsule polymerases of Nm serogroup A by the donor-acceptor ratio is highly unexpected as the full length capsule polymerases of Nm serogroups X, Y and W-135 cannot be easily regulated by donor-acceptor ratio.

Furthermore, the inventors of the present invention astonishingly found that, when terminally truncated, also the capsule polymerase of Nm serogroup X (CP-X) can be regulated via the donor-acceptor ratio in order to produce capsular polysaccharides with a uniform and defined length. Moreover, as shown in the illustrating appended examples, this terminally truncated version of the capsule polymerase of Nm serogroup X has the additional advantage that it can also be regulated by the reaction time. Thus, as shown in the appended examples, by choosing a suitable reacting time (e.g. 3 to 45 minutes), the terminally truncated version of the capsule polymerase of Nm serogroup X can be forced to produce capsular polysaccharides with a uniform and defined length of DP10 to DP60. This length is needed for effective vaccine production. It is noted that the inventive truncated (e.g. terminally truncated) capsular polymerase of NmX has the additional advantage that it has a significantly improved activity as compared to its full length counterpart. This is a surprising finding as the prior art has shown that truncated versions of the capsule polymerase of Nm serogroup B (CP-B) have the same or even less activity as compared to the full length CP-B (Keys, Analytical Biochemistry 427, 60-68 (2012)).

Thus, the present invention paves the way for efficient, economical and fast in vitro production methods for Nm capsule polysaccharides, which are suitable for vaccine development. Furthermore, in context of the present invention two important features of the capsule polymerase of NmA (also called CP-A or CsaB) have been identified: (i) the minimal efficient acceptor is the dimer and (ii) the reducing end phosphate group can be extended with rather large chemical groups (such as decyl-ester groups). This latter finding bears the perspective that chain elongation can be primed with reagents of very high purity and functional groups that facilitate conjugation of glycans to carrier proteins in the vaccine production chain.

Moreover, in context of the present invention it was further found that an O-acetyltransferase (e.g. the CsaC of NmA) can be applied in the inventive in vitro production methods and directly effecting O-acetylation of the produced capsular polysaccharides. This is of advantage as usually for vaccine production Nm capsular polysaccharides must be O-acetylated. In addition, O-acetylation has also an effect on the immunogenicity of the produced capsular polysaccharides. Natural capsule polysaccharides of NmA are O-acetylated in position 3-O and to a minor extend in position 4-O of ManNAc (Gudlavalleti, Carbohydr. Res. (2006) 341: 557-562). It has been shown that capsular polysaccharides of NmA are immunogenic only if they are O-acetylated (Berry et al., 2002 Infection and immunity 70 (7), 3707-3713). As demonstrated in the appended examples, during in vitro synthesis of CPS an O-acetyltransferase (such as the CsaC of NmA) can be directly added to the mixture comprising the capsule polymerase, the donor carbohydrate(s) and the acceptor carbohydrate(s). Thus, in vitro production and O-acetylation can be performed in a one-pot reaction. Accordingly, the O-acetyltransferase may be used in step (a) of the herein described in vitro method for producing Nm capsular polysaccharides. In addition or alternatively, O-acetylation may be performed as an additional step after the synthesis of the Nm capsular polysaccharides. Thus, in the herein described in vitro method for producing Nm capsular polysaccharides, O-acetylation may be performed after step (a) in the additional step (a').

Accordingly, the present invention provides for effective in vitro methods for producing exactly the type of Nm capsular polysaccharides which is required for vaccine production (i.e. capsular polysaccharides which have a defined length and which are O-acetylated). Thereby, the previously used cost- and time-intensive vaccine production processes can be avoided.

In vitro methods for producing synthetic capsular polysaccharides of *Neisseria meningitidis* have been described in the prior art (WO 2011/023764 A1). However, the prior art does not disclose how to generate synthetic Nm capsular polysaccharides which have a uniform and defined length and the prior art does not disclose that an O-acetyltransferase can be applied in the in vitro production of capsular polysaccharides to obtain O-acetylated capsular polysaccharides.

By contrast, in the methods of the present invention, isolated Nm capsular polymerases are regulated by the donor-acceptor ratio and/or by the reaction time to allow for the production of Nm capsular polysaccharides which have a uniform and defined length. Accordingly, the invention provides for methods for producing Nm capsular polysaccharides, wherein the capsular polymerases are regulated by the donor-acceptor ratio and/or the reaction time so as to produce capsular polysaccharides which have a uniform and defined length.

Moreover, a further advantageous property of the methods of the invention is that they can be combined with an O-acetyltransferase to generate O-acetylated capsular polysaccharides which can directly be used for vaccine production.

Thus, the present invention relates to an in vitro method for producing *Neisseria meningitidis* capsular polysaccharides which have a defined length, said method comprising the steps:

(a) incubating at least one capsule polymerase with at least one donor carbohydrate and at least one acceptor carbohydrate; wherein the ratio of donor carbohydrate to acceptor carbohydrate is a ratio from about 10:1 to about 400:1; and (b) isolating the resulting capsular polysaccharides, wherein the capsule polymerase is the capsule polymerase of *Neisseria meningitidis* serogroup A or a truncated version of the capsule polymerase of *Neisseria meningitidis* serogroup X, and wherein in step (a) the corresponding capsular polysaccharide is produced. Said production method is an in vitro production method and allows for isolation of capsular polysaccharides from the incubation mixture as defined in step (a); i.e. this isolation allows for the separation of the produced capsular polysaccharides from the capsule polymerase(s), the donor carbohydrate(s) and/or the acceptor carbohydrate(s).

The appended examples demonstrate that capsular polysaccharides which have the desired length of DP10 to DP60 can be produced by using CP-A or a terminally truncated version of CP-X and a ratio of donor carbohydrate to acceptor carbohydrate which is approximately between 10:1 and 400:1. Therefore, in the herein described methods, if the length of the Nm capsular polysaccharides is regulated via the ratio of donor carbohydrate to acceptor carbohydrate, than the donor:acceptor ratio is 10:1 to 400:1 (e.g. 20:1 to 400:1). For example, the ratio may be 10:1, 20:1, 40:1, 60:1, 80:1, 100:1, 150:1, 200:1, 220:1, 240:1, 250:1, 300:1, 350:1 or 400:1. In particular aspects of the invention also other donor acceptor ratios, e.g. ratios from 2:1 to 2000:1 may be used.

If CP-A is used in the in vitro methods described herein, than the ratio of donor carbohydrate to acceptor carbohydrate is preferably from 10:1 to 240:1, and more preferably from 10:1 to 80:1, and even more preferably from 10:1 to 75:1, and even more preferably from 20:1 to 75:1, and most preferably from 20:1 to 60:1 (e.g. 40:1 to 60:1 or 50:1). The term "CP-A" includes a polypeptide which has the amino acid sequence of SEQ ID NO: 9 or 10 and a polypeptide which has at least 80% (preferably at least 90%) sequence identity to SEQ ID NO: 9 (CP-A wildtyp/full-length) or to SEQ ID NO: 10 (ΔN69-CP-A).

If the terminally truncated CP-X is used and if it is regulated via the ratio of donor carbohydrate to acceptor carbohydrate (and not via the reaction time) then the following ratios are preferably used. For example, if the capsule polymerase is a polypeptide which has the amino acid sequence of SEQ ID NO: 28 or which has at least 80% (preferably at least 90%) sequence identity to SEQ ID NO: 28 (ΔC99-CP-X), then the ratio of donor carbohydrate to acceptor carbohydrate is preferably from 10:1 to 80:1, more preferably from 20:1 to 60:1, even more preferably from 20:1 to 50:1, and most preferably from 33:1 to 50:1. In addition, if the capsule polymerase is a polypeptide which has the amino acid sequence of SEQ ID NO: 25 or which has at least 80% (preferably at least 90%) sequence identity to SEQ ID NO: 25 (ΔN58-CP-X), then the ratio of donor carbohydrate to acceptor carbohydrate is preferably from 10:1 to 80:1, more preferably from 20:1 to 50:1, and most preferably from 20:1 to 33:1 (e.g. 33:1). Furthermore, if the capsule polymerase is a polypeptide which has the amino acid sequence of SEQ ID NO: 29 or which has at least 80% (preferably at least 90%) sequence identity to SEQ ID NO: 29 (ΔN58ΔC99-CP-X), then the ratio of donor carbohydrate to acceptor carbohydrate is preferably from 50:1 to 400:1, more preferably from 80:1 to 400:1, even more preferably from 100:1 to 400:1, and most preferably from 100:1 to 200:1.

All capsule polymerases which are applied in the herein described methods are functional. For example, a polypeptide which has at least 80% (preferably at least 90%) sequence identity to any one of the sequences of SEQ ID NOs: 9, 10, 25, 28, and 29 is considered to be functional, i.e. to have the same function as the polypeptide which has the sequence of SEQ ID NO: 9, 10, 25, 28, or 29, respectively. In particular, the function of a polypeptide having the sequence of SEQ ID NO: 9 or 10 is the ability to transfer ManNAc-1P (or a derivative thereof) from UDP-ManNAc (or a derivative thereof) onto an acceptor carbohydrate. Preferably, at least 80% of the acceptor carbohydrates are polysaccharides with a DP of ≥4. In addition, the function of a polypeptide having the sequence of any one of SEQ ID NOs: 25, 28, and 29 is the ability to transfer GlcNAc-1P (or a derivative thereof) from UDP-GlcNAc (or a derivative thereof) onto an acceptor carbohydrate.

If (in the herein described in vitro methods for producing Nm capsular polysaccharides (Nm CPS) which have a defined length) the length of the produced capsular polysaccharides is regulated via the donor:acceptor ratio, then 50-100 nM of the capsular polymerase may be used. The amount of donor carbohydrate may be 1-100 mM, e.g. 5-10 mM. The amount of acceptor carbohydrate is adjusted to the amount of donor carbohydrate so as to result in the desired donor:acceptor ratio ratio. For example, the amount of acceptor carbohydrate may be 1-1000 μM, e.g. 10-40 μM. Preferably, at least 80% of the acceptor carbohydrates are polysaccharides with a DP of ≥4.

For example, if in the herein described methods for producing Nm polysaccharides with a defined length the CP-A is used, then 1-100 nM (preferably 70-100 nM) of CP-A, 10 mM donor carbohydrate (e.g. a dimer of ManNAc-1-phosphate), and an amount of acceptor carbohydrate (e.g. purified capsular polysaccharides of NmA) resulting in a ratio of donor carbohydrate to acceptor carbohydrate which is from 10:1 to 400:1, preferably from 10:1 to 240:1, more preferably from 10:1 to 80:1, even more preferably from 10:1 to 75:1, even more preferably from 20:1 to 75:1, and most preferably from 20:1 to 60:1 (e.g. 40:1 to 60:1 or 50:1) may be used. In a particular example of the herein described methods for producing Nm polysaccharides with a defined length, 70-100 nM of CP-A, 10 mM donor carbohydrate (e.g. UDP-ManNAc; or UDP-GlcNAc, wherein in step (a)

the capsule polymerase is further incubated with the UDP-GlcNAc-epimerase), and an amount of acceptor carbohydrate (e.g. purified capsular polysaccharides of NmA of which at least 80% have a DP of ≥4) resulting in a ratio of donor carbohydrate to acceptor carbohydrate which is from 20:1 to 60:1 is used. The term "CP-A" includes a polypeptide having the amino acid sequence as shown in SEQ ID NO: 9 (CP-A wildtyp/full-length) or SEQ ID NO: 10 (ΔN69-CP-A) and a polypeptide with an amino acid sequence having at least 80% (preferably at least 90%) sequence identity to SEQ ID NO: 9 or to SEQ ID NO: 10 and being functional.

In another particular example of the herein described methods, the length of the produced Nm polysaccharides is regulated via the donor:acceptor ratio and 50-70 nM of a polypeptide having the amino acid sequence of SEQ ID NO: 25 (ΔN58-CP-X), 28 (ΔC99-CP-X), or 29 (ΔN58ΔC99-CP-X), or having an amino acid sequence which is at least 80% (preferably at least 90%) identical to SEQ ID NO: 25, 28, or 29 and being functional; 10 mM donor carbohydrate (e.g. UDP-GlcNAc), and an amount of acceptor carbohydrate (e.g. purified capsular polysaccharides of NmX of which at least 80% have a DP of ≥4) resulting in the desired ratio of donor carbohydrate to acceptor carbohydrate is used.

In another example of the invention, the length of the Nm CPS is regulated by the reaction time, and 50-70 nM capsular polymerase (e.g. ΔC99-CP-X or ΔN58ΔC99-CP-X), 10 mM donor carbohydrate (e.g. UDP-GlcNAc) and 10-30 μM acceptor carbohydrate (e.g. purified capsular polysaccharides of NmX of which at least 80% have a DP of ≥4) is used.

Step (a) of the herein provided in vitro method may be performed by incubating the capsule polymerase, the donor carbohydrate and the acceptor carbohydrate in a reaction buffer (e.g. a buffer comprising 50 mM Tris pH 8.0 and 20 mM $MgCl_2$). The incubation in step (a) may be performed at a temperature range between 20° C. and 40° C., preferably between 25° C. and 37° C., more preferably between 30 and 37° C.

In context of the present invention it has surprisingly and unexpectedly been found that in the herein described methods, if the length of the Nm capsular polysaccharides is regulated via the ratio of donor carbohydrate to acceptor carbohydrate (and not via the reaction time) and if the CP-A or a C-terminally truncated version of the CP-X is used (e.g. ΔC99-CP-X), then the donor:acceptor ratio (i.e. the donor: acceptor quotient) reflects the avDP (i.e. the length of the major species within the produced capsular polysaccharides). For example, if the donor:acceptor ratio is 15:1, then the CP-A or the C-terminally truncated CP-X produces capsular polysaccharides which have an avDP15. Or, if the donor:acceptor ratio is 50:1, then the CP-A or the C-terminally truncated CP-X produces capsular polysaccharides which have an avDP50 (see, e.g., FIG. 1A, 2C, 2F). Or, in other words, if the donor:acceptor ratio is 15:1 (or 50:1, respectively), then the major species (i.e. the main components) of the produced capsular polysaccharides have a length around DP15 (or DP50, respectively). Or, in other words, the product pool has an avDP15 (or avDP50, respectively) and is narrowly distributed around the major species having a DP of 15 (or 50, respectively). In line with this, if the donor:acceptor ratio is from 15:1 to 20:1, then the major species of the produced capsular polysaccharides have a length of avDP15 to avDP20.

Accordingly, the present invention relates to an in vitro method for producing *Neisseria meningitidis* capsular polysaccharides which have a defined length, said method comprising the steps:

(a1) incubating at least one capsule polymerase with at least one donor carbohydrate and at least one acceptor carbohydrate; and thereby producing capsule polysaccharides, wherein at least 60% (preferably at least 80% and most preferably at least 90%) of the produced capsular polysaccharides have a length or in other words a degree of polymerisation corresponding to the ratio of donor carbohydrate to acceptor carbohydrate −20/+30 repeating units; and (b) isolating the resulting capsular polysaccharides, wherein the capsule polymerase is the CP-A or a C-terminally truncated version of the CP-X. The C-terminally truncated version of the CP-X may be a polypeptide which comprises:

(i) an amino acid sequence encoded by a nucleic acid molecule which comprises the nucleic acid sequence of SEQ ID NO: 20 (ΔC99-CP-X); or a nucleic acid sequence having at least 80% (preferably at least 90%) identity to the nucleic acid sequence of SEQ ID NO: 20 and encoding a functional polypeptide; wherein the function comprises the ability to transfer GlcNAc-1P from UDP-GlcNAc onto an acceptor carbohydrate; or (ii) the amino acid sequence of SEQ ID NO: 28 (ΔC99-CP-X); or an amino acid sequence having at least 80% (preferably at least 90%) identity to SEQ ID NO: 28 and being functional, wherein the function comprises the ability to transfer GlcNAc-1P from UDP-GlcNAc onto an acceptor carbohydrate.

As indicated, in the above described method, the produced capsular polysaccharides comprise as a main component capsular polysaccharides having a DP corresponding to about the ratio of donor carbohydrate to acceptor carbohydrate. Preferably, at least 80% of the acceptor carbohydrates are polysaccharides with a DP of ≥4. Thus, the length of the produced capsular polysaccharides can easily be regulated via the donor:acceptor ratio. One aspect of the invention relates to the above described method, wherein the donor:acceptor ratio is from 15:1 to 20:1, and wherein at least 60% (preferably 80%, most preferably 90%) of the produced capsular polysaccharides have a length, or in other words, a degree of polymerisation corresponding to the ratio of donor carbohydrate to acceptor carbohydrate −20/+30 repeating units.

Herein the term "*Neisseria meningitidis* capsular polysaccharides which have a defined length" means that the produced capsular polysaccharides have a defined DP (degree of polymerization) or a defined avDP (average degree of polymerization), e.g. a DP between 10 and 60 or an avDP between 15 and 20. The term "*Neisseria meningitidis* capsular polysaccharides which have a defined length" preferably means that at least 60% (more preferably at least 80%, most preferably at least 90%) of the produced capsular polysaccharides have a length between DP10 and DP60. For example, the DP may be between DP20 and DP60. The DP indicates the number of monosaccharide-units which built up the capsular polysaccharide. For example, a DP of 10 means that the capsular polysaccharide consists of 10 monosaccharide-units and a DP of 60 means that the capsular polysaccharide consists of 60 monosaccharide-units. Accordingly, a NmX capsular polysaccharide having DP10 means that the capsular polysaccharide consists of 10 GlcNAc-1P repeating units. Acidic hydrolysis used to produce oligosaccharide fragments form long polysaccharide chains, results in fragments of different lengths, which in subsequent chromatographic steps can be separated into size classes. The average DP (avDP) describes the dispersion of chains with one class and can be calculated according to established protocols as described, e.g. in Berti (2012) Vaccine 30 (45), 6409-6415. Or, in other words, the avDP describes the average length of a polysaccharide pool. Alternative ways to determine the DP of oligosaccharides are high percentage polyacrylamide gel electrophoresis or HPLC-anion-exchange chromatography as demonstrated in the appended examples. The avDP may be determined by the protocol described in Berti (2012) 30(45): 6409-15., which includes $^{31}$P NMR and High Performance Anionic Exchange Chromatography with Pulsed Amperometric Detection (HPAEC-PAD). For vaccine production usually capsular polysaccharides having an avDP of 15 to 20 is used. The product pool of polysaccharides with an avDP of 15 to 20 consists of polysaccharides having a DP of 10 to 60. The herein provided in vitro methods have the advantage that capsule polysaccharides with the length which is desired for vaccine production (i.e. DP10 to DP60) can directly be produced. Herein the term "*Neisseria meningitidis* capsular polysaccharides which have a defined length" also means that the produced capsular polysaccharides have a low dispersity (i.e. a narrow product distribution).

In the above described in vitro method, if the capsule polymerase of Nm serogroup A is used, than capsule polysaccharides of Nm serogroup A are produced. Analogously, if a truncated version of the capsule polymerase of Nm serogroup X is used, that capsule polysaccharides of Nm serogroup X are produced.

As described herein and illustrated in the appended examples, one aspect of the present invention relates to the identification of terminally truncated versions of the capsule polymerase of Nm serogroup X (CP-X, also designated as CsxA). These terminally truncated proteins have the advantage that they have an increased activity as compared to the full length CP-X. A further advantageous property of these terminally truncated proteins is that they can be regulated by the ratio of donor carbohydrates to acceptor carbohydrates such that they produce capsular polysaccharides which have a uniform and defined length. This is surprising since the full length CP-X cannot be regulated by the donor-acceptor ratio. Furthermore, in context of the present invention it has astonishingly been found that these terminally truncated versions of the CP-X can also be regulated by the reaction time so as to produce capsular polysaccharides which have a uniform and defined length. More specifically, the time how long the terminally truncated CP-X is incubated with the donor carbohydrates (and, optionally, the acceptor carbohydrates) regulates the length of the produced capsule polysaccharides. Accordingly, an incubation time can be chosen which results in the production of capsule polysaccharides of NmX which have the length which is desired for vaccine production (i.e. DP10 to DP60). Accordingly, one embodiment of the invention relates to an in vitro method for producing *Neisseria meningitidis* capsular polysaccharides which have a defined length, said method comprising the steps:
(a) incubating at least one capsule polymerase with at least one donor carbohydrate and at least one acceptor carbohydrate; wherein the incubation time ranges from 3 to 45 minutes; and
(b) isolating the resulting capsular polysaccharides,
wherein the capsule polymerase is a truncated version of the capsule polymerase of *Neisseria meningitidis* serogroup X.

Or, in other words, the invention relates to an in vitro method for producing *Neisseria meningitidis* capsular polysaccharides which have a defined length, said method comprising the steps:
(a) incubating at least one capsule polymerase with at least one donor carbohydrate and at least one acceptor carbohydrate; wherein the incubation time ranges from about 3 to about 45 minutes; and
(b) isolating the resulting capsular polysaccharides,
wherein the capsule polymerase is a truncated version of the capsule polymerase of *Neisseria meningitidis* serogroup X, and wherein in step (a) the corresponding capsular polysaccharide is produced. Said production method is an in vitro production method and allows for isolation of capsular polysaccharides from the incubation mixture as defined in step (a); i.e. this isolation allows for the separation of the produced capsular polysaccharides from the capsule polymerase(s), the donor carbohydrate(s) and/or the acceptor carbohydrate(s).

Due to the distributive nature of the elongation mechanism used by the truncated CP-X, the reaction can be stopped at any time whereby the resulting avDP depends on the reaction time. Therefore, if the truncated version of the CP-X is regulated via the reaction time, then the ratio of donor carbohydrate to acceptor carbohydrate is not relevant. For example, the ratio of donor carbohydrate to acceptor carbohydrate can range from 1:1 to 50000:1, preferably from 10:1 to 10000:1 [Hier wurde entsprechend der Ansprüche 10:1 to 10000:1 gewählt] (e.g. from 200:1 to 10000:1, or more preferably from 100:1 to 8000:1).

In context of the present invention it has surprisingly been found that the herein described capsule polymerases are active even if they are coupled to a solid phase. Immobilizing a component on a solid phase has the advantage that it reduces labor in the isolating step (b). More specifically, immobilizing a component to a solid phase omits further purification steps to remove the produced capsular polysaccharides from the reaction mixture of step (a). Thus, in the herein provided in vitro methods for producing Nm capsular polysaccharides, one of the components may be immobilized (i.e. bound/coupled) on a solid phase. For example, the donor carbohydrate or the capsule polymerase may be immobilized on a solid phase. The solid phase may be column, such as a His-Trap column (i.e. a column having His-Trap beads). In a particular aspect of the inventive in vitro methods, the capsule polymerase is immobilized on a solid phase. For example, a polypeptide which has the amino acid sequence of SEQ ID NO: 29 (ΔN58ΔC99-CP-X) or which has at least 80% (preferably at least 90%) sequence identity to SEQ ID NO: 29 and being functional may be immobilized on a solid phase.

It is noted that the capsule polymerase of Nm serogroup X is capable of a de novo synthesis of capsular polysaccharides. Or, in other words, the CP-X is able to synthesize capsular polysaccharides in the absence of acceptor carbohydrates (Fiebig, Glycobiology (2014) 24:150-8). Thus, if the terminally truncated version of CP-X is regulated by the reaction time, the presence of acceptor carbohydrates is optional. Accordingly, one aspect of the invention relates to an in vitro method for producing Nm capsular polysaccharides of NmX which have a defined length, said method comprising the steps:
(a) incubating a terminally truncated version of the CP-X with at least one donor carbohydrate (and, optionally, with at least one acceptor carbohydrate); wherein the incubation time ranges from 3 to 45 minutes; and
(b) isolating the resulting capsular polysaccharides.

As described herein and illustrated in the appended examples, the inventive terminally truncated versions of the capsule polymerase of Nm serogroup X can be regulated by both, the donor-acceptor ratio and the reaction time (i.e. the time how long the terminally truncated version of the CP-X is incubated with the donor saccharides and the acceptor saccharides).

As mentioned above, if the truncated version of the CP-X is regulated via the reaction time, then the ratio of donor carbohydrate to acceptor carbohydrate is not relevant. Thus, as also demonstrated in the appended Examples, if the length of the Nm capsular polysaccharides is regulated by the reaction time, then higher donor-acceptor ratios can be used (to produce *Neisseria meningitidis* capsular polysaccharides which have a defined length) as compared to the method wherein the length of the Nm capsular polysaccharides is regulated via the donor-acceptor ratio (and not via the reaction time). Accordingly, one aspect of the invention relates to an in vitro method for producing *Neisseria meningitidis* capsular polysaccharides which have a defined length, said method comprising the steps:
(a) incubating at least one capsule polymerase with at least one donor carbohydrate and at least one acceptor carbohydrate; wherein
  (i) the ratio of donor carbohydrate to acceptor carbohydrate is a ratio from 10:1 to 10000:1 [Hier wurde entsprechend der Ansprüche 10:1 to 10000:1 gewählt], and
  (ii) the incubation time ranges from 3 to 45 minutes; and
(b) isolating the resulting capsular polysaccharides,
wherein the capsule polymerase is a truncated version of the capsule polymerase of *Neisseria meningitidis* serogroup X.

Or, in other words, the invention relates to an in vitro method for producing *Neisseria meningitidis* capsular polysaccharides which have a defined length, said method comprising the steps:
(a) incubating at least one capsule polymerase with at least one donor carbohydrate and at least one acceptor carbohydrate; wherein
  (i) the ratio of donor carbohydrate to acceptor carbohydrate is a ratio from about 10:1 to about 10000:1, and
  (ii) the incubation time ranges from about 3 to about 45 minutes; and
(b) isolating the resulting capsular polysaccharides,
wherein the capsule polymerase is a truncated version of the capsule polymerase of *Neisseria meningitidis* serogroup X; and wherein in step (a) the corresponding capsular polysaccharide is produced. Said production method is an in vitro production method and allows for isolation of capsular polysaccharides from the incubation mixture as defined in step (a); i.e. this isolation allows for the separation of the produced capsular polysaccharides from the capsule polymerase(s), the donor carbohydrate(s) and/or the acceptor carbohydrate(s).

Or, in other words, the invention relates to an in vitro method for producing Nm capsular polysaccharides of NmX which have a defined length, said method comprising the steps:
(a) incubating a terminally truncated version of CP-X with at least one donor carbohydrate and at least one acceptor carbohydrate; wherein
  (i) the ratio of donor carbohydrate to acceptor carbohydrate is a ratio from 10:1 to 10000:1, and
  (ii) the incubation time ranges from 3 to 45 minutes; and
(b) isolating the resulting capsular polysaccharides.

The appended examples demonstrate that capsular polysaccharides of NmX which have the desired length of DP10 to DP60 can be produced by using a terminally truncated version of CP-X and a ratio of donor carbohydrate to acceptor carbohydrate which is approximately between 10:1 and 400:1. The appended Examples also demonstrate that higher donor-acceptor ratios (e.g., 200:1 or 8000:1) can be used to produce Nm capsule polysaccharides which have a defined length, if the terminally truncated version of the CP-X is regulated via the reaction time (i.e. if the reaction time is from 3 to 45 min).

Accordingly, if the length of the Nm capsular polysaccharides is regulated by the reaction time, then the ratio of donor carbohydrate to acceptor carbohydrate is not relevant. For example, the donor:acceptor ratio can be from 10:1 to 10000:1, preferably from 100:1 to 8000:1 (e.g. from 200:1 to 1000:1)

For example, if the terminally truncated CP-X is regulated by the reaction time, then the ratio of donor carbohydrate to acceptor carbohydrate of 10:1, 20:1, 40:1, 60:1, 80:1, 100:1, 120:1, 140:1, 160:1, 180:1, 200:1, 220:1, 240:1, 250:1, 300:1, 350:1, 400:1, 450:1, 500:1, 550:1, 600:1, 650:1, 700:1, 750:1, 800:1, 850:1, 900:1, 950:1, 1000:1, 2000:1, 3000:1, 4000:1, 5000:1, 6000:1, 7000:1, 8000:1, 9000:1, or 10000:1 may be used.

In the herein described and provided in vitro methods, if the length of the produced capsule polysaccharides in regulated via the reaction time, it is envisaged that the truncated version of the CP-X is used in a concentration ranging from 20 to 500 nM, preferably from 20 to 200 nM, or more preferably from 50 to 100 nM (e.g. 50 nM). In addition, it is envisaged herein that said truncated version of the CP-X is incubated with a donor concentration of 1 to 100 mM, preferably of 1 to 50 mM, more preferably of 2 to 20 mM, even more preferably of 5 to 10 mM, or most preferably of 10 mM UDP-GlcNAc; and with an acceptor concentration resulting in a donor to acceptor ratio from 10:1 to 10000:1, preferably from 100:1 to 8000:1, (e.g. from 200:1 to 1000:1) and that the reaction time ranges from 3 to 45 minutes, more preferably from 5 to 30 minutes, or most preferably from 5 to 10 minutes. Preferably, at least 80% of the acceptor carbohydrates are polysaccharides with a DP of ≥4.

Or, in other words, if the length of the Nm capsular polysaccharides is regulated by the reaction time, it is envisaged that the concentration of the truncated version of the CP-X (e.g. a capsule polymerase having at least 80% (preferably at least 90%) identity to any one of the sequences of SEQ ID NOs: 25, 28 and 29 and being functional) ranges from 20 to 500 nM, preferably from 20 to 200 nM, or more preferably from 50 to 100 nM (e.g. 50 nM). In addition, it is envisaged herein that said truncated version of the CP-X is incubated with a donor concentration of 1 to 100 mM, preferably of 1 to 50 mM, more preferably of 2 to 20 mM, even more preferably of 5 to 10 mM, or most preferably of 10 mM UDP-GlcNAc; and with an acceptor concentration resulting in a donor to acceptor ratio from 10:1 to 10000:1, preferably from 100:1 to 8000:1 (e.g. 200:1 to 1000:1); and that the reaction time ranges from 3 to 45 minutes. Preferably, at least 80% of the acceptor carbohydrates are polysaccharides with a DP of ≥4.

As indicated above, if the length of the Nm capsular polysaccharides is regulated by the reaction time, then the reaction time ranges (i.e. is) from 3 to 45 minutes. Preferably, the reaction time ranges from 5 to 30 minutes, more preferably from 5 to 10 minutes (e.g. 5 or 10 min). For example, if the capsule polymerase is a polypeptide which has at least 80% (preferably at least 90%) sequence identity to SEQ ID NO: 28 (ΔC99-CP-X) and being functional, then the reaction time ranges preferably from 5 to 10 minutes, and is most preferably 5 minutes. In addition, if the capsule polymerase is a polypeptide which has at least 80% (preferably at least 90%) sequence identity to SEQ ID NO: 25 (ΔN58-CP-X) and being functional, then the reaction time ranges preferably from 5 to 30 minutes. Furthermore, if the capsule polymerase is a polypeptide which has at least 80% (preferably at least 90%) sequence identity to SEQ ID NO: 29 (ΔN58ΔC99-CP-X) and being functional, then the reaction time ranges preferably from 5 to 30 minutes and is most preferably 10 minutes.

In the inventive in vivo methods, the temperature in the incubation step (a) may be from 20° C. to 40° C., preferably from 25° C. to 37° C., more preferably from 30° C. to 37° C., and most preferably 37° C.

As indicated above, if the length of the Nm CPS is regulated by the reaction time, the reaction time may be 3-45 min, preferably 5-30 minutes. For example, the reaction time may be 3 min, 5 min, 10 min, 15 min, 20 min, 25 min 30 min, 35 min, 40 min or 45 min. In addition, if the length of the Nm CPS is regulated by the reaction time, it is preferred that a C- and N-terminally truncated version of the CP-X (such as ΔN58ΔC99-CP-X) is used. This truncated version of the CP-X may be a polypeptide having the amino acid sequence of SEQ ID NO: 29 or a polypeptide having an amino acid sequence which has at least 80% homology to SEQ ID NO: 29 and being functional.

If the length of the Nm CPS is regulated by the ratio of donor carbohydrate to acceptor carbohydrate, then the reaction time may be, e.g., 4-7 hours.

In step (b) of the herein described in vitro methods for producing Nm CPS which have a defined length (i.e. which have low dispersity in terms of length), the resulting CPS are isolated. Isolation of the synthesized CPS may be performed, e.g., by anion exchange chromatography (AEC). For example, the produced CPS may be purified via AEC by using a MonoQ HR5/5 column (Pharmacia biotech) at a flow rate of 1 mL/min and a linear sodium chloride gradient or by High Performance Anionic Exchange Chromatography with Pulsed Amperometric Detection (HPAEC-PAD) as described (Berti et al. 2012 Vaccine. (2012) 30:6409-15).

In accordance with the present invention, the ingredients which are used in the herein described methods for producing Nm CPS can be packed together as a composition. Accordingly, one aspect of the invention relates to a composition comprising:
(i) at least one capsule polymerase;
(ii) at least one donor carbohydrate; and
(iii) at least one acceptor carbohydrate,
wherein the ratio of donor carbohydrate to acceptor carbohydrate is a ratio from 10:1 to 10000:1 (e.g. 20:1 to 1000:1), and wherein the capsule polymerase is the capsule polymerase of *Neisseria meningitidis* serogroup A or a truncated capsule polymerase of *Neisseria meningitidis* serogroup X.

The skilled person understands that, depending on the exactness of the measurements, the exact ratio can slightly deviate from 10:1 to 10000:1. Accordingly, the methods of the invention can also be performed with a ratio of about 10:1 to 10000:1. Thus, one aspect of the invention relates to a composition comprising:
(i) at least one capsule polymerase;
(ii) at least one donor carbohydrate; and
(iii) at least one acceptor carbohydrate,
wherein the ratio of donor carbohydrate to acceptor carbohydrate is a ratio from about 10:1 to about 10000:1 (e.g. about 20:1 to about 1000:1), and wherein the capsule polymerase is the capsule polymerase of *Neisseria meningitidis* serogroup A or a truncated capsule polymerase of *Neisseria meningitidis* serogroup X.

For example, in the herein provided compositions, 20 nM to 500 µM (preferably 20 to 200 nM, more preferably 50 to 100 nM, e.g. 50-70 nM) of the capsular polymerase (e.g. ΔC99-CP-X, ΔN58ΔC99-CP-X or ΔN58-CP-X, or a polypeptide having at least 80% (preferably at least 90%) identity to any one of SEQ ID NOs: 25, 28 and 29 and being functional) may be used. The amount of donor carbohydrate (e.g. UDP-GlcNAc) may be 1-100 mM, preferably 1 to 50 mM, more preferably 2 to 20 mM (e.g. 5-10 mM). The acceptor carbohydrate may be purified capsular polysaccharides of NmX. Preferably, the amount of the acceptor carbohydrate is adjusted to result in a ratio of donor carbohydrate to acceptor carbohydrate of 10:1 to 10000:1, preferably of 100:1 to 8000:1 (e.g. of 200:1 to 1000:1). For example, the amount of the acceptor carbohydrate may be 1-1000 µM, e.g. 10-40 µM.

In the herein provided compositions, the ratio of donor carbohydrate to acceptor carbohydrate is 10:1 to 10000:1, e.g. 20:1, 40:1, 60:1, 80:1, 100:1, 150:1, 200:1, 220:1, 240:1, 250:1, 300:1, 350:1, 400:1, 450:1, 500:1, 550:1, 600:1, 650:1, 700:1, 750:1, 800:1, 850:1, 900:1, 950:1, 1000:1, 2000:1, 3000:1, 4000:1, 5000:1, 6000:1, 7000:1, 8000:1, 9000:1 or 10000:1. For example, the donor-acceptor-ratio may be from 2:1 to 2000:1. One aspect of the invention relates to the herein described composition, wherein the ratio of donor carbohydrate to acceptor carbohydrate is a ratio from 20:1 to 240:1.

The composition of the invention may be suitable for storage (e.g. storage under cold temperatures to prevent that the synthesis of capsular polysaccharides starts). For instance, the composition may be suitable for storage in 4° C., 0° C., −10° C., −20° C. or −80° C.

The inventive compositions and in vitro methods comprise "at least one" capsule polymerase. Therefore, the inventive compositions and in vitro methods can comprise several capsular polymerases of different types in one reaction mixture (e.g. CP-A together with the terminally truncated CP-X). However, it is preferred that the inventive compositions and in vitro methods comprise only capsule polymerases of one type (e.g. only CP-A or only the terminally truncated version of CP-X).

The in vitro methods of the invention may be realized by using an appropriate kit. Accordingly, another embodiment of the invention relates to a kit for carrying out the in vitro methods of the invention, comprising the above described composition. The embodiments disclosed in connection with the in vitro method of the present invention apply, mutatis mutandis, to the composition and the kit of the present invention.

Advantageously, the kit of the present invention further comprises, optionally (a) reaction buffer(s), storage solutions, wash solutions and/or remaining reagents or materials required for the conduction of the assays as described herein. Furthermore, parts of the kit of the invention can be packaged individually in vials or bottles or in combination in containers or multicontainer units. These vials/bottles/containers or multicontainers may, in addition to the capsule polymerases and donor carbohydrates and acceptor carbohydrates as described herein, comprise preservatives or buffers for storage. In addition, the kit may contain instructions for use.

The composition of the present invention or the kit of the present invention may be advantageously used for carrying out the in vitro methods as described herein (i.e. for producing Nm capsular polysaccharides of NmX which have a defined length). The manufacture of the kit of the present invention follows preferably standard procedures which are known to the person skilled in the art.

In the methods and compositions of the invention, the capsule polymerase of NmA (CP-A also designated as CsaB) may be used. The DNA sequence of the wild type full length CP-A is shown herein as SEQ ID NO: 1. The DNA sequence of the full length CP-A which is optimized for expression in *E. coli* (i.e. a codon optimized DNA sequence) is shown herein as SEQ ID NO: 2. The polypeptide resulting from the expression of the wild type or codon optimized CP-A polynucleotide is identical. The amino acid sequence of the full length CP-A is given in SEQ ID NO: 9.

Of note, within the DNA sequence of the CP-A, the inventors of the present invention identified an additional ATG start codon and cloned the corresponding truncation ΔN69-CP-A (which starts from the alternative ATG). The designation "ΔN69-CP-A" means that 69 amino acids are lacking at the N-terminus of the CP-A protein. Herein, "ΔN69-CP-A" is also designated as "dN69-CsaB". The polynucleotide sequence of a codon optimized version of ΔN69-CP-A is shown in SEQ ID NO: 3. The polynucleotide sequence of the wild type ΔN69-CP-A is shown in SEQ ID NO: 46. The amino acid sequence of the expressed wild type or codon optimized ΔN69-CP-A is identical and in SEQ ID NO: 10. Surprisingly, ΔN69-CP-A is advantageous over the full length CP-A. In particular, as demonstrated in the appended illustrative examples, while increased degradation and concomitantly reduced expression was seen for the codon optimized full length CP-A, the codon optimized ΔN69-CP-A is well expressed and no degradation is detectable. In addition, as shown in the appended examples, by using the radioincorporation assay as described in Fiebig, Glycobiology (2014) 24:150-8, it was demonstrated the ΔN69-CP-A protein is active (i.e. is capable of producing NmA capsular polysaccharides). Furthermore, the appended examples also show that the ΔN69-CP-A and the full length CP-A show identical activity profiles. This is surprising since several other tested truncated versions of CP-A (i.e. ΔN97-CP-A, ΔN167-CP-A, ΔN235-CP-A, ΔC45-CP-A and ΔC25-CP-A) were demonstrated to be not active. It is mentioned that herein, in particular in the appended examples, "Δ" is also designated as "d" or "delta".

Accordingly, one aspect of the present invention relates to a truncated version of the CP-A (i.e. Δ69-CP-A), wherein said truncated version of the CP-A is the polypeptide of any one of (a) to (f):

(a) a polypeptide comprising an amino acid sequence encoded by a nucleic acid molecule having the nucleic acid sequence of SEQ ID NO: 3 or 46;

(b) a polypeptide comprising the amino acid sequence of SEQ ID NO: 10;

(c) a polypeptide encoded by a nucleic acid molecule encoding a polypeptide comprising the amino acid sequence of SEQ ID NO: 10 or of a functional fragment thereof, wherein the function comprises the ability to transfer ManNAc-1P or a derivative thereof from UDP-ManNAc or a derivative thereof onto an acceptor carbohydrate;

(d) a polypeptide comprising an amino acid sequence encoded by a nucleic acid molecule hybridizing under stringent conditions to the complementary strand of a nucleic acid molecule as defined in (a) or (c) and encoding a functional polypeptide; or a functional fragment thereof, wherein the function comprises the ability to transfer ManNAc-1P or a derivative thereof from UDP-ManNAc or a derivative thereof onto an acceptor carbohydrate;

(e) a polypeptide having at least 80%, preferably at least 85%, more preferably at least 90%, even more preferably at least 95%, even more preferably at least 96%, even more preferably at least 97%, even more preferably at least 98%, or even more preferably at least 99% homology to the polypeptide of any one of (a) to (d), whereby said polypeptide is functional; or a functional fragment thereof, wherein the function comprises the ability to transfer ManNAc-1P or a derivative thereof from UDP-ManNAc or a derivative thereof onto an acceptor carbohydrate; and (f) a polypeptide comprising an amino acid sequence encoded by a nucleic acid molecule being degenerate as a result of the genetic code to the nucleotide sequence of a nucleic acid molecule as defined in (a), (c), and (d).

As indicated above, the herein provided truncated version of the CP-A comprises the ability to transfer ManNAc-1P or a derivative thereof from UDP-ManNAc or a derivative thereof onto an acceptor carbohydrate (i.e. onto the hydroxyl group of C6 of a capsular polysaccharide from NmA or a derivative thereof). Accordingly, this function can be the ability to transfer ManNAc-1P from UDP-ManNAc onto an acceptor carbohydrate. The acceptor carbohydrate may be extended/activated at the reducing end or the reducing end phosphate. In addition, the size of the produced capsular polysaccharides can be controlled by the ratio of donor and acceptor carbohydrate when the ratio is in the range of 10:1 to 400:1, preferably from 10:1 to 240:1, more preferably from 10:1 to 80:1, even more preferably from 10:1 to 75:1, even more preferably from 20:1 to 75:1, and most preferably from 20:1 to 60:1 (e.g. 40:1 to 60:1 such as 50:1). Within this range, only one product distribution corresponding in size to the calculated donor-acceptor ratio is obtained at reaction endpoints.

The transfer of ManNAc-1P (or a derivative thereof) from UDP-ManNAc (or a derivative thereof) onto an acceptor carbohydrate may be performed by incubating a truncated version of the CP-A (i.e. ΔN69-CP-A) with UDP-ManNAc (or a derivative thereof) and an acceptor carbohydrate (e.g. a tetramer or a dimer consisting of ManNAc-1P units linked together by phosphodiester bonds). Whether a transfer from ManNAc-1P (or a derivative thereof) from UDP-ManNAc (or a derivative thereof) onto an acceptor carbohydrate has occurred can be tested, e.g. by high percentage PAGE and developed by alcian blue/silver staining (Fiebig, Glycobiology (2014) 24:150-8). in the presence of a size marker or by $^{31}P$ NMR monitoring the characteristic phosphodiester signal, or by High Performance Anionic Exchange Chromatography with Pulsed Amperometric Detection (HPAEC-PAD) as described (Berti Vaccine (2012) 30:6409-15).

A derivative of ManNAc-1P may be ManNAc-3-O-Ac or ManNAc-4-O-Ac or ManNAc-3,4-di-O-Ac. A derivative of UDP-ManNAc may be UDP-ManNAc-3-O-Ac or UDP-ManNAc-4-O-Ac or UDP-ManNAc-3,4-di-O-Ac.

One aspect of the present invention relates to the above described truncated version of the CP-A (i.e. ΔN69-CP-A), wherein the function comprises the ability to transfer ManNAc-1P (or a derivative thereof) from UDP-ManNAc (or a derivative thereof) onto an acceptor carbohydrate, wherein the truncated version of the CP-A shows the same activity profile as the full length CP-A. An activity profile means that elongated products are of similar or identical dispersity.

The full length CP-A, the codon optimized CP-A, the ΔN69-CP-A or the codon optimized ΔN69-CP-A may be used in the herein described in vitro methods for producing Nm capsular polysaccharides or compositions. Accordingly, one embodiment of the present invention relates to the in vitro method of the invention or the composition of the invention, wherein the capsule polymerase of *Neisseria meningitidis* serogroup A is the polypeptide of any one of (a) to (f):

(a) a polypeptide comprising an amino acid sequence encoded by a nucleic acid molecule having the nucleic acid sequence of any one of SEQ ID NO: 1 to 3;

(b) a polypeptide comprising the amino acid sequence of SEQ ID NO: 9 or 10;

(c) a polypeptide encoded by a nucleic acid molecule encoding a polypeptide comprising the amino acid sequence of SEQ ID NO: 9 or 10, or of a functional fragment thereof;

(d) a polypeptide comprising an amino acid sequence encoded by a nucleic acid molecule hybridizing under stringent conditions to the complementary strand of a nucleic acid molecule as defined in (a) or (c) and encoding a functional polypeptide; or a functional fragment thereof;

(e) a polypeptide having at least 80%, more preferably at least 85%, even more preferably at least 90%, even more preferably at least 95%, even more preferably at least 96%, even more preferably at least 97%, even more preferably at least 98% or most preferably at least 99% identity to the polypeptide of any one of (a) to (d), whereby said polypeptide is functional; or a functional fragment thereof; and (f) a polypeptide comprising an amino acid sequence encoded by a nucleic acid molecule being degenerate as a result of the genetic code to the nucleotide sequence of a nucleic acid molecule as defined in (a), (c), and (d).

A particular embodiment of the present invention relates to the in vitro method of the invention or the composition of the invention, wherein the capsule polymerase of *Neisseria meningitidis* serogroup A is the polypeptide of any one of (a) to (f):

(a) a polypeptide comprising an amino acid sequence encoded by a nucleic acid molecule having the nucleic acid sequence of any one of SEQ ID NO: 1 to 3;

(b) a polypeptide comprising the amino acid sequence of SEQ ID NO: 9 or 10;

(c) a polypeptide encoded by a nucleic acid molecule encoding a polypeptide comprising the amino acid sequence of SEQ ID NO: 9 or 10, or of a functional fragment thereof, wherein the function comprises the ability to transfer ManNAc-1P or a derivative thereof from UDP-ManNAc or a derivative thereof onto an acceptor carbohydrate;

(d) a polypeptide comprising an amino acid sequence encoded by a nucleic acid molecule hybridizing under stringent conditions to the complementary strand of a nucleic acid molecule as defined in (a) or (c) and encoding a functional polypeptide; or a functional fragment thereof, wherein the function comprises the ability to transfer ManNAc-1P or a derivative thereof from UDP-ManNAc or a derivative thereof onto an acceptor carbohydrate;

(e) a polypeptide having at least 80%, more preferably at least 85%, even more preferably at least 90%, even more preferably at least 95%, even more preferably at least 96%, even more preferably at least 97%, even more preferably at least 98% or most preferably at least 99% identity to the polypeptide of any one of (a) to (d), whereby said polypeptide is functional; or a functional fragment thereof, wherein the function comprises the ability to transfer ManNAc-1P or a derivative thereof from UDP-ManNAc or a derivative thereof onto an acceptor carbohydrate; and (f) a polypeptide comprising an amino acid sequence encoded by a nucleic acid molecule being degenerate as a result of the genetic code to the nucleotide sequence of a nucleic acid molecule as defined in (a), (c), and (d).

As indicated, the function of the above under items (a) to (f) described capsule polymerase of *Neisseria meningitidis* serogroup A comprises the ability to transfer ManNAc-1P or a derivative thereof from UDP-ManNAc or a derivative thereof onto an acceptor carbohydrate. Preferably, at least 80% of the acceptor carbohydrates are polysaccharides with a DP of ≥4. For example, the acceptor (or at least 80% of the acceptor carbohydrates) may be DP4, DP5 or DP6; preferably the acceptor (or at least 80% of the acceptor carbohydrates) is a tetramer or pentamer of ManNAc-1P with a free reducing end.

As described, the full length CP-A, the codon optimized CP-A or the codon optimized ΔN69-CP-A (i.e. the polypeptide described above under items (a) to (f)) may be used in the herein described in vitro methods for producing Nm capsular polysaccharides or in the herein described compositions. For example, if one of these capsule polymerases is used in the in vitro methods or compositions described herein, than the ratio of donor carbohydrate to acceptor carbohydrate is from 10:1 to 400:1, preferably from 10:1 to 240:1, and more preferably from 10:1 to 80:1, and even more preferably from 10:1 to 75:1, even more preferably from 20:1 to 75:1, and most preferably from 20:1 to 60:1 (e.g. 40:1 to 60:1 such as 50:1).

In a prioritized aspect of the invention, the codon optimized ΔN69-CP-A is used in the herein described in vitro methods for producing Nm CPS which have a defined length or in the herein described compositions.

The inventors of the present invention surprisingly identified truncated versions of the capsule polymerase of Nm serogroup X (CP-X). For example, the CP-X-fragment ΔN67ΔC99-CP-X (wherein 67 amino acids are lacking at the N-terminus and 99 amino acids are lacking at the C-terminus) was demonstrated to be functional (i.e. able to transfer GlcNAc-1P (or a derivative thereof) from UDP-GlcNAc (or a derivative thereof) onto an acceptor carbohydrate. Preferably, at least 80% of the acceptor carbohydrates are polysaccharides with a DP of ≥4. For example, the acceptor (or at least 80% of the acceptor carbohydrates) may be DP4, DP5, or DP6 (see, e.g., FIG. 3E); preferably, the acceptor (or at least 80% of the acceptor carbohydrates) is a tetramer or pentamer of GlcNAc-1P with a free reducing end as shown in FIG. 3. The DNA sequence of ΔN67ΔC99-CP-X is provided herein as SEQ ID NO: 23 and the amino acid sequence is shown herein as SEQ ID NO: 31. In context of the present invention it is expected that the C-terminally truncated ΔC136-CP-X (wherein 136 amino acids are lacking at the C-terminus) is active, as several C-terminal mutations (except of a mutation at position 351) do not affect activity of the CP-X (unpublished data, see also FIG. 6C). In addition also the fragment ΔN83ΔC136-CP-X (wherein 83 amino acids are lacking at the N-terminus and 136 amino acids are lacking at the C-terminus) is considered to be active because the CP-A is still active if it carries a mutation at amino acid 250 (in the N-terminus) which corresponds to amino acid 84 in CP-X.

As demonstrated in the appended examples, the inventors of the present invention surprisingly found that, when terminally truncated, the CP-X can be regulated via the donor-acceptor ratio such that it produces CPS with a uniform and defined length. Furthermore, these terminally truncated versions of the CP-X have the additional advantage that they can also be regulated by the reaction time. Moreover, the inventive terminally truncated versions of CP-X have the superior property that they have a significantly improved activity as compared to the full length CP-X. The DNA sequence of the full length CP-X is shown herein as SEQ ID NO: 16 and the amino acid sequence of the full length CP-X is shown herein as SEQ ID NO: 24.

The illustrative appended examples demonstrate several truncated versions of the CP-X which are capable of producing NmX capsular polysaccharides. For example, the proteins ΔN58-CP-X (wherein 58 amino acids are lacking at the N-terminus of CP-X and which comprises approximately 88% of the full length CP-X), ΔC99-CP-X (wherein 98 amino acids are lacking at the C-terminus of CP-X and which comprises approximately 80% of the full length CP-X) and ΔN58ΔC99-CP-X (wherein 58 amino acids are lacking at the N-terminus and 98 amino acids are lacking at the C-terminus and which comprises approximately 68% of the full length CP-X) have been demonstrated to be functional capsular polysaccharides. Herein, in particular in the appended examples, "ΔN58-CP-X", "ΔC99-CP-X" and "ΔN58ΔC99-CP-X" are also designated as "dN58-CsxA", "dC99-CsxA" and "dN58dC99-CsxA", respectively. Regarding the designation "ΔC99" it is noted that this designation has been chosen as the DNA sequence which was used to generate the ΔC99-CP-X construct ends with codon 387 of the CP-X sequence. However, this DNA sequence was cloned to have an XhoI restriction site (CTCGAG) at the 3' end. The codon CTC within this site encodes leucine. Amino acid 388 of wild type CP-X is also a leucine (however encoded by CTT). Therefore, in the proteins ΔC99-CP-X and ΔN58ΔC99-CP-X, 98 (instead of 99) amino acids are lacking at the C-terminus. In this regard it is further noted that if the herein provided polynucleotide encoding ΔC99-CP-X (i.e. SEQ ID NO: 20) is expressed in a host cell, then the resulting polypeptide has the sequence as given herein in SEQ ID NO: 28. Analogously, if the herein provided polynucleotide encoding ΔN58ΔC99-CP-X (i.e. SEQ ID NO: 21) is expressed in a host cell, then the resulting polypeptide has the sequence as given herein in SEQ ID NO: 29. Herein, in particular in the appended examples, "ΔC99-CP-X" and "ΔN58ΔC99-CP-X" are also designated as "dC99-CsxA" and "dN58dC99-CsxA", respectively.

As mentioned, the inventors of the present invention surprisingly found that truncated versions of the CP-X have a considerably higher activity as compared to the full length CP-X. More specifically, by using a radioincorporation assay, the appended illustrative examples demonstrate that truncated versions of the CP-X (e.g. ΔN58-CP-X, ΔC99-CP-X or ΔN58ΔC99-CP-X) are more active (i.e. assemble more saccharide monomers to capsule polysaccharides) as compared to the full length CP-X. In the herein described and provided in vitro methods and compositions, the truncated version of the CP-X may preferably be a terminally truncated version of the CP-X. Accordingly, a further embodiment of the present invention relates to a truncated version of the CP-X, which is a polypeptide comprising:

(a) an amino acid sequence encoded by a nucleic acid molecule which is a terminally truncated version of the nucleic acid sequence of SEQ ID NO: 16 and comprises maximal 50-95% of the nucleic acid sequence of SEQ ID NO: 16;

(b) an amino acid sequence which is a terminally truncated version of the amino acid sequence of SEQ ID NO: 24 and comprises maximal 50-95% of the amino acid sequence of SEQ ID NO: 24;

(c) a polypeptide encoded by a nucleic acid molecule encoding a polypeptide having an amino acid sequence which is a terminally truncated version of the amino acid sequence of SEQ ID NO: 24 and comprises maximal 50-95% of the amino acid sequence of SEQ ID NO: 24;

(d) a polypeptide encoded by a nucleic acid molecule hybridizing under stringent conditions to the complementary strand of a nucleic acid molecule as defined in (a) or (c) and encoding a functional polypeptide;

(e) a polypeptide having at least 80%, more preferably at least 85%, even more preferably at least 90%, even more preferably at least 95%, even more preferably at least 96%, even more preferably at least 97%, even more preferably at least 98% or most preferably at least 99% identity to the polypeptide of any one of (a) to (d), whereby said polypeptide is functional; or (f) a polypeptide comprising an amino acid sequence encoded by a nucleic acid molecule being degenerate as a result of the genetic code to the nucleotide sequence of a nucleic acid molecule as defined in (a), (c) or (d).

The function of the terminally truncated version of the CP-X comprises the ability to transfer GlcNAc-1P from UDP-GlcNAc onto an acceptor carbohydrate. Preferably, at least 80% of the acceptor carbohydrates are polysaccharides with a DP of ≥4. For example, the acceptor (or at least 80% of the acceptor carbohydrates) may be DP4, DP5, or DP6; preferably, the acceptor (or at least 80% of the acceptor carbohydrates) is a tetramer or pentamer of GlcNAc-1P with a free reducing end as shown in FIG. 3. The terminally truncated version of CP-X which is applied herein has also the ability to transfer derivatives of GlcNAc-1P from derivatives of UDP-GlcNAc onto an acceptor carbohydrate. Thus, the function of the terminally truncated version of the CP-X comprises the ability to transfer GlcNAc-1P or a derivative thereof from UDP-GlcNAc or a derivative thereof onto an acceptor carbohydrate. Therefore, the present invention also relates to a truncated version of the CP-X, which is a polypeptide comprising:

(a) an amino acid sequence encoded by a nucleic acid molecule which is a terminally truncated version of the nucleic acid sequence of SEQ ID NO: 16 and comprises maximal 50-95% of the nucleic acid sequence of SEQ ID NO: 16;

(b) an amino acid sequence which is a terminally truncated version of the amino acid sequence of SEQ ID NO: 24 and comprises maximal 50-95% of the amino acid sequence of SEQ ID NO: 24;

(c) a polypeptide encoded by a nucleic acid molecule encoding a polypeptide having an amino acid sequence which is a terminally truncated version of the amino acid sequence of SEQ ID NO: 24 and comprises maximal 50-95% of the amino acid sequence of SEQ ID NO: 24;

(d) a polypeptide encoded by a nucleic acid molecule hybridizing under stringent conditions to the complementary strand of a nucleic acid molecule as defined in (a) or (c) and encoding a functional polypeptide; wherein the function comprises the ability to transfer GlcNAc-1P or a derivative thereof from UDP-GlcNAc or a derivative thereof onto an acceptor carbohydrate;

(e) a polypeptide having at least 80%, more preferably at least 85%, even more preferably at least 90%, even more preferably at least 95%, even more preferably at least 96%, even more preferably at least 97%, even more preferably at least 98% or most preferably at least 99% identity to the polypeptide of any one of (a) to (d), whereby said polypeptide is functional; wherein the function comprises the ability to transfer GlcNAc-1P or a derivative thereof from UDP-GlcNAc or a derivative thereof onto an acceptor carbohydrate; or (f) a polypeptide comprising an amino acid sequence encoded by a nucleic acid molecule being degenerate as a result of the genetic code to the nucleotide sequence of a nucleic acid molecule as defined in (a), (c) or (d).

As described above, the herein provided terminally truncated version of the CP-X comprises maximal 50-95% of the full length CP-X. It is envisaged, that the terminally truncated version of the CP-X comprises minimal 50% of the full length CP-X and maximal 95% of the full length CP-X. For example, the terminally truncated CP-X of the invention may comprise 50-95%, 55-90%, 60-85% or 65-80% of the full length CP-X. For example, the terminally truncated CP-X may comprise 50%, 55%, 60%, 65%, 70%, 75%, 80%, 85%, 90% or 95% or the full length CP-X.

Figure 3:
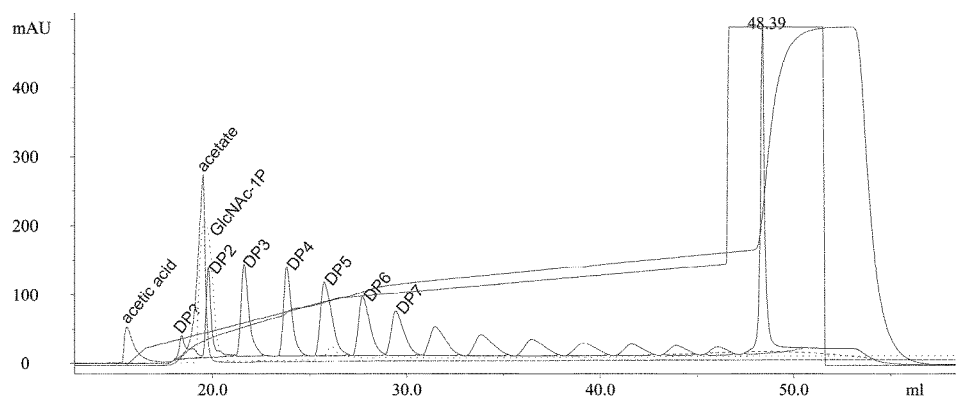
Figure 3:
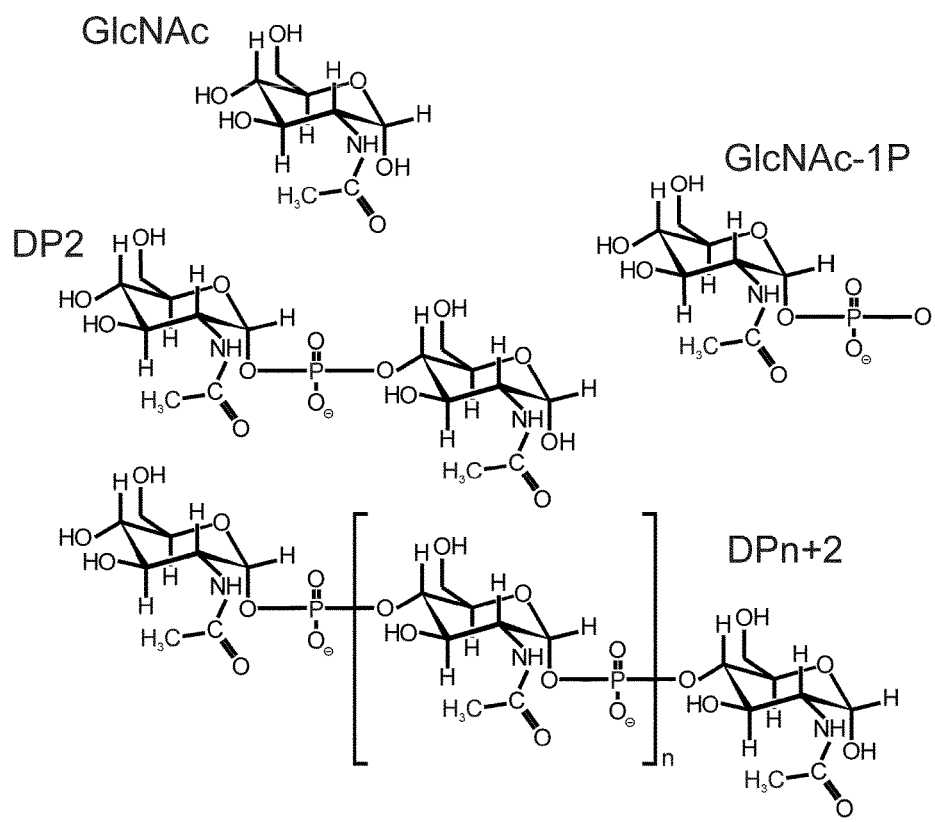
Figure 3:
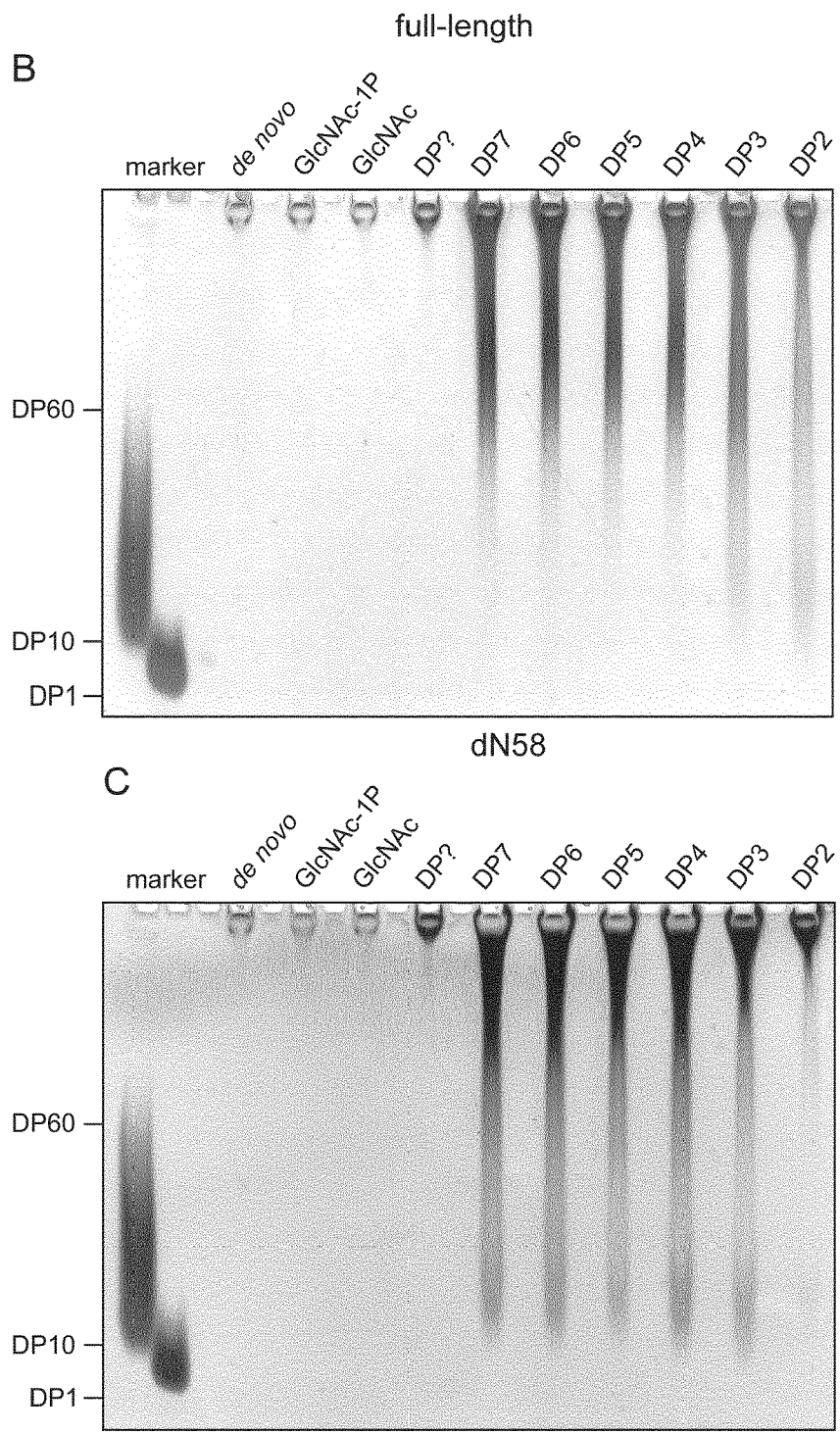
Figure 3:
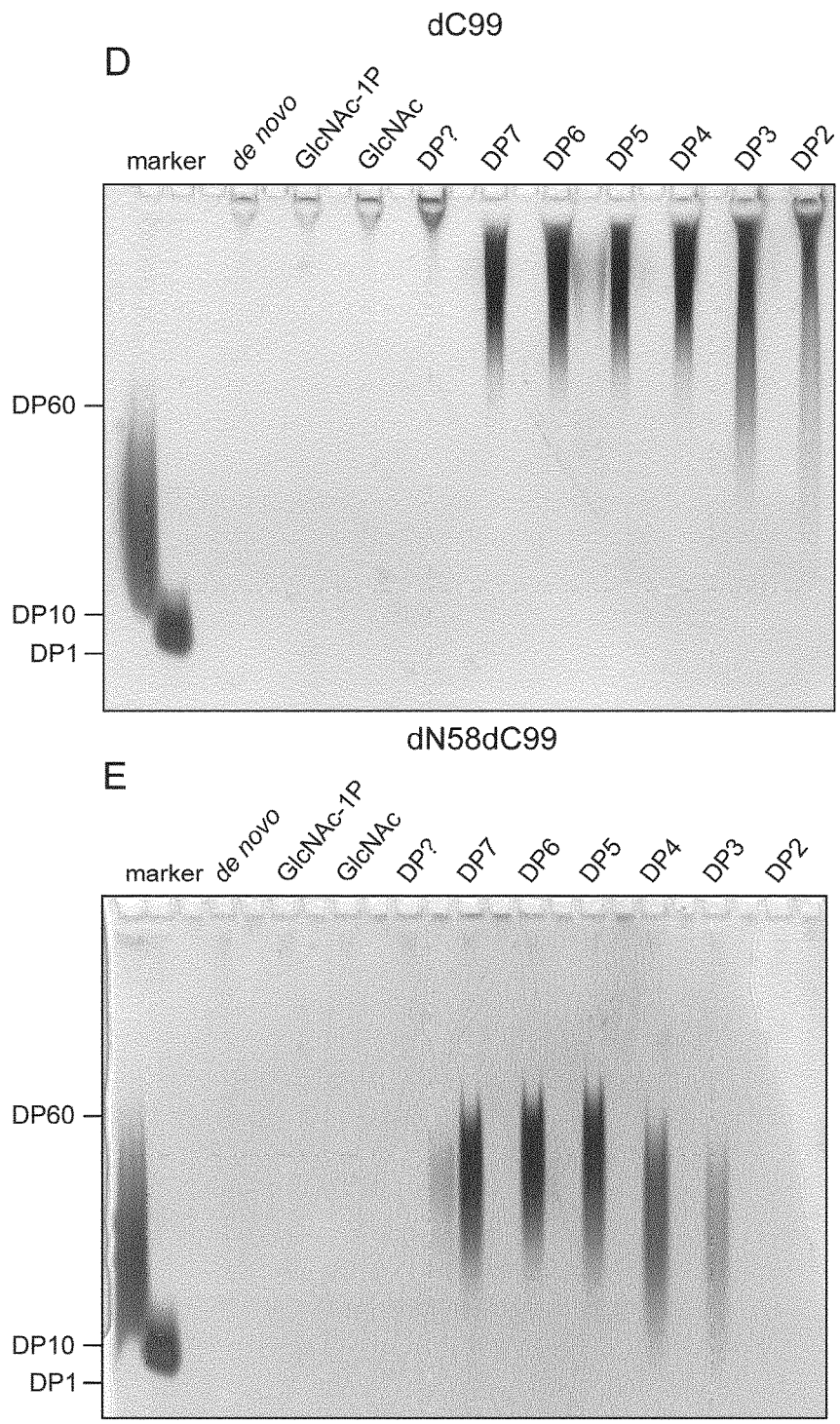

The herein provided terminally truncated version of the CP-X comprises the ability to transfer GlcNAc-1P (or a derivative thereof) from UDP-GlcNAc (or a derivative thereof) onto an acceptor carbohydrate (i.e. onto the hydroxyl group of C4 of a capsular polysaccharide from NmX (or a derivative thereof)). The acceptor carbohydrate may be extended/activated at the reducing end or the reducing end phosphate. Preferably, at least 80% of the acceptor carbohydrates are polysaccharides with a DP of ≥4. For example, the acceptor (or at least 80% of the acceptor carbohydrates) may be DP4, DP5, or DP6; preferably, the acceptor (or at least 80% of the acceptor carbohydrates) is a tetramer or pentamer of GlcNAc-1P with a free reducing end as shown in FIG. 3. In addition, the size of the produced capsular polysaccharides can be controlled by the ratio of donor and acceptor carbohydrate when the ratio is in the range of 10:1-400:1. Within this range, only one product distribution with a low dispersity (compared to full-length CP-X) is obtained at reaction endpoints. More specifically, within this range, only one product distribution with a low dispersity is obtained during all time points of the reaction.

The transfer GlcNAc-1P (or a derivative thereof) from UDP-GlcNAc (or a derivative thereof) onto an acceptor carbohydrate may be performed by incubating a truncated version of the CP-X (e.g. ΔC99-CP-X, ΔN58-CP-X or ΔN58ΔC99-CP-X) with UDP-GlcNAc (or a derivative thereof) and an acceptor carbohydrate and in reaction buffer (50 mM Tris pH 8.0, and 20 mM MgCl$_2$, and optionally 1-2 mM (e.g. 1 mM) DTT) and incubated for 1 h—over night (preferably for 4-7 hours) at 25-37° C. (preferably between 30 and 37° C.) (Fiebig et al., 2014; Glycobiology. 2014 February; 24(2):150-8). Preferably, at least 80% of the acceptor carbohydrates are polysaccharides with a DP of ≥4. For example, the acceptor (or at least 80% of the acceptor carbohydrates) may be DP4, DP5, or DP6; preferably, the acceptor (or at least 80% of the acceptor carbohydrates) is a tetramer or pentamer of GlcNAc-1P with a free reducing end as shown in FIG. 3.

Whether a transfer from GlcNAc-1P (or a derivative thereof) from UDP-GlcNAc (or a derivative thereof) onto an acceptor carbohydrate has occurred can be tested, e.g. by high percentage PAGE and developed by alcian blue/silver staining (Fiebig et al., Glycobiology. 2014 February; 24(2): 150-8) in the presence of a size marker or by $^{31}$P NMR monitoring the characteristic phosphodiester signal (Fiebig et al., Glycobiology. 2014 February; 24(2):150-8), or by High Performance Anionic Exchange Chromatography with Pulsed Amperometric Detection (HPAEC-PAD) as described (Berti et al. Vaccine. 2012 Oct. 5; 30(45):6409-15; Fiebig et al., Glycobiology. 2014 February; 24(2):150-8).

In context of the present invention it was surprisingly found that the C-terminally truncated CP-X as well as the C- and N-terminally truncated CP-X can be regulated via the donor-acceptor ratio and/or via the reaction time so as to produce capsular polysaccharides that have a uniform and defined length. In particular, the appended examples show that the truncated proteins ΔC99-CP-X and ΔN58ΔC99-CP-X can be regulated via the donor-acceptor ratio or via the reaction time such that they produce capsular polysaccharides which have a uniform and defined length. Accordingly, one aspect the invention relates to a terminally truncated version of the CP-X, which is a C-terminally or a C- and N-terminally truncated version of the full length CP-X.

Thus, the invention relates to the herein provided terminally truncated version of the CP-X, comprising:

(a) an amino acid sequence which is a C-terminally or C- and N-terminally truncated version of the amino acid sequence of SEQ ID NO: 24 and comprises maximal 50-95% of the amino acid sequence of SEQ ID NO: 24;

(b) a polypeptide encoded by a nucleic acid molecule encoding a polypeptide having an amino acid sequence which is a C-terminally or C- and N-terminally truncated version of the amino acid sequence of SEQ ID NO: 24 and comprises maximal 50-95% of the amino acid sequence of SEQ ID NO: 24; or (c) a polypeptide having at least 80%, more preferably at least 85%, even more preferably at least 90%, even more preferably at least 95%, even more preferably at least 96%, even more preferably at least 97%, even more preferably at least 98% or most preferably at least 99% identity to the polypeptide of (a) or (b), whereby said polypeptide is functional; wherein the function comprises the ability to transfer GlcNAc-1P or a derivative thereof from UDP-GlcNAc or a derivative thereof onto an acceptor carbohydrate.

In one aspect of the present invention, the terminally truncated version of the CP-X which is described and provided herein is the construct ΔN58-CP-X, ΔC99-CP-X or ΔN58ΔC99-CP-X.

Thus, the invention relates to the herein provided terminally truncated version of the CP-X, comprising (a) a polypeptide comprising an amino acid sequence encoded by a nucleic acid molecule having the nucleic acid sequence of any one of SEQ ID NO: 17, 20 or 21;

(b) a polypeptide comprising the amino acid sequence of any one of SEQ ID NO: 25, 28 or 29;

(c) a polypeptide comprising an amino acid sequence encoded by a nucleic acid molecule hybridizing under stringent conditions to the complementary strand of a nucleic acid molecule as defined in (a) and encoding a functional polypeptide; wherein the function comprises the ability to transfer GlcNAc-1P or a derivative thereof from UDP-GlcNAc or a derivative thereof onto an acceptor carbohydrate;

(d) a polypeptide having at least 80%, more preferably at least 85%, even more preferably at least 90%, even more preferably at least 95%, even more preferably at least 96%, even more preferably at least 97%, even more preferably at least 98% or most preferably at least 99% identity to the polypeptide of any one of (a) to (c), whereby said polypeptide is functional; wherein the function comprises the ability to transfer GlcNAc-1P or a derivative thereof from UDP-GlcNAc or a derivative thereof onto an acceptor carbohydrate; and (e) a polypeptide comprising an amino acid sequence encoded by a nucleic acid molecule being degenerate as a result of the genetic code to the nucleotide sequence of a nucleic acid molecule as defined in (a) or (c).

Accordingly, in one aspect the invention relates to the terminally truncated version of the CP-X comprising:

(i) an amino acid sequence encoded by a nucleic acid molecule which comprises the nucleic acid sequence of SEQ ID NO: 17, 20 or 21; or a nucleic acid sequence having at least 80%, more preferably at least 85%, even more preferably at least 90%, even more preferably at least 95%, even more preferably at least 96%, even more preferably at least 97%, even more preferably at least 98% or most preferably at least 99% identity to the nucleic acid sequence of any one of SEQ ID NO: 17, 20 or 21 and encoding a functional polypeptide; wherein the function comprises the ability to transfer GlcNAc-1P or a derivative thereof from UDP-GlcNAc or a derivative thereof onto an acceptor carbohydrate; or (ii) the amino acid sequence of SEQ ID NO: 25, 28 or 29; or an amino acid sequence having at least 80%, more preferably at least 85%, even more preferably at least 90%, even more preferably at least 95%, even more preferably at least 96%, even more preferably at least 97%, even more preferably at least 98% or most preferably at least 99% identity to any one of SEQ ID NOs: 25, 28 or 29 and being functional, wherein the function comprises the ability to transfer GlcNAc-1P or a derivative thereof from UDP-GlcNAc or a derivative thereof onto an acceptor carbohydrate.

A particular embodiment of the invention relates to the above described terminally truncated version of the CP-X wherein the function comprises the ability to transfer GlcNAc-1P or a derivative thereof from UDP-GlcNAc or a derivative thereof onto an acceptor carbohydrate; wherein the produced polymers have a DP between 10 and 60 or an avDP between 15 and 20, when the ratio of donor carbohydrate to acceptor carbohydrate is in the range of 10:1 to 400:1. Preferably, at least 80% of the acceptor carbohydrates are polysaccharides with a DP of ≥4. For example, the acceptor (or at least 80% of the acceptor carbohydrates) may be DP4, DP5, or DP6; preferably, the acceptor (or at least 80% of the acceptor carbohydrates) is a tetramer or pentamer of GlcNAc-1P with a free reducing end as shown in FIG. 3.

As described, the terminally truncated version of the CP-X (i.e. the polypeptide described above under items (i) and (ii)) may be used in the herein described in vitro methods for producing Nm capsular polysaccharides or in the herein described compositions.

For example, if the terminally truncated CP-X is regulated via the ratio of donor carbohydrate to acceptor carbohydrate (and not via the reaction time) then the following preferred ratios can produce a product distribution with a low dispersity. Or, in other words, if the terminally truncated version of the CP-X is regulated via the ratio of donor carbohydrate to acceptor carbohydrate, then the following preferred ratios can produce capsular polysaccharides of which at least 60%, (preferably at least 80%) have a defined length between DP10 and DP60 or between avDP15 and avDP20. Moreover, the following capsule polymerases and ratios are preferably used in the compositions described herein.

For example, if the capsule polymerase is a polypeptide which has at least 80% (preferably at least 85%, even more preferably at least 90%, even more preferably at least 95%, even more preferably at least 96%, even more preferably at least 97%, even more preferably at least 98% or most preferably at least 99%) sequence identity to a polypeptide encoded by a nucleic acid molecule which comprises the nucleic acid sequence of SEQ ID NO: 20 (ΔC99-CP-X) and being functional, then the ratio of donor carbohydrate to acceptor carbohydrate is preferably from 10:1 to 80:1, more preferably from 20:1 to 60:1, even more preferably from 20:1 to 50:1, and most preferably from 33:1 to 50:1. In addition, if the capsule polymerase is a polypeptide which has at least 80% (preferably at least 85%, even more preferably at least 90%, even more preferably at least 95%, even more preferably at least 96%, even more preferably at least 97%, even more preferably at least 98% or most preferably at least 99%) sequence identity to a polypeptide encoded by a nucleic acid molecule which comprises the nucleic acid sequence of SEQ ID NO: 17 (ΔN58-CP-X) and being functional, then the ratio of donor carbohydrate to acceptor carbohydrate is preferably from 10:1 to 80:1, more preferably from 20:1 to 50:1, and most preferably from 20:1 to 33:1 (e.g. 33:1). Furthermore, if the capsule polymerase is a polypeptide which has at least 80% (preferably at least 85%, even more preferably at least 90%, even more preferably at least 95%, even more preferably at least 96%, even more preferably at least 97%, even more preferably at least 98% or most preferably at least 99%) sequence identity to a polypeptide encoded by a nucleic acid molecule which comprises the nucleic acid sequence of SEQ ID NO: 21 (ΔN58ΔC99-CP-X) and being functional, then the ratio of donor carbohydrate to acceptor carbohydrate is preferably from 50:1 to 400:1, more preferably from 80:1 to 400:1, even more preferably from 100:1 to 400:1, and most preferably from 100:1 to 200:1. In addition, if the capsule polymerase is a polypeptide which comprises an amino acid sequence which has at least 80% (preferably at least 85%, even more preferably at least 90%, even more preferably at least 95%, even more preferably at least 96%, even more preferably at least 97%, even more preferably at least 98% or most preferably at least 99%) sequence identity to SEQ ID NO: 28 (ΔC99-CP-X) and being functional, then the ratio of donor carbohydrate to acceptor carbohydrate is preferably from 10:1 to 80:1, more preferably from 20:1 to 60:1, even more preferably from 20:1 to 50:1, and most preferably from 33:1 to 50:1. Furthermore, if the capsule polymerase is a polypeptide which comprises an amino acid sequence which has at least 80% (preferably at least 85%, even more preferably at least 90%, even more preferably at least 95%, even more preferably at least 96%, even more preferably at least 97%, even more preferably at least 98% or most preferably at least 99%) sequence identity to SEQ ID NO: 25 (ΔN58-CP-X) and being functional, then the ratio of donor carbohydrate to acceptor carbohydrate is preferably from 10:1 to 80:1, more preferably from 20:1 to 50:1, and most preferably from 20:1 to 33:1 (e.g. 33:1). Moreover, if the capsule polymerase is a polypeptide which comprises an amino acid sequence which has at least 80% (preferably at least 85%, even more preferably at least 90%, even more preferably at least 95%, even more preferably at least 96%, even more preferably at least 97%, even more preferably at least 98% or most preferably at least 99%) sequence identity to SEQ ID NO: 29 (ΔN58ΔC99-CP-X) and being functional, then the ratio of donor carbohydrate to acceptor carbohydrate is preferably from 50:1 to 400:1, more preferably from 80:1 to 400:1, even more preferably from 100:1 to 400:1, and most preferably from 100:1 to 200:1.

In context of the invention the terminally truncated version of the CP-X may also be a polypeptide comprising the construct ΔN65ΔC10-CP-X (which is shown in SEQ ID NOs: 22 and 30) or ΔN67ΔC99-CP-X (which is shown in SEQ ID NOs: 23 and 31) which have been demonstrated to be active (data not shown) and which can be regulated via the donor-acceptor ratio or via the reaction time such that they produce capsular polysaccharides with a uniform and defined length.

Accordingly, the terminally truncated version of the CP-X of the present invention may be a polypeptide comprising the amino acid of any one of SEQ ID NOs: 25, 28, 29, 30 or 31. Also encompassed by the present invention are terminally truncated versions of the CP-X comprising the amino acid sequence of any one of SEQ ID NOs: 25, 28, 29, 30 or 31 wherein one, two, three or more amino acid residues are added, deleted or substituted. The polypeptides may have the function of the terminally truncated version of the CP-X (i.e. the ability to transfer GlcNAc-1P or a derivative thereof from UDP-GlcNAc or a derivative thereof onto an acceptor carbohydrate). Preferably, at least 80% of the acceptor carbohydrates are polysaccharides with a DP of ≥4. The amino acid sequence of the polypeptides may be at least 80%, more preferably at least 85%, more preferably at least 90%, more preferably at least 95%, more preferably at least 96%, more preferably at least 97%, more preferably at least 98%, and most preferably at least 99% identical to SEQ ID NO: 25, 28, 29, 30 or 31. The polypeptides may have the function of a truncated version of the CP-X. Preferably, the function comprises the ability to transfer GlcNAc-1P (or a derivative thereof) from UDP-GlcNAc (or a derivative thereof) onto an acceptor carbohydrate; wherein at least 60% (preferably at least 80%) of the produced polymers have a DP between 10 and 60 or an avDP between 15 and 20, when the ratio of donor carbohydrate to acceptor carbohydrate is in the range of 10:1 to 400:1. Preferably, at least 80% of the acceptor carbohydrates are polysaccharides with a DP of ≥4. For example, the acceptor (or at least 80% of the acceptor carbohydrates) may be DP4, DP5, or DP6; preferably, the acceptor (or at least 80% of the acceptor carbohydrates) is a tetramer or pentamer of GlcNAc-1P with a free reducing end as shown in FIG. 3.

The herein described terminally truncated versions of the CP-X may be linked (e.g. operatively linked) to additional, heterologous sequences. E.g. the nucleic acid molecule encoding a truncated version of the CP-X may be linked to additional, heterologous nucleic acid sequences in a recombinant nucleic acid molecule. For example, said additional nucleic acid sequence may be a coding gene.

The term "recombinant nucleic acid molecule" relates to nucleic acid molecules originating from a different genetic context and combined by molecular biological methods. Here, the term "different genetic context" relates to genomes from different species, varieties or individuals or different positions within a genome. Recombinant nucleic acid molecules can contain not only natural sequences but also sequences, which, compared to the natural ones are mutated or chemically modified or else, the sequences are altogether newly synthesized sequences.

As indicated above, the terminally truncated version of the CP-X may be linked to an additional heterologous molecule. Said additional heterologous molecule may be a nucleic acid molecule which is preferably operatively linked to a truncated version of the CP-X. Said additional heterologous nucleic acid molecule may originate from a different genetic context than the truncated version of the CP-X. Non-limiting examples of additional heterologous molecules comprise in particular marker molecules, like luciferase, galactosidase, GFP, EGFP, DsRed, etc. or tag-molecules, like Flag-tags, CBP and others. In a particular aspect of the invention, said additional heterologous molecule is a tag, such as a StrepII-tag, a thrombin-tag, a his-tag, a MBP-tag or a S3N10-tag. In a further aspect of the invention, said additional heterologous molecule is a nucleic acid molecule encoding a restriction site (e.g. a restriction site of the enzymes BamHI/BgIII, XhoI or NdeI). It is also envisaged that the truncated CP-X of the invention is linked to several additional sequences (e.g. several tags or several restriction sites). Yet, as detailed below, also sequences which optimize (e.g. enhance) the expression of the terminally truncated CP-X may be operatively linked to the nucleic acid sequence of the truncated CP-X. Such a sequence may be a particular promoter sequence. A suitable promoter for the expression of the terminally truncated version of the CP-X may be, e.g., Tac-, T7-, or Lacpromoter.

One embodiment of the present invention relates to a nucleic acid molecule encoding the herein described truncated version of the CP-X. The invention also relates to a vector comprising said nucleic acid molecule. The present invention further relates to vectors containing a nucleic acid molecule of the present invention encoding a terminally truncated version of the CP-X. The present invention relates also to a vector comprising the nucleic acid construct encoding the herein described truncated version of the CP-X.

The term "vector" relates to circular or linear nucleic acid molecules which can autonomously replicate in host cells into which they are introduced. The "vector" as used herein particularly refers to plasmids, cosmids, viruses, bacteriophages and other vectors commonly used in genetic engineering. In a preferred embodiment, the vectors of the invention are suitable for the transformation of cells, like fungal cells, cells of microorganisms such as yeast or prokaryotic cells. In a particularly preferred embodiment such vectors are suitable for stable transformation of bacterial cells, for example to express the truncated version of the CP-X of the present invention.

Accordingly, in one aspect of the invention, the vector as provided is an expression vector. Generally, expression vectors have been widely described in the literature. As a rule, they may not only contain a selection marker gene and a replication-origin ensuring replication in the host selected, but also a promoter, and in most cases a termination signal for transcription. Between the promoter and the termination signal there is preferably at least one restriction site or a polylinker which enables the insertion of a nucleic acid sequence/molecule desired to be expressed.

It is to be understood that when the vector provided herein is generated by taking advantage of an expression vector known in the prior art that already comprises a promoter suitable to be employed in context of this invention (for example expression of a truncated version of the CP-X as described herein above) the nucleic acid construct is inserted into that vector in a manner that the resulting vector comprises only one promoter suitable to be employed in context of this invention. The skilled person knows how such insertion can be put into practice. For example, the promoter can be excised either from the nucleic acid construct or from the expression vector prior to ligation.

A non-limiting example of the vector of the present invention is the plasmid vector pET22b comprising a nucleic acid construct of the present invention. Further examples of vectors suitable to comprise a nucleic acid construct of the present invention to form the vector of the present invention are known in the art and are, for example other vectors for bacterial expression systems such as vectors of the pET series (Novagen) or pQE vectors (Qiagen).

In an additional embodiment, the present invention relates to a host cell comprising the herein described vector. In particular, the invention relates to a host cell comprising a nucleic acid construct encoding a terminally truncated version of the CP-X and/or the vector of the present invention. Preferably, the host cell of the present invention may be a prokaryotic cell, for example, a bacterial cell. As a non limiting example, the host cell of the present invention may be *Escherichia coli*. The host cell provided herein is intended to be particularly useful for generating the terminally truncated version of the CP-X of the present invention.

Generally, the host cell of the present invention may be a prokaryotic or eukaryotic cell, comprising a nucleic acid construct of the invention or the vector of the invention or a cell derived from such a cell and containing a nucleic acid construct of the invention or the vector of the invention. In a preferred embodiment, the host cell is genetically modified with a nucleic acid construct of the invention or the vector of the invention in such a way that it contains the nucleic acid construct of the present invention integrated into the genome. For example, such host cell of the invention, but also the host cell of the invention in general, may be a bacterial, yeast, or fungus cell.

In one particular aspect, the host cell of the present invention is capable to express or expresses a terminally truncated version of the CP-X as defined herein and as illustrative characterized in SEQ ID NOs: 17, 20, 21, 22 or 23, for example in SEQ ID NO: 21. An overview of examples of different corresponding expression systems to be used for generating the host cell of the present invention is for instance contained in Methods in Enzymology 153 (1987), 385-516, in Bitter et al. (Methods in Enzymology 153 (1987), 516-544), in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), and in Griffiths et al., (Methods in Molecular Biology 75 (1997), 427-440).

The transformation or genetically engineering of the host cell with a nucleic acid construct of the invention or the vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990.

The nucleic acid molecules, vectors, host cells and polypeptides described herein may be used for producing (i.e. synthesizing) Nm capsular polysaccharides which have a defined length.

As mentioned, in the herein provided in vitro methods for producing Nm CPS which have a defined length or in the compositions of the invention, the terminally truncated version of the CP-X as described herein may be used.

As for vaccine production the Nm CPS have preferably a DP of 10 to 60 (i.e. an avDP of 15 to 20), it is preferred that the Nm CPS which are produced by the herein described in vitro methods have this size. Advantageously, if in the herein described in vitro methods the CP-A or a terminally truncated version of the CP-X is used, then the produced Nm CPS have a DP or 10 to 60 (i.e. an avDP of 15 to 20), if the donor-to-acceptor-ratio is in the range from 10:1 to 400:1. In addition, if in herein described in vitro methods the truncated version of the CP-X is used, then the produced Nm CPS have a DP of 10 to 60 (i.e. an avDP of 15 to 20) if the incubation time ranges from 3 to 45 minutes. Thus, one aspect of the invention relates to the herein provided in vitro methods, wherein the capsular polysaccharides have a DP of 10 to 60 or an avDP of 15 to 20. In a preferred aspect of the herein provided in vitro methods, at least 60% (more preferably at least 80%) of the capsular polysaccharides have a DP of 10 to 60 or an avDP of 15 to 20. In addition, a further embodiment of the invention relates to the in vitro methods of the invention or the composition of the invention, wherein (i) the ratio of donor carbohydrate to acceptor carbohydrate is a ratio from 20:1 to 80:1; and the capsule polymerase is either a polypeptide comprising maximal 80% of the amino acid sequence of SEQ ID NO: 24 (CP-X) and comprising the amino acid sequence of SEQ ID NO: 28 (ΔC99-CP-X), or a polypeptide comprising the amino acid sequence of SEQ ID NO: 9 (CP-A); or (ii) the ratio of donor carbohydrate to acceptor carbohydrate is a ratio from 100:1 to 400:1; and the capsule polymerase is a polypeptide comprising maximal 68% of the amino acid sequence of SEQ ID NO: 24 (CP-X) and comprising the amino acid sequence of SEQ ID NO: 29 (ΔN58ΔC99-CP-X).

In item (i) of the above described embodiment, the ratio of donor carbohydrate to acceptor carbohydrate may be 50:1.

According to the inventive in vitro method, the donor carbohydrate which is contacted with at least one purified capsule polymerase (CP) may further be activated during step (a). Thus, one embodiment of the invention relates to the in vitro methods of the invention, wherein said donor carbohydrate is activated or wherein said donor carbohydrate is activated during step (a). Said activation during step (a) may be performed by contacting said donor carbohydrate with an activating enzyme. In addition, during this in step (a) of the inventive in vitro methods, said donor carbohydrate may be further contacted with PEP and/or at least one activating nucleotide. Analogously, in the herein provided composition said donor carbohydrate may be activated. In the methods or in the composition of the invention, said donor carbohydrate may be activated by linkage to an activating nucleotide. Said activating nucleotide may be, e.g. CMP, CDP, CTP, UMP, UDP, TDP, AMP or UTP, preferably UDP.

For example, the activation may be mediated by linkage of an activating nucleotide such as CMP, UDP, TDP or AMP. Preferably, the activating nucleotide is UDP. The activation of a carbohydrate by linkage of a nucleotide may be catalyzed by several activating enzymes which are known in the art. Such activating enzymes may be incubated with the at least one donor carbohydrate, at least one acceptor carbohydrate and the at least one CP during step (a) of the in vitro method provided herein. UDP-ManNAc is preferably synthesized from UDP-GlcNAc using the enzyme UDP-GlcNAc-epimerase. In SEQ ID NO: 32, the nucleotide sequence of UDP-GlcNAc-epimerase cloned from *Neisseria meningitidis* serogroup A is shown, the corresponding polypeptide sequence of UDP-GlcNAc-epimerase is shown in SEQ ID NO: 33.

One particular embodiment of the present invention relates to the herein provided in vitro methods or the herein provided composition, wherein the capsule polymerase is a truncated version of the capsule polymerase of *Neisseria meningitidis* serogroup X and wherein at least one donor carbohydrate is UDP-GlcNAc. However, another embodiment of the present invention relates to the herein provided in vitro methods or the herein provided composition, wherein the capsule polymerase is a truncated version of the capsule polymerase of *Neisseria meningitidis* serogroup X and wherein at least one donor carbohydrate is GlcNAc-1-P.

In a further embodiment of the herein described in vitro methods or compositions the capsule polymerase is the capsule polymerase of *Neisseria meningitidis* serogroup A and at least one donor carbohydrate is UDP-ManNAc. The sugar building block UDP-ManNAc is commercially not available. Therefore, a further advantage of the present invention is that UDP-ManNAc can be synthesized (during the inventive in vitro method for producing Nm capsular polysaccharides) from cheap UDP-GlcNAc. Thus, another embodiment of the present invention relates to the inventive in vitro methods or the inventive composition, wherein the capsule polymerase is the capsule polymerase of *Neisseria meningitidis* serogroup A and wherein at least one donor carbohydrate is UDP-GlcNAc.

In context of the present invention, UDP-ManNAc is preferably synthesized from UDP-GlcNAc using the enzyme UDP-GlcNAc-epimerase. In SEQ ID NO: 32, the nucleotide sequence of UDP-GlcNAc-epimerase cloned from *Neisseria meningitidis* serogroup A is shown, the corresponding polypeptide sequence of UDP-GlcNAc-epimerase is shown in SEQ ID NO: 33. Thus, one aspect of the invention relates to the herein provided in vitro methods, wherein in step (a) the capsule polymerase is further incubated with the UDP-GlcNAc-epimerase. In addition, one embodiment of the invention relates to the herein provided composition, further comprising the UDP-GlcNAc-epimerase. For example, in the in vitro methods or compositions of the present invention, the UDP-GlcNAc-epimerase (e.g. CsaA of NmA) may be used in a concentration of 1-2000 nmol, e.g. 10 nmol.

In another embodiment of the inventive in vitro methods and compositions, the capsular polymerase (CP) may be a truncated version of the CP-X or a functional derivative thereof and at least one donor carbohydrate may be GlcNAc-1-phosphate. Said donor carbohydrate GlcNAc-1-phosphate may be further contacted with at least one nucleotide and/or phosphoenolpyruvate (PEP) and auxiliary enzymes. Said nucleotide can be, e.g., UMP, UDP or UTP. Said donor carbohydrate GlcNAc-1-phosphate may further be activated during incubation with the terminally truncated CP-X. In accordance with the herein presented in vitro method, this activation may yield the activated sugar nucleotide UDP-GlcNAc.

Thus, the CP to be applied in the means and methods described herein may be a truncated version of CP-X or a functional derivative thereof and at least one donor carbohydrate may be UDP-GlcNAc or a derivative thereof. Examples for derivatives of UDP-GlcNAc may be compounds that are alkylated or hydroxylated or that comprise additional functional groups, such as carboxylic acids, azides, amides, acetyl groups or halogen atoms; see also "Carbohydrate chemistry" Volumes 1-34, Cambridge [England], Royal Society of Chemistry, loc. cit.

Generally, in context of the present invention, the saccharides described herein may also be labelled forms of these saccharides. For example, the saccharides may be labelled radioactively, such as [$^{14}$C] or [$^{3}$H]. Such labelling may be inter alia useful in diagnostic applications and uses of the saccharides described herein. Such diagnostic applications and uses will be further described herein below.

In accordance with the inventive method, the terminally truncated version of the CP-X is contacted with at least one donor carbohydrate and with at least one acceptor carbohydrate during the incubation step (a) of the in vitro method presented herein. Said acceptor carbohydrate may be oligomeric or polymeric CPS of *Neisseria meningitidis* serogroup X (CPSX), and/or a carbohydrate structure containing terminal GlcNAc residues such as hyaluronic acid, heparin, heparin sulphate or protein-linked oligosaccharides.

In the herein provided methods for producing Nm capsular polysaccharides which have a defined length, it is preferred that the acceptor carbohydrate has a DP≥4. Or, in other words, acceptor carbohydrates with a length of DP≥4 are particularly preferred in the herein described methods for producing Nm capsular polysaccharides which have a defined length. Normally, the acceptor carbohydrates are purified capsular polysaccharides of the respective serogroup and have different length. However, in the herein provided methods for producing capsular polysaccharides with a defined length, and in the herein provided compositions, it is preferred that at least 80% of the acceptor carbohydrates are polysaccharides with a DP of ≥4. The acceptor carbohydrates may also consist of polysaccharides with a DP of ≥4. For example, if the CP-A is used, then the acceptor (or at least 80% of the acceptor carbohydrates) is preferably DP4, DP5, or DP6; more preferably the acceptor (or at least 80% of the acceptor carbohydrates) is a tetramer or pentamer of ManNAc-1P with a free reducing end. If a terminally truncated version of the CP-X is used, then the acceptor (or at least 80% of the acceptor carbohydrates) is preferably DP4, DP5, or DP6; more preferably, the acceptor (or at least 80% of the acceptor carbohydrates) is a tetramer or pentamer of GlcNAc-1P with a free reducing end as shown in FIG. 3.

An example of the present invention relates to the in vitro method for producing Nm capsular polysaccharides of NmX which have a defined length, said method comprising the steps:
(a) incubating a truncated version of the CP-X with UDP-GlcNAc and hydrolysed capsular polysaccharides of NmX; wherein the ratio of UDP-GlcNAc to hydrolysed capsular polysaccharides of NmX is a ratio from 10:1 to 400:1 (e.g. 20:1 to 400:1); and
(b) isolating the resulting capsular polysaccharide.

A further example of the present invention relates to the in vitro method for producing Nm capsular polysaccharides of NmX which have a defined length, said method comprising the steps:
(a) incubating a truncated version of the CP-X with UDP-GlcNAc and hydrolysed capsular polysaccharides of NmX; wherein the incubation time ranges from 3 to 45 minutes; and
(b) isolating the resulting capsular polysaccharide.

Another example of the present invention relates to the in vitro method for producing Nm capsular polysaccharides of NmX which have a defined length, said method comprising the steps:
(a) incubating a truncated version of the CP-X with UDP-GlcNAc and hydrolysed capsular polysaccharides of NmX; wherein
  (i) the ratio of donor carbohydrate to acceptor carbohydrate is a ratio from 10:1 to 10000 (e.g. 200:1 to 1000:1), and
  (ii) the incubation time ranges from 3 to 45 minutes; and
(b) isolating the resulting capsular polysaccharide.

In the above examples also other combinations of activated or non-activated donor carbohydrates and acceptor carbohydrates as described herein can be applied. Such other combinations do not defer from the gist of the present invention.

In one embodiment of the present in vitro method, the CP to be used is CP-A or a functional derivative thereof and at least one donor carbohydrate may be UDP-ManNAc or a derivative thereof. Examples for derivatives of UDP-ManNAc may be compounds that are alkylated or hydroxylated or that comprise additional functional groups such as carboxylic acids, azides, amides, acetyl groups or halogen atoms; see also "Carbohydrate chemistry" Volumes 1-34: monosaccharides, disaccharides, and specific oligosaccharides, Reviews of the literature published during 1967-2000, Cambridge (England), Royal Society of Chemistry.

In another embodiment of the in vitro method described herein, the CP is CP-A or a functional derivative thereof and at least one donor carbohydrate is ManNAc-1-phosphate or a derivative thereof. Examples for derivatives of ManNAc-1-phosphate ManNAc-3-O-Ac or ManNAc-4-O-Ac or ManNAc-3,4-di-O-Ac. In the herein provided in vitro method, said donor carbohydrate ManNAc-1-phosphate (ManNAc-1-P) may be contacted with at least one nucleotide and/or phosphoenolpyruvate (PEP) and auxiliary enzymes during step (a) of the in vitro method. Said nucleotide can be, e.g., UMP, UDP and UTP. Said donor carbohydrate ManNAc-1-phosphate may be activated during incubation with CP-A. In accordance with the herein presented in vitro method, this activation may yield the activated sugar nucleotide UDP-ManNAc, or its derivatives UDP-ManNAc-3-O-Ac or UDP-ManNAc-4-O-Ac or UDP-ManNAc-3,4-di-O-Ac. Thus, one aspect of the invention relates to the herein provided in vitro methods, wherein the capsule polymerase is the capsule polymerase of *Neisseria meningitidis* serogroup A and wherein at least one donor carbohydrate is ManNAc-1-P.

In the herein provided in vitro method, CP-A or a functional derivative thereof is contacted with at least one donor carbohydrate and with an acceptor carbohydrate during the incubation step (a) of the inventive in vitro method. In accordance with the inventive in vitro method presented herein, the acceptor carbohydrate may be oligomeric or polymeric CPS of *Neisseria meningitidis* serogroup A (CPSA) and/or a carbohydrate structure containing terminal GlcNAc or ManNAc residues such as hyaluronic acid, heparin, heparin sulphate or protein-linked oligosaccharides. As described above, in the herein provided in vitro methods, the acceptor carbohydrate of CP-A may be the cheap and easily commercially available UDP-GlcNAc, as the UDP-GlcNAc-epimerase can be used to convert UDP-GlcNAc into UDP-ManNAc.

An example of the present invention relates to the in vitro method for producing Nm capsular polysaccharides of NmA which have a defined length, said method comprising the steps:
(a) incubating CP-A with UDP-GlcNAc, UDP-GlcNAc-epimerase and hydrolysed capsular polysaccharides of NmA; wherein the ratio of UDP-GlcNAc to hydrolysed capsular polysaccharides of NmA is a ratio from 10:1 to 400:1 (e.g. 20:1 to 400:1); and
(b) isolating the resulting capsular polysaccharide.

A further example of the present invention relates to the in vitro method for producing Nm capsular polysaccharides of NmA which have a defined length, said method comprising the steps:

(a) incubating CP-A with UDP-ManNAc and hydrolysed capsular polysaccharides of NmA; wherein the ratio of UDP-ManNAc to hydrolysed capsular polysaccharides of NmA is a ratio from 10:1 to 400:1 (e.g. 20:1 to 400:1); and
(b) isolating the resulting capsular polysaccharide.

Again, the skilled person readily understands that also other combinations of activated or non-activated donor carbohydrates and acceptor carbohydrates as described herein can be applied. Such other combinations do not defer from the gist of the present invention.

As described herein and illustrated in the appended examples, the acceptor carbohydrate is preferred by the CP (e.g. CP-A) if it is presented in non-acetylated form. Moreover, the acceptor is even more preferred if presented in non-acetylated, de-phosphorylated form. Accordingly, one embodiment of the present invention relates to the herein provided in vitro methods or the herein provided composition, wherein the acceptor carbohydrate is non-acetylated and/or dephosphorylated, preferably non-acetylated and dephosphorylated.

Within a CPS obtainable by the inventive method described hereinabove, one or more carbohydrates of the CPS-subunits may be derivatized and may contain, for example, additional functional groups such as acetyl groups, amino groups, alkyl groups, hydroxyl groups, carboxylic acids, azides, amides, or halogen atoms; see also "Carbohydrate chemistry" Volumes 1-34: monosaccharides, disaccharides, and specific oligosaccharides, Reviews of the literature published during 1967-2000, Cambridge (England), Royal Society of Chemistry. Thus, in one embodiment of the inventive in vitro method or composition, the acceptor carbohydrate carries one or more additional functional groups at its reducing end. Said additional functional groups, may be, e.g., acetyl groups, carboxylic acids, azides, amides, or halogen atoms; see also "Carbohydrate chemistry" Volumes 1-34, Cambridge [England], Royal Society of Chemistry, loc. cit.

One embodiment of the present invention relates to the herein provided in vitro method or the herein provided composition, wherein said acceptor carbohydrate is capsule polysaccharide of *Neisseria meningitidis* serogroup A or X or a carbohydrate structure containing terminal GlcNAc residues. Said carbohydrate structure containing terminal GlcNAc-residues may be hyaluronic acid, heparin sulphate, heparan sulphate or protein-linked oligosaccharides.

As demonstrated in the appended examples, the inventors of the present invention analyzed the minimal length of the priming acceptor for CP-A. Therefore, synthetic compounds which are shown in FIG. 25 which vary not only in length, but also with respect to O-acetylation (compounds 2, 4, 6 are 3-O-acetylated) and reducing end modifications have been used. In compounds 1, 2, 5, 6 the reducing ends are occupied by a decyl-phosphate-ester, while a methyl group (OMe) is present in the compounds 3 and 4. As evident from the appended examples, the activity of the codon optimized ΔN69-CP-A did not go beyond background (no acceptor) with compounds 1-4, but, intriguingly, steeply increased with disaccharides carrying a decyl-phosphate-ester at the reducing end (compounds 5, 6) (FIG. 25). With the non-acetylated compound 5, activity values similar to those obtained with the optimized acceptor $CPSA_{hyd(deOAc)}$-deP were measured. Interestingly, O-acetylation of compound 5 (resulting in compound 6) reduced the quality of the acceptor. Based on these data, the minimal acceptor recognized by CP-A or a derivative of CP-A (such as ΔN69-CP-A) can be defined as the dimer of ManNAc-1P units linked together by phosphodiester bonds. The presence of a phosphodiester at the reducing end seems obligatory, because compounds ending with OMe groups are not used by the capsule polymerase.

Thus, in context of the present invention, a dimer of ManNAc-1P carrying a phosphodiester at the reducing end was identified as minimal acceptor for CP-A or derivatives of CP-A (such as ΔN69-CP-A).

Accordingly, the inventors of the present invention identified two important features of CP-A: (i) the minimal efficient acceptor is a dimer and (ii) the reducing end phosphate group can be extended with rather large chemical groups (such as decyl-ester). This latter finding bears the perspective that chain elongation can be primed with reagents of very high purity and functional groups that facilitate conjugation of glycans to carrier proteins in the vaccine production chain (Costantino (2011) Expert opinion on drug discovery 6 (10), 1045-1066; Bardotti (2008) Vaccine 26 (18), 2284-2296). Besides decyl-ester, chain elongation may be primed with a number of functional groups that allow conjugation to carrier proteins, e.g., Alkyl-azides, Alkyl-aminedes or sulfhydryl-reagents chemical functions as described in Costantino et al., 2011 Expt. Opin. Drug. Discov. 6:1053; Table 2.

Accordingly, one embodiment of the present invention relates to the in vitro method of the invention or the composition of the invention, wherein said acceptor carbohydrate is a dimer of ManNAc carrying a phosphodiester at the reducing end. In this embodiment of the present invention, the capsule polymerase may be the capsule polymerase of *Neisseria meningitidis* serogroup A. Moreover, the phosphate group at the reducing end may be extended with alkyl-azides, alkyl-aminedes or sulfhydryl-groups and chemical functions as described in Costantino (2011) Expt. Opin. Drug. Discov. 6:1053; Table 2. For example, in the herein provided in vitro methods or composition, the acceptor carbohydrate may be a disaccharide carrying a decyl-phosphate-ester at the reducing end. As mentioned, in this embodiment of the present invention, the capsule polymerase may be the capsule polymerase of *Neisseria meningitidis* serogroup A.

If in the herein described in vitro methods or compositions the acceptor is a dimer of ManNAc carrying a phosphodiester at the reducing end (which may be extended with large chemical groups such as a decyl-ester), then the capsular polymerase may be CP-A or a derivative of CP-A (such as ΔN69-CP-A).

The capsule polymerase (CP) which is incubated with the at least one donor carbohydrate in the presented in vitro methods and compositions may be purified. Said CP (or a functional fragment or derivative thereof) may be isolated from *Neisseria meningitidis* lysates or recombinantly produced. Recombinant production of a CP (or a functional fragment or derivative thereof) may be performed by transferring the DNA coding for the CP (or the functional fragment or derivative thereof) into a vector and using a host (e.g. eukaryotic host cells such as insect cells or yeast or prokaryotic host cells such as *Escherichia coli*) to express the CP (or the functional fragment or derivative thereof). After expression, the CP (or the functional fragment or derivative thereof) may be purified from the cell lysate. The purification may be carried out following the instructions of the Qiaexpressionist (http://www.qiagen.com/literature/render.aspx?id=128, Qiagen) for bacterial protein purification or by using BD Bioscience Baculo Gold instruction (Cat. No. 560138) for insect cell protein production and purification. For instance, the CP (or the functional fragment or derivative thereof) may be produced by purifying the recombinant CP (or the functional fragment or derivative thereof) from bacteria via his-tag purification following the instructions of the Qiaexpressionist. A CP (or a functional fragment or derivative thereof) may also be synthetically or chemically produced. Therefore solid phase peptide synthesis (SPPS) may be applied.

The donor carbohydrates which are used in the herein provided means and methods may be obtained from commercial sources or may be chemically synthesized (Wolf, Chemistry (2009) 15:7656-64; Wolf, Eur J Cell Biol. (2010) 89:63-75. The acceptor carbohydrates which are used in the inventive means and methods may be obtained by purifying them from *Neisseria meningitidis* cultures and can be chemically synthesized as described in the attached manuscript (Black (2010) Synthesis of structures corresponding to the capsular polysaccharide of *Neisseria meningitidis* group A. 4th Baltic Meeting on Microbial Carbohydrates, Abstracts, p. 56 (abstract 5), Hyytiälä Forestry Field Station, Finland; Black (2011) Towards synthetic glycoconjugates based on the structure of *Neisseria meningitidis* group A capsular polysaccharide. 16th European Carbohydrate Symposium, Abstracts, p. 61 (OL-02), Sorrento, Italy; Nikolaev (2011) From phosphosaccharide chemistry to potential anti-parasite and anti-bacterial carbohydrate vaccines. Carbohydrate Gordon Research Conference, Abstracts, p. 4, Colby College, Waterville, Me., USA.). One embodiment of the invention relates to the herein provided in vitro methods or composition, wherein said acceptor carbohydrate is purified.

As mentioned, the acceptor carbohydrate which is contacted with the donor carbohydrate and the CP may be purified according to the in vitro method described herein. If said acceptor carbohydrate is oligomeric or polymeric CPS of *Neisseria meningitidis*, it may be hydrolysed. Thus, one aspect of the invention relates to the herein provided in vitro methods or composition, wherein said acceptor capsule polysaccharide is hydrolysed.

It is known in the art that capsule polysaccharides of NmA are immunogenic only if O-acetylated (Berry (2002) Infection and immunity 70 (7), 3707-3713). Therefore, in the herein described in vitro methods for producing capsular polysaccharides an O-acetyltransferase can be used which is able to perform this modification in a nature identical form. Accordingly, one embodiment of the invention relates to the herein provided in vitro method, further comprising O-acetylation of the produced capsule polysaccharides. Said O-acetylation may be performed by contacting the produced capsule polysaccharides with an O-acetyltransferase. Also provided herein is the composition of the invention, further comprising an O-acetyltransferase.

The O-acetyltransferase which is used in the inventive methods and compositions may be, e.g. the CsaC of NmA. Accordingly, one aspect of the invention relates to the in vitro methods of the invention or the composition of the invention, wherein, wherein the O-acetyltransferase is the polypeptide of any one of (a) to (f):

(a) a polypeptide comprising an amino acid sequence encoded by a nucleic acid molecule having the nucleic acid sequence of SEQ ID NO: 53;

(b) a polypeptide comprising the amino acid sequence of SEQ ID NO: 54;

(c) a polypeptide encoded by a nucleic acid molecule encoding a polypeptide comprising the amino acid sequence of SEQ ID NO: 54 or of a functional fragment thereof;

(d) a polypeptide comprising an amino acid sequence encoded by a nucleic acid molecule hybridizing under stringent conditions to the complementary strand of a nucleic acid molecule as defined in (a) or (c) and encoding a functional polypeptide; or a functional fragment thereof;

(e) a polypeptide having at least 80%, more preferably at least 85%, even more preferably at least 90%, even more preferably at least 95%, even more preferably at least 96%, even more preferably at least 97%, even more preferably at least 98% or most preferably at least 99% identity to the polypeptide of any one of (a) to (d), whereby said polypeptide is functional; or a functional fragment thereof; and (f) a polypeptide comprising an amino acid sequence encoded by a nucleic acid molecule being degenerate as a result of the genetic code to the nucleotide sequence of a nucleic acid molecule as defined in (a), (c), and (d).

The function of this O-acetyltransferase comprises the ability to transfer Acetyl-groups from the donor Acetyl-Coenzyme A onto hydroxyl-groups of UDP-ManNAc or oligo- and polymeric structures consisting of ManNAc-1-phosphate units linked together by phosphodiester linkages. Or, in other words this O-acetlytransferase catalyses the formation of an ester-bond between an Acetyl-group and a hydroxyl-group of ManNAc-1-phosphate containing molecule. Thus, one aspect of the invention relates to the in vitro methods of the invention or the composition of the invention, wherein the O-acetyltransferase is the polypeptide of any one of (a) to (f):

(a) a polypeptide comprising an amino acid sequence encoded by a nucleic acid molecule having the nucleic acid sequence of SEQ ID NO: 53;

(b) a polypeptide comprising the amino acid sequence of SEQ ID NO: 54;

(c) a polypeptide encoded by a nucleic acid molecule encoding a polypeptide comprising the amino acid sequence of SEQ ID NO: 54 or of a functional fragment thereof, wherein the function comprises the ability to transfer Acetyl-groups from the donor Acetyl-Coenzyme A onto hydroxyl-groups of UDP-ManNAc or oligo- and polymeric structures consisting of ManNAc-1-phosphate units linked together by phosphodiester linkages;

(d) a polypeptide comprising an amino acid sequence encoded by a nucleic acid molecule hybridizing under stringent conditions to the complementary strand of a nucleic acid molecule as defined in (a) or (c) and encoding a functional polypeptide; or a functional fragment thereof, wherein the function comprises the ability to transfer Acetyl-groups from the donor Acetyl-Coenzyme A onto hydroxyl-groups of UDP-ManNAc or oligo- and polymeric structures consisting of ManNAc-1-phosphate units linked together by phosphodiester linkages;

(e) a polypeptide having at least 80%, more preferably at least 85%, even more preferably at least 90%, even more preferably at least 95%, even more preferably at least 96%, even more preferably at least 97%, even more preferably at least 98% or most preferably at least 99% identity to the polypeptide of any one of (a) to (d), whereby said polypeptide is functional; or a functional fragment thereof, wherein the function comprises the ability to transfer Acetyl-groups from the donor Acetyl-Coenzyme A onto hydroxyl-groups of UDP-ManNAc or oligo- and polymeric structures consisting of ManNAc-1-phosphate units linked together by phosphodiester linkages; and (f) a polypeptide comprising an amino acid sequence encoded by a nucleic acid molecule being degenerate as a result of the genetic code to the nucleotide sequence of a nucleic acid molecule as defined in (a), (c), and (d).

In context of the present invention, production and O-acetylation of capsular polysaccharides (e.g. of capsular polysaccharides of NmA) may be performed by using a two-step protocol or in a one-pot reaction.

For example, the O-acetylation of capsular polysaccharides may be performed by incubating in vitro synthesized capsular polysaccharides (e.g. 1 mg) in the presence of an O-acetyltransferase (e.g. 1.2 nmol CsaC of NmA) in a total volume of 0.5 mL. The reaction may be performed in reaction buffer (e.g. a buffer comprising 25 mM Tris pH 7.5 and 50 mM NaCl), started by the addition of an equimolar amount of Acetyl-CoA (e.g. 14 mM final) and allowed to proceed for 4 h at 37° C. Obviously, this protocol may be up or down scale depending on the needed amount of O-acetylated capsular polysaccharides.

As mentioned above, capsule polysaccharides of NmA are only immunogenic if they are O-acetylated. In addition, natural capsule polysaccharides of NmA are O-acetylated in positions 3 and 4 of ManNAc. Thus, if the herein provided in vitro methods are combined with O-acetylation of the produced capsule polysaccharides, then the used capsule polymerase may be CP-A. Thus, one aspect of the invention relates to the herein provided in vitro methods or composition, wherein the capsule polymerase is the capsule polymerase of *Neisseria meningitidis* serogroup A. The capsule polysaccharides produced by the inventive in vitro methods may be O-acetylated in positions 3 and 4 of ManNAc.

As described herein, the capsule polysaccharides (e.g. the O-acetylated capsular polysaccharides) which are produced by the herein described methods may be used for glycoconjugate vaccine production. Thus, one embodiment of the present invention relates to a method for producing a vaccine comprising the herein provided in vitro method. Said method for producing a vaccine may further comprise covalently attaching the produced capsular polysaccharides to a carrier molecule. Said carrier molecule may be tetanus toxoid or $CRM_{197}$ (Cross-Reacting Material 197), an inactive form of diphteria-toxin (Micoli et al., 2013; PNAS).

Thus, the invention relates to a method for the production of a vaccine against a strain genus *Neisseria* comprising the steps of:

(a) In vitro production of (a) Nm capsule polysaccharide(s) as defined above; and (b) combining said Nm capsule polysaccharide(s) with a pharmaceutically acceptable carrier.

Accordingly, the invention relates to a method for the production of a vaccine against a strain or strains of the genus *Neisseria*, in particular *N. meningitidis* by combining (a) Nm capsular polysaccharide(s) of the invention with a biologically acceptable carrier.

Another embodiment of the present invention also relates to a capsular polysaccharide which has been produced by the in vitro method of the present invention. The CPS obtainable by the in vitro methods described hereinabove are useful as pharmaceuticals, e.g., as vaccines. In particular, the herein described CPS are advantageous as vaccines in the prophylaxis and treatment of diseases caused by *Neisseria meningitidis*, such as neisserial *meningitidis*. Accordingly, one embodiment of the present invention relates to the capsular polysaccharide of the invention for use as a medicament.

As mentioned, the synthetic CPS obtainable by the inventive in vitro method may be used as vaccines. In a preferred embodiment of the present invention, they are used in vaccination of a human subject. Also disclosed is the use of the CPS obtainable by the inventive in vitro method for the preparation of a vaccine. In a specific embodiment of the present invention, the CPS obtainable by the in vitro methods described herein are used as vaccines against meningococcal *meningitidis* caused by *Neisseria meningitidis* serogroup A or X. Thus, the medicaments disclosed herein may be useful in pharmaceutical and vaccination purposes, i.e.

for the treatment of *Neisseria*-induced diseases or the vaccination against these pathogens. Therefore, one embodiment of the present invention relates to a vaccine comprising the capsular polysaccharide of the invention, optionally further comprising a pharmaceutically acceptable carrier. Also provided herein is the capsular polysaccharide of the invention or the vaccine of the invention for use in vaccination of a subject. Accordingly, the present invention provides for a method for treating and/or preventing a meningococcal *meningitidis* comprising the administration of (a) capsular polysaccharide(s) of the present invention or the vaccine(s) of the present invention to a subject in need of such a treatment. Preferably said subject is a human patient.

A "patient" or "subject" for the purposes of the present invention includes both humans and other animals, particularly mammals, and other organisms. Thus, the methods are applicable to both human therapy and veterinary applications. In the preferred embodiment the patient is a mammal, and in the most preferred embodiment the patient is human being. As indicated, the herein provided capsular polysaccharide(s) or vaccine(s) may be used for the vaccination against meningococcal *meningitidis* caused by *Neisseria meningitidis* serogroup A or X.

The medicaments provided herein are pharmaceutical compositions and may comprise the CPS of the present invention. The pharmacological compositions may further comprise antibodies specifically directed against the CPS of the present invention. Such CPS as well as the antibodies directed against the same may be used, inter alia, in vaccination protocols, either alone or in combination. Therefore, the pharmaceutical compositions of the present invention which comprise the CPS of the invention or antibodies directed against these CPS, may be used for pharmaceutical purposes such as effective therapy of infected humans or animals and/or, preferably for vaccination purposes. Accordingly, the present invention relates to pharmaceutical compositions comprising the CPS as described herein and/or antibodies or antibody fragments against the CPS as described herein and, optionally, a pharmaceutically acceptable carrier. In context with the present invention, the pharmaceutical compositions described herein may be used, inter alia, for the treatment and/or prevention of *Neisseria*-induced diseases and/or infections. Preferably, the pharmaceutical composition of the invention is used as a vaccine as will be further described herein below.

As mentioned, the present invention also relates to pharmaceutical compositions comprising the capsular polysaccharides described herein. Said capsular polysaccharides may be isolated but it is also envisaged that these capsular polysaccharides are to be used in context with other structures, e.g., toxins, adjuvants and the like. Such toxins may, inter alia, function as carriers for the capsular polysaccharides produced by the herein described methods. Numerous methods have been developed to link oligosaccharides covalently to carriers (Lit: (a) Vince Pozsgay, Oligosaccharide-protein conjugates as vaccine candidates against bacteria, Advances in Carbohydrate Chemistry and Biochemistry, Academic Press, 2000, Volume 56, Pages 153-199, (b) Jennings, H. J., R. K. Sood (1994) Synthetic glycoconjugates as human vaccines; in Lee, Y. C. R. T. Lee (eds): Neoglycoconjugates. Preparation and Applications. San Diego, Academic Press, pp 325-371, (c) Pozsgay, V.; Kubler-Kielb, J., Conjugation Methods toward Synthetic Vaccines, Carbohydrate-Based Vaccines, American Chemical Society, Jul. 2, 2008, 36-70); (D) Carl E. Frasch, Preparation of bacterial polysaccharide-protein conjugates: Analytical and manufacturing challenges, Vaccine, In Press, Corrected Proof, Available online 24 Jun. 2009, ISSN 0264-410X, DOI: 10.1016/j.vaccine.2009.06.013.) One example is the covalent coupling of the synthetic CPS molecules provided herein to protein amino-groups by means of reductive amination. As indicated above, for producing a vaccine, the herein produced CPS may be coupled to tetanus toxoid or other carrier proteins to generate a conjugate vaccine.

Thus, the capsular polysaccharide produced by the herein described methods may preferably used as a vaccine, i.e. the compounds provided herein can be employed for the vaccination of a subject. Such a subject may be a mammal and, in a particular embodiment, a human being. The vaccines provided herein are particularly useful in the vaccination against *Neisseria*.

The medicament/pharmaceutical composition (e.g. the vaccine) of the present invention comprises the CPS produced by the in vitro methods of the invention and may further comprise a pharmaceutically acceptable carrier, excipient and/or diluent. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The pharmaceutical composition of the present invention, particularly when used for vaccination purposes, may be employed at about 0.01 µg to 1 g CPS per dose, or about 0.5 µg to 500 µg CPS per dose, or about 1 µg to 300 µg CPS per dose. However, doses below or above this exemplary ranges are envisioned, especially considering the aforementioned factors. Administration of the suitable compositions may be effected by different ways, e.g., by intravenous, intraperitoneal, subcutaneous, intramuscular, topical or intradermal administration. However, in particular in the pharmaceutical intervention of the present invention, *Neisseria* infections can demand an administration to the side of infection, like the brain. Progress can be monitored by periodic assessment. The compositions of the invention may be administered locally or systemically. Administration will generally be parenterally, e.g., intravenously. The compositions of the invention may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as interleukins and/or interferons depending on the intended use of the pharmaceutical composition. The pharmaceutical composition (e.g. the vaccine) of the invention may also be administered as co-therapy together with at least one other active agent. This at least other active agent may be a medicament which is conventionally used as adjuvant or for preventing and/or treating Nm infections. The other active agent may be, e.g., a vaccine, an antibiotic, an anti-inflammatory agent, an interleukin or an interferon.

In a preferred embodiment of the present invention, the pharmaceutical composition as defined herein is a vaccine.

Vaccines may be prepared, inter alia, from one or more CPS as described herein, or from one or more antibodies as described herein, i.e. antibodies against the CPS as disclosed herein. Accordingly, in context with the present invention, vaccines may comprise one or more CPS as described herein and/or one or more antibodies, fragments of said antibodies or derivatives of the antibodies of the invention, i.e. antibodies against the CPS as disclosed herein.

The CPS or the antibodies, fragments or derivatives of said antibodies of the invention which are used in a pharmaceutical composition may be formulated, e.g., as neutral or salt forms. Pharmaceutically acceptable salts, such as acid addition salts, and others, are known in the art. Vaccines can be, inter alia, used for the treatment and/or the prevention of an infection with pathogens, e.g. *Neisseria*, and are administered in dosages compatible with the method of formulation, and in such amounts that will be pharmacologically effective for prophylactic or therapeutic treatments.

A vaccination protocol can comprise active or passive immunization, whereby active immunization entails the administration of an antigen or antigens (like the capsule polysaccharides of the present invention or antibodies directed against these CPS) to the subject/patient in an attempt to elicit a protective immune response. Passive immunization entails the transfer of preformed immunoglobulins or derivatives or fragments thereof (e.g., the antibodies, the derivatives or fragments thereof of the present invention, i.e. specific antibodies directed against the CPS obtained by the means and methods provided herein) to a subject/patient. Principles and practice of vaccination and vaccines are known to the skilled artisan, see, for example, in Paul, "Fundamental Immunology" Raven Press, New York (1989) or Morein, "Concepts in Vaccine Development", ed: S. H. E. Kaufmann, Walter de Gruyter, Berlin, N.Y. (1996), 243-264; Dimitriu S, editor. "Polysaccharides in medicinal application"; New York: Marcel Dekker, pp 575-602. Typically, vaccines are prepared as injectables, either as liquid solutions or suspensions; solid forms suitable for solution in or suspension in liquid prior to injection may also be prepared. The preparation may be emulsified or the protein may be encapsulated in liposomes. The active immunogenic ingredients are often mixed with pharmacologically acceptable excipients which are compatible with the active ingredient. Suitable excipients include but are not limited to water, saline, dextrose, glycerol, ethanol and the like; combinations of these excipients in various amounts also may be used. The vaccine may also contain small amounts of auxiliary substances such as wetting or emulsifying reagents, pH buffering agents, and/or adjuvants which enhance the effectiveness of the vaccine. For example, such adjuvants can include aluminum compositions, like aluminumhydroxide, aluminumphosphate or aluminumphosphohydroxide (as used in "Gen H-B-Vax®" or "DPT-Impfstoff Behring"), N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxyphaosphoryloxy)-ethylamine (CGP 19835A, also referred to as MTP-PE), MF59 and RIBI (MPL+TDM+CWS) in a 2% squalene/Tween-80® emulsion.

The vaccines are usually administered by intravenous or intramuscular injection. Additional formulations which are suitable for other modes of administration include suppositories and, in some cases, oral formulations. For suppositories, traditional binders and carriers may include but are not limited to polyalkylene glycols or triglycerides. Oral formulation include such normally employed excipients as, for example, pharmaceutical grades of mannitol, lactose, starch, magnesium stearate, sodium saccharine, cellulose, magnesium carbonate and the like. These compositions may take the form of solutions, suspensions, tables, pills, capsules, sustained release formulations or powders and contain about 10% to about 95% of active ingredient, preferably about 25% to about 70%.

Vaccines are administered in a way compatible with the dosage formulation, and in such amounts as will be prophylactically and/or therapeutically effective. The quantity to be administered generally is in the range of about 0.01 µg to 1 g antigen per dose, or about 0.5 µg to 500 µg antigen per dose, or about 1 µg to 300 µg antigen per dose (in the present case CPS being the antigen), and depends upon the subject to be dosed, the capacity of the subject's immune system to synthesize antibodies, and the degree of protection sought. Precise amounts of active ingredient required to be administered also may depend upon the judgment of the practitioner and may be unique to each subject. The vaccine may be given in a single or multiple dose schedule. A multiple dose is one in which a primary course of vaccination may be with one to ten separate doses, followed by other doses given at subsequent time intervals required to maintain and/or to reinforce the immune response, for example, at one to four months for a second dose, and if required by the individual, a subsequent dose(s) after several months. The dosage regimen also will be determined, at least in part, by the need of the individual, and be dependent upon the practitioner's judgment. It is contemplated that the vaccine containing the immunogenic compounds of the invention may be administered in conjunction with other immunoregulatory agents, for example, with immunoglobulins, with cytokines or with molecules which optimize antigen processing, like listeriolysin.

For diagnosis and quantification of pathogens like *Neisseria*, pathogenic fragments, their derivatives, their (poly) peptides (proteins), their polynucleotides, etc. in clinical and/or scientific specimens, a variety of immunological methods, as well as molecular biological methods, like nucleic acid hybridization assays, PCR assays or DNA Enzyme Immuno Assays (DEIA; Mantero et al., Clinical Chemistry 37 (1991), 422-429) have been developed and are well known in the art. In this context, it should be noted that the nucleic acid molecules of the invention may also comprise PNAs, modified DNA analogs containing amide backbone linkages. Such PNAs are useful, inter alia, as probes for DNA/RNA hybridization. The proteins of the invention may be, inter alia, useful for the detection of anti-pathogenic (like, e.g., anti-bacterial or anti-viral) antibodies in biological test samples of infected individuals. It is also contemplated that antibodies of the invention and compositions comprising such antibodies of the invention may be useful in discriminating acute from non-acute infections. The CPS as provided herein can also be used in diagnostic settings, for example as "standards", in, e.g., chromatographic approaches. Therefore, the present CPS can be used in comparative analysis and can be used either alone or in combination to diagnostic methods known in the art.

The diagnostic compositions of the invention optionally comprise suitable means for detection. The CPS as disclosed and described herein as well as specific antibodies or fragments or derivatives thereof directed or raised specifically against these CPS are, for example, suitable for use in immunoassays in which they can be utilized in liquid phase or bound to a solid phase carrier. Solid phase carriers are known to those in the art and may comprise polystyrene beads, latex beads, magnetic beads, colloid metal particles, glass and/or silicon chips and surfaces, nitrocellulose strips, membranes, sheets, animal red blood cells, or red blood cell ghosts, duracytes and the walls of wells of a reaction tray, plastic tubes or other test tubes. Suitable methods of immobilizing nucleic acids, (poly)peptides, proteins, antibodies, microorganisms etc. on solid phases include but are not limited to ionic, hydrophobic, covalent interactions and the like. Examples of immunoassays which can utilize said proteins, antigenic fragments, fusion proteins, antibodies or fragments or derivatives of said antibodies of the invention are competitive and non-competitive immunoassays in either a direct or indirect format. Commonly used detection assays can comprise radioisotopic or non-radioisotopic methods. Examples of such immunoassays are the radioimmunoassay (RIA), the sandwich (immunometric assay) and the Western blot assay. Furthermore, these detection methods comprise, inter alia, IRMA (Immune Radioimmunometric Assay), EIA (Enzyme Immuno Assay), ELISA (Enzyme Linked Immuno Assay), FIA (Fluorescent Immuno Assay), and CLIA (Chemioluminescent Immune Assay). Other detection methods that are used in the art are those that do not utilize tracer molecules. One prototype of these methods is the agglutination assay, based on the property of a given molecule to bridge at least two particles.

The CPS of the invention can be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention.

A variety of techniques are available for labeling biomolecules. Theses techniques are well known to the person skilled in the art and comprise, inter alia, covalent coupling of enzymes or biotinyl groups, iodinations, phosphorylations, biotinylations, random priming, nick-translations, tailing (using terminal transferases) or labeling of carbohydrates. Such techniques are, e.g., described in Tijssen, "Practice and theory of enzyme immuno assays", Burden, R H and von Knippenburg (Eds), Volume 15 (1985), "Basic methods in molecular biology"; Davis L G, Dibmer M D; Battey Elsevier (1990), Mayer et al., (Eds) "Immunochemical methods in cell and molecular biology" Academic Press, London (1987), or in the series "Methods in Enzymology", Academic Press, Inc., or in Fotini N. Lamari, Reinhard Kuhn, Nikos K. Karamanos, "Derivatization of carbohydrates for chromatographic, electrophoretic and mass spectrometric structure analysis", Journal of Chromatography B, Volume 793, Issue 1, Derivatization of Large Biomolecules, (2003), Pages 15-36.

Detection methods comprise, but are not limited to, autoradiography, fluorescence microscopy, direct and indirect enzymatic reactions, etc.

The CPS described herein may be detected by methods known in the art as well as described and exemplified herein. For example, an ELISA (Enzyme-linked immunosorbent assay) based method described herein may be used for the detection and quantification of the chimeric CPS described herein. In this context, the chimeric CPS described herein may be immobilized by an antibody or other binding molecule, such as a lectine or similar, contacting one part or building block of the chimeric CPS. Detection of a second part or building block of the chimeric CPS described herein can be achieved by, e.g., contacting with an antibody or other binding molecule as described herein which is labeled for further detection or a secondary antibody or other binding molecule as described which is labeled for further detection.

As indicated above, the present invention further relates to antibodies specifically binding to the synthetic CPS obtainable by the in vitro methods described herein. The term "antibody" herein is used in the broadest sense and specifically encompasses intact monoclonal antibodies, polyclonal antibodies, multispecific antibodies (e.g., bispecific antibodies) formed from at least two intact antibodies, and antibody fragments, so long as they exhibit the desired biological activity. Also human, humanized, camelized or CDR-grafted antibodies are comprised.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler, G. et al., Nature 256 (1975) 495, or may be made by recombinant DNA methods (see, e.g., U.S. Pat. No. 4,816,567). "Antibody fragments" comprise a portion of an intact antibody. In context of this invention, antibodies specifically recognize CPS obtainable by the in vitro method described herein. Antibodies or fragments thereof as described herein may also be used in pharmaceutical and medical settings such as vaccination/immunization, particularly passive vaccination/immunization.

The term "antibody" includes antigen-binding portions, i.e., "antigen binding sites," (e.g., fragments, subsequences, complementarity determining regions (CDRs)) that retain capacity to bind an antigen (such as CPS produced by the herein described methods), comprising or alternatively consisting of, for example, (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward; 1989; Nature 341; 544-546), which consists of a VH domain; and (vi) an isolated complementarity determining region (CDR). Antibody fragments or derivatives further comprise F(ab')2, Fv or scFv fragments or single chain antibodies.

The antibodies of the present invention may be used for vaccinating against, treating and/or diagnosing meningococcal *meningitidis* caused by *Neisseria meningitidis* serogroup A or X.

The term "carbohydrate" as used herein comprises building blocks such as saccharides and sugars in any form as well as aldehydes and ketones with several hydroxyl groups added. A carbohydrate may contain one or more of said building blocks linked via covalent bonds such as glycosidic linkages. A carbohydrate may be of any length, i.e. it may be monomeric, dimeric, trimeric or multimeric. A carbohydrate may also contain one or more building blocks as side chains linked to the main chain via covalent bonds. A carbohydrate may also contain one or more activated saccharides such as nucleotide sugars. Examples of nucleotide sugars are UDP-GlcNAc, UDP-ManNAc, UDP-GlcUA, UDP-Xyl, GDP-Man and GDP-Fuc.

Herein, the term "nucleic acid molecule" or "polynucleotide" refers to DNA or RNA or hybrids thereof or any modification thereof that is known in the state of the art (see, e.g., U.S. Pat. Nos. 5,525,711, 4,711,955, 5,792,608 or EP 302175 for examples of modifications). The polynucleotide sequence may be single- or double-stranded, linear or circular, natural or synthetic. For instance, the polynucleotide sequence may be genomic DNA, cDNA, mRNA, antisense RNA, ribozymal or a DNA encoding such RNAs or chimeroplasts (Gamper, Nucleic Acids Research, 2000, 28, 4332-4339). Said polynucleotide sequence may be in the form of a plasmid or of viral DNA or RNA. For example, the present invention relates to a nucleic acid molecule having the nucleotide sequence of any one of SEQ ID NOs: 1-8, 16-23 and 32. The present invention also encompasses nucleic acid molecules comprising the nucleic acid molecule of any one of SEQ ID NO: 1-8, 16-23 and 32 wherein one, two, three or more nucleotides are added, deleted or substituted. Such a nucleic acid molecule may encode a polypeptide being active (i.e. functional). The term "activity", "functionality" or "being functional" as used herein refers in particular to the ability of having substantially the same function as the non-modified polynucleotide.

The present invention further relates to nucleic acid molecules which are complementary to the nucleic acid molecules described above. Also encompassed are nucleic acid molecules which are able to hybridize to nucleic acid molecules described herein. A nucleic acid molecule of the present invention may also be a fragment of the nucleic acid molecules described herein. Particularly, such a fragment is a functional fragment, which means that the fragment has the same function as the non-modified polynucleotide.

The term "hybridization" or "hybridizes" as used herein in context of nucleic acid molecules/polynucleotieds/DNA sequences may relate to hybridizations under stringent or non-stringent conditions. If not further specified, the conditions are preferably stringent. Said hybridization conditions may be established according to conventional protocols described, for example, in Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions. Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

In accordance to the invention described herein, low stringent hybridization conditions for the detection of homologous or not exactly complementary sequences may, for example, be set at 6×SSC, 1% SDS at 65° C. As is well known, the length of the probe and the composition of the nucleic acid to be determined constitute further parameters of the hybridization conditions.

Hybridizing nucleic acid molecules also comprise fragments of the above described molecules. Furthermore, nucleic acid molecules which hybridize with any of the aforementioned nucleic acid molecules also include complementary fragments, derivatives and allelic variants of these molecules. Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands.

The term "hybridizing sequences" preferably refers to sequences which display a sequence identity of at least 80%, more preferably at least 85%, even more preferably at least 90%, even more preferably at least 95%, even more preferably at least 96%, even more preferably at least 97%, even more preferably at least 98% and most preferably at least 99% identity with a nucleic acid sequence as described above.

The polypeptides and nucleic acid molecule provided herein preferably show a homology, determined by sequence identity, of at least 80%, more preferably of at least 85%, even more preferably of at least 90%, even more preferably of at least 95%, even more preferably of at least 96%, even more preferably of at least 97%, even more preferably of at least 98, and most preferably of at least 99% identity to a sequence as shown in any one of SEQ ID NOs: 1-3, 9, 10, 16, 17, 20-25 or 28-33 as defined herein above.

The polypeptides and nucleic acid molecules to be employed in accordance with this invention preferably show a homology, determined by sequence identity, to the sequences indicated under any one of SEQ ID NOs: 1-3, 9, 10, 16, 17, 20-25 or 28-33, preferably over the entire length of the sequences compared. The homologous sequences are preferably fragments having a length of at least 100, more preferably at least 200, more preferably at least 300, more preferably at least 400 and more preferably at least 500, more preferably at least 600, more preferably at least 700, more preferably at least 800 and most preferably at least 900 nucleotides which have an identity of at least 80%, more preferably of at least 85%, even more preferably of at least 90%, even more preferably of at least 95%, even more preferably of at least 96%, even more preferably of at least 97%, even more preferably of at least 98, and most preferably of at least 99% with the sequence shown under any one of SEQ ID NOs: 1-3, 9, 10, 16, 17, 20-25 or 28-33, respectively.

If two sequences which are to be compared with each other differ in length, sequence identity preferably relates to the percentage of the (amino acid or nucleotide) residues of the shorter sequence which are identical with the (amino acid or nucleotide) residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711), CLUSTALW computer program (Thompson; 1994; Nucl Acids Res; 2; 4673-4680) or FASTDB (Brutlag; 1990; Comp App Biosci; 6; 237-245). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides or amino acids in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson, Methods in Enzymology 183 (1990), 63-98, appended examples and http://workbench.sdsc.edu/). For this purpose, the "default" parameter settings may be used.

The in vitro methods described herein may also be used for automated high-throughput approaches using robotic liquid dispensing workstations. Generally in such high-throughput approaches a plurality of assay mixtures are run in parallel. These mixtures may have the same or different concentrations of the respective ingredients. Typically, one of these mixtures serves as a negative control, i.e. at zero concentration or below the limits of assay detection.

These and other embodiments are disclosed and obvious to a skilled person and embraced by the description and the Examples of the present invention. Additional literature regarding one of the above-mentioned methods, means and uses, which can be applied within the meaning of the present invention can be obtained from the prior art, for instance in public libraries, e.g. with the use of electronic means. For this purpose, public data bases, such as "Medline", can be accessed via the internet, for instance under the address http://www.ncbi.nlm.nih.gov/PubMed/medline.html. Additional data bases and addresses are known to a skilled person and can be taken from the internet, for instance under the address http://www.lycos.com. An overview of sources and information regarding patents or patent applications in biotechnology is given in Berks, TIBTECH 121 (1994), 352-364.

A number of documents including patent applications, manufacturer's manuals and scientific publications are cited herein. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The present invention is further described by reference to the following non-limiting figures and examples.

The Figures show:

FIG. 1. The donor:acceptor ratio influences the product distribution and the product length of CsaB- and CsxA-reactions in a different manner By using CP-A (i.e. CsaB), the product distribution as well as the product length can be controlled via the donor:acceptor ratio. By using full length CP-X (i.e. CsxA), the product distribution as well as the product length cannot be controlled via the donor:acceptor ratio. Here two product pools are produced, one having small and the other having large polymers.

A: CPSA distribution obtained after CsaB (in particular ΔN69-CP-A) reactions in the presence of 2 mM UDP-GlcNAc and varying amounts of short CPSA oligos (DP1-DP10). It is mentioned that, in pilot experiments, a similar product length control by varying the donor-acceptor ratio was seen for the full length CP-A. The designation "expected DP" indicates the major species of the produced capsular polysaccharides (i.e. the main component) and also specifies the donor-acceptor ratio (i.e. the donor:acceptor quotient). Thus, the concentrations of the acceptor CPSX range from 40-4 µM. Accordingly, from left to right, the used ratios of donor carbohydrate to acceptor carbohydrate are 50:1, 75:1, 100:1, 200:1 and 500:1.

B: Purification of CsxA truncations.

C: Design of CsaB and CsaX truncations. Active truncations are indicated by and asterisk *.

D: CPSX distribution obtained after CsxA reactions in the presence of 5 mM UDP-GlcNAc and varying amounts of short CPSX oligos (DP1-DP7). The fact that the highest amount of acceptor sugar is not detectable in the gel indicates that all detected molecule are synthesised by CsxA. The marker consists of polymer of the size which is used in vaccine production.

E: CPSX distribution obtained after CsxA reactions in the presence of 5 mM UDP-GlcNAc and varying amounts of long CPSX oligos (DP10-DP70). The marker consists of polymer of the size which is used in vaccine production.

Figure 2:
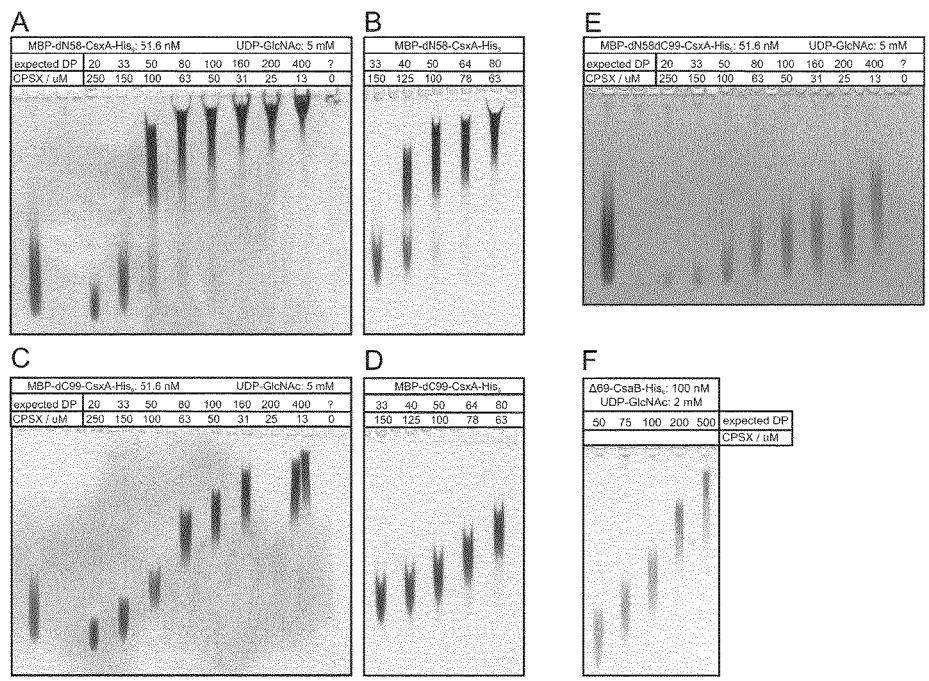

FIG. 2. The donor:acceptor ratio influences the product distribution and the product length of the truncated version of the CsxA By using a truncated version of CP-X (i.e. dC99-CsxA or dN58dC99-CsxA), the product distribution as well as the product length can be controlled via the donor:acceptor ratio. The designation "expected DP" indicates the major species (i.e. the main component) of the produced capsular polysaccharides and also specifies the donor-acceptor ratio (i.e. the donor:acceptor quotient). For example, an "expected DP" of 20, 33, 40, 50, 64, 75, 80, 100, 160, 200, 400, or 500 means a ratio of donor carbohydrate to acceptor carbohydrate of 20:1, 33:1, 40:1, 50:1, 64:1, 75:1, 80:1, 100:1, 160:1, 200:1, 400:1, or 500:1.
A/B: CPSX distribution obtained after dN58-CsxA reactions in the presence of 5 mM UDP-GlcNAc and varying amounts of short CPSX oligos (DP1-DP7).
C/D: CPSX distribution obtained after dC99-CsxA reactions in the presence of 5 mM UDP-GlcNAc and varying amounts of short CPSX oligos (DP1-DP7).
E: CPSX distribution obtained after dN58dC99-CsxA reactions in the presence of 5 mM UDP-GlcNAc and varying amounts of short CPSX oligos (DP1-DP7).
F: CPSA distribution obtained after dN69-CsaB reactions in the presence of 2 mM UDP-GlcNAc and varying amounts of short CPSA oligos (DP1-DP10).

FIG. 3. Determination of the minimal acceptor of full length CsxA and truncated CsxA
A: Purification of single CPSX oligos.
B-D: Finding the minimal acceptor of CsxA full-length and CsxA truncations.

Figure 4:
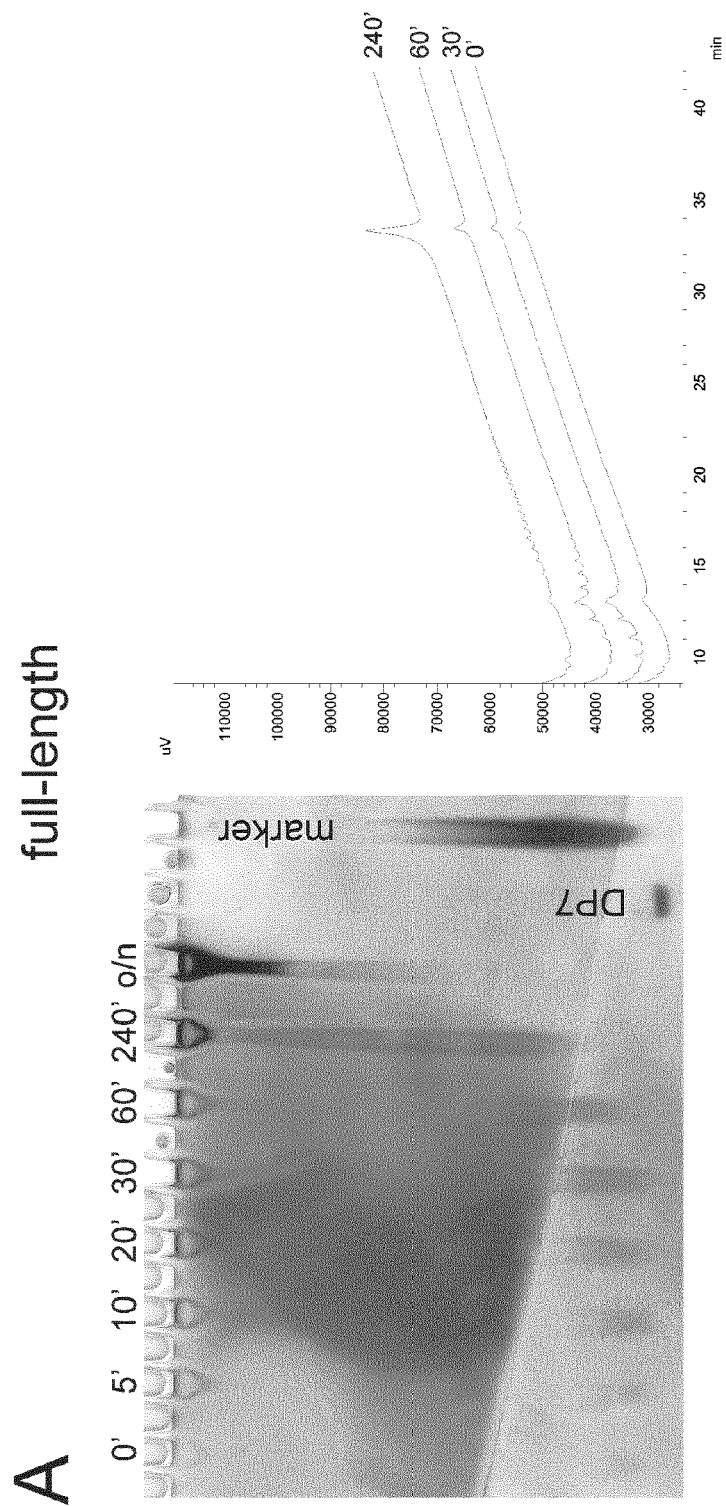
Figure 4:
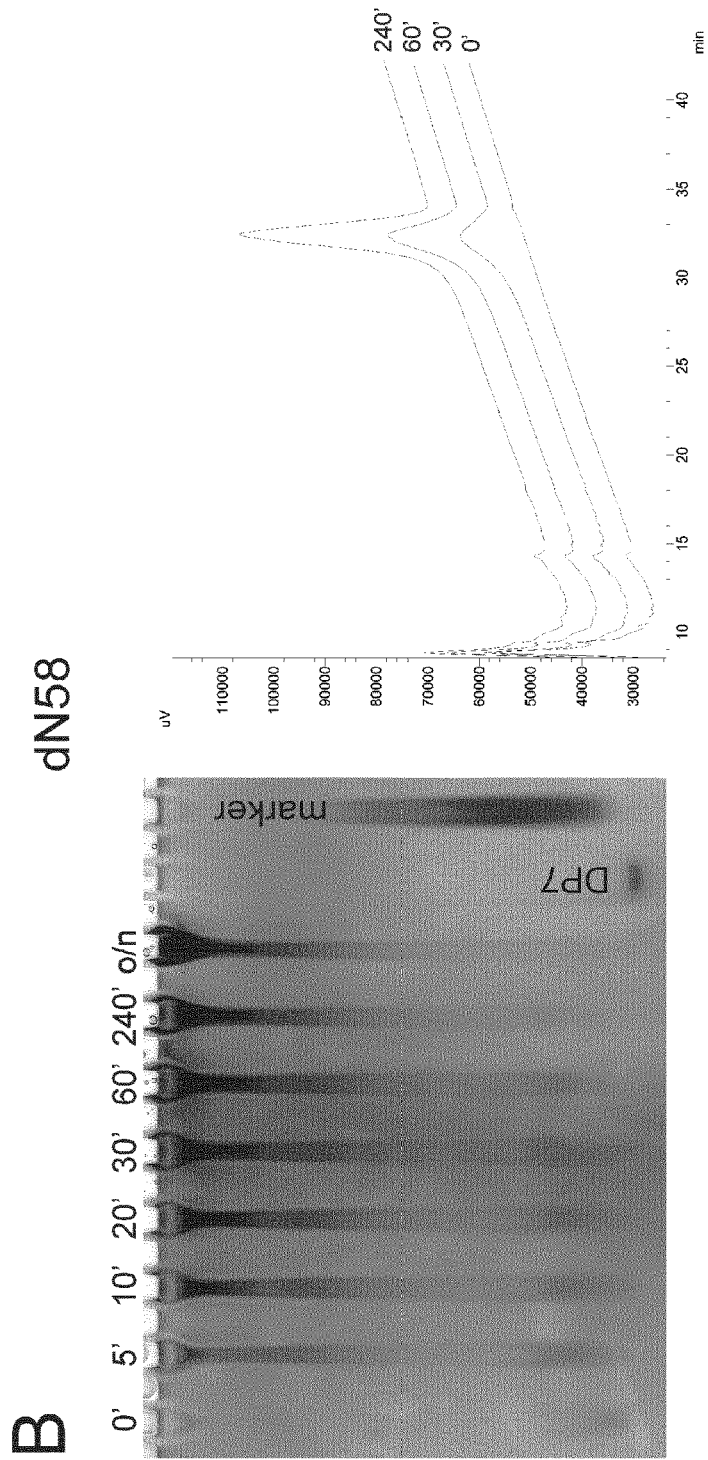
Figure 4:
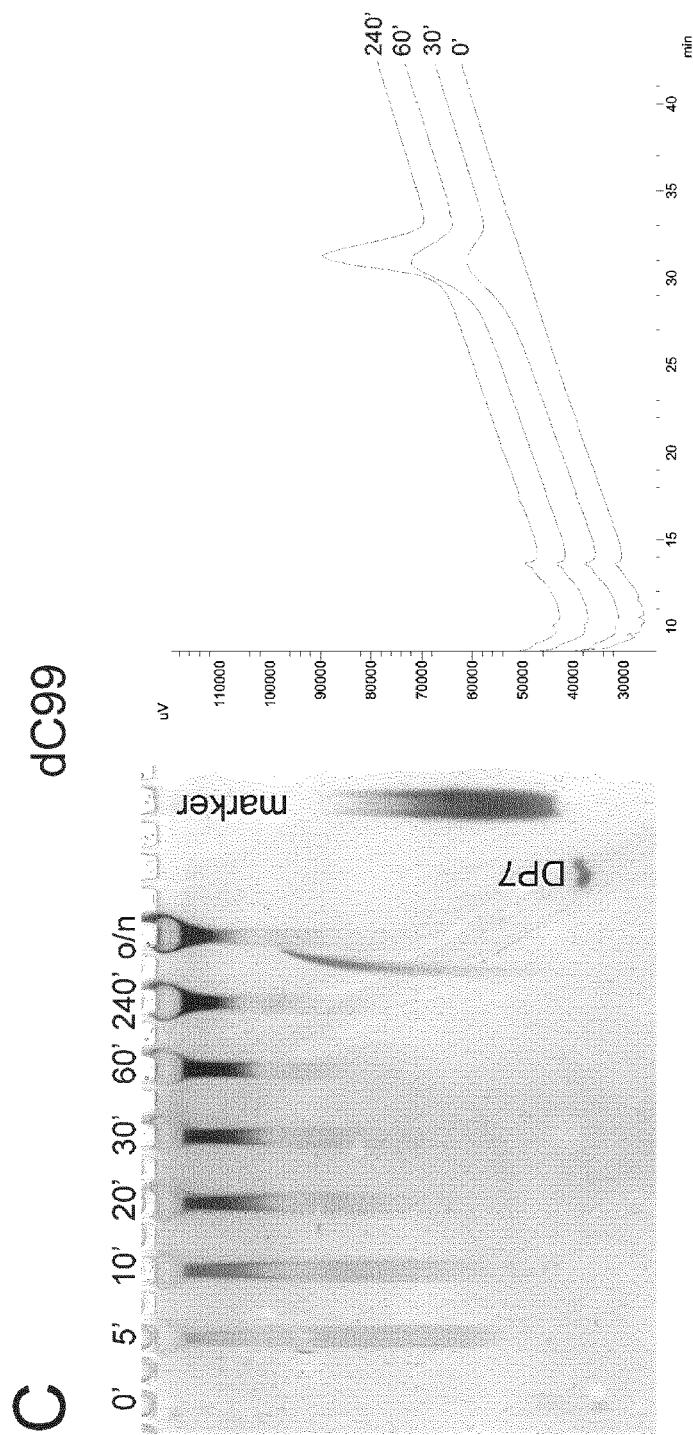
Figure 4:
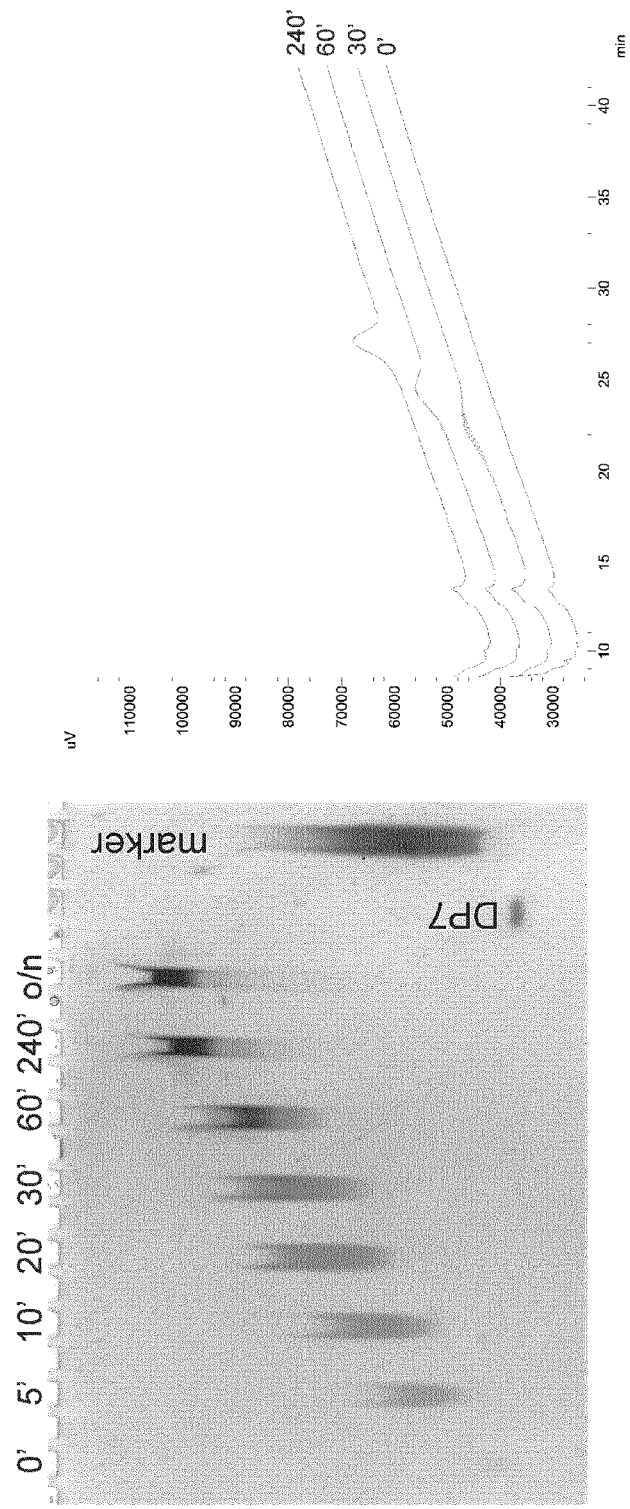
Figure 4:
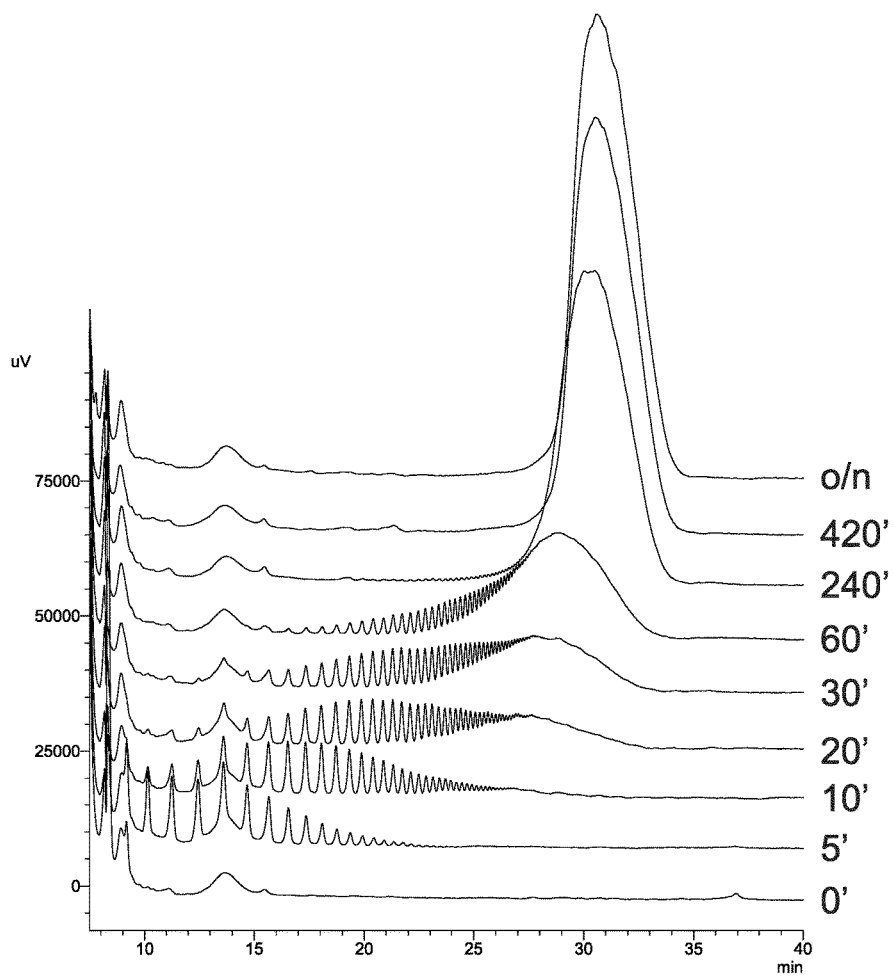
Figure 4:
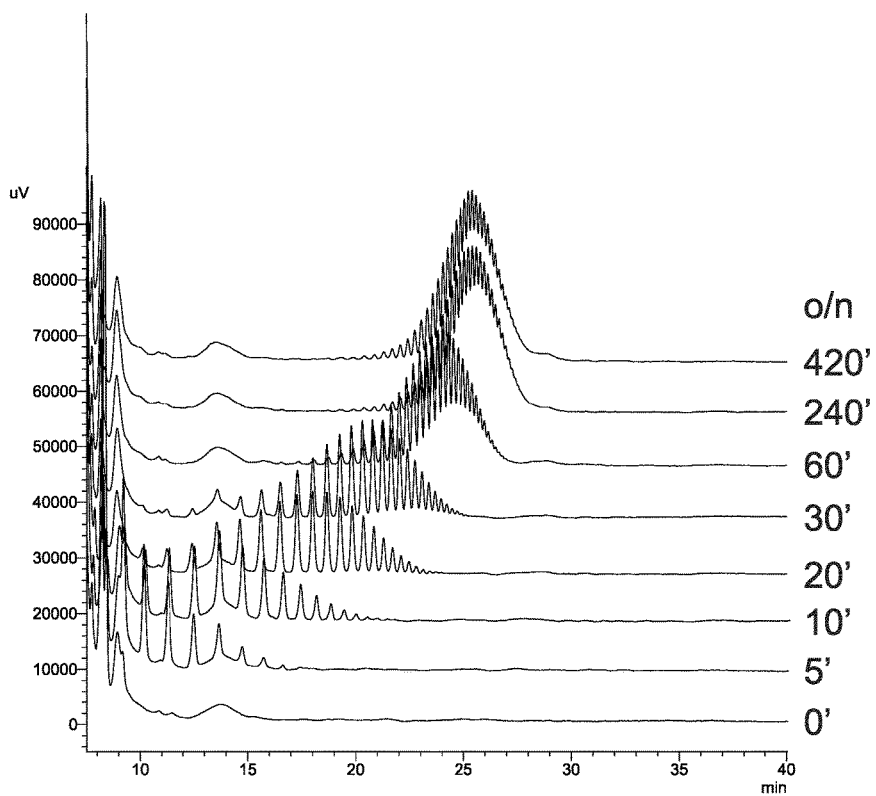

FIG. 4. The reaction time influences the product distribution and the product length of the truncated versions of the CsxA By using constant donor-acceptor ratios and truncated versions of the CsxA (i.e. dC99-CsxA, dN58-CsxA or dC99dN58-CsxA) the avDP of the produced products can be controlled via the reaction time. 50 nM of capsule polymerase have been used. The marker indicates length from DP10 to DP60.
A: Analysis of the CPSX distribution obtained at different time-points during a CsxA reaction in the presence of 10 mM UDP-GlcNAc and DP7. The ratio of donor carbohydrate to acceptor carbohydrate is approximately 8000:1.
B: Analysis of the CPSX distribution obtained at different time-points during a dN58-CsxA reaction in the presence of 10 mM UDP-GlcNAc and DP7. The ratio of donor carbohydrate to acceptor carbohydrate is approximately 8000:1.
C: Analysis of the CPSX distribution obtained at different time-points during a dC99-CsxA reaction in the presence of 10 mM UDP-GlcNAc and DP7. The ratio of donor carbohydrate to acceptor carbohydrate is approximately 8000:1.
D: Analysis of the CPSX distribution obtained at different time-points during a dN58dC99-CsxA reaction in the presence of 10 mM UDP-GlcNAc and DP7. The ratio of donor carbohydrate to acceptor carbohydrate is approximately 8000:1.
E: Analysis of the CPSX distribution obtained at different time-points during a dC99-CsxA reaction in the presence of 10 mM UDP-GlcNAc and DP5. The ratio of donor carbohydrate to acceptor carbohydrate is approximately 200:1.
F: D: Analysis of the CPSX distribution obtained at different time-points during a dN58dC99-CsxA reaction in the presence of 10 mM UDP-GlcNAc and DP7. The ratio of donor carbohydrate to acceptor carbohydrate is approximately 200:1. A calibration showed that the product pool in the 20' fraction has an avDP of 15 and the product pool in the 20' fraction has an avDP of 20.

Figure 5:
Figure 5:
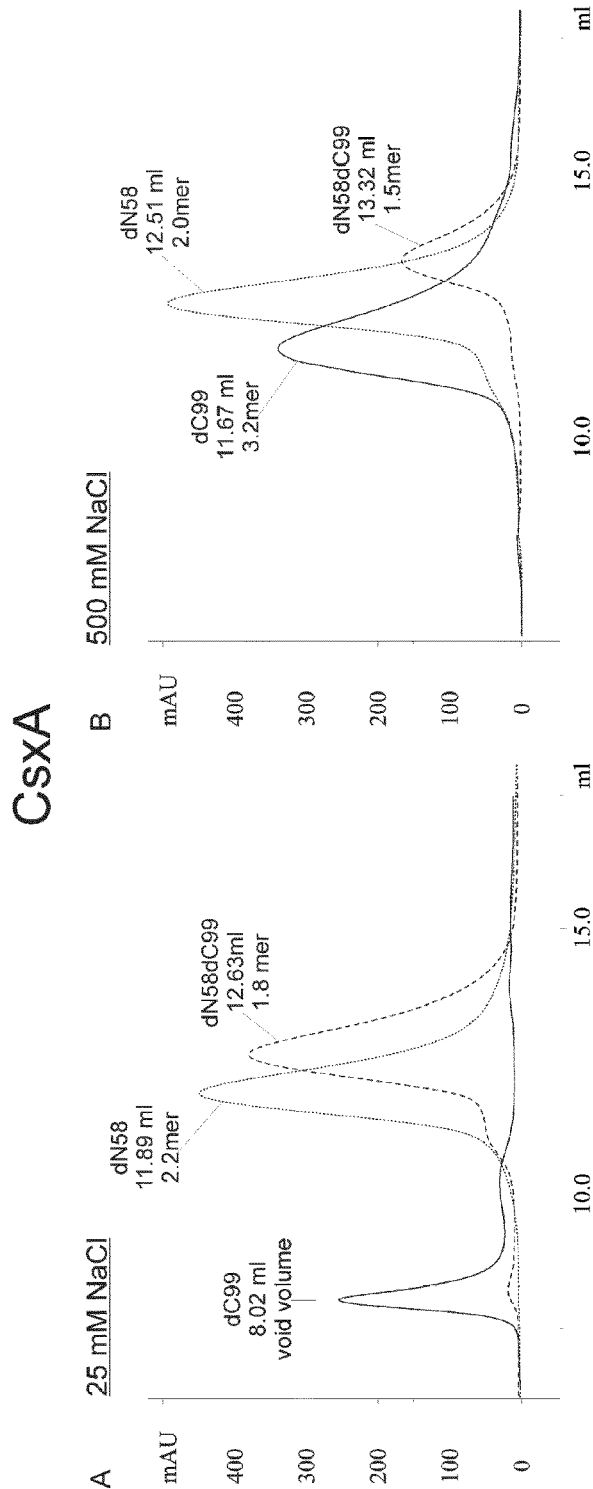

FIG. 5. The oligomerisation status of CP-A (CsaB; upper panel) and CP-X (CsxA; lower panel) was analysed by size exclusion and different salt concentrations. CP-A elutes in the void volume with 25 mM NaCl and elutes as a broad smeared peak in the presence of 500 mM salt, indicating that the full length enzyme forms aggregates in solution that are distorted but not dissociated into monomers in the presence of 500 mM salt.

In case of CP-X (CsxA) the C-terminal truncation (dC99) is not sufficient to prevent aggregate formation at low salt concentrations, however, the protein migrates with an apparent molecular mass resembling the trimer if 500 mM salt are present. In contrast the N-terminal truncation (dN58) prevents larger aggregate formation. The mutant dN58 similar to dN58dC99 migrates with an apparent molecular mass that suggest dimer formation already at low salt concentrations (25 mM NaCl). The dimers formed seem to be stable also in the presence of 500 mM salt.

Figure 6:
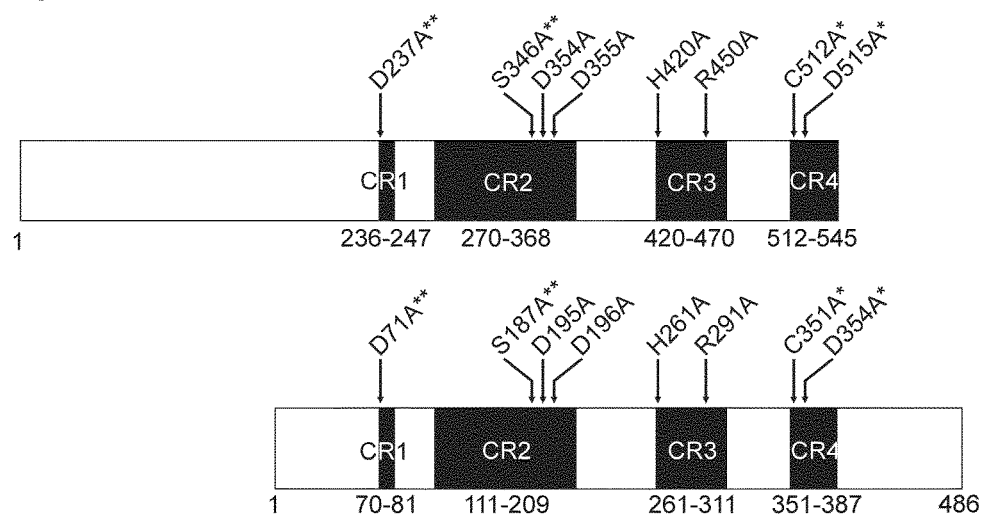
Figure 6:
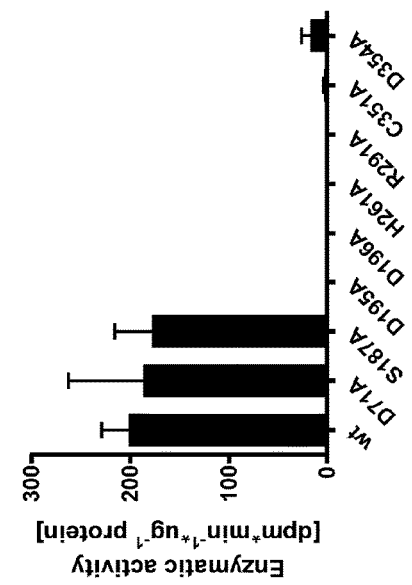
Figure 6:
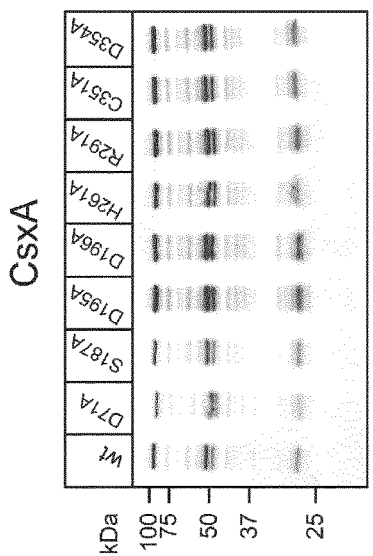
Figure 6:
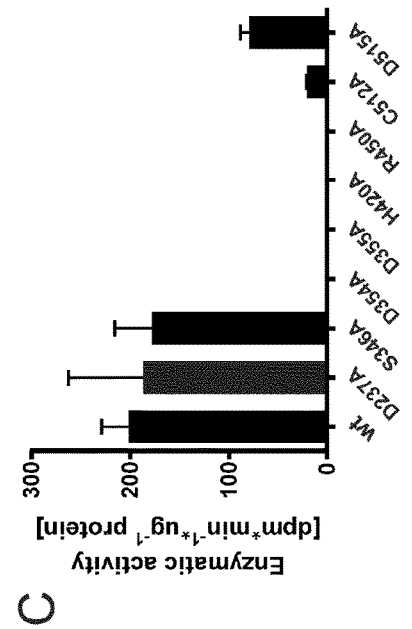
Figure 6:
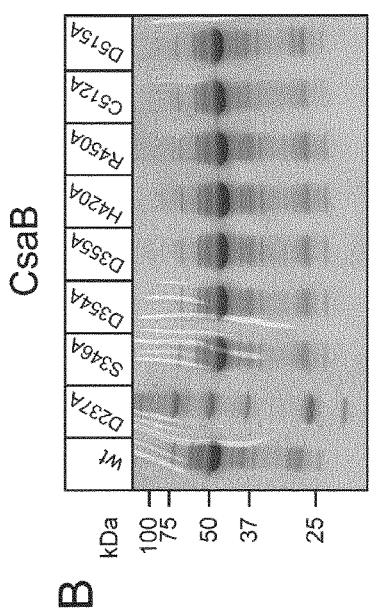

FIG. 6. A: schematic representation of CP-A (upper bar) and CP-X (lower bar) illustrating the conserved motives existing in these proteins and positions were point mutations have been introduced. Point mutants with reduced- or no activity are marked with one and double star (*), respectively. B: All protein variants could be expressed as recombinant proteins and purified in high quality. C: A radioactive incorporation assay was used to determine the enzymatic activity.

Figure 7:
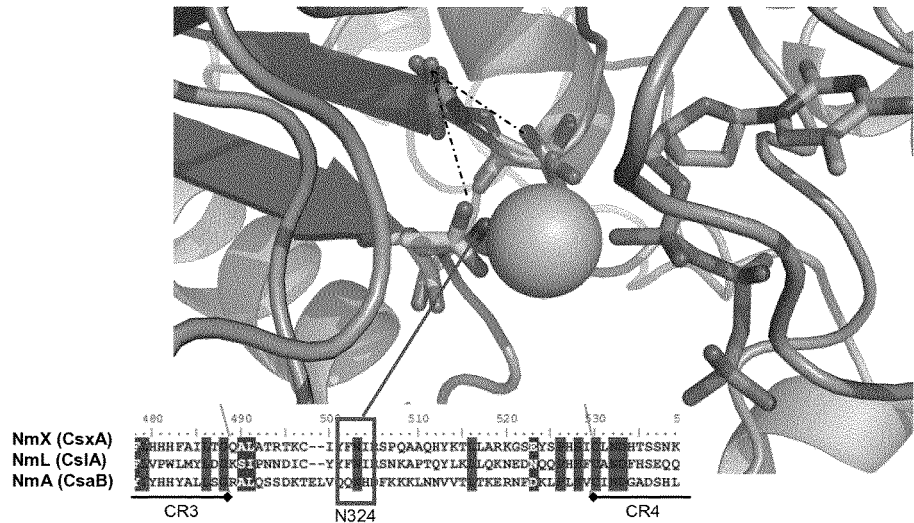

FIG. 7. Multi-sequence alignment including the bacterial capsule polymerases that are hexosylphosphate transferases identified a novel conserved asparagine-residue (N324 in CP-X) outside of the conserved motifs. Based on a hypothetic model of CP-X (top) N324 may be involved in the coordination of the catalytically important divalent cation (large gray ball in the middle). Replacement of this asparagine by alanine in CP-A and CP-X inactivated enzymatic activity. Remarkably, the respective enzyme isolated from non-pathogenic NmL had no activity neither as wildtype nor after mutation of this position.

Figure 8:
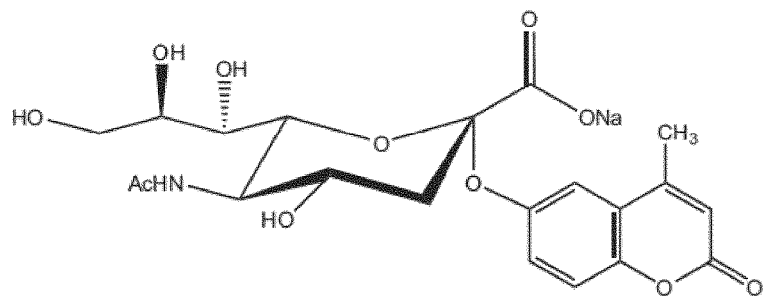
Figure 8:
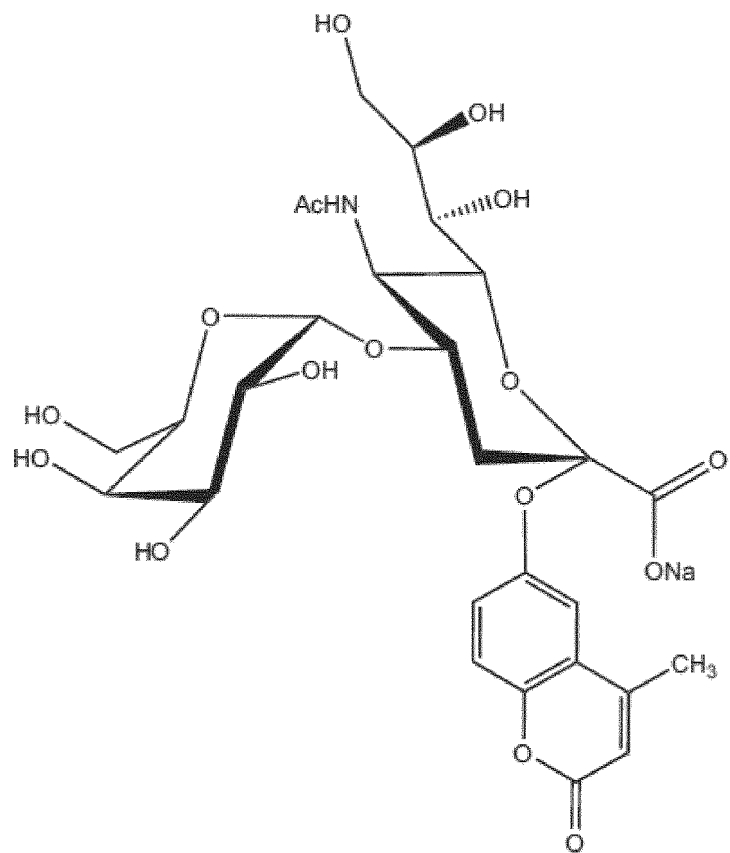
Figure 8:
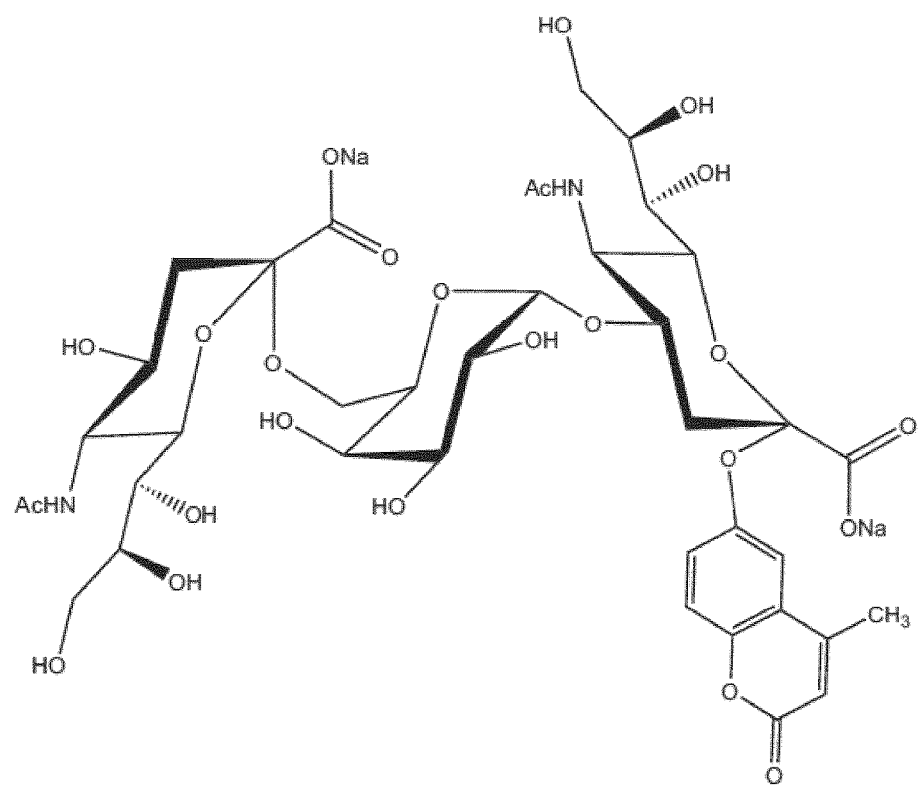

FIG. 8. Fluorescently labelled primers for the separate testing of hexosyl- and sialyltransferase activity.

Starting from 4-MU-Sia, monovalent forms of $SiaD_{W-135}$/$SiaD_Y$ were used in iterative steps to generate labelled acceptors suited to separately assay hexosyl- and sialyltransferase activity in the chimeric capsule polymerases of NmW-135 and NmY. Exemplarily shown are the acceptors with Gal as hexose. For simplicity DP—degree of polymerization—is used to describe the different 4-MU-labelled saccharides.

Figure 9:
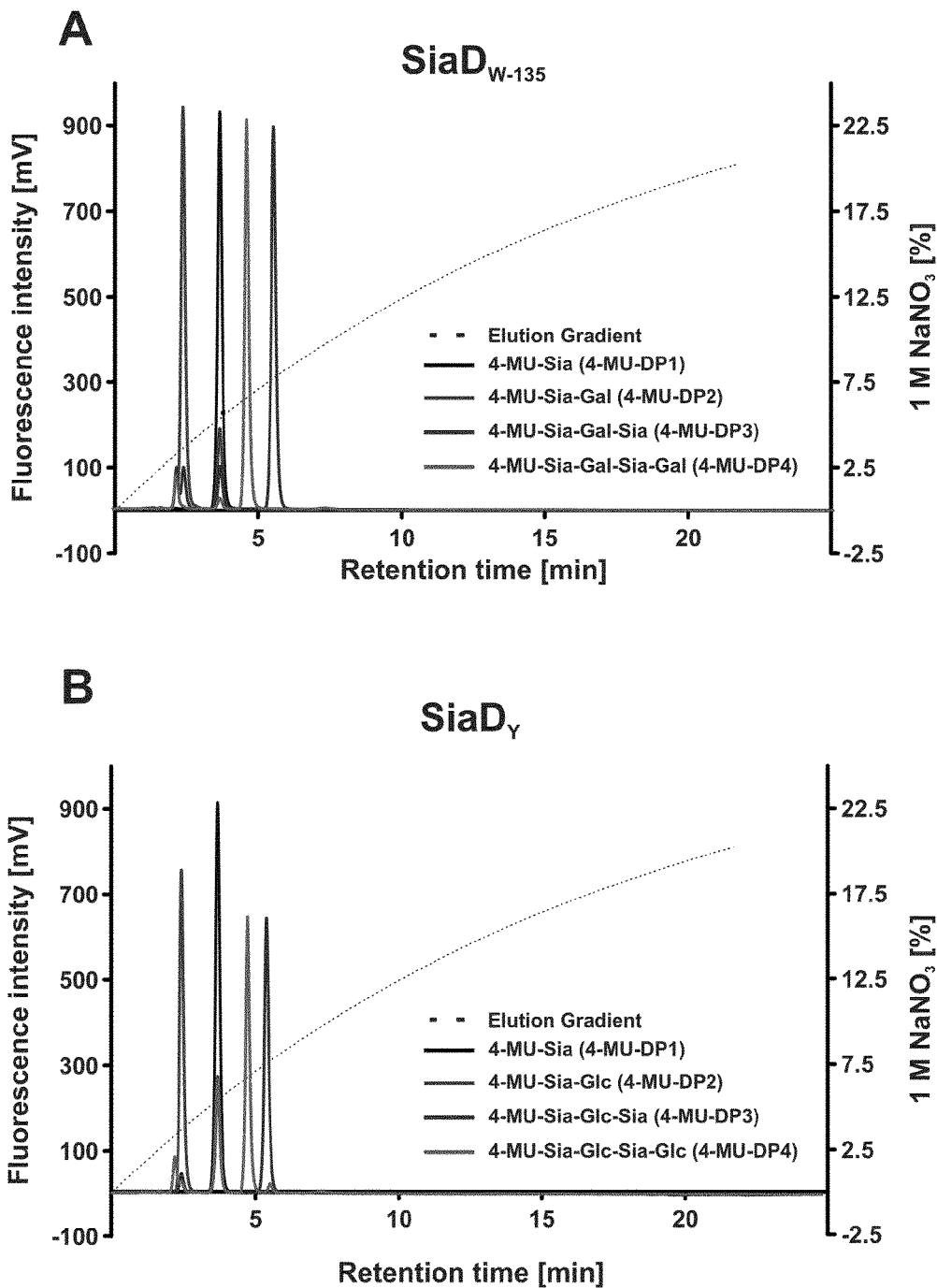

FIG. 9. Chromatographic behaviour of 4-MU-labelled oligomers in anion exchange chromatography.

In consecutive enzymatic reactions 4-MU-Sia (4-MU-DP1) was elongated to 4-MU-DP4. Before the start of a new reaction 0.01% of the sample was loaded onto a CarboPac® PA-100 column and products eluted with a curved $NaNO_2$ gradient as shown. MU fluorescence was detected at 375 nm. Overlays of chromatograms obtained with the monovalent forms of $SiaD_{W-135}$ (A) and $SiaD_Y$ (B) are shown. Baseline separation of peaks allowed the determination of precise retention times. Of note, the chromatograms show that the conversion of 4-MU-DP1 to 4-MU-DP2 was incomplete under the conditions used, while all other that reactions proceeded to completion.

Figure 10:
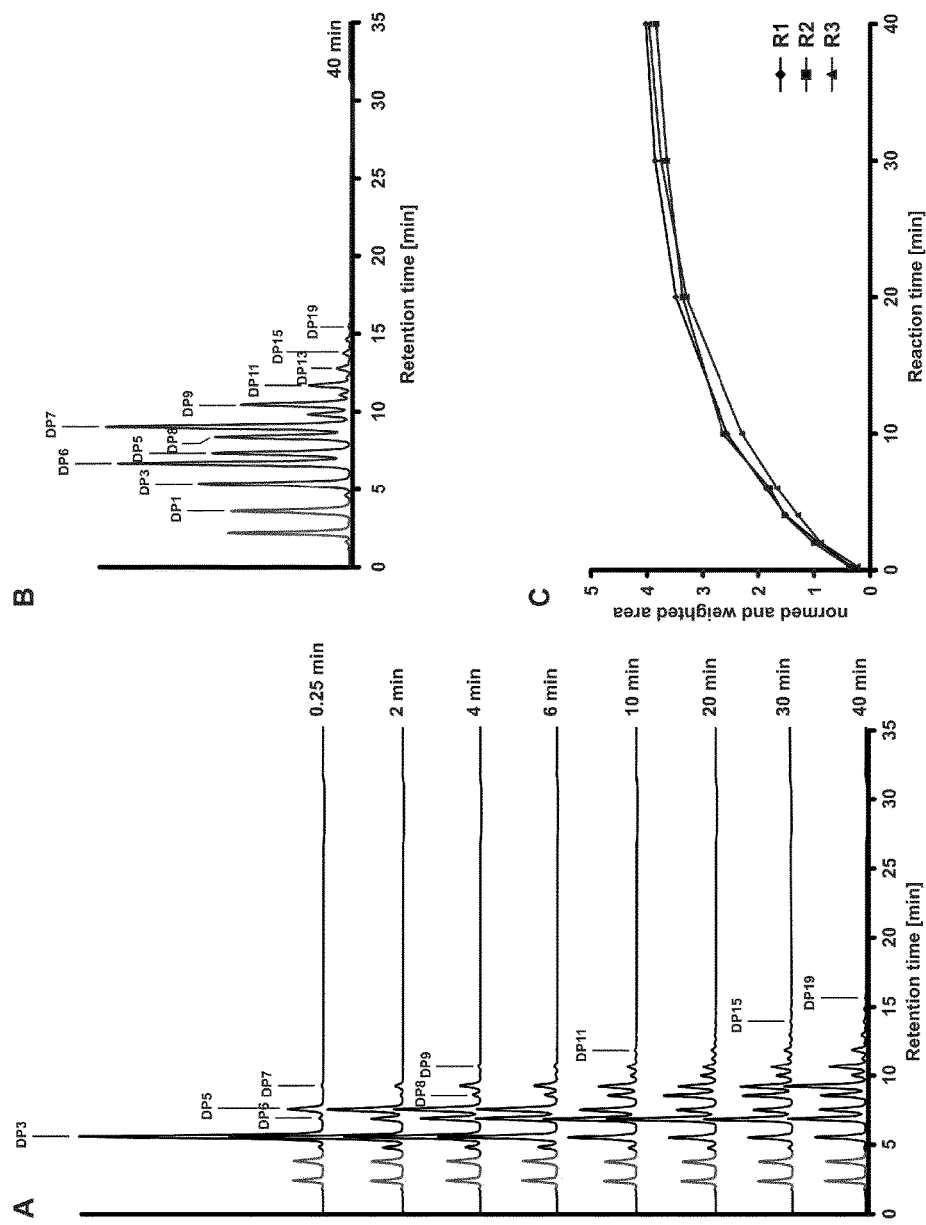

FIG. 10. Time lapse recording of the SiaD$_{W-135}$ reaction.

(A) SiaD$_{W-135}$ was primed with 1 mM 4-MU-Sia-Gal-Sia (4-MU-DP3) in the presence of 2 mM UDP-Gal and 2 mM CMP-Sia. At indicated time points, product profiles were recorded by HPLC-FD. (B) Enlarged display of the HPLC-FD profile obtained at 40 min and labelling of individual DPs. (C) Normed and weighted peak areas were calculated for each time point and used to construct progress curves. Progress curves obtained in three independent experiments (R1-R3) are shown and document the high reproducibility of the reaction. Peaks marked red represent 4-MU-DP1 and 4-MU, which represent contaminants in the 4-MU-DP3 pool, whereby 4-MU is already present in the starting solution of the substrate 4-MU-Sia and represents the hydrolysis of the substrate. Both peaks remain unchanged over the entire reaction, confirming a step increase in acceptor quality from DP2 to DP3.

Figure 11:
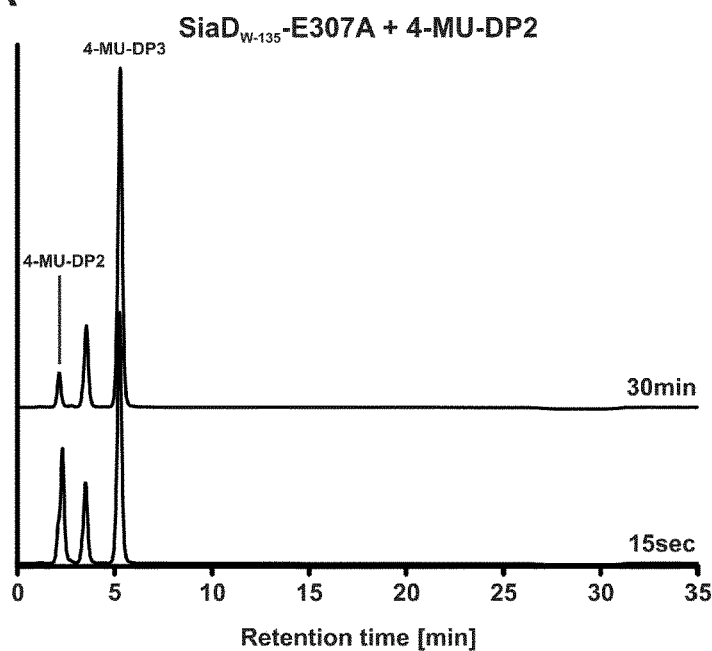
Figure 11:
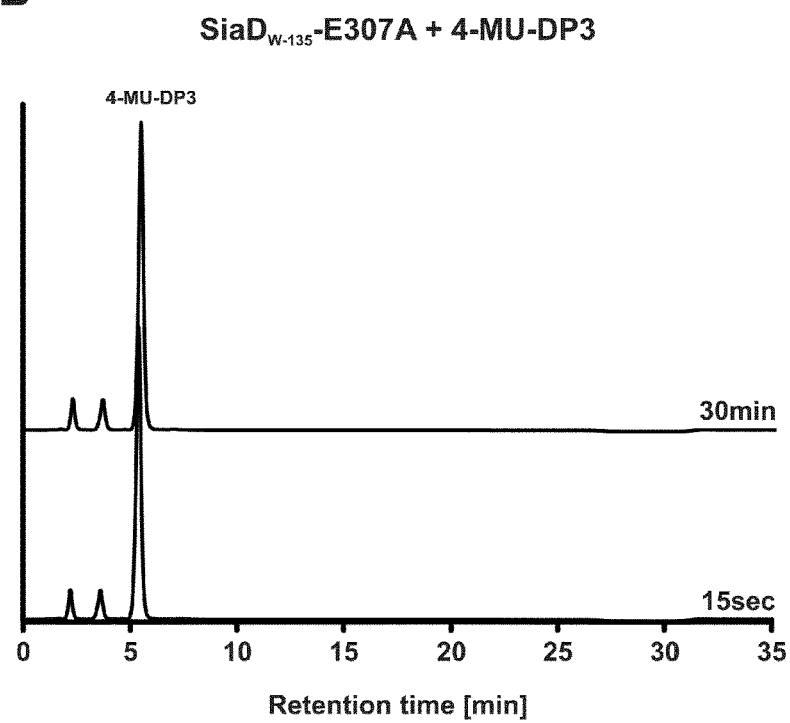
Figure 11:
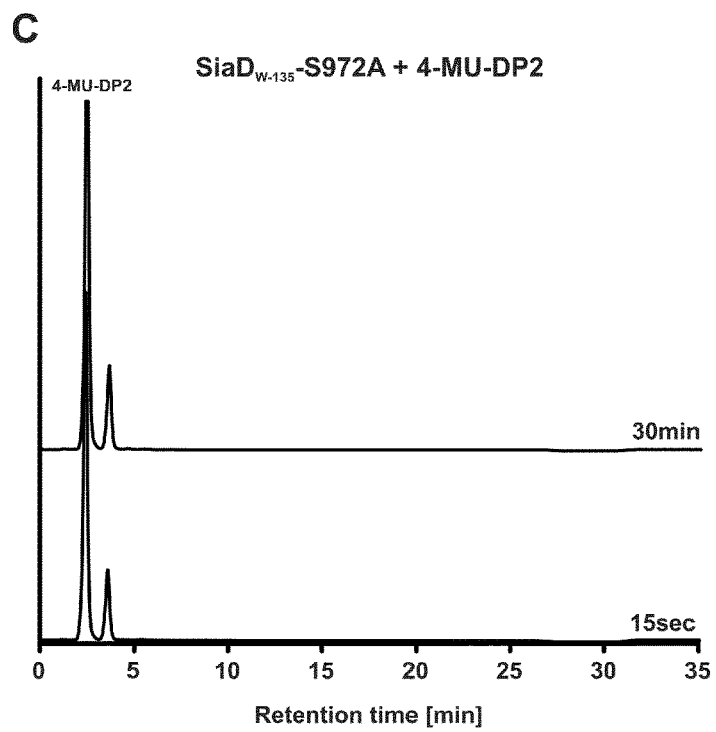
Figure 11:
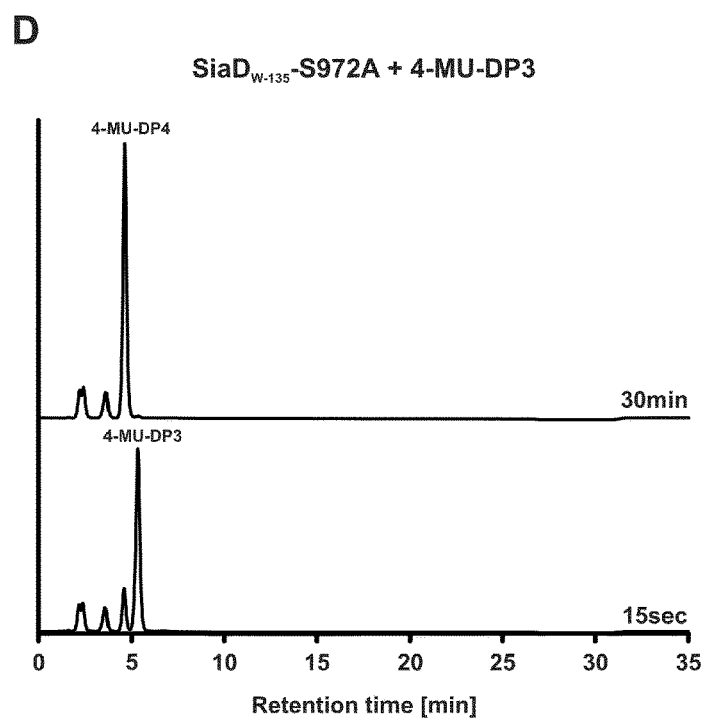

FIG. 11. Use of fluorescent primers to monitor the reaction profiles of single point mutant enzymes Reaction profiles of the monovalent point mutants NmW-135-(E307A)-His$_6$ and NmW-135-(S972A)-His$_6$ were recorded in the presence of both donor sugars using the appropriate or false fluorescent primer. Reactions were run over 30 min with samples taken after 15 sec and 30 min. A: NmW-135-(E307A)-His$_6$ with 4-MU-DP2. The only reaction product formed is 4-MU-DP3. B: NmW-135-(E307A)-His$_6$ primed with 4-MU-DP3. No product is formed. C: NmW-135-(S972A)-His$_6$ primed with 4-MU-DP2. No product was formed. D: NmW-135-(S972A)-His$_6$ primed with 4-MU-DP3. The only product formed is 4-MU-DP4.

Figure 12:
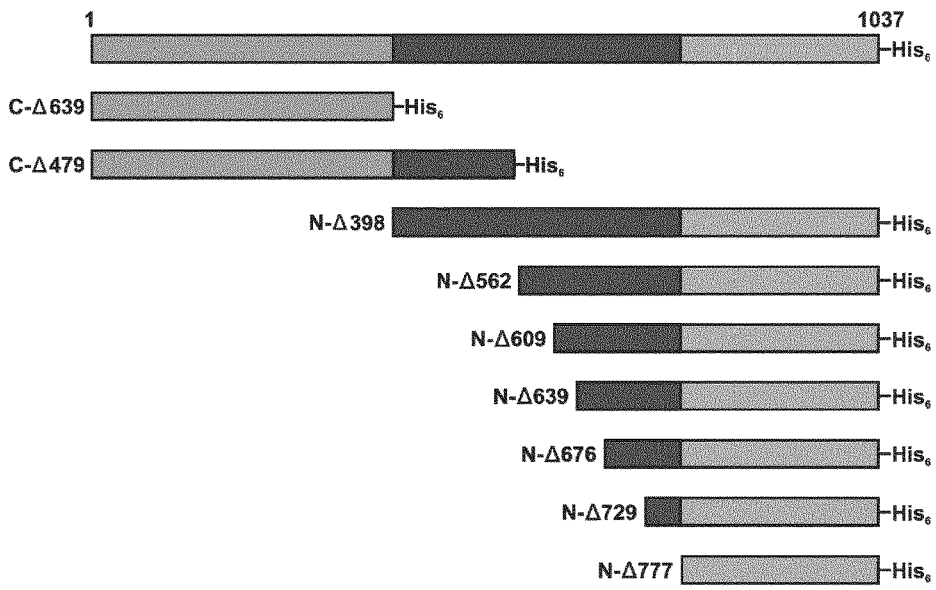
Figure 12:
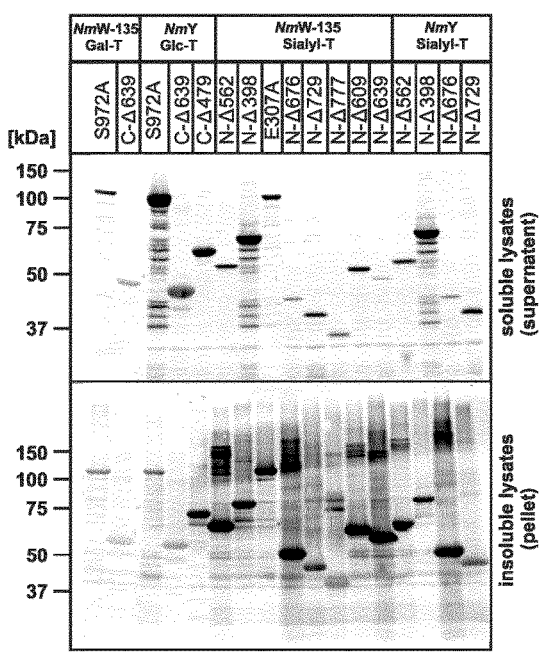

FIG. 12. Schematic representation of the capsule polymerases from NmW-135 and NmY and illustration of deletion mutants made thereof.

A: Schematic illustration of the full length capsule polymerases NmW-135 and NmY. The GT-B folds predicted to comprise hexosyl- and sialyltransferase domain are highlighted in green and purple, respectively. The linker region connecting the GT-B folded domains is shown in black. Mutants made in the course of this project were named according the introduced deletion. All proteins were expressed with N-terminal His$_6$-tag. B: Western blot analysis of expressed proteins as indicated. Lysates prepared from transformed BL21(DE3) cells were separated into soluble and insoluble fraction and after separation on 10% SDS-PAGE analysed by western blotting using an anti-penta-His antibody.

Figure 13:
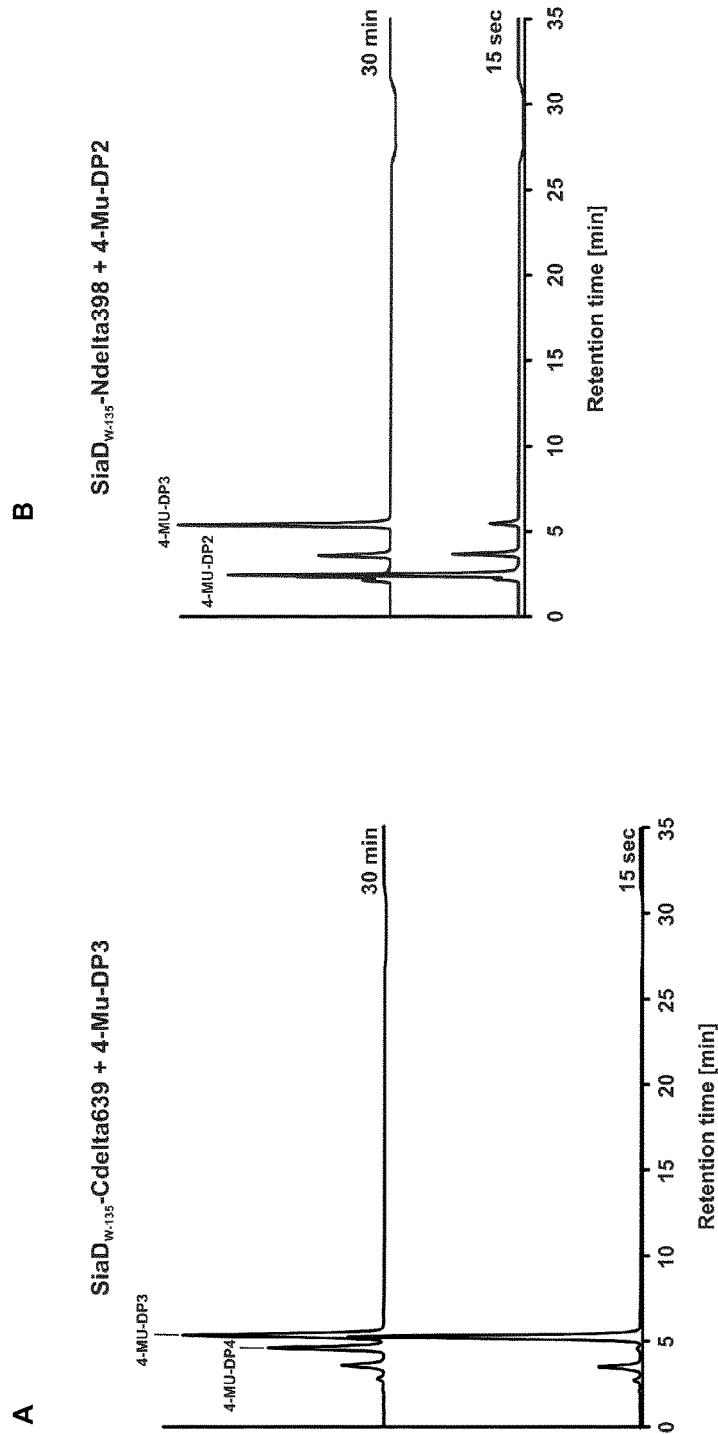

FIG. 13. Product Profiles of the reactions obtained with CΔ639-His$_6$ and with NΔ398-His$_6$.

Reaction profiles of the truncates variants NmW-135-(CΔ639)-His$_6$ and NmW-135-(NΔ398)-His$_6$ were recorded in the presence of both donor sugars using the corresponding acceptor. Reactions were run over 30 min with samples taken after 15 sec and 30 min. A: NmW-135-(CΔ639)-His$_6$ with 4-MU-DP3 catalyze the transfer of UDP-Gal by creating 4-MU-DP4. B: NmW-135-(NΔ398)-His$_6$ primed with 4-MU-DP2 catalyze the transfer of CMP-Sia by producing 4-MU-DP3.

Figure 14:
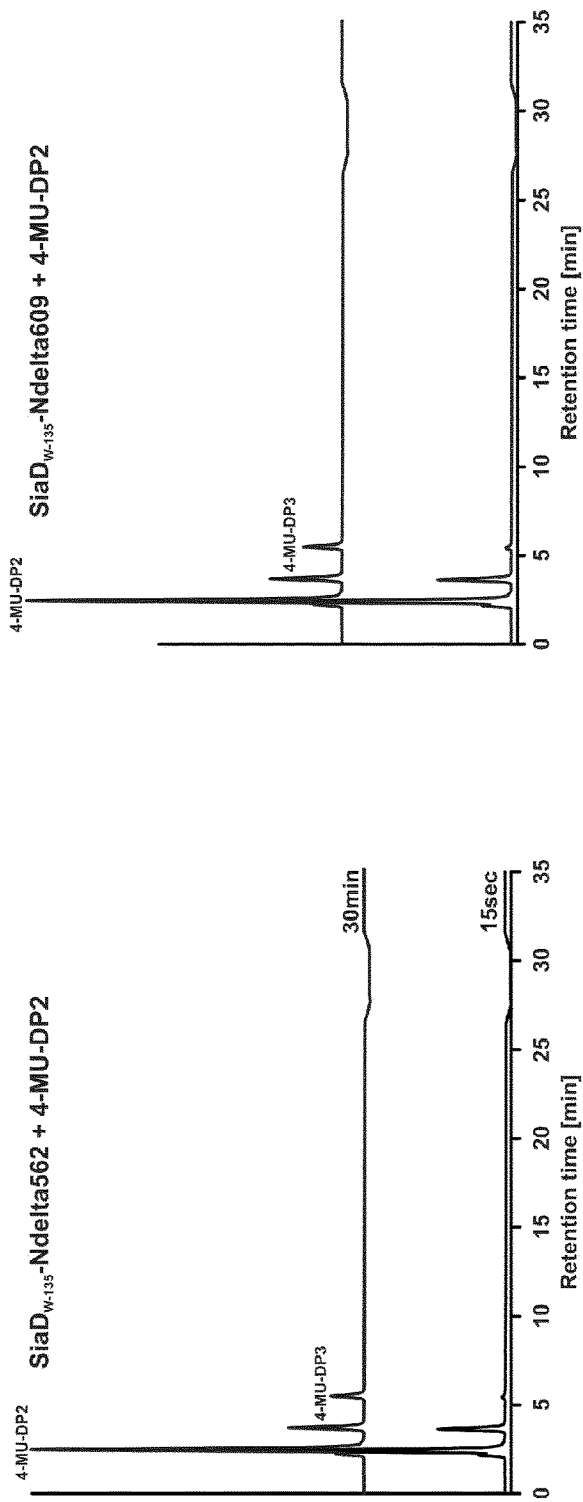

FIG. 14. Product profiles of NΔ562 and NΔ609 constructs.

Reaction profiles of the truncates variants NmW-135-(NΔ562)-His$_6$ and NmW-135-(NΔ609)-His$_6$ were recorded in the presence of both donor sugars using the corresponding acceptor. Reactions were run over 30 min with samples taken after 15 sec and 30 min. A: NmW-135-(NΔ562)-His$_6$ with 4-MU-DP2 catalyze the transfer of CMP-Sia by creating 4-MU-DP3. B: NmW-135-(NΔ609)-His$_6$ primed with 4-MU-DP2 catalyze the transfer of CMP-Sia by producing 4-MU-DP3.

Figure 15:
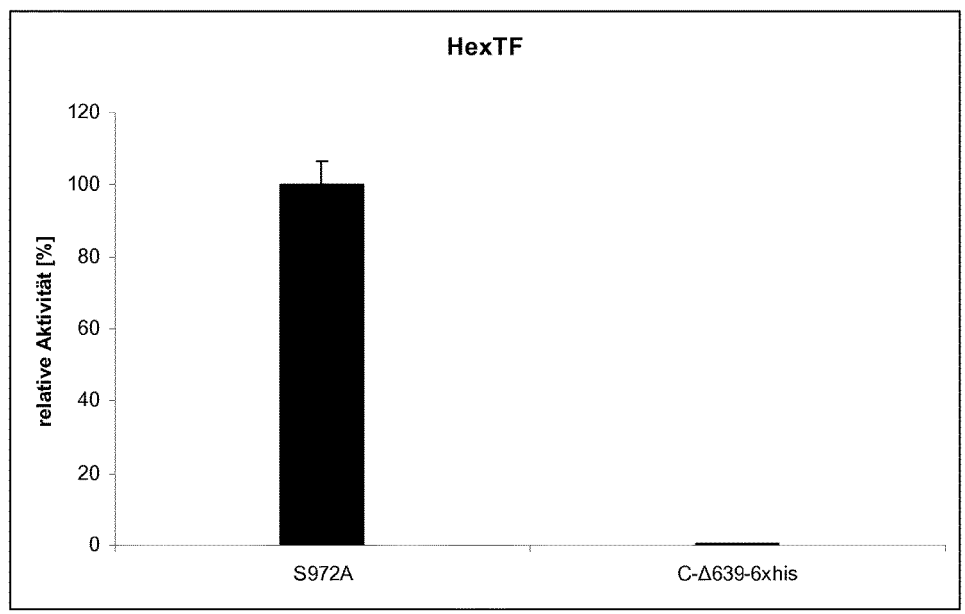
Figure 15:
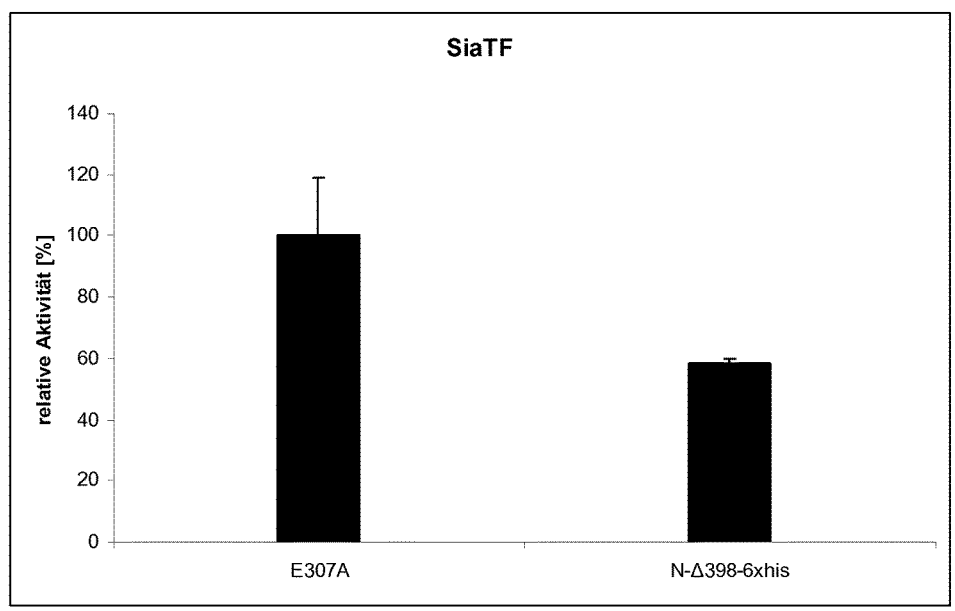

FIG. 15. Quantification of enzymatic activity obtained with mutants.

The enzymatic activity of mutant forms was determined in an HPLC-based assay using fractions of purified enzymes. The HexTF catalysis is shown under A which were incubated with 4-MU-DP3 and the SiaTF catalysis is indicated under B which were incubated with 4-MU-DP2. Values represent means of three independent experiments.

Figure 16:
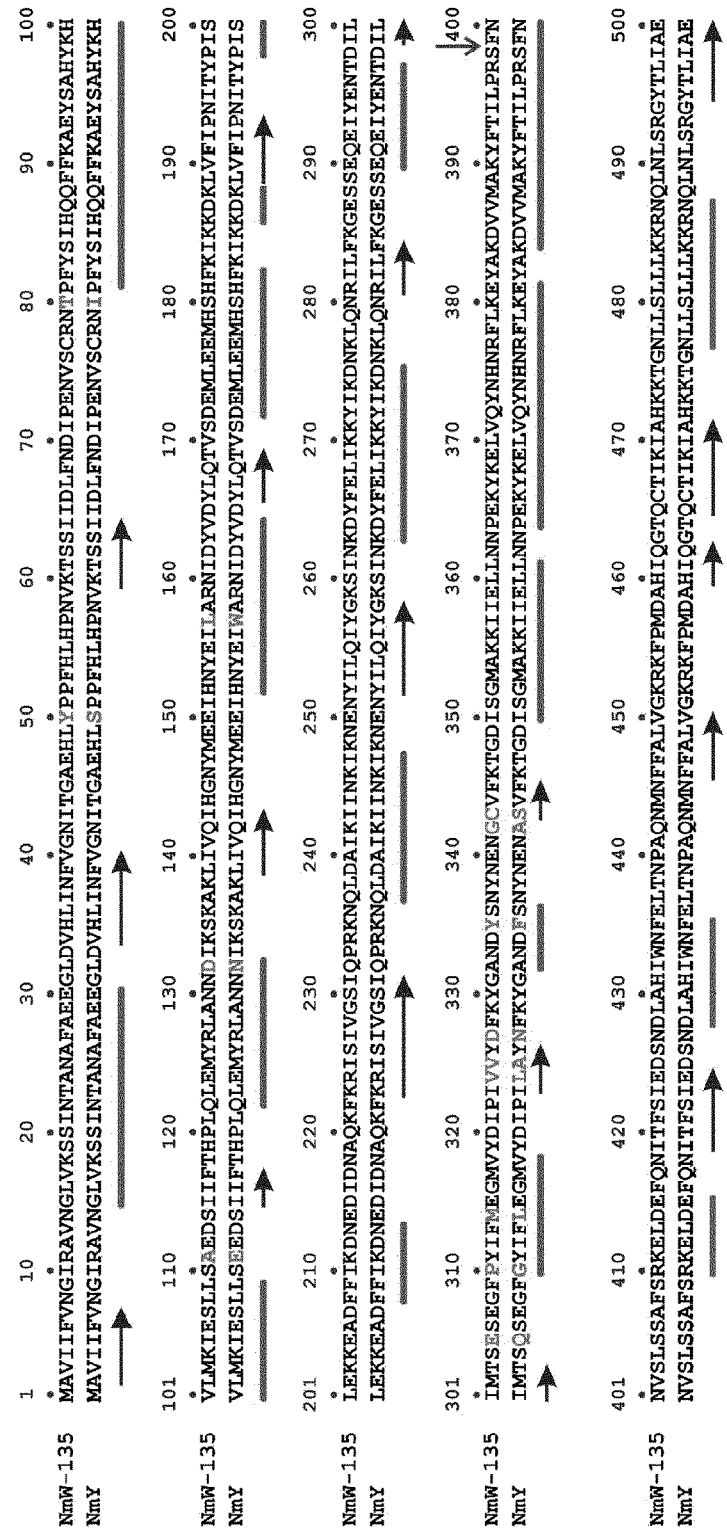
Figure 16:
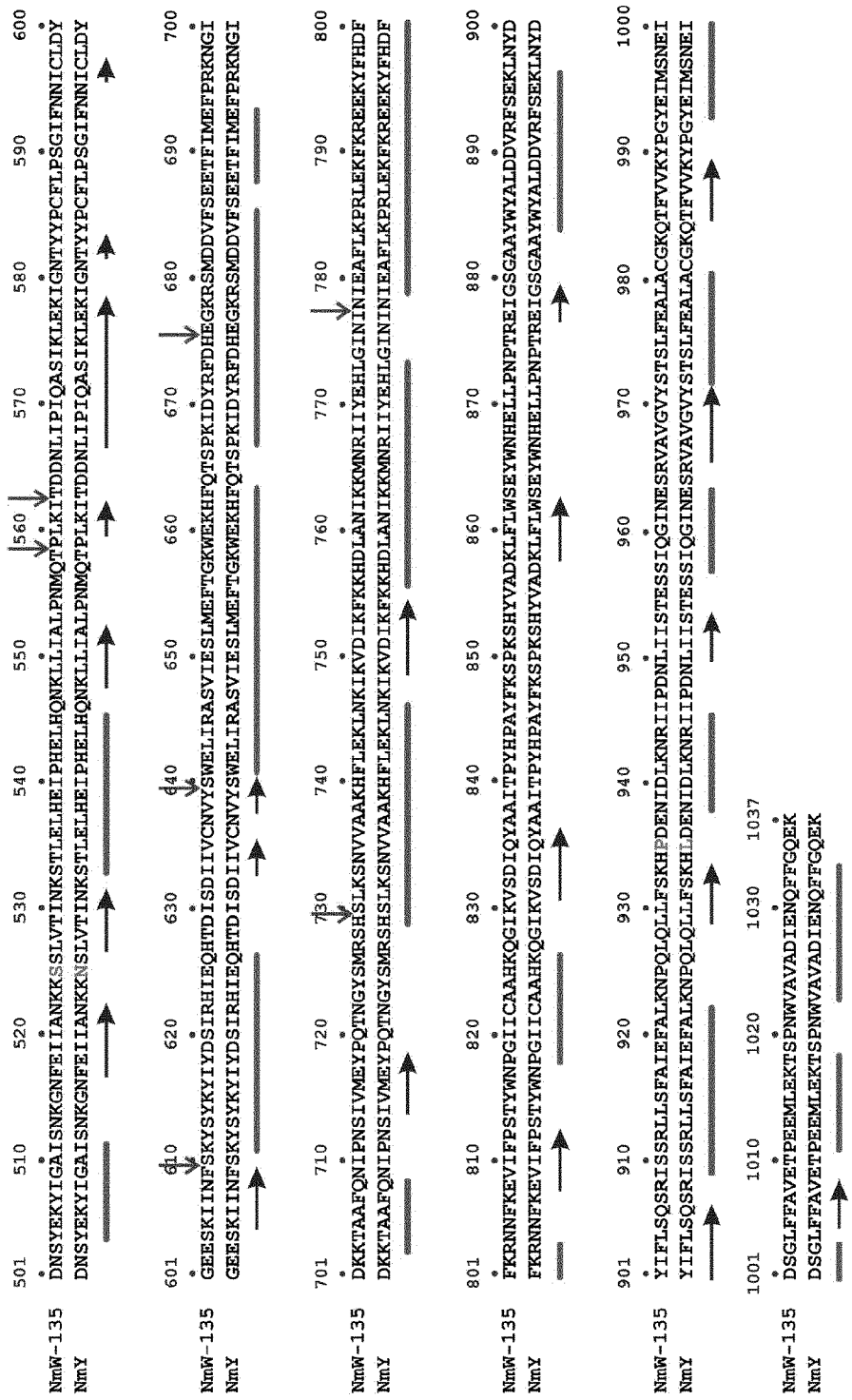

FIG. 16. Secondary structure-based alignment predicted for SiaD$_{W-135}$ and SiaD$_Y$.

The sequence alignment was performed using the ClustalW2 alignment and secondary structure motif predictions The symbols below the sequence illustrate β-strands (black arrows) and α-helices (lines). Positions where truncations were introduced are indicated with arrows above the sequences. The selected sequence accession numbers from the GenBank are Y13970 (SiaD$_{W-135}$) and Y13969 (SiaD$_Y$).

Figure 17:
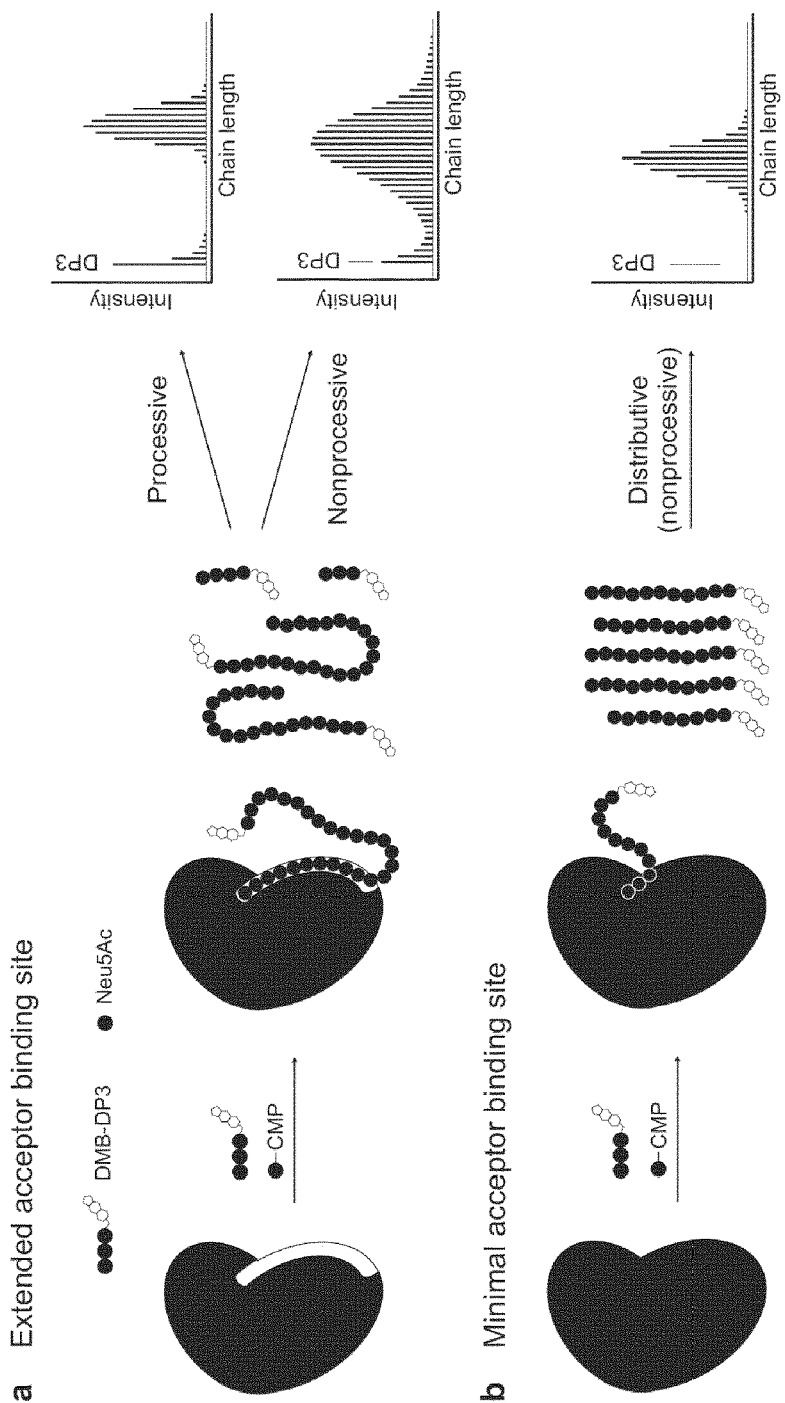

FIG. 17. Mechanisms of polysaccharide synthesis. Polymerization occurs by repeated transfer of a sugar residue (Neu5Ac) from a nucleotide sugar precursor (CMP-Neu5Ac) onto an acceptor substrate (DMB-DP3).

The mechanism of elongation and product distribution are determined by the nature and extent of interaction with the growing polysaccharide chain. Schematic HPLC profiles of the product distributions are shown at right (DP, degree of polymerization). (a) An extended acceptor binding site confers an increased affinity for longer chains which occupy more of the binding subsites, resulting in uneven chain elongation and a skewed product distribution. For highly processive elongation, the acceptor is retained through many transfer cycles and no intermediates between short and long chains will be observed (top, right). Strict nonprocessive elongation involves dissociation of the enzyme-acceptor complex after each sugar transfer, therefore, all intermediates can be observed in the product distribution (bottom, right). In practice, the precise mechanism is often unclear because the product distributions of less processive and nonprocessive enzymes are indistinguishable16. (b) In the absence of an extended acceptor binding site, the enzyme interacts only with the growing end of the polysaccharide, elongation is nonprocessive and distributive, resulting in uniform elongation of all acceptors. The product profile has a narrow, Poissonian distribution (right).

Figure 18:
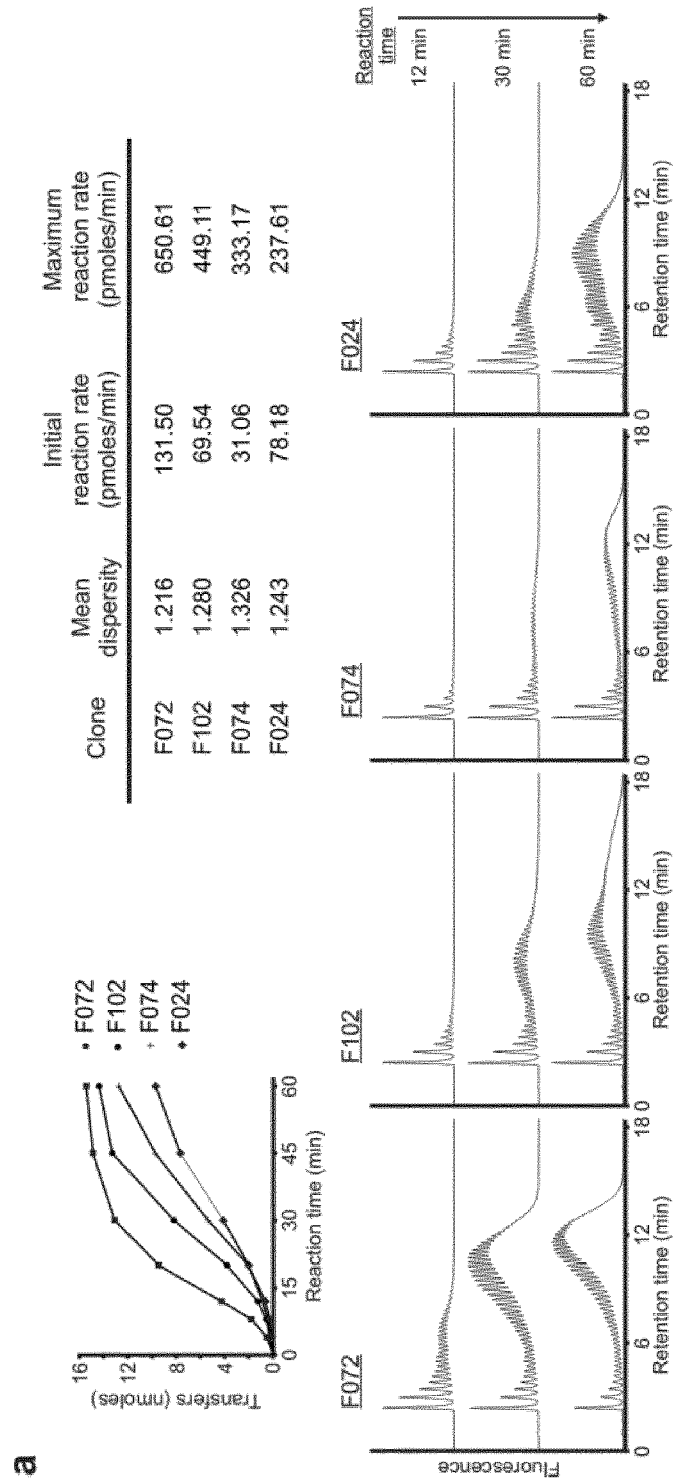
Figure 18:
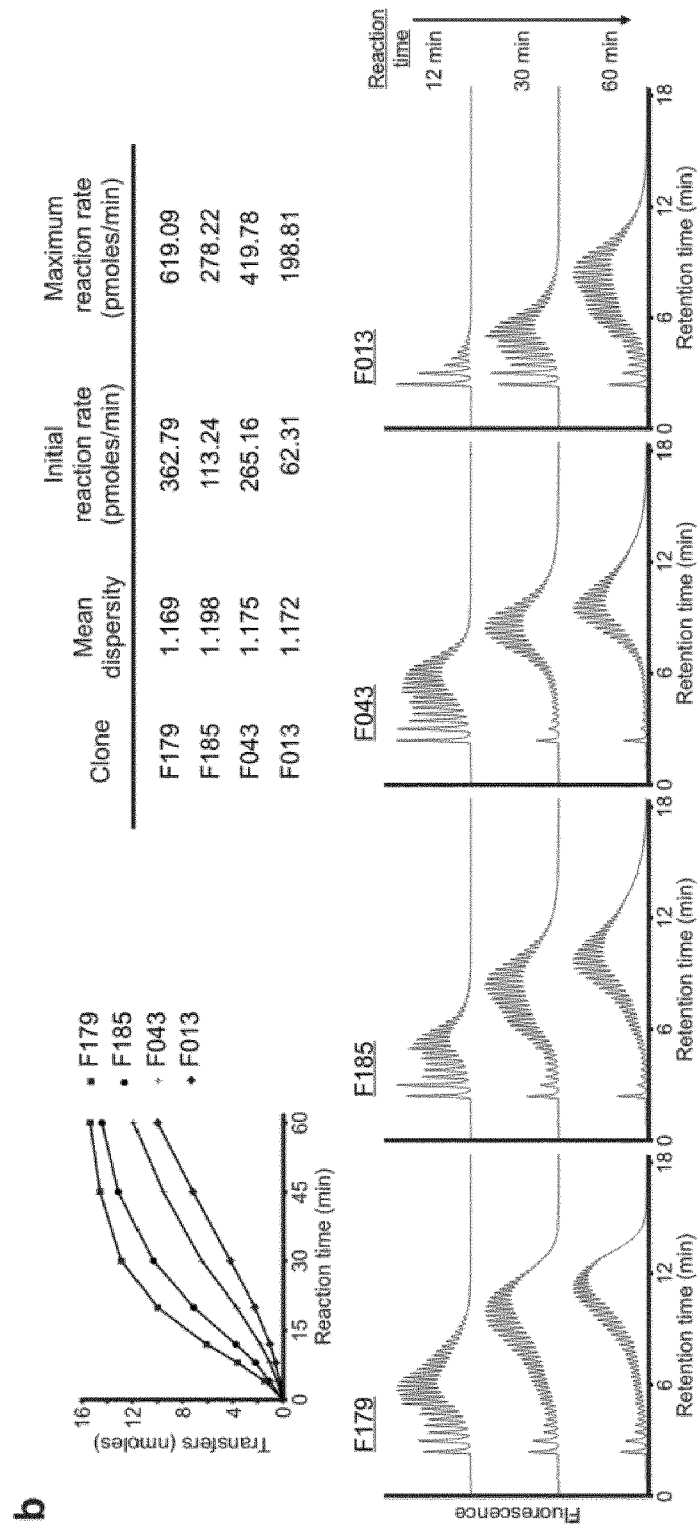
Figure 18:
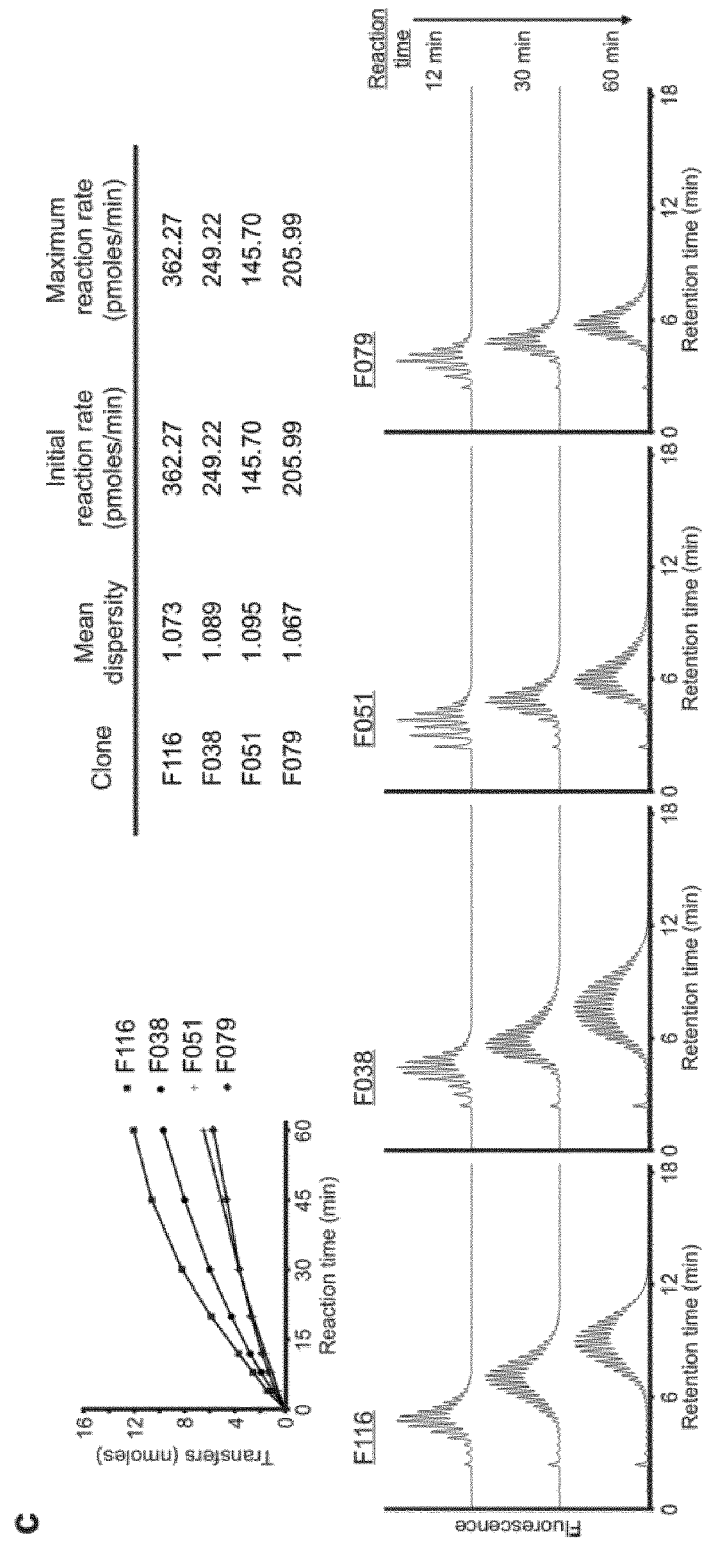

FIG. 18. Drifted polySTs exhibit diverse patterns of chain elongation.

Clones were sorted into three categories based on their average product dispersity. For each category, the reaction time course (top left), HPLC product profiles at three reaction time points (bottom), and an extract from Supplementary Table 1 (top right) are displayed for four representative clones. (a) High dispersity clones (mean dispersity >1.2) exhibit an exacerbated kinetic lag phase, maximum reaction rates up to 10 times greater than the initial rate, and product profiles strongly skewed towards longer chains. (b) Medium dispersity clones (mean dispersity of 1.1-1.2) exhibit a mild lag phase and less skewed product distributions. (c) Low dispersity clones (mean dispersity <1.1) have no lag phase (initial rate is the maximum reaction rate) and uniformly elongate chains resulting in narrow product distributions. Results for all 51 neutral drift clones are given in Supplementary Data Set 2 and Supplementary Table 1.

Figure 19:
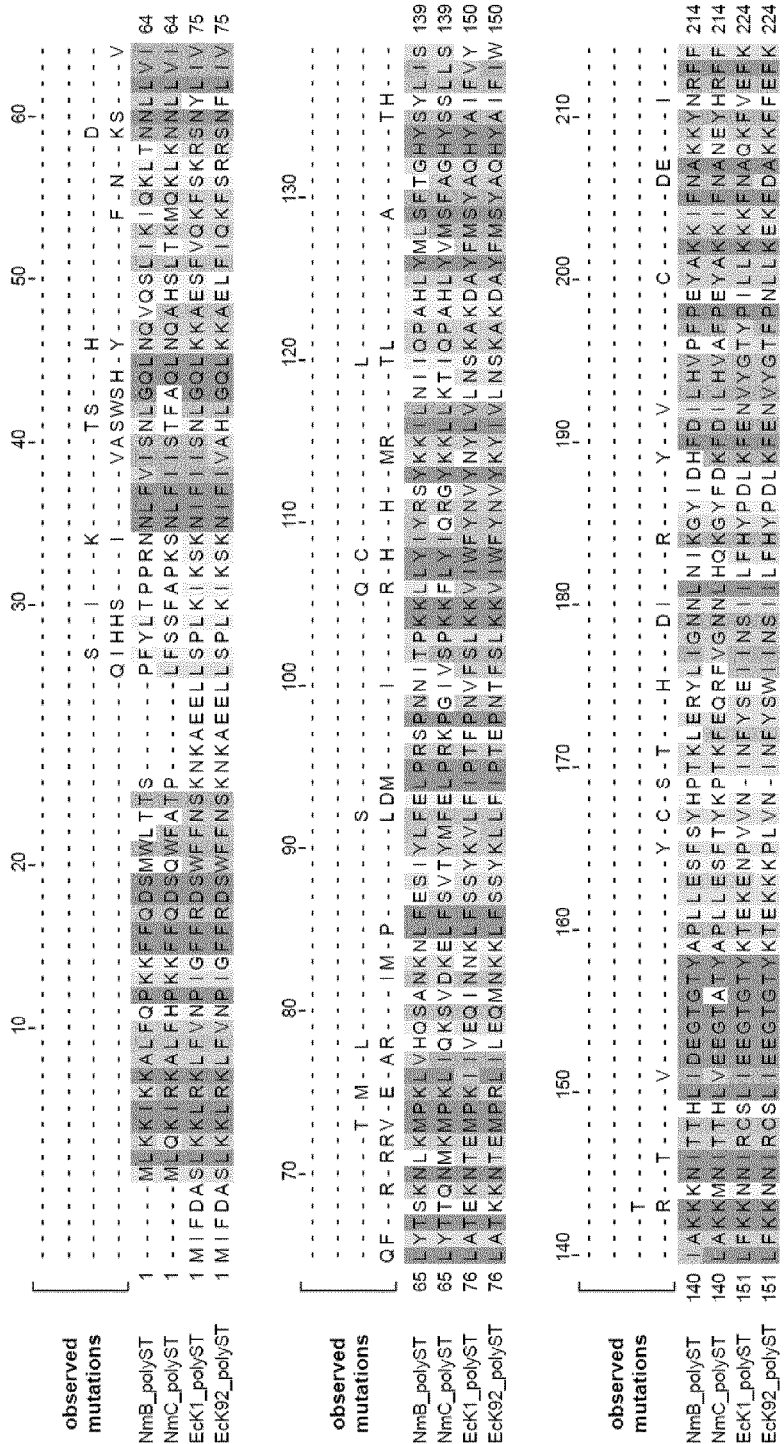
Figure 19:
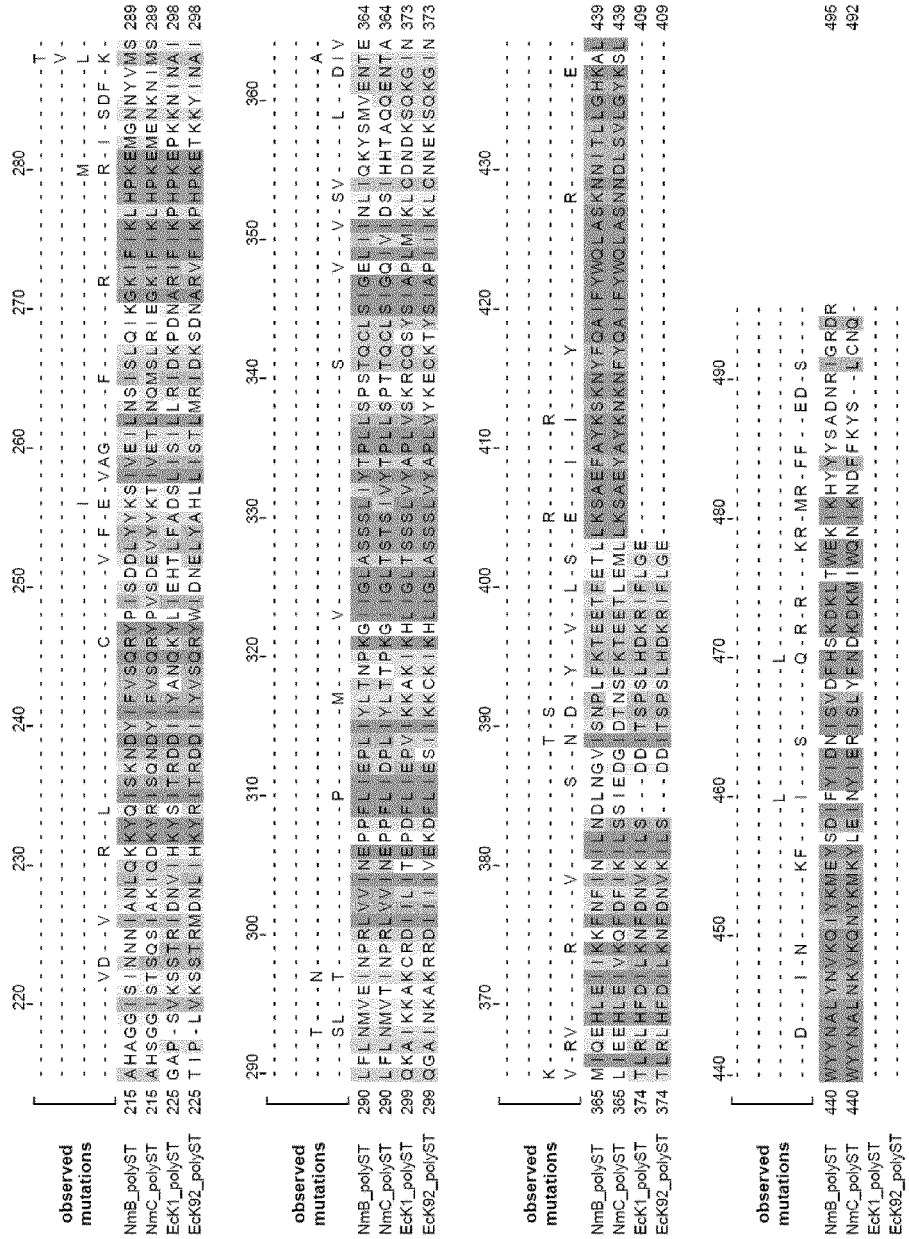

FIG. 19. Distribution of mutations across the polyST sequence.

Sequencing of 122 'neutral' variants from the first round of screening revealed 163 mutations across the $\Delta 25$polyST$_{NmB}$ sequence. Here the mutations are plotted on an alignment of the four bacterial polySTs from *Neisseria meningitidis* serogroup B (NmB), *Neisseria meningitidis* serogroup C (NmC), *Escherichia coli* K1 (EcK1) and *Escherichia coli* K92 (EcK92). Similarities of homology are shown in different gray scales. Numbering above the alignment indicates residue number in the polyST$_{NmB}$ sequence. Of note is that the mutations are unevenly distributed across the sequence with targeted positions and short clusters showing high mutability.

Figure 20:
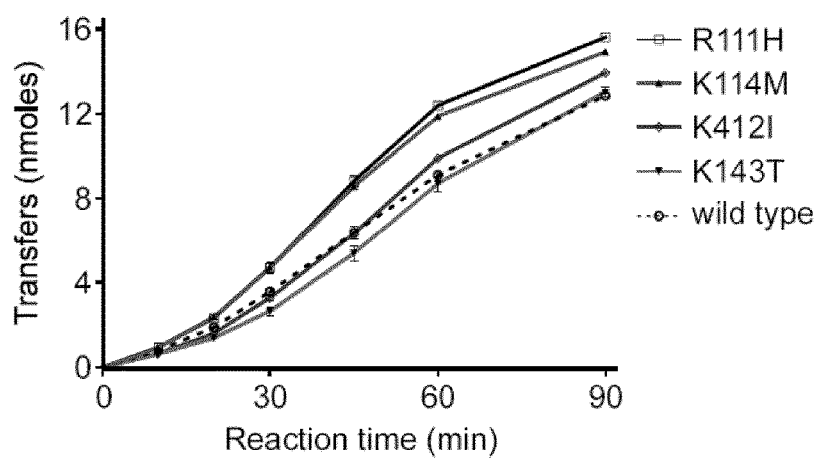
Figure 20:
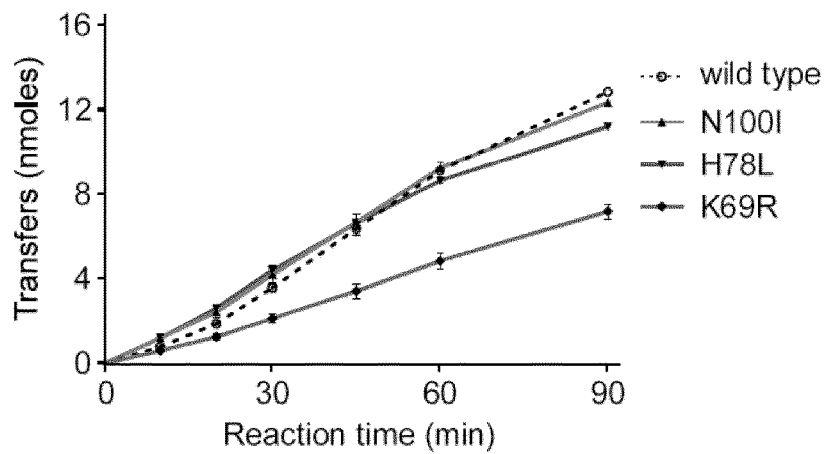
Figure 20:
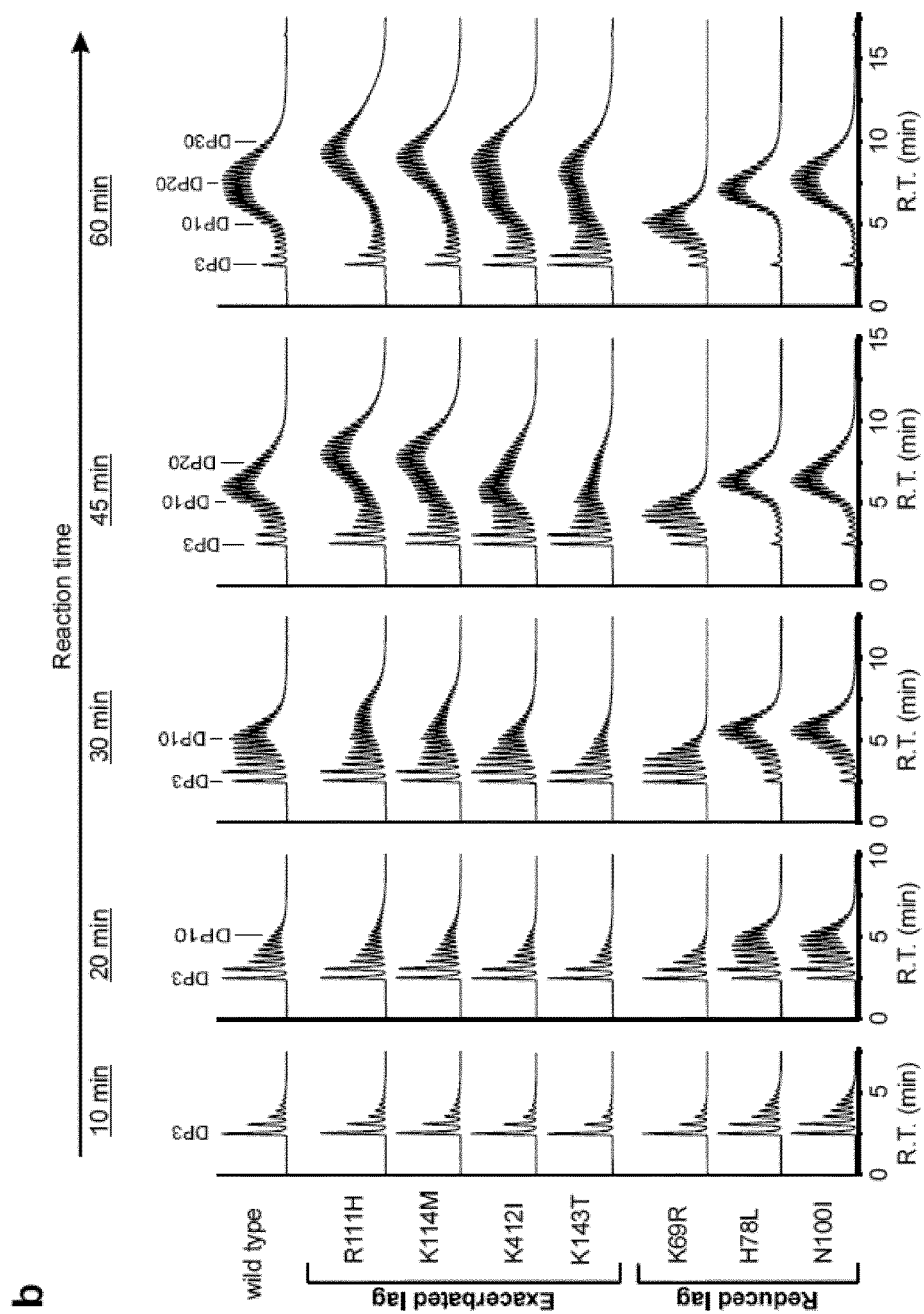

FIG. 20. Single amino acid exchanges alter the mode of chain elongation. (a) Reaction time course for single mutatnts which exhibit either an exacerbated (top) or reduced (bottom) kinetic lag phase compared to the $\Delta 25$polyST$_{NmB}$ (wild type) reference sequence (dotted line). Error bars indicate the standard error of three separate enzyme preparations (from different colonies) analysed in a single experiment. (b) Time lapse HPLC product profiles throughout the polymerization reaction of each of the clones. The $\Delta 25$polyST$_{NmB}$ reference chromatograms (top) are displayed for comparison, and chain lengths are indicated (DP, degree of polymerization; R.T., retention time). Enzymes with an exacerbated lag phase show a broadening of the product distribution specifically after synthesis of chains >DP10, which corresponds in time to the increase in reaction rate observed in the reaction time courses. Enzymes with a reduced lag phase show more uniform chain elongation, and considerably less broadening of the product distribution.

Figure 21:
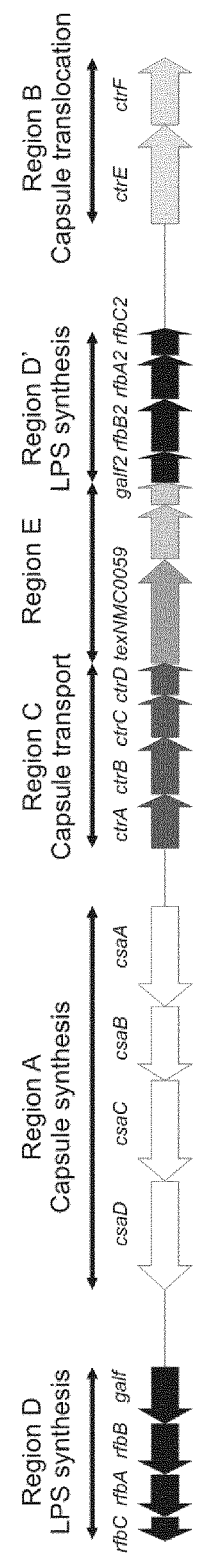

FIG. 21: Schematic representation of the chromosomal locus (cps) of NmA. Products of genes forming region A are involved in the synthesis of the capsule polysaccharide and are serogroup-specific. For more information, see text [adapted from Harrison et al. (2013)].

Figure 22:
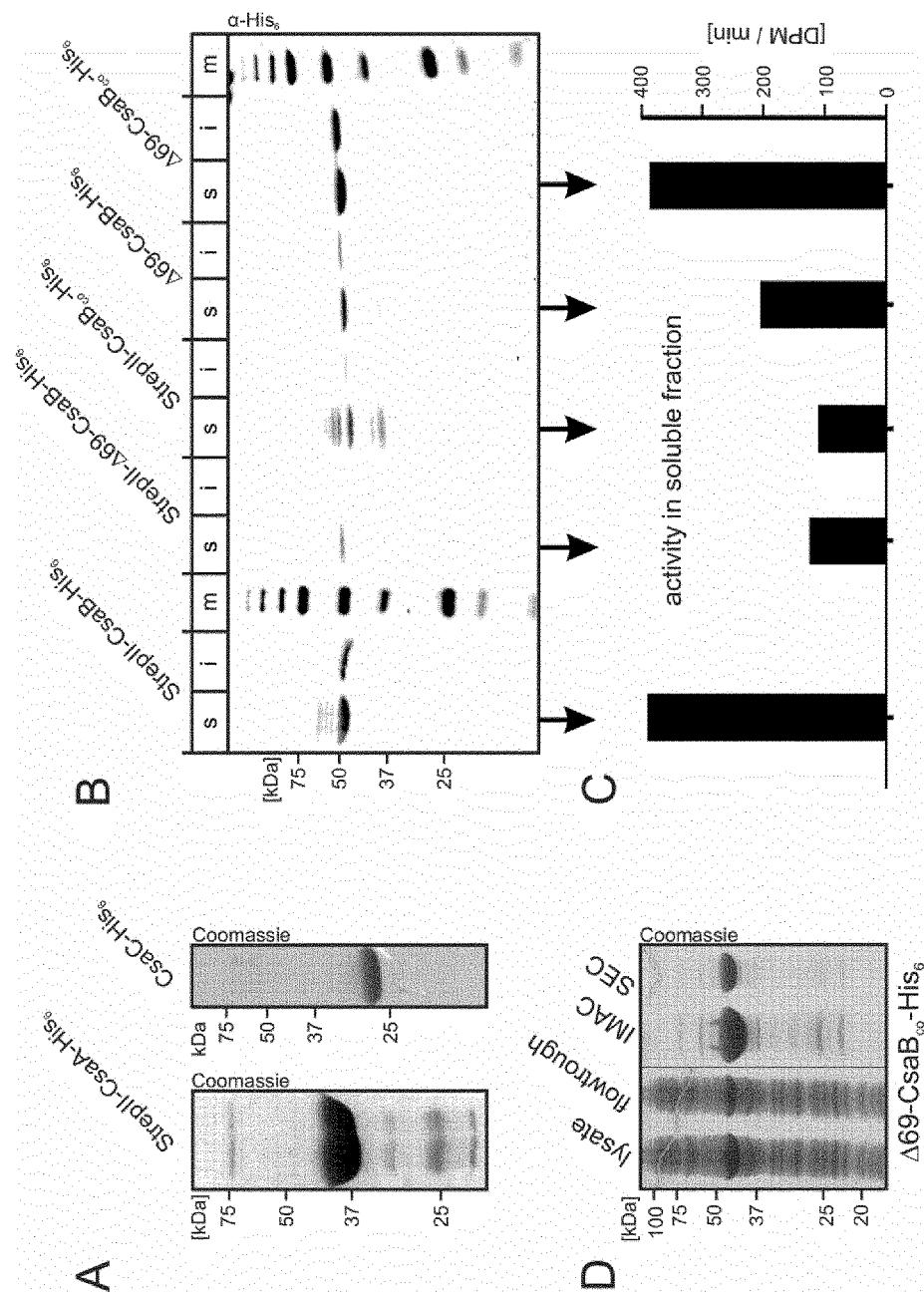

FIG. 22: (A) Coomassie stained SDS-PAGE of purified StrepII-CsaA-His$_6$ (left panel) and CsaC-His$_6$ (right panel). (B) To select the construct most suited for the production of active recombinant CsaB the wildtype and a codon optimized (CsaB$_{co}$) version of the CsaB sequence were cloned (full length or after N-terminal truncation, $\Delta 69$) to produce proteins with tags on either both (StrepII and His$_6$) or only one end (His$_6$) as indicated. Transformed bacteria were lysed, separated into soluble (s) and insoluble (i) fraction and fractions separately run on 10% PAGE. After transfer onto nitrocellulose, the blot was developed with an anti-penta-His antibody. (C) Soluble fractions were used to measure CsaB activity in a radioactive incorporation assay. (D) Coomassie stained gel demonstrating the purification result for $\Delta 69$-CsaB$_{co}$-His$_6$ (IMAC; immobilized metal ion affinity chromatography; SEC size exclusion chromatography).

Figure 23:
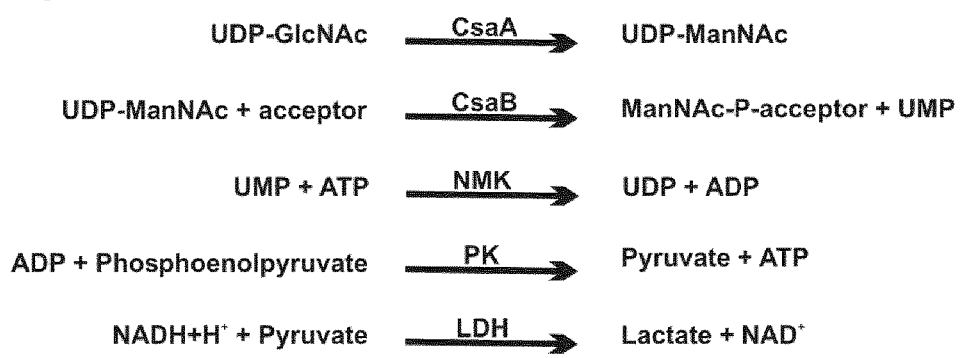

FIG. 23: Schematic representation of the multi-enzyme assay used to continuously follow CsaB activity.

Figure 24:
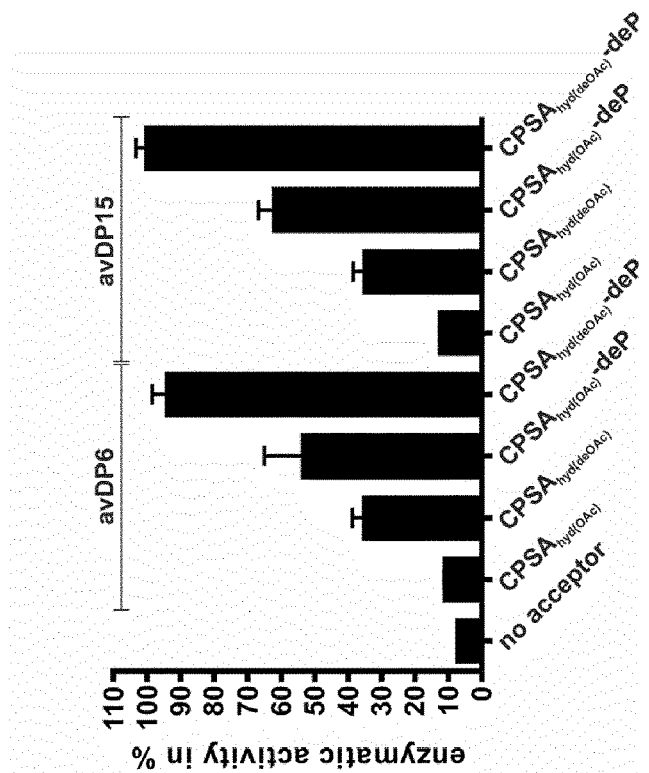
Figure 24:
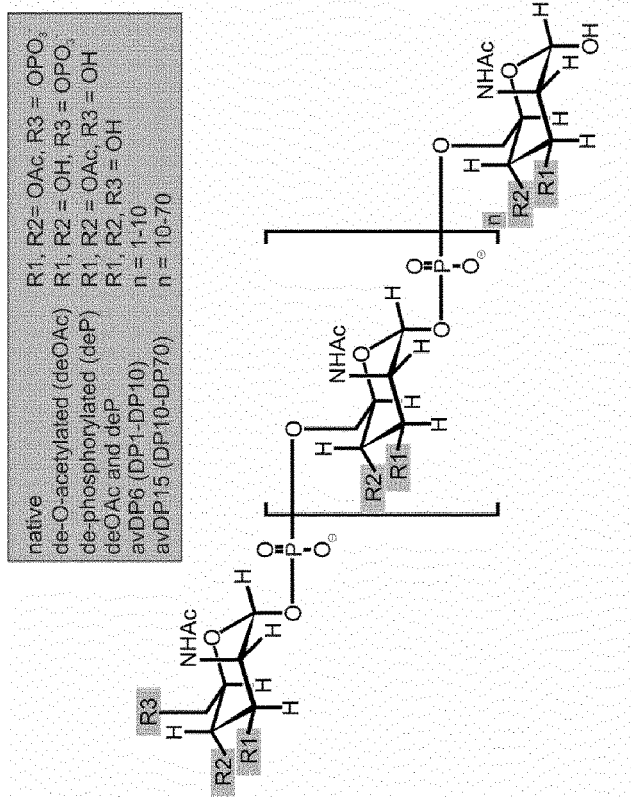

FIG. 24: (A) The chemical properties of the primers used to test the acceptor preference of $\Delta 69$-CsaB$_{co}$-His$_6$ are displayed. (B) $\Delta 69$-CsaB$_{co}$-His$_6$ activity was followed using the spectrophotometric assay in the presence of CPSA$_{hyd}$ of avDP6 and avDP15, in either native O-acetylated form (CPSA$_{hyd(OAc)}$) or after de-O-acetylation (CPSA$_{hyd(deOAc)}$). Because earlier studies showed that the non-reducing ends in CPSA$_{hyd}$ are phosphorylated, samples were additionally tested before and after phosphatase treatment (deP). Samples designated with $_{(deOAc)}$deP were subject of de-acetylation and de-phosphorylation.

Figure 25:
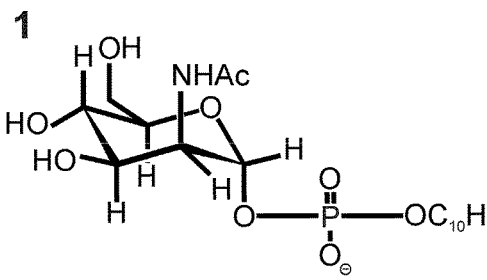
Figure 25:
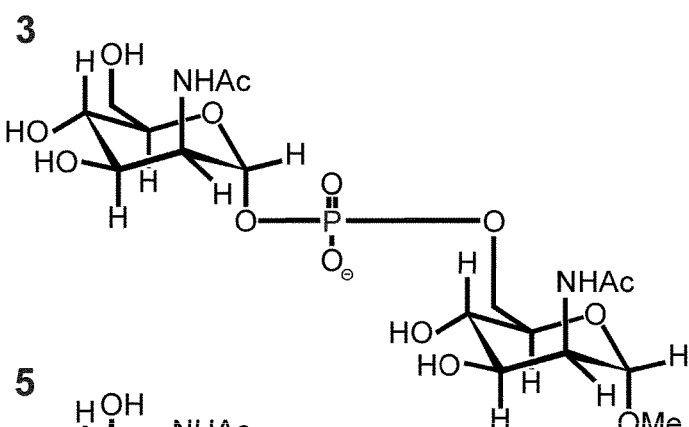
Figure 25:
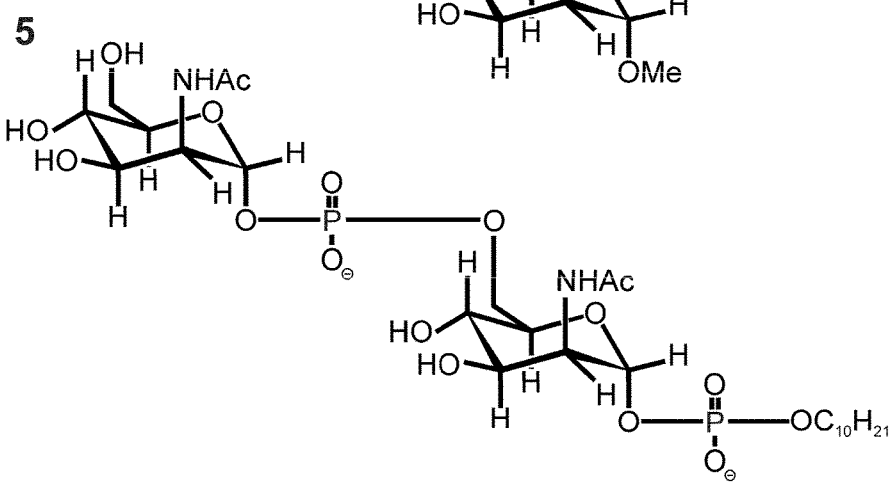
Figure 25:
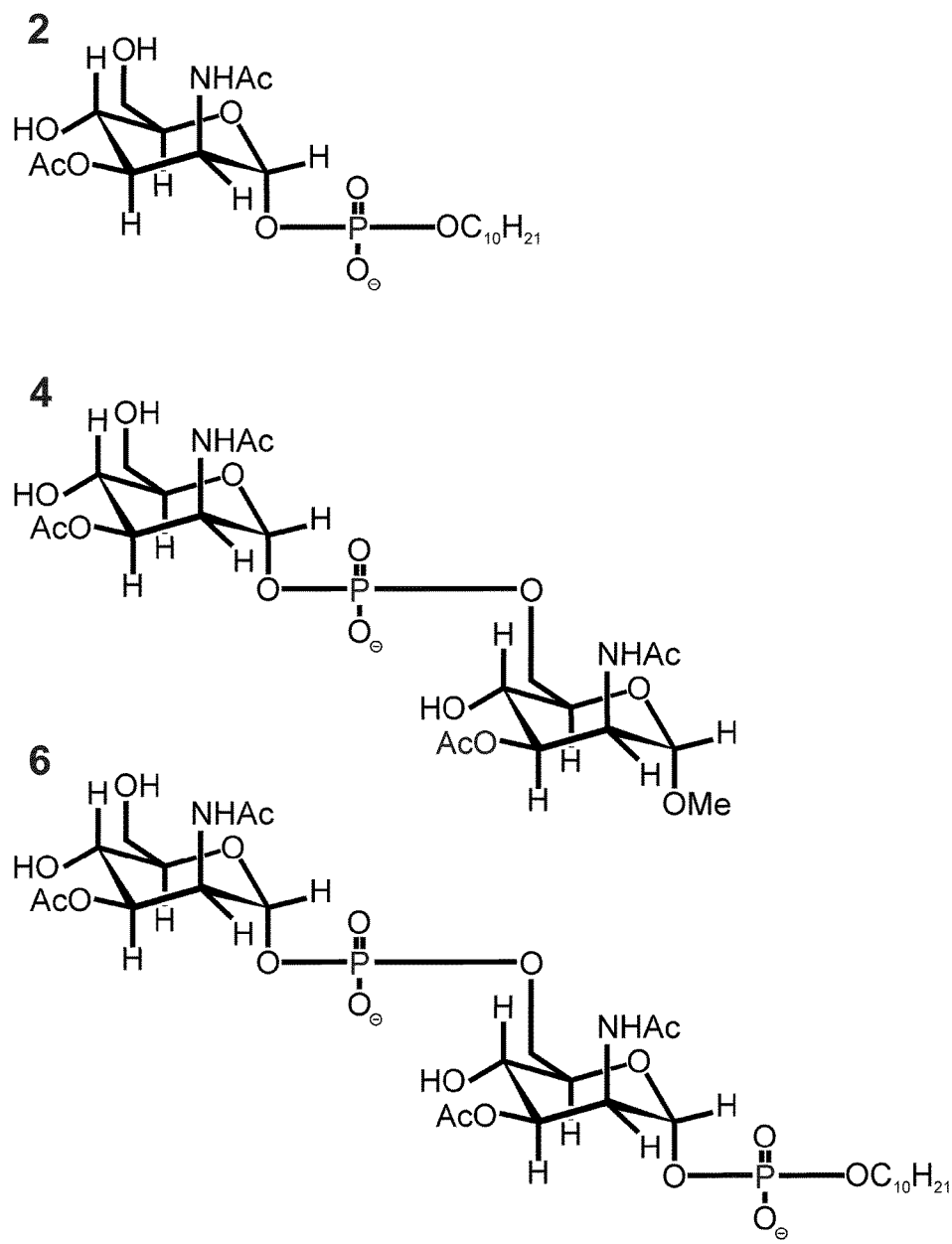
Figure 25:
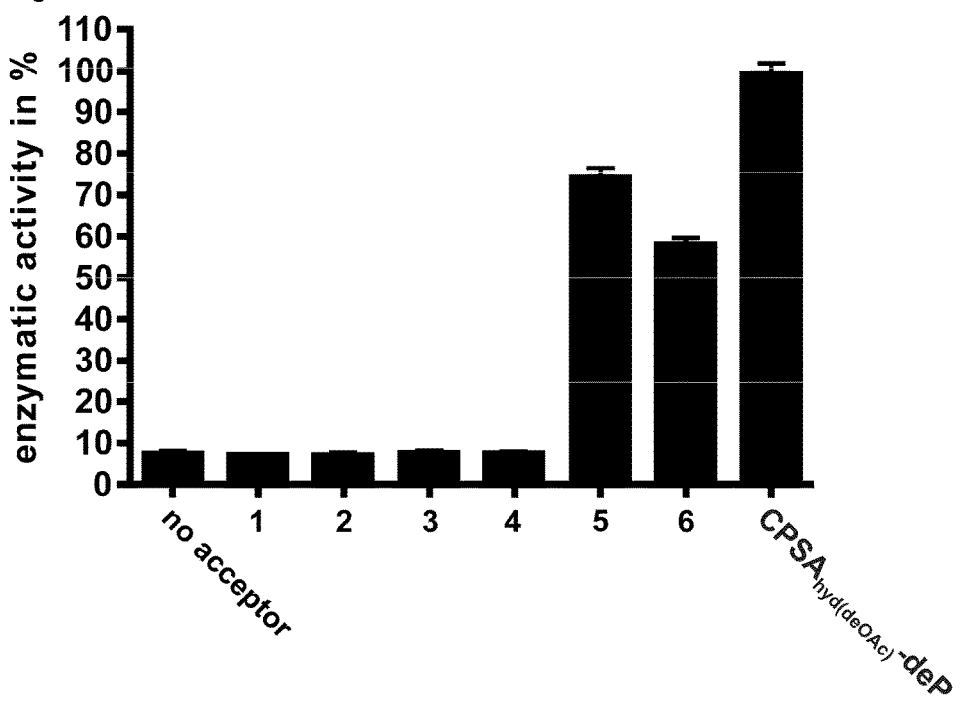

FIG. 25: Derivatives of ManNAc ending at the reducing end with a methyl group (compounds 3, 4) or a phosphodecyl-ester (compounds 1, 2, 5, 6) were synthesized and used to prime the $\Delta 69$-CsaB$_{co}$-His$_6$ reaction in the continues spectrophotometric assay. The dimer of ManNAc-1P carrying a phosphodiester at the reducing end was identified as minimal acceptor. Importantly, compound 5 showed acceptor quality identical to CPSA$_{hyd(deOAc)}$-deP and O-acetylation (compound 6) reduced the acceptor quality to approximately the same extend as seen for CPSA$_{hyd}$.

Figure 26:
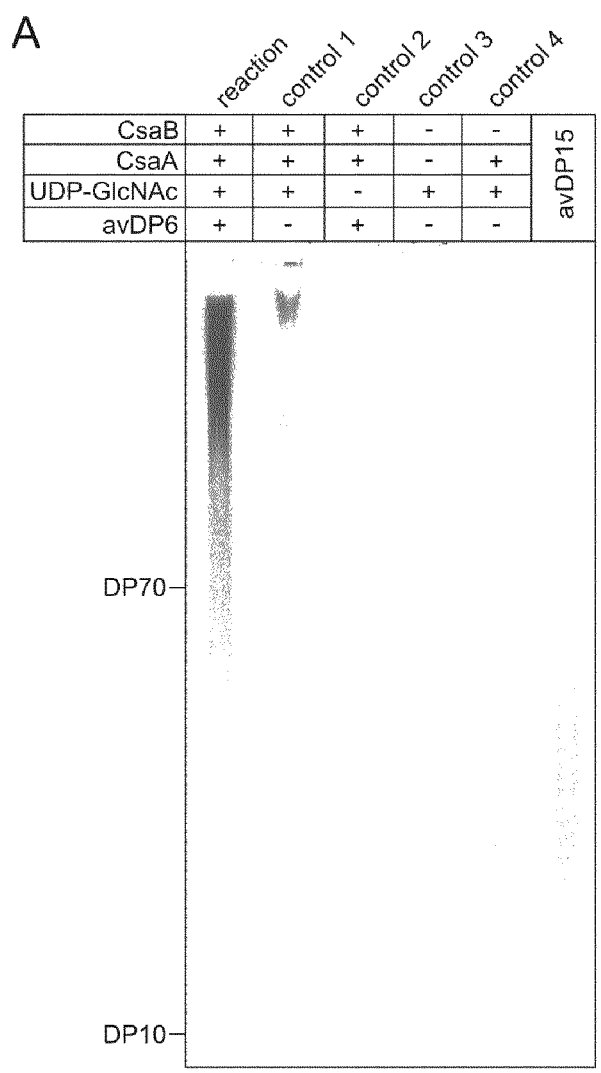
Figure 26:
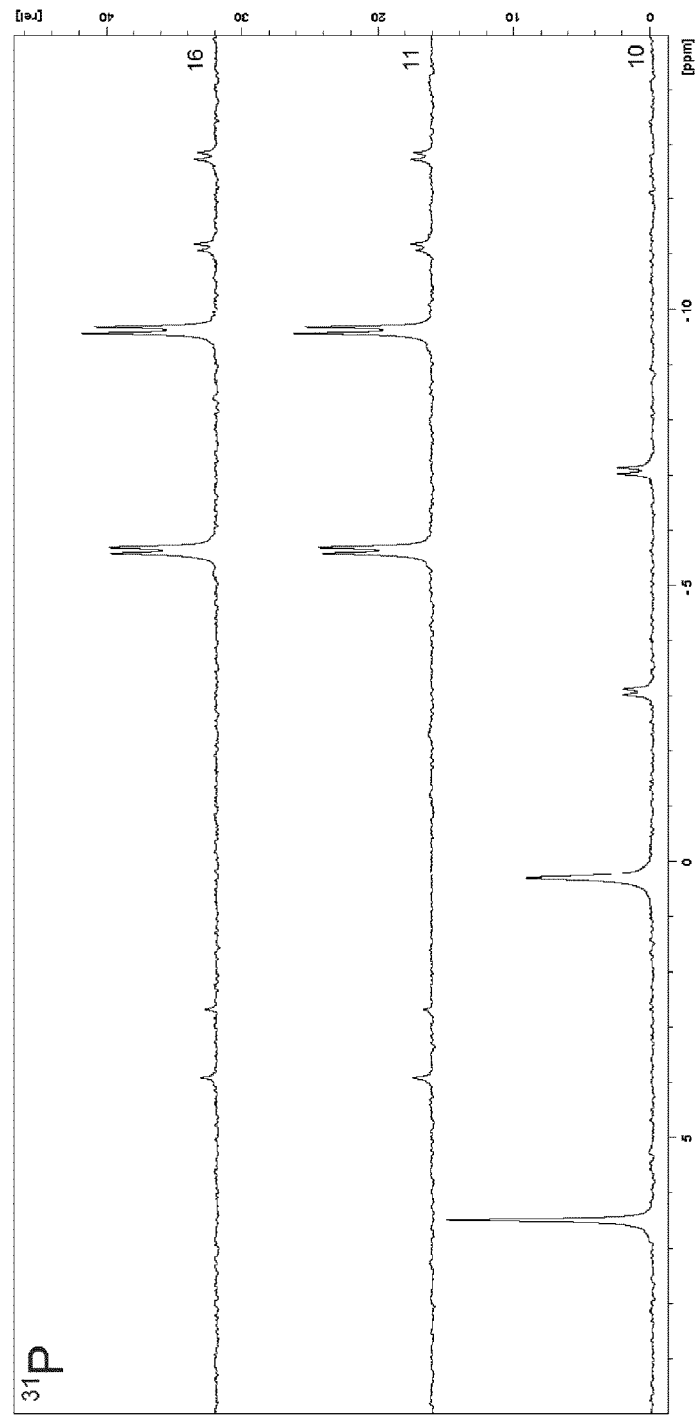
Figure 26:
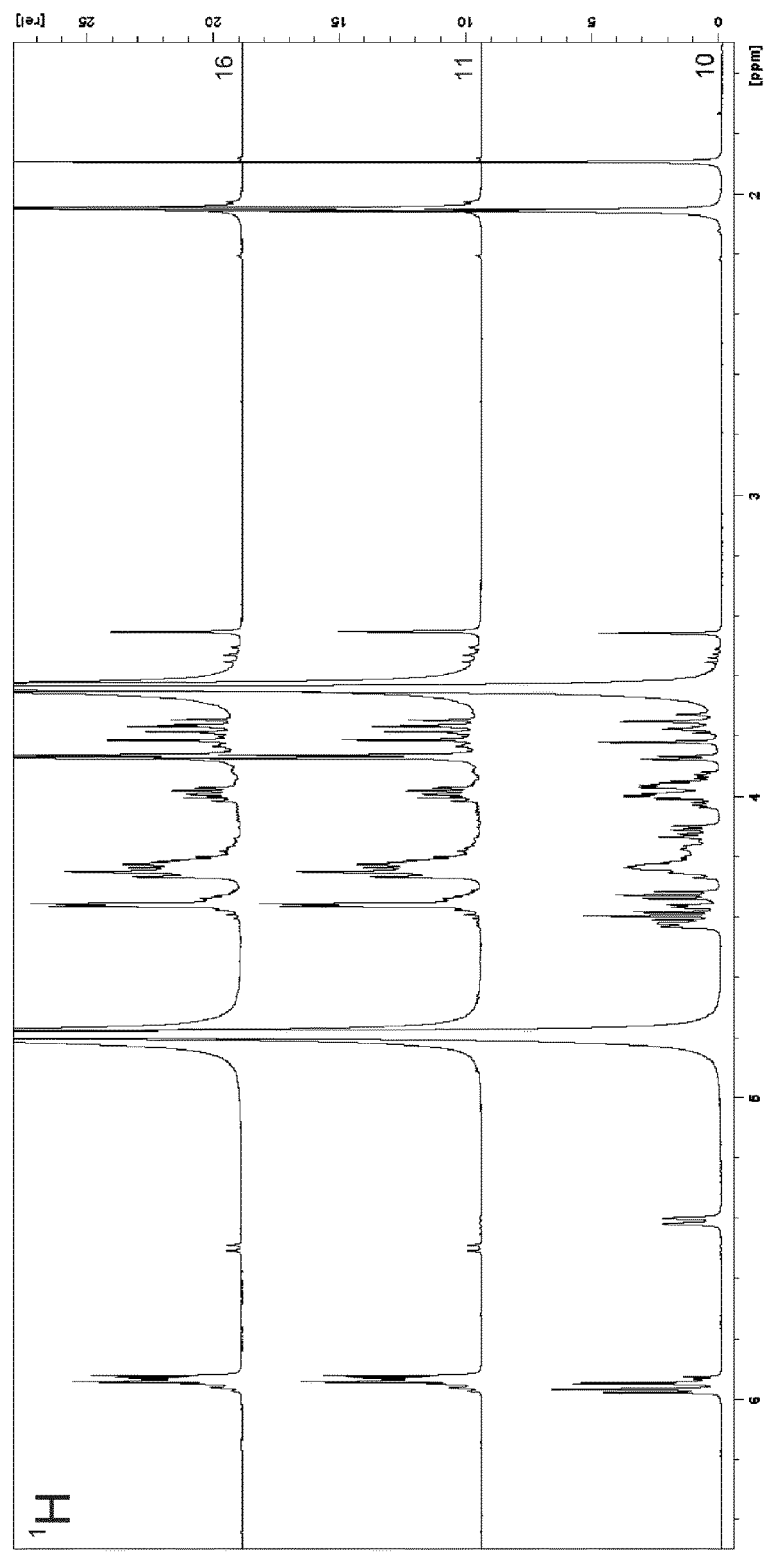
Figure 26:
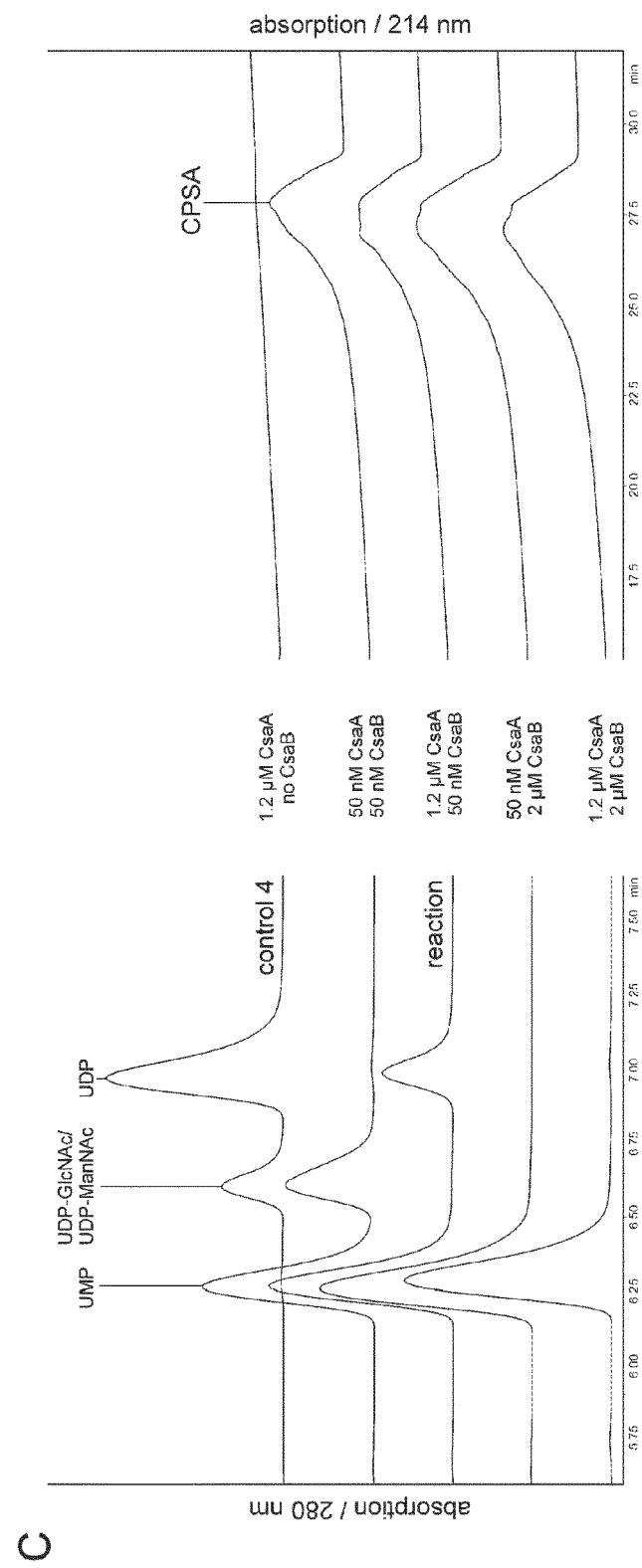

FIG. 26. (A) Products synthesized in the CsaA/CsaB reaction in the presence of UDP-GlcNAc and CPSA$_{hyd}$ of avDP6 were analysed by high percentage PAGE and a combined alcian blue/silver staining. Long chains were produced in the presence of all reactants (reaction) and, though in small amounts, also in control-1 were no priming oligosaccharides were added. The production of long CPSA-chains in control-1 argues for the capacity of CsaB to start chains de novo. (B) Corresponding $^1$H- and $^{31}$P NMR analysis. (C) HPLC analysis of products obtained in reactions were the ratio between CsaA:CsaB was varied as indicated. This experiment clearly shows that UDP-formation is a side activity of CsaA, which can be prevented if the CsaB concentration is equal or higher than the concentration of CsaA. UMP, UDP and UDP-GlcNAc/UDP-ManNAc were detected at 280 nm and CPSA at 224 nm.

Figure 27:
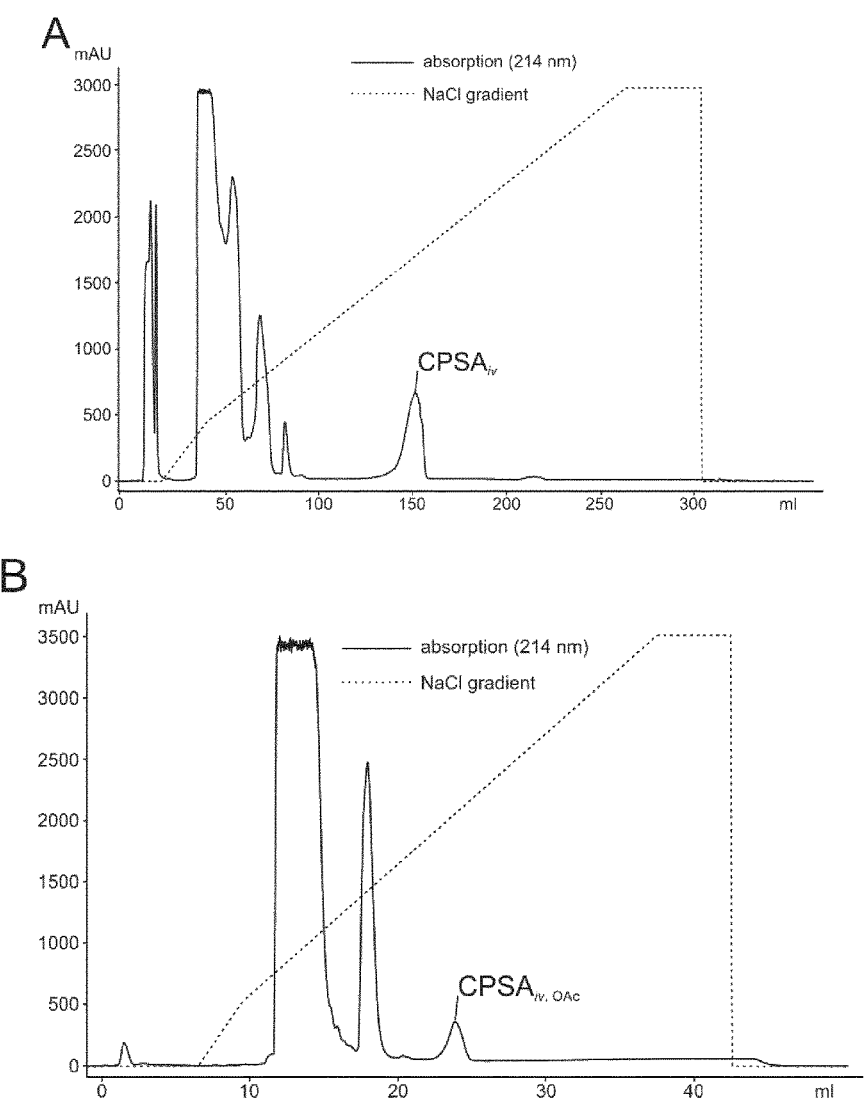
Figure 27:
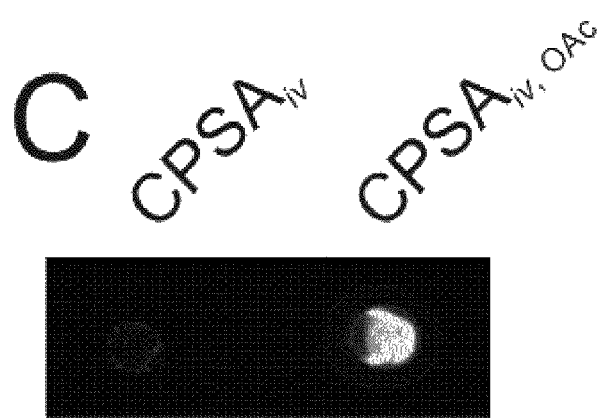
Figure 27:
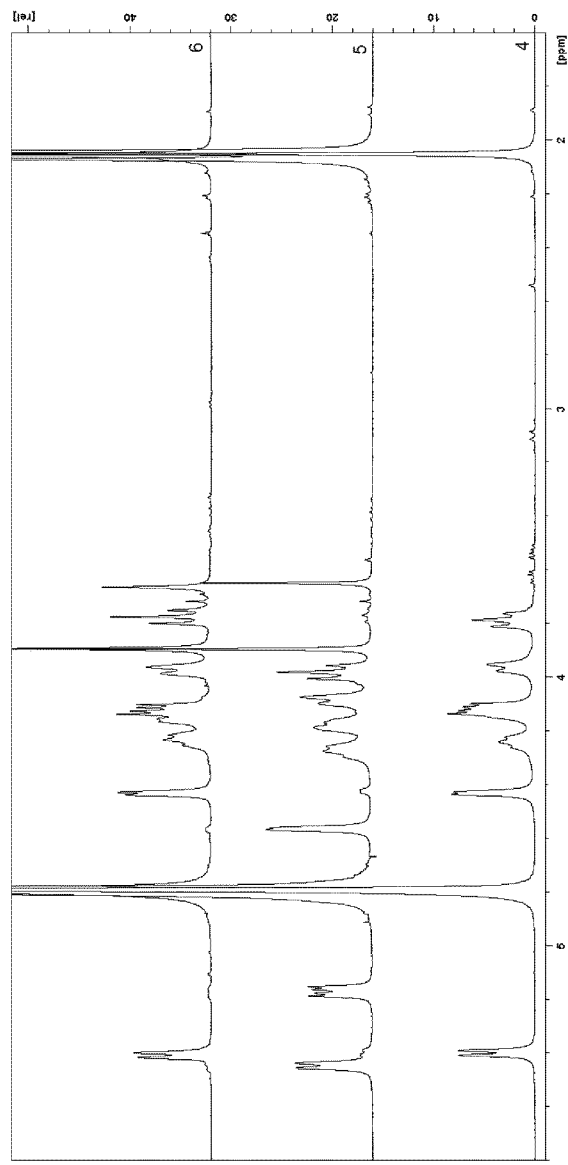
Figure 27:
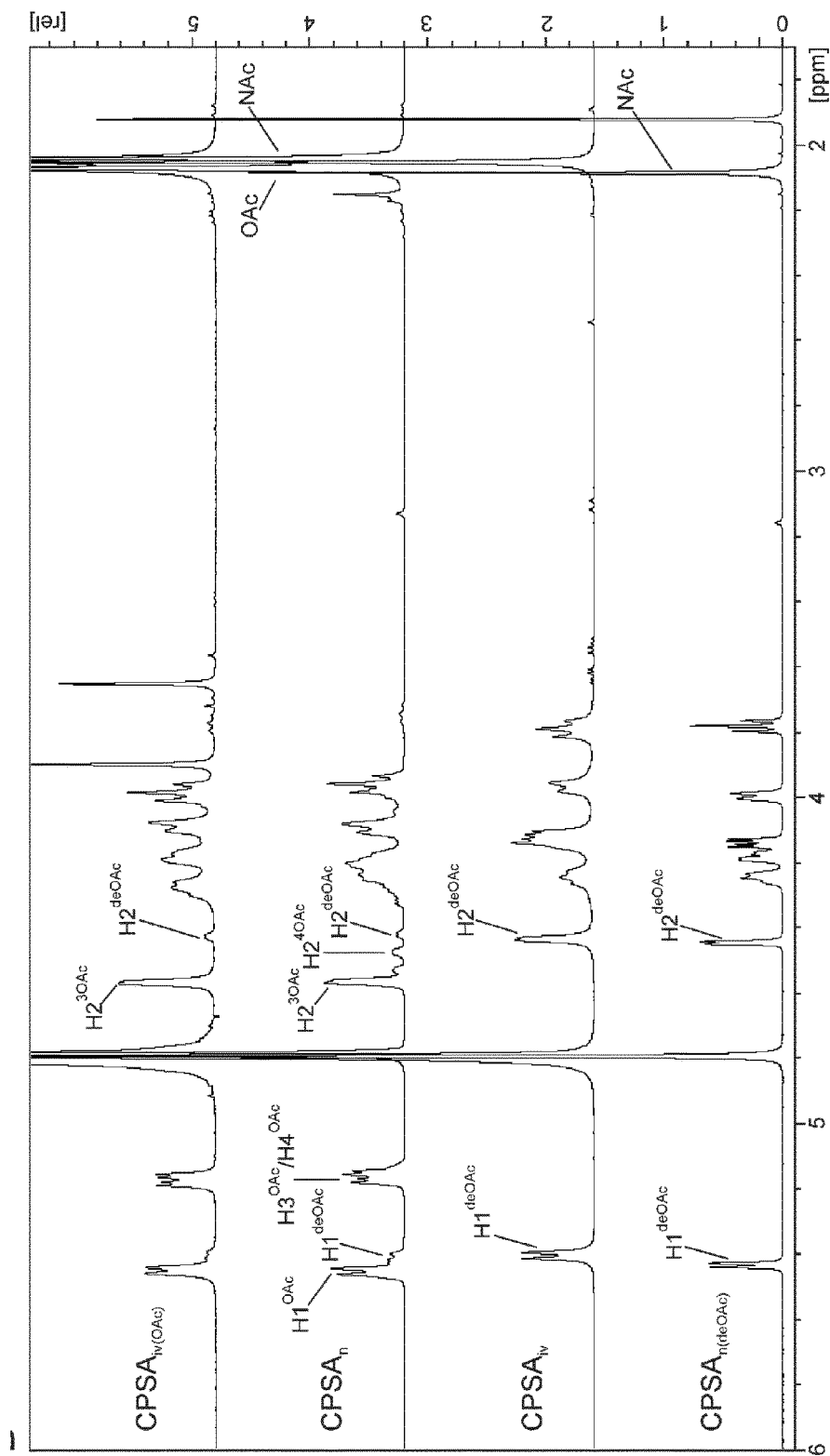

FIG. 27. (A) In vitro synthesized CPSA (CPSA$_{iv}$) was separated from all contaminating reaction products using anion exchange chromatography with the indicated sodium chloride gradient. (B) Purified CPSAiv after O-acetylation (CPSA$_{iv/OAc}$ was re-chromatographed under the same conditions resulting in a well separated product peak, which in dot (C) was recognized by mAb 932. (D) Corresponding $^1$H NMR analysis of the produced CPSA in comparison to CPSA from natural source.

Figure 28:
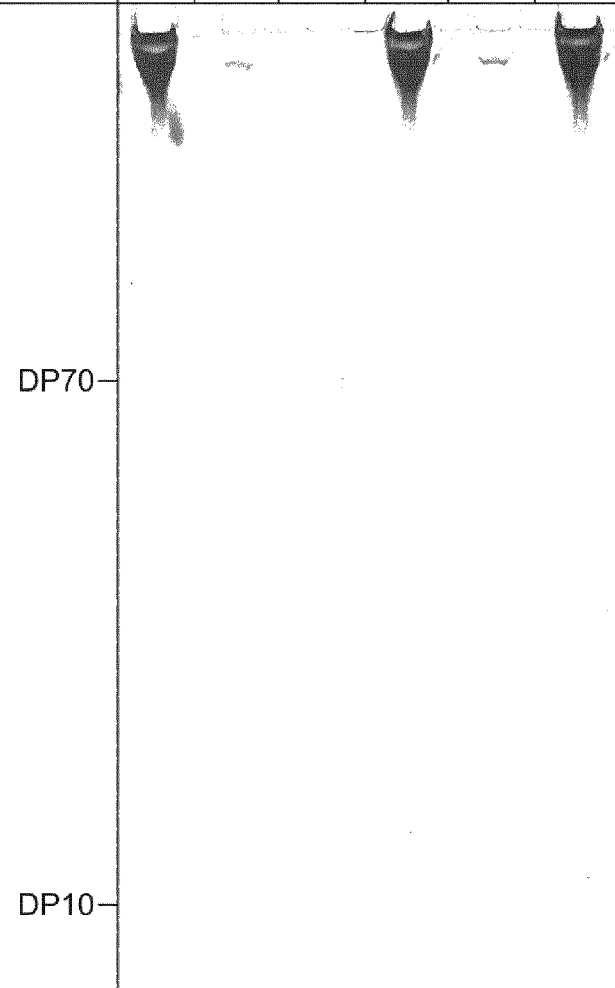
Figure 28:

FIG. 28. (A) In vitro synthesis of O-acetylated and non-O-acetylated CPSA using all enzymes CsaA-C in a one pot reaction. To control product formation, substrates and enzymes were added as indicated. After overnight incubation, products were displayed on high percentage PAGE by a combined alcian blue/silver staining. Long chains were synthesized in all reactions containing CsaA, CsaB and UDP-GlcNAc. (B) Products obtained in the reaction where CsaC and acetyl-CoA were present, were detected with mAb 932 specifically directed against the CPSA$_{OAc}$.

Figure 29:
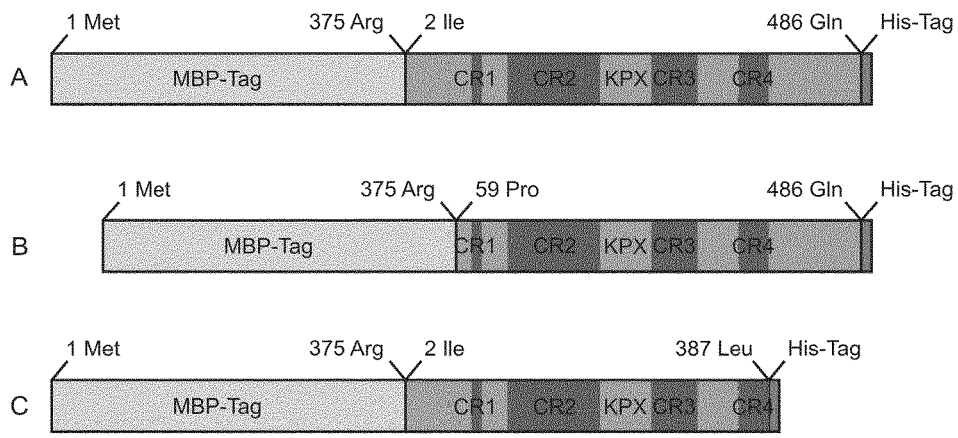

FIG. 29. Schematic representation of the truncated CsxA constructs. (A) Full-length, (B) $\Delta$N58 truncation, (C) $\Delta$C99 truncation.

Figure 30:
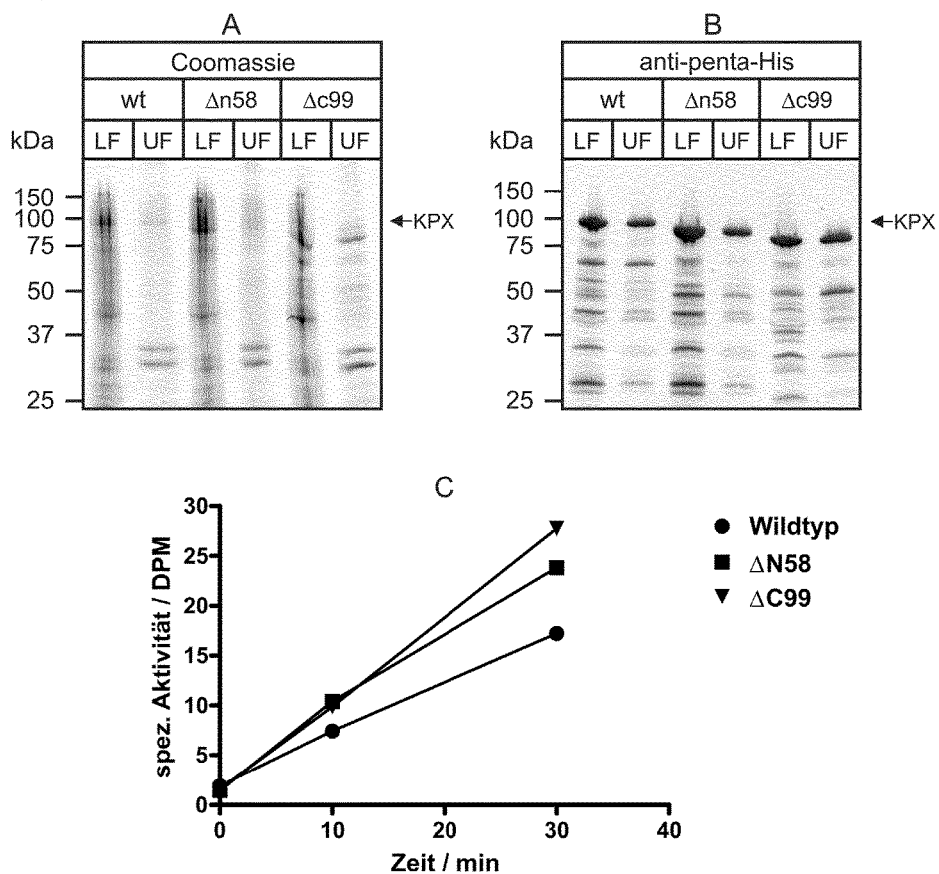

FIG. 30. Truncation studies. (A) 10% SDS-PAGE followed by Coomassie staining of the soluble (LF) and the insoluble (UF) fraction of lysed BL21(DE3)Gold expressing the constructs as indicated. (B) Corresponding western blot developed against the His$_6$-tag. (C) Normalized activities from soluble fractions of full-length (wildtyp) and truncated constructs.

Figure 31:
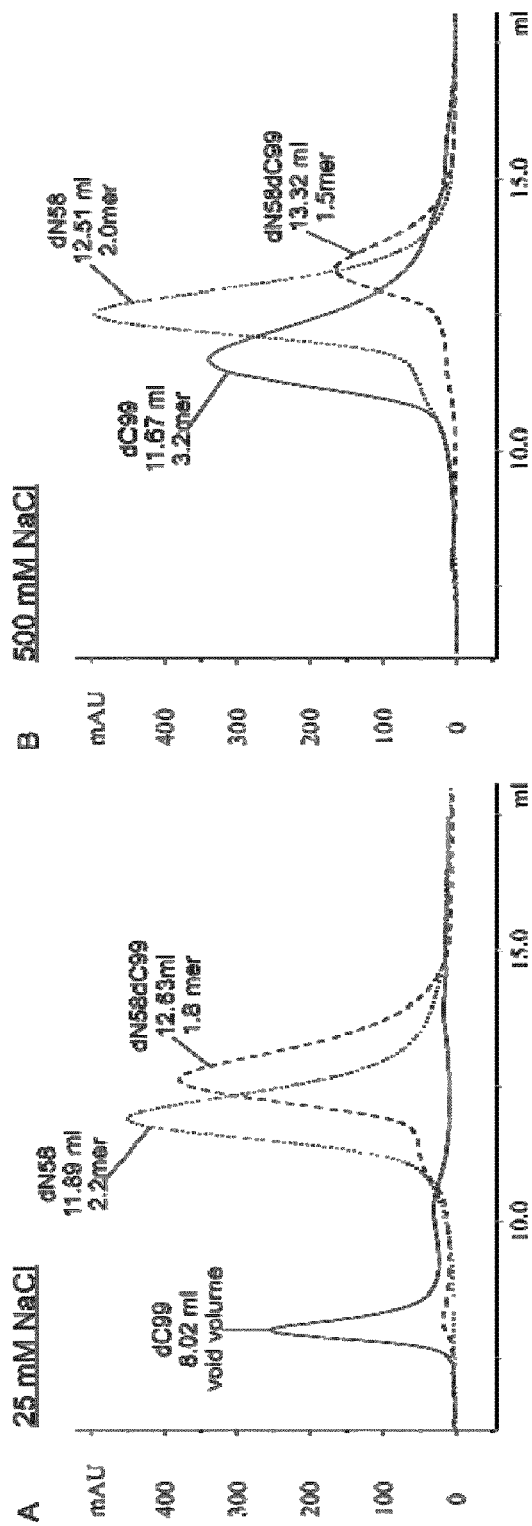
Figure 31:
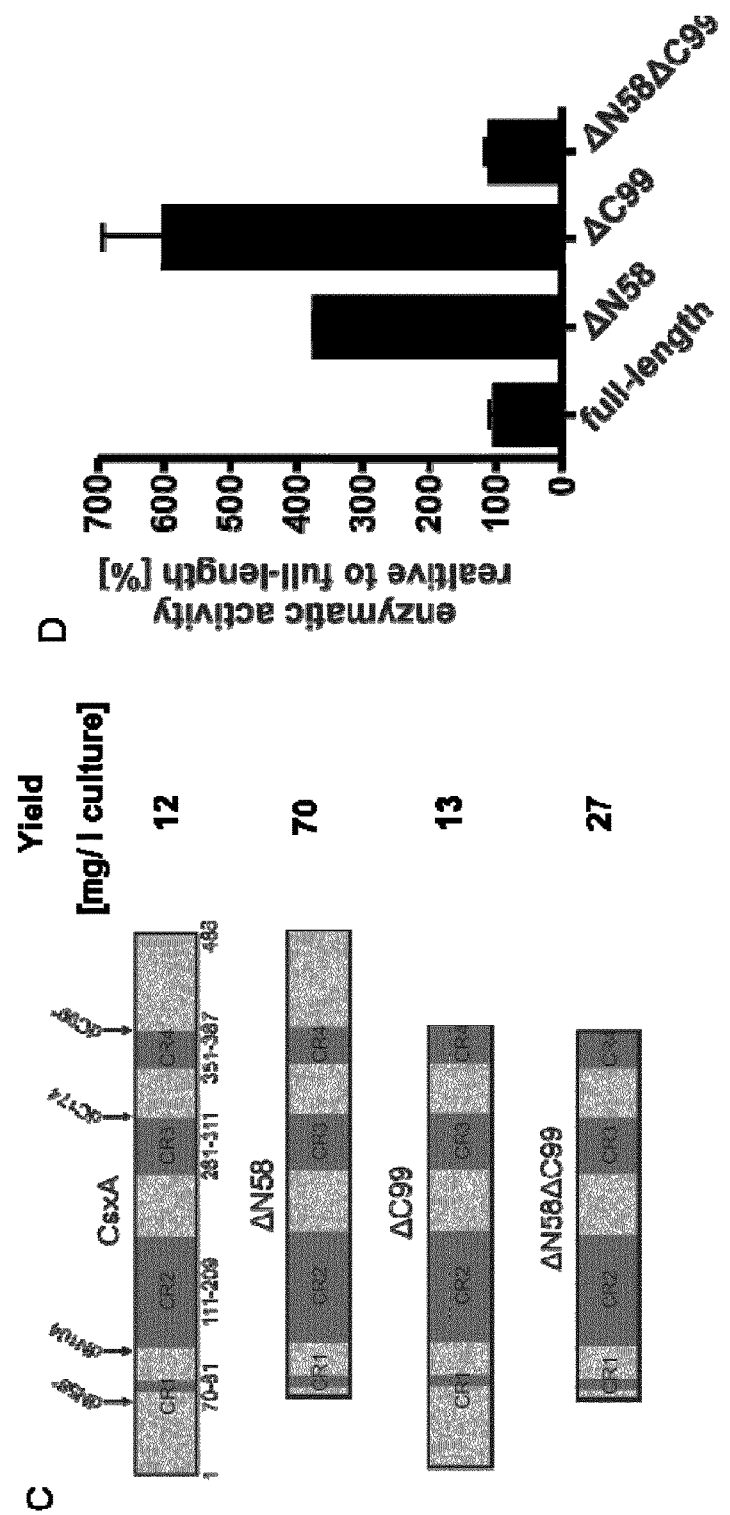

FIG. 31. (A) Analytical size exclusion chromatography in low-salt buffer (25 mM NaCl). (B) Analytical size exclusion chromatography in high-salt buffer (500 mM NaCl). (C) Schematic representation of the constructs tested in A, B and D. (D) Enzymatic activity of the constructs measured using and adaption of the multi-enzyme assay published by Freiberger et al. (2007, Molecular Microbiology 65, 1258-1275).

Figure 32:
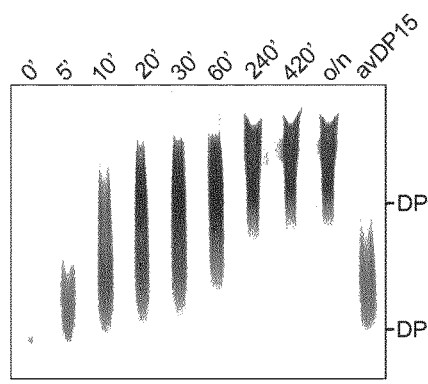
Figure 32:
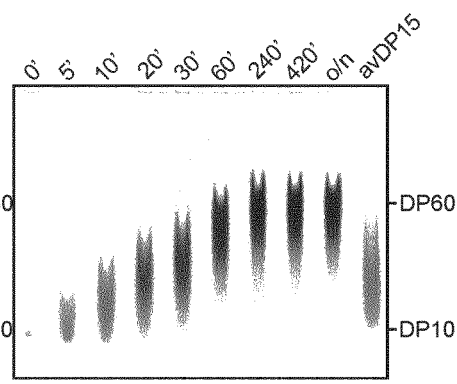

FIG. 32. Elongation of an acceptor carbohydrate having DP5 by using 50 nM $\Delta$C99-CP-X (A) or 50 nM $\Delta$N58$\Delta$C99-

CP-X (B). The reaction times are indicated at the top. The used marker is avDP15, which is the material which is (coupled to a toxoid) often used in vaccines. The marker indicates length from DP10 to DP60. The donor acceptor ratio is approximately 200:1. As can be seen ΔN58ΔC99-CP-X (B) produces capsular polysaccharides with a lower degree of dispersity as compared to ΔC99-CP-X (A).

Figure 33:
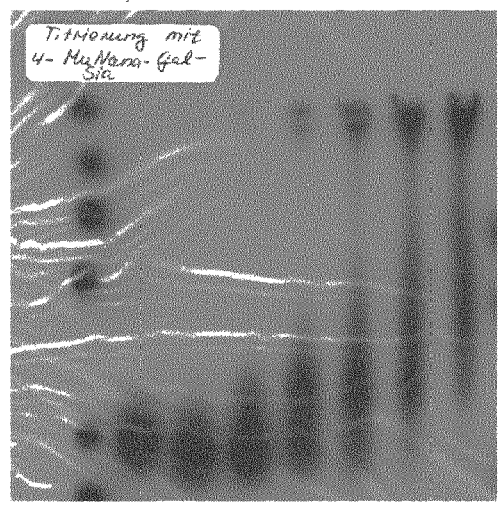

FIG. 33. The capsule polymerase of NmW-135 cannot be regulated via the donor-acceptor ratio. Extension of the synthetic acceptor 4-Mu-Sia-Gal-Sia by CP-W-135 is shown. The concentration of CMP-Sia and UDP-Gal is 2 mM. The designation "ratio" specifies the donor-acceptor-ratio. Even at a ratio of 4 the synthesized polymers are rather long (approximately >200 repeating units).

FIG. 34. (A) The amount of acceptor was experimentally determined in over-night reactions by incubating ΔN58ΔC99 CsxA in the presence of 10 mM UDP-GlcNAc and varying amounts of DP2-DP10. (B) The progress of the reaction could be determined following the consumption of UDP-GlcNAc and the corresponding production of UMP by HPLC-AEC. (C) The obtained CPSX pool is well in the range of the avDP15 material which is commonly used for vaccine production showing that ΔN58ΔC99 CsxA is active and remains distributive even if coupled to a solid phase (His-Trap beads). (D) The fact that ΔN58ΔC99 CsxA can be eluted from the column after the reaction had been performed demonstrates that the construct was coupled to the solid phase during the whole period of the reaction.

The Examples illustrate the invention.

EXAMPLE 1

Biochemical Characterisation of the Capsule Polymerases of NmA (CsaB) and NmX (CsxA)

Materials and Methods

Freshly transformed *E. coli* BL21(DE3) were grown at 15° C. in PowerBroth medium for 18 h. At an optical density of $OD_{600}$=1.0 protein expression was induced by addition of 0.1 mM IPTG and allowed to proceed for a period of approximately 20 h. Pellets from 125 mL expression culture were pelleted by centrifugation (6,000×g, 10 min, 4° C.). After a washing step with PBS, cells were re-suspended in 7.5 ml binding buffer (50 mM Tris pH 8.0, 300 mM NaCl) complemented with 40 µg/ml Bestatin (Sigma), 1 µg/ml Pepstatin (Applichem), 100 µM PMSF (Stratagene) and sonified (Branson Digital Sonifier, 50% amplitude, 8×30 s, interrupted by cooling on ice). After centrifugation at 27,000×g for 30 min, the soluble fractions were directly loaded onto a HisTrap column (GE Healthcare) to enrich the recombinant proteins by immobilized metal ion affinity chromatography (IMAC). Columns were washed with binding buffer (50 mM Tris pH 8.0, 300 mM NaCl) and proteins eluted in step gradients using 10%, 30%, 50% and 100% elution buffer (binding buffer containing 500 mM imidazol). Fractions containing recombinant protein were pooled and the buffer exchanged to storage buffer (50 mM Tris pH 8.0, 50 mM NaCl for CsaA/CsaB; 50 mM Hepes pH 7.05, 100 mM NaCl, 5 mM $MgCl_2$ and 1 mM EDTA for CsaC) using the HiPrep 26/10 Desalting column (GE Healthcare). Isolated proteins were concentrated using Amicon Ultra centrifugal devices (Millipore 30 MWCO). After separation into aliquots, samples were snap frozen in liquid nitrogen and stored at −80° C.

For activity testing a radioactive assay system, which is an adaptation of a protocol described by Weisgerber (1990; J. Biol. Chem. 265, 1578-1587) was used. Briefly, assays were carried out with 5 µl of the soluble fractions of bacterial lysates expressing either recombinant CsaB and CsaA or CsxA or the respective purified and epitope-tagged proteins in a total volume of 25 µl assay buffer (50 mM Tris pH 8.0 or various pH for determination of the pH optimum). Divalent cations were added from stock solutions. The reaction was primed with 5 ng of the respective priming oligosaccharides (hydrolysates of the respective capsule polysaccharides) and started by the addition of 0.05 µmol UDP-GlcNAc (Calbiochem) containing 0.05 µCi UDP-[$^{14}$C]-GlcNAc (American Radiolabeled Chemicals). Samples were incubated at 37° C. and 5 µl aliquots spotted onto Whatman 3MM CHR paper after 0, 5, 10 and 30 min. Following descending paper chromatography, the chromatographically immobile $^{14}$C-labeled CPSA was quantified by scintillation counting.

Activity Testing of CsaB (Together with CsaA) and CsxA by Use of a Multi-Enzyme Spectrophotometric Assay—

1.2 µM of CsaA and 1 µM CsaB were assayed in the presence of 0.25 mM UDP-GlcNAc (Calbiochem), 20 mM $MgCl_2$ and 50 mM Tris pH 8.0 in a total volume of 100 µL. The consumption of UDP-GlcNAc was coupled to nicotinamide adenine dinucleotide (NADH) consumption using the following enzymes/substrates: 0.25 mM adenosine triphosphate (ATP, Roche), 1 mM phosphoenolpyruvate (PEP, ABCR), 0.3 mM (NADH, Roche), 9-15 units/ml pyruvate kinase, 13.5-21 units/ml lactic dehydrogenase (PK/LDH mix Sigma), 0.05 mg/ml nucleoside monophosphate kinase (Roche). Absorption was measured at 340 nm every 30 min using a Biotek EL 808 96-well plate reader.

Results

The Donor:Acceptor Ratio Influences the Product Distribution of CsaB- and CsxA-Reactions in a Different Manner Previous studies have suggested that conjugate vaccines made with intermediate chain-length oligosaccharides, as opposed to high-molecular-weight polysaccharides, are more immunogenic and better at eliciting T cell-dependent antibody responses" (Bröker M, Fantoni S. Minerva Med. (2007) 98(5):575-89). Very effective glycoconjugate vaccines are made of polysaccharides of intermediate size like for example the quadrivalent glycoconjugate vaccine Menveo (Novartis).

In two recent studies we demonstrated that the capsule polymerases from NmA (CsaB) and NmX (CsxA) were able to synthesise CPS chains in vitro which makes them a very attractive target for in vitro vaccine development. However, the synthesised chains were very long and thus not ready for immediate coupling to the toxin.

With the aim of producing oligosaccharide chains that can be readily coupled to a carrier protein, we wanted to investigate in this study if the product distribution produced by these enzymes can be manipulated.

In a first experiment, we incubated catalytic amounts of the enzymes (50 nM) in the presence of different ratios of UDP-GlcNAc, the donor sugar, and a mixture of small oligosaccharides ranging in size from DP1-DP10, the acceptor sugars. The reaction was allowed to proceed over night and the resulting products were analysed using high percentage PAGE stained with a combination of Alcian blue/silver. The expected DPs, indicated above the gels (FIG. 1), were calculated from the donor:acceptor ratio.

As a molecular weight marker, we used hydrolysed CPSA and CPSX samples that were used in the manufacturing process of Menveo. This way, we could judge immediately if the produced product pool had the desired size.

Indeed, CsaB was able to produce the desired product pool (see FIG. 1A, marker) containing chains ranging from ~DP20-DP60. Moreover, the observed chains lengths correlate very well with the expected DPs in the respective reaction. This finding emphasizes that the chain lengths produced by CsaB are controlled by the donor:acceptor ratio, indicating a distributive elongation mechanism. It is of note that the repetition of the experiment in the presence of an excess of the epimerase CsaA lead to the same results, emphasizing that the observed finding are not due to limited supply with UDP-ManNAc.

In contrast, we observed a completely different elongation behaviour from CsxA (FIG. 1D). At very low donor: acceptor ratios CsxA produced only very short chains. However, with increasing donor:acceptor ratio we observed a second product distribution containing chains with a DP much higher than expected. The fact that no intermediate chain lengths were observed indicates that chains with a certain DP are elongated preferably while short chain are disregarded. To test this hypothesis, we repeated the experiment with CPSX oligos ranging from DP10-DP70. Again, the intermediate chain lengths disappeared emphasizing the possibility that those chains are elongated preferably.

Determination of the Minimal Active Domain of CsaB and CsxA

Both CsxA and CsaB belong to the family of stealth proteins that are involved in protecting pathogens from to the host immune defense system (Sperisen, PLoS Comput Biol. (2005) 1(6):e63). All members of stealth harbour, on amino acid level, four conserved regions separated and/or extended by non-conserved regions of varying length. FIG. 1C, showing a schematic alignment of CsxA and CsaB, illustrates that the two enzymes differ mostly by the length of their terminal extensions. Thus, we hypothesised that the difference in elongation behaviour might be encoded in the enzymes termini. Example 4 demonstrates that an N-terminal Δ69-truncation of CsaB was active and very well expressed. The experiment shown in FIG. 1A was repeated with this construct and led to the same results, indicating that the N-terminal 69 aa are not important for the product distribution.

Determination of the Minimal Active Domain of CsaB and CsxA

Both CsxA and CsaB belong to the family of stealth proteins (Sperisen et al., 2005). All members of stealth harbour four conserved regions on amino acid level separated and/or extended by non-conserved regions of varying length. Based on these sequence characteristics, a schematic alignment of CsaB and CsxA shows that the two enzymes differ mainly in their terminal extensions (FIG. 1C). Thus, we hypothesised that the difference in elongation behaviour might be encoded in the enzyme's termini and designed truncated constructs (FIG. 1C). Starting with CsxA, primers were designed annealing in regions that were predicted to be unstructured by the secondary structure prediction software PHYRE2 (Kelley and Sternberg, 2009) to make sure that no important structural elements were destroyed. Like the full-length enzyme, the CsxA truncations were expressed as N-terminally MBP- and C-terminally $His_6$-tagged fusion constructs. The radioactive incorporation assay was used to monitor enzymatic activity from lysates (Fiebig et al., 2014a). While no activity could be detected from constructs lacking CR1 (ΔN104-CsxA) and CR4 (ΔC174-CsxA), truncations of the N- (ΔN58-CsxA) and/or C-terminal (ΔC99-CsxA) extensions were active. A combination of IMAC and SEC was used for the purification of the active constructs. Interestingly, the truncation of the N-terminus led to a nearly six fold increase of purification yield for ΔN58-CsxA (70 mg/l culture) and a two fold increase for ΔN58ΔC99-CsxA (27 mg/l culture) compared to full-length-CsxA (12 mg/l culture) or ΔC99-CsxA (13 mg/l culture) and also reduced the co-purification of degradation products (FIG. 1B). To compare the enzymatic activity of the purified constructs to full-length-CsxA, an adaption of the spectrophotometric assay established for CsaB was used (Fiebig et al., 2014b). Interestingly, the activity of both single truncations was dramatically increased while the activity of the double truncation was comparable to full-length-CsxA (FIG. 31D).

Analysis of the Oligomerisation State

We recently demonstrated that MBP-CsxA-$His_6$ forms complexes >669 kDa in the presence of low amounts of NaCl (25 mM) and partly dissociates into tri- to tetrameric assemblies in high salt conditions (700 mM NaCl) (Fiebig et al., 2014a). The preparative SEC step included in the purification procedure of the truncated CsxA constructs indicated that the termini might influence the oligomerisation behavior of this enzyme. To further interrogate this finding, analytical size exclusion chromatography was performed. ΔC99-CsxA showed salt-dependent oligomerisation behavior similar to full-length-CsxA, suggesting that the C-terminus is not involved in the formation of the correct oligomeric state (FIG. 5). However, the truncation of the N-terminus resulted in roughly dimeric assemblies that could be observed at both high and low NaCl concentrations for both ΔN58-CsxA and ΔN58ΔC99-CsxA (FIG. 5).

In contrast to CsxA, no data is available about the oligomerisation state of CsaB. Since full-length-CsaB is almost exclusively expressed as ΔN69-truncation (Fiebig et al., 2014b), we used ΔN69-CsaB for SEC analysis. Like CsxA, this construct also forms high-molecular weight complexes >669 kDa in low-salt buffer (FIG. 5). However, at high-salt conditions, no defined oligomerisation state could be detected.

The Termini of CsxA Influence its Elongation Mechanism

Asking if the truncations ΔN58-CsxA, ΔC99-CsxA and ΔN58ΔC99-CsxA showed a difference in their d/a-dependent product profiles, we repeated the experiment shown in FIG. 1 with these constructs. The product profile obtained for ΔN58-CsxA was comparable to the profile of full-length-CsxA (compare FIGS. 1D and 2A) and a repetition of the experiment at additional d/a confirmed the appearance of two distinct product populations (FIG. 2B). Remarkably, the product profile of ΔC99-CsxA (FIG. 2C) is unlike that of the full-length-CsxA, but resembles that of the distributive enzyme CsaB. Combined with testing at further d/a (FIG. 2D), these results demonstrate the absence of a processive step in chain elongation, and suggest that processivity is mediated by the truncated C-terminus of CsxA. Interestingly, this construct shares both elongation behaviour and its C-terminus, ending directly behind CR4, with the CsaB enzyme (FIG. 1C). In comparison to the product profiles obtained for ΔC99-CsxA, ΔN58ΔC99-CsxA requires a far greater d/a to produce products of a similar size (compare FIGS. 2C and E).

Full-length-CsaB is mostly expressed as ΔN69 truncation with only residual amounts of the original construct present in the purified sample (Fiebig et al., 2014b). Consequently, so far, only the product profile of ΔN69-CsaB has been analysed (FIG. 1A). However, to investigate if the minor amounts of full-length-CsaB can influence the product profile, we also repeated the experiment shown in FIG. 1A with purified full-length-CsaB. No influence on the product profile could be observed (FIG. 2F) indicating that the first 69 amino acids are not important for the elongation behaviour of this polymerase.

Determination of the Minimal Acceptor Used by CsaB- and CsxA-Constructs

Protocols in glycoconjugate vaccine manufacturing often require free reducing ends for the conjugation of saccharides to the carrier protein (Costantino et al., 2011). Thus, we wanted to determine the minimal length of CPS acceptors with a free reducing end needed for chain elongation for each of the active constructs. We were especially interested if the d/a-dependent length control of ΔN69-CsaB, ΔC99-CsxA and ΔN58ΔC99-CsxA would be influenced by the DP of the acceptor. Acceptors of a single DP were purified from a mixture of hydrolysed, dephosphorylated CPSX and CPSA using anion exchange chromatography (FIG. 3A). The DP of purified material was confirmed by HPAEC-PAD and $^1$H NMR using established protocols (Costantino et al., 1992; Berti et al., 2012). ManNAc-1P could already be excluded as acceptor for CsaB in an earlier study (Fiebig et al., 2014b). Consequently, the acceptor quality of monomeric compounds (GlcNAc, GlcNAc-1P) was only tested for CsxA. Since both CsaB and CsxA exhibit a de novo polymerisation activity which is considerably less efficient than elongation of an acceptor, we considered acceptors stimulating an increased amount of product synthesis compared to the de novo reaction to be acceptors for the enzymes.

Full-length-CsxA and the single truncations ΔN58-CsxA and ΔC99-CsxA were able to elongate acceptors with a DP≥2 while the presence of the monomers GlcNAc-1P and GlcNAc did not lead to product signals beyond de novo background (FIG. 3 C, D, F). Interestingly, a repetition of the experiment with an acceptor concentration increased by 10-fold showed that acceptors of a DP≥4 are particularly useful for the d/a-dependent length-control of ΔC99-CsxA (FIG. 3E). Repeatedly no CPSX was synthesised by ΔN58ΔC99-CsxA in the presence of DP2 and activity seemed to be impaired also in reactions complemented with DP3 (FIG. 3G). It is of note that the products of ΔN58ΔC99-CsxA were considerably smaller than those of ΔC99-CsxA under the same reaction conditions (compare FIGS. 3D and G).

For ΔN69-CsaB, a first screening of short CPSA acceptors of a single DP showed elongation for chains ≥DP2 (FIG. 3I). In agreement with an earlier study suggesting that a phosphate, i.e. a phosphodiester (instead of a methyl-group) at the reducing end is helpful for DP2-uptake (Fiebig et al., 2014b), DP2 with a free reducing end was elongated less efficiently even though HPLC-AEC analysis of DP2 and DP3 at 214 nm indicated that the concentration used in the experiment was comparable for both acceptors. Interestingly, an increase of the acceptor concentration by 25-fold led to an increase in enzymatic activity in the presence of DP2 (FIG. 3J). However, in agreement with the observation for ΔC99-CsxA, the best length-control of the product pool was achieved with acceptors of DP≥4 (FIG. 3J) and even after a further 10-fold increase (compared to the concentrations used in FIG. 3J), the size of the product population in the presence of DP2 was not significantly reduced (FIG. 3H).

Analysis of the Time-Resolved Elongation Behavior of CsaB and CsxA

To provide further insight into the elongation mechanism used by the different constructs, we analysed the time-course of the polymerase reactions. For this analysis the donor and acceptor concentrations were increased to allow detection by HPLC-AEC at 214 nm while maintaining a d/a sufficient for the production of long chains. Samples of each reaction were heat-inactivated after the indicated time-points and analyzed via PAGE followed by Alcian-blue/silver staining or HPLC-AEC, which was calibrated using the purified DPs (FIG. 3A).

During the first 60 minutes, full-length-CsxA mainly synthesized short chains (FIG. 4A) that were at later time-point converted into a broad production population consisting of high-molecular weight material. Similar to the full-length construct, ΔN58-CsxA showed the characteristics of a processive enzyme and a preference for intermediate chain lengths (FIG. 4B).

The fact that the product profile of ΔC99-CsxA is perfectly controllable via the d/a suggests distributive elongation (FIG. 2C). However, this construct produces broad product profiles with high dispersity over time, which is an indication for a certain degree of processivity (FIG. 4E). Nevertheless, compared to full-length- and ΔN58-CsxA (FIGS. 4A and B), no gap indicating biased acceptor binding could be detected (FIG. 4E and FIG. 32 A).

ΔN58ΔC99-CsxA appears to be fully distributive over time and again, produces much shorter chains and narrower distributions compared to ΔC99-CsxA (compare FIGS. 4E/F and 32 A/B). However, a repeat of the experiment with lower acceptor concentrations indicated that the synthesis of longer chains is possible (FIG. 4D).

Experimental Procedures

General Cloning—The generation of MBP-csxA-His$_6$, csaB$_{co}$-His$_6$ and d69-csaB$_{co}$-His$_6$ has been reported elsewhere (Fiebig et al., 2014b; Fiebig et al., 2014a). All truncated constructs described herein were amplified by polymerase chain reaction (PCR) using the primers shown in Table 1 and genomic DNA of Nm strain Z2491, csaB$_{co}$ (Fiebig et al., 2014b) or pHC19 (for CsxA sequences)(Fiebig et al., 2014a) as template. After restriction digest using BamHI/XhoI csaB truncations were cloned into pET22b-Strep (Schwarzer et al., 2009) and csxA truncations were cloned into MBP-csxA-His$_6$ (T7) or MBP-csxA-His$_6$ (tac) (Fiebig et al., 2014a).

TABLE 1

Primers used in this study.
Restriction sites are highlighted in bold.

| Primer pair | Resulting construct |
|---|---|
| GCAGATCTATTGATTTAGT ATTTACTTGG CCGCTCGAGTTTCTCAAAT GATGATGGTAATG | StrepII-ΔN235-CsaB-His$_6$ |
| GCAGATCTACTTTAAGTTC ATCTATATCT CCGCTCGAGTTTCTCAAAT GATGATGGTAATG | StrepII-ΔN167-CsaB-His$_6$ |
| GCAGATCTCCTTCTAATCT TACTCTTAAGC CCGCTCGAGTTTCTCAAAT GATGATGGTAATG | StrepII-ΔN97-CsaB-His$_6$ |
| GCAGATCTTTTATACTTAA TAACAGAAAATGGC CGCCTCGAGAAAATTCCTT TCTTTAGTTAAGG | StrepII-ΔC41-CsaB-His$_6$ |
| GCAGATCTTTTATACTTAA TAACAGAAAATGGC CGCCTCGAGGGTGACTATCA GCACCATCG | StrepII-ΔC25-CsaB-His$_6$ |

TABLE 1-continued

Primers used in this study.
Restriction sites are highlighted in bold.

| Primer pair | Resulting construct |
|---|---|
| CGGGATCCCCAATTGAAGA<br>TCCATACCCAGTA<br>CCCTCGAGTTGTCCACTA<br>GGCTGTGATG | MBP-ΔN58-CsxA-His$_6$ |
| GCGGATCCATTATGAGCAA<br>AATTAGCAAATTG<br>CCCTCGAGGAGAATTTCT<br>GCTTCTGATACATC | MBP-ΔC99-CsxA-His$_6$* |
| CGGGATCCCCAATTGAAGA<br>TCCATACCCAGTA<br>CCCTCGAGGAGAATTTCT<br>GCTTCTGATACATC | MBP-ΔN58ΔC99-CsxA-His$_6$ |
| CGGGATCCGAAAGCACCGA<br>TATTGCAAGATTCC<br>CCCTCGAGGAGAATTTCT<br>GCTTCTGATACATC | MBP-ΔN104-CsxA-His$_6$ |
| GCGGATCCATTATGAGCAA<br>AATTAGCAAATTG<br>CCCTCGAGTTGGCCTGTC<br>AAAATGGCAAATGGTGG | MBP-ΔC174-CsxA-His$_6$ |

*Leucin 388 of the CsxA sequence, normally encoded by ctt, is encoded by ctc from the XhoI site used for cloning.

Expression and Purification of Recombinant CsaB- and CsxA-Constructs—Expression and purification of all CsaB- and CsxA-based sequences was performed as described in (Fiebig et al., 2014b) and (Fiebig et al., 2014a), respectively. For activity testing from lysates and subsequent analysis using the radioactive incorporation assay, csxA and its truncations were expressed from MBP-csxA-His$_6$ (T7)-based constructs using BL21(DE3) as expression host (Fiebig et al., 2014a). Purification was performed using MBP-csxA-His$_6$ (tac)-based constructs and M15(pREP4) as expression host.

Activity testing from lysates was performed using the radioactive incorporation assay as described before (Fiebig et al., 2014b; Fiebig et al., 2014a). The spectrophotometric assay published for CsaB (Fiebig et al., 2014b) was adapted for CsxA resulting in the alterations as follows; (i) no CsaA (epimerase) was used in the reaction mixture, (ii) the reaction was performed using 54 nM of the respective CsxA construct in the presence of (iii) 37 ng CPSX oligosaccharides of avDP18.6.

SDS-PAGE and Immunoblotting—SDS-PAGE and immunoblotting was performed as described before (Fiebig et al., 2014b; Fiebig et al., 2014a).

Purification of CPSA and CPSX Oligosaccharides—CPSA and CPSX oligosaccharide mixtures (Fiebig et al., 2014b; Fiebig et al., 2014a) were dephosphorylated using either acid phosphatase (Sigma) or alkaline phosphatase (CIP, NEB) according to the manufacturer's guidelines. Anion exchange chromatography (AEC) was performed on an ÄKTA$_{FPLC}$ (GE Healthcare) equipped with a MonoQ HR 5/5 column (Pharmacia Biotech) at a flow-rate of 1 ml/min. H$_2$O and 1 M NaCl were used as mobile phases M$_1$ and M$_2$, respectively. Samples were separated using a combination of linear gradients (0% to 5% over 1 ml, 5% to 20% over 10 ml, 20% to 30% over 20 ml). The amount of oligosaccharide in each fraction was estimated from the peak area obtained at 214 nm under the assumption that each residue contributes equally to the absorbance of the respective oligomer. Fractions were dialysed against water (ZelluTrans, Roth, 1 kDa MWCO), freeze-dried and equal concentrations were adjusted with H$_2$O. The identity and DP of the oligosaccharide fractions was confirmed by HPLC-PAD and $^1$H NMR using established protocols (Berti et al., 2012; Ravenscroft et al., 1999; Costantino et al., 1992).

Analysis of CsaB and CsxA Reaction Products—For the d/a dependent analysis, 100 nM CsaB and 50 nM CsxA constructs were incubated in 25-100 uL reaction buffer (50 mM Tris pH 8.0, 20 mM MgCl$_2$, (2 mM DTT, only for CsxA)) in the presence of 2 mM (CsaB) or 5 mM (CsxA) UDP-GlcNAc and acceptors in a concentration resulting in the d/a ratios indicated in FIGS. 1 and 4. CsaB reactions were supplemented with 0.1 μM (FIG. 1A) or 1 μM (FIG. 4A) CsaA for in situ UDP-ManNAc production.

For the time-dependent analysis, the reaction volume was upscaled to 700 uL. The UDP-GlcNAc concentration was increased to 10 mM and the CsaB concentration was decreased to 50 nM. Aliquots were snap-frozen after the indicated time-points and heat-inactivated for 3-5 min at 98° C. HPLC-AEC and high percentage PAGE followed by Alcian blue/silver staining was performed as described before (Fiebig et al., 2014b).

Analytical Size-Exclusion Chromatography—Roughly 300 ug of recombinant protein was analysed at 280 nm on an ÄKTA$_{FPLC}$ (GE Healthcare) equipped with a Superdex 10/300 GL column (GE Healthcare) using 50 mM Tris pH 8.0 elution buffer supplemented with NaCl as indicated in FIG. 3. For the analysis of CsxA constructs, 1 mM of DTT was added. The column was calibrated using the Gel Filtration Markers Kit for Protein Molecular Weights 29,000-700,000 Da (Sigma) according to the manufacturer's guidelines.

REFERENCE LIST

Berti F, Romano M, Micoli F, Pinto V, Cappelletti E, Gavini M, Proietti D, Pluschke G, MacLennan C, Costantino P (2012) Relative stability of meningococcal serogroup A and X polysaccharides. *Vaccine* 30: 6409-6415

Costantino P, Rappuoli R, Berti F (2011) The design of semi-synthetic and synthetic glycoconjugate vaccines. *Expert Opin Drug Discov* 6: 1045-1066

Costantino P, Viti S, Podda A, Velmonte M, Nencioni L, Rappuoli R (1992) Development and phase 1 clinical testing of a conjugate vaccine against meningococcus A and C. *Vaccine* 10: 691-698

Fiebig T, Berti F, Freiberger F, Pinto V, Claus H, Romano M R, Proietti D, Brogioni B, Stummeyer K, Berger M, Vogel U, Costantino P, Gerardy-Schahn R (2014a) Functional expression of the capsule polymerase of *Neisseria meningitidis* serogroup X: a new perspective for vaccine development. *Glycobiology* 24: 150-158

Fiebig T, Freiberger F, Pinto V, Romano M R, Black A, Litschko C, Bethe A, Yashunsky D, Adamo R, Nikolaev A, Berti F, Gerardy-Schahn R (2014b) Molecular cloning and functional characterisation of components of the capsule biosynthesis complex of *Neisseria meningitidis* serogroup A: towards in vitro vaccine production. *J Biol Chem*

Kelley L A, Sternberg M J (2009) Protein structure prediction on the Web: a case study using the Phyre server. *Nat Protoc* 4: 363-371

Ravenscroft N, Averani G, Bartoloni A, Berti S, Bigio M, Carinci V, Costantino P, D'Ascenzi S, Giannozzi A, Norelli F, Pennatini C, Proietti D, Ceccarini C, Cescutti P (1999) Size determination of bacterial capsular oligosaccharides used to prepare conjugate vaccines. *Vaccine* 17: 2802-2816

Schwarzer D, Stummeyer K, Haselhorst T, Freiberger F, Rode B, Grove M, Scheper T, von Itzstein M, Muhlenhoff M, Gerardy-Schahn R (2009) Proteolytic release of the intramolecular chaperone domain confers processivity to endosialidase F. *J Biol Chem* 284: 9465-9474

Sperisen P, Schmid C D, Bucher P, Zilian O (2005) Stealth proteins: in silico identification of a novel protein family rendering bacterial pathogens invisible to host immune defense. *PLoS Comput Biol* 1: e63

EXAMPLE 2

Dissection of Hexosyl- and Sialyltransferase-Domain in the Bi-Functional Capsule Polymerases from *Neisseria meningitidis* W-135 and Y Provides Evidence for the Existence of a New Sialyltransferase Family Abstract Crucial virulence determinants of disease causing *Neisseria meningitidis* (Nm) species are their extracellular polysaccharide capsules (CPSs). In the serogroups W-135 and Y these are heteropolymers of the repeating units [→6)-α-D-Gal-(1→4)-α-Neu5Ac-(2→]$_n$ in NmW-135 and [→6)-α-D-Glc-(1→4)-α-Neu5Ac-(2→]$_n$ in NmY. We recently showed that the capsule polymerases, SiaD$_{W-135}$ and SiaD$_Y$, which synthesise these highly unusual polymers, are composed of two GT-B folded glycosyltransferase domains (an N-terminal hexosyl- and a C-terminal sialyltransferase domain) and a linker region (amino acids 399-762) of unknown function. Here we use a mutational approach and synthetic fluorescent substrates to define the boundaries of the hexosyl- and sialyltransferase domains. Our results reveal that the active sialyltransferase domain encompasses a large portion of the linker region and indeed may define a new family in the CAZy classification.

Experimental Procedures

Generation of truncation mutants and purification of recombinant proteins. To separate hexosyl- and sialyltransferase the clones pHC4 (SiaD$_{W-135}$) and pHC5 (SiaD$_Y$) (Claus (1997) Mol. Gen. Genet. 257, 28-34) were used as templates and truncation mutants were generated by PCR as shown in FIG. 12 and FIG. 16. Hot start Phusion-DNA-Polymerase (Thermo Scientific; Fermentas) was used in these experiments primers containing NdeI or XhoI sites and PCR conditions were: 1 cycle of 98° C./120 s; 30 cycles 98° C./15 s, 65° C./30 s, 72° C./30 s, and 1 cycle 72° C./300 s. Used primers together with the obtained truncation variants are listed in Table 2. PCR-products after digestion with NdeI and XhoI (New England BioLabs®$_{ICn.}$) were purified and ligated into the respective sites of the expression vector pET22-b (Novagen). After transformation into *E. coli* XL-1 Blue (Stratagene), transformed colonies where selected on ampicillin and constructs controlled by restriction analysis and sequencing. Expressed proteins carried a C-terminal His$_6$-epitope. Purification of recombinant proteins was carried out as described (Romanow, J Biol Chem. (2013) 26; 288(17):11718-30).

TABLE 1

Bacterial strains, plasmids and primers used in this study.

| Strains/plasmids/primers | Description or sequence | Reference |
|---|---|---|
| *E. coli* strains | | |
| BL21(DE3) | B; F⁻ ompT hsdS$_B$(r$_B$⁻m$_B$⁻) gal dcm (DE3) | Novagen |
| XL1-Blue | RecA1 ebdA1 gyrA96 thi-1 hsdR17 supE44 | Stratagene |
| Plasmids | | |
| pET-22b(+) | | Novagen |
| Primers | | |
| KS422/KS273 wt NmW-135 | 5'-GCATCT<u>CATATG</u>GCTGTTATTATATTTGTTAACG-3'<br>5'-CCG<u>CTCGAG</u>TTTTTCTTGGCCAAAAAACTG-3' | |
| KS422/KS273 wt NmY | 5'-GCATCT<u>CATATG</u>GCTGTTATTATATTTGTTAACG-3'<br>5'-CCG<u>CTCGAG</u>TTTTTCTTGGCCAAAAAACTG-3' | |
| Point mutants SiaD$_{W-135}$ | | |
| KS350/KS351 E307A | 5'-CTGATCATGACATCAGAAAGT<u>GC</u>GGGATTTCCATATATATTTATG-3'<br>5'-CATAAATATATATGGAAATCCC<u>GC</u>ACTTTCTGATGTCATGATCAG-3' | |
| KS370/KS371 S972A | 5'-ATCTCGCGTTGCTGTAGGTGTTTAT<u>GCA</u>ACTAGCTTATTTG-3'<br>5'-CAAATAAGCTAGT<u>TGC</u>ATAAACACCTACAGCAACGCGAGAT-3' | |
| Point mutants SiaDγ | | |
| AR11/AR12 E307A | 5'-ATACAGATATCCTAATCATGACATCTCAAAGC<u>GC</u>AGGCTTTGGTTATATAT-3'<br>5'-ATATATAACCAAAGCCT<u>GC</u>GCTTTGAGATGTCATGATTAGGATATCTGTAT-3' | |
| Truncations SiaD$_{W-135}$ | | |
| KS422/KS421 C-Δ639 | 5'-GCATCT<u>CATATG</u>GCTGTTATTATATTTGTTAACG-3'<br>5'-CCG<u>CTCGAG</u>GCTGCGCGGAAGAATAGTG-3' | |

TABLE 1-continued

Bacterial strains, plasmids and primers used in this study.

| Strains/plasmids/primers | Description or sequence | Reference |
|---|---|---|
| AR2/KS273 N-Δ398 | 5'-GCATCTCATATGTTTAATAACGTATCATTATCGTC-3'<br>5-'CCGCTCGAGTTTTTCTTGGCCAAAAAACTG-3' | |
| AR1/KS273 N-Δ562 | 5'-GCATCTCATATGACTGATGATAATTTAATACCTAT-3'<br>5-'CCGCTCGAGTTTTTCTTGGCCAAAAAACTG-3' | |
| AR9/AR273 N-Δ609 | 5'-GCATCTCATATGAAATATTCTTATAAATATATCTA-3'<br>5-'CCGCTCGAGTTTTTCTTGGCCAAAAAACTG-3' | |
| AR10/KS273 N-Δ639 | 5'-GCATCTCATATGTCTTGGGAACTTATTCGTGCCTC-3'<br>5-'CCGCTCGAGTTTTTCTTGGCCAAAAAACTG-3' | |
| KS433/KS273 N-Δ676 | 5'-GCATCTCATATGGGTAAGCGTTCGATGGATG-3'<br>5-'CCGCTCGAGTTTTTCTTGGCCAAAAAACTG-3' | |
| KS434/KS273 N-Δ729 | 5'-GCATCTCATATGTCACTGAAAAGTAATGTAGTTG-3'<br>5-'CCGCTCGAGTTTTTCTTGGCCAAAAAACTG-3' | |
| KS435/KS273 N-Δ777 | 5'-GCATCTCATATGAATATCGAAGCATTTCTAAAACC-3'<br>5-'CCGCTCGAGTTTTTCTTGGCCAAAAAACTG-3' | |
| Truncations SiaDγ | | |
| KS422/KS421 C-Δ639 | 5'-GCATCTCATATGGCTGTTATTATATTTGTTAACG-3'<br>5'-CCGCTCGAGGCTGCGCGGAAGAATAGTG-3' | |
| KS422/KS374 C-Δ479 | 5'-GCATCTCATATGGCTGTTATTATATTTGTTAACG-3'<br>5'-CCGCTCGAGCGTTTGCATGTTGGGTAAAG-3' | |
| AR2/KS273 N-Δ398 | 5'-GCATCTCATATGTTTAATAACGTATCATTATCGTC-3'<br>5-'CCGCTCGAGTTTTTCTTGGCCAAAAAACTG-3' | |
| AR1/KS273 N-Δ562 | 5'-GCATCTCATATGACTGATGATAATTTAATACCTAT-3'<br>5-'CCGCTCGAGTTTTTCTTGGCCAAAAAACTG-3' | |
| KS433/KS273 N-Δ676 | 5'-GCATCTCATATGGGTAAGCGTTCGATGGATG-3'<br>5-'CCGCTCGAGTTTTTCTTGGCCAAAAAACTG-3' | |
| KS434/KS273 N-Δ729 | 5'-GCATCTCATATGTCACTGAAAAGTAATGTAGTTG-3'<br>5-'CCGCTCGAGTTTTTCTTGGCCAAAAAACTG-3' | |
| Recloning primer | 5'-GCATCTCATATGGGTAAGCGTTCGATGGATG-3'<br>5'-CCGCTCGAGTTTTTCTTGGCCAAAAAACTG-3' | |

Synthesis and purification of fluorescently labelled acceptors to prime SiaD$_{W-135}$ and SiaD$_Y$ Reactions. Because activity testing in the classical radioactive incorporation assay depends on polymer formation (short oligosaccharide primers are washed out in the paper chromatography step (Weisgerber and Troy (1990) J. Biol. Chem. 265, 1578-1587), the reliable testing of monovalent mutants needed a test system in which single sugar transfers can be identified. We exploited the capability of SiaD$_{W-135}$ and SiaD$_Y$ to extend sialic acid derivatives carrying the fluorescent label 2-(4-methylumbelliferyl) (4-MU) at the reducing end. The recombinant C-terminally His$_6$-tagged monovalent full length enzymes NmW-135-(S972A)-His$_6$ and NmY-(S972A)-His$_6$ were used as hexosyltransferases and NmW-135-(E307A)-His$_6$ and NmY-(E307A)-His$_6$ as sialyltransferases. 4-MU-Sia-Gal/Glc were obtained by mixing 4 mM 4-MU-Sia*Na (Sigma or Iris Biotech GmbH) with 4 mM donor sugar UDP-Gal/UDP-Glc (Sigma) and 20 μg ml$^{-1}$ of the respective hexosyltransferase (NmW-135-(S972A)-His$_6$ or NmY-(S972A)-His$_6$) in reaction buffer (20 mM Tris/HCl pH 8.0, 20 mM MgCl$_2$, and 2 mM DTT). After 24 h at 25° C. enzymes were removed by ultra-filtration (Amicon®Ultra 10 Molecular Weight Cut-Off (MWCO) Millipore) and filtrates containing the reaction products (4-MU-Sia-Gal or 4-MU-Sia-Glc) were lyophilised (Christ; Alpha 1-2 LD plus). After dissolution in water, samples were desalted on P2-gel filtration columns (Bio-Rad). Reaction products were identified by high-performance liquid chromatography using an UFLC-RX system (Shimadzu) coupled to a fluorescence detector (RF-10A XL). Samples were excited at 315 nm and monitored at 375 nm. Although, under the conditions used, this reaction did not give product yields >90% (see FIG. 9) further product purification was omitted because the acceptor quality increased exponential from 4-MU-Sia to 4-MU-Sia-Hex-Sia, making 4-MU-Sia an irrelevant contaminant, which was however useful as an internal standard in consecutive HPLC runs. Obtained 4-MU-Sia-Gal/Glc were then the starting material for Sia transfer to obtain 4-MU-Sia-Gal/Glc-Sia. This reaction was carried out with either NmW-135-(E307A)-His$_6$ or NmY-(E307A)-His$_6$ in the presence of 2 mM CMP-Neu5Ac (Nacalai tesque). Reaction conditions were identical to those described in the first reaction step. However, due to significantly improved acceptor, the sialylation of the starting material was complete after 1 h incubation, after removal of enzyme and desalting, obtained compounds were used in iterative rounds to synthesise primers of the needed size.

Enzyme testing. Radioactive incorporation assays were performed as described (Romanow, J Biol Chem. (2013) 26; 288(17):11718-30). For activity testing with fluorescent compounds, reactions were carried out in a total volume of 25 μl. Mixtures contained 50 mM Tris/HCl pH 8.0, 20 mM $MgCl_2$, 2 mM DTT, 1 mM acceptor (4-MU-Sia-Gal/Glc, 4-MU-Sia-Gal/Glc-Sia, or 4-MU-Sia-Gal/Glc-Sia-Gal/Glc) plus 2 mM of the nucleotide sugar (UDP-Gal/Glc; Sigma and/or 2 mM CMP-Neu5Ac; Nacalai tesque) depending on the tested enzyme. Reactions were started by addition of 20 μg $ml^{-1}$ purified enzyme or, if the soluble fraction of bacterial lysates was used as enzyme source, with 72-100 μg $ml^{-1}$ total protein. After appropriate incubation times, reactions were stopped by shock freezing in liquid nitrogen.

Synthesised polymers were analysed and quantified via the fluorescent tag. Separation of 4-MU-labelled oligo- and polysaccharides was achieved by anion exchange chromatography (CarboPac® PA-100 column, Dionex) using an ultrafast HPLC system (UFLC-RX, Shimadzu) with coupled fluorescence detection (FD; detector RF-10A XL). Before loading onto the CarboPac® PA-100 column, samples were 500-fold diluted in water. For the elution the buffer components A (20 mM $NaNO_3$) and B (1 M $NaNO_3$) were used to establish a curved gradient, reaching 21.65% buffer B over 35 min. The flow rate was set to 0.6 ml $min^{-1}$ and the column temperature to 50° C. The curved portion of the gradient is described by the following formula in with the index −1.425 describes the slope (LS Solution; Shimadzu; Keys, Glycobiology (2013); 23(5):613-8).

$$B\% = \frac{21.65*(e^{-1.425t/25}-1)}{(e^{-1.425}-1)}$$

Elution profiles were monitored via fluorescence emission at 375 nm with 315 nm as extinction wave length. Under these conditions the separation of polysaccharides up to a degree of polymerisation (DP)>18 was easily achieved (see results).

SDS-PAGE and immunoblotting. SDS-PAGE was performed under reducing conditions using 2.5% (v/v) β-mercaptoethanol. Western blot analysis was done on a PVDF membrane (Millipore). For detection of the hexahistidine tag, penta-His antibody (Qiagen) was used as first antibody at a concentration of 1 μg $ml^{-1}$ and detected with 0.05 μg $ml^{-1}$ $IgG_1$ anti mouse IR Dye800 antibody (Odyssey Infrared Imaging®). Protein bands were visualised and quantified with the infrared fluorescence detection system (LI-COR®) according to the manufacturer's instructions.

Results

Synthesis of Fluorescently Labelled Oligosaccharides. With the intention to physically separate hexosyl (Hex)- and sialyl (Sia)-transferase and functionally express the individual enzyme domains, it was prerequisite to have specific acceptors available that would allow the unequivocal detection of single sugar transfers. As detailed in Experimental Procedures the monovalent mutants NmW-135-(S972A)-$His_6$ and NmY-(S972A)-$His_6$, bearing only HexTF activity were used to generate 4-MU-Sia-Hex (4-MU-DP2), which then was substrate for the monovalent enzymes bearing only SiaTF activity (NmW-135-(E307A)-$His_6$ and NmY-(E307A)-$His_6$). 4-MU-Sia-Hex-Sia (4-MU-DP3) resulting from this reaction, was an efficient acceptor for the HexTFs.

The structures of the generated acceptors (exemplarily shown for oligosaccharides with Gal as hexose) are given in FIG. 8.

Based on previous experiences with the separation and purification of Sia-containing oligo- and polymers (Glycobiology (2013) 23(5):613-8) a CarboPac® PA-100 column and a curved $NaNO_3$ gradient were used to determine the elution positions of 4-MU-Sia and of the elongated products 4-MU-DP2-4-MU-DP4. Shown in FIGS. 9A and 9B, respectively, are the products formed with NmW-135-(S972A)-$His_6$ and NmY-(S972A)-$His_6$ as HexTFs and NmW-135-(E307A)-$His_6$ or NmY-(E307A)-$His_6$ as SiaTFs. Baseline separation was obtained for all tested compounds. Of note, transfer of the neutral sugar (Gal and Glc in the case of NmW-135 and NmY, respectively) shifted the product peaks left in relation to their precursors (compare 4-MU-DP2 and 4-MU-DP4 to 4-MU-DP1 and 4-MU-DP3, respectively), indicating that the surface charge density is decisive for the elution behaviour of the oligosaccharides. The chromatograms also show that the first hexosyl-transfer onto 4-MU-DP1 remained incomplete under the conditions used, while subsequent transfer reactions proceeded to completion.

It is important at this point to mention that trials to start the reaction with 4-MU-Gal and 4-MU-Glc as potential substrates for the SiaTF domains were unsuccessful with both, the wild-type enzymes and the monovalent point mutants NmW-135-(E307A)-$His_6$ and NmY-(E307A)-$His_6$. This finding strongly suggested that the SiaTF domain needs at least a disaccharide to be active or, alternatively, recognition of the acceptor may need the presence of at least one sialic acid residue.

The new assay system was then used to record the wild-type $SiaD_{W-135/Y}$ reactions over time. To visualize the initial reaction steps, the enzymes were primed with 1 mM 4-MU-DP3 in the presence of limited substrate concentrations (CMP-Sia and UDP-Gal/Glc, 2 mM each) and reactions run up to 40 min. Samples were taken between 0.25 min and 40 min as indicated (FIG. 10) and products displayed by HPLC-FD. Exemplarily shown are the results obtained with $SiaD_{W-135}$. Under the conditions used the successive elongation of the 4-MU-DP3 primer up to DP19 (in the case of $SiaD_Y$ DP16) could be recorded. The well separated peaks migrated at precisely identical positions in three independent replicates and thus allowed the assignation of retention times to the individual DP (see also Table 2).

To quantify product formation over time, the relative abundance of each synthesized DP at a given time point was calculated and with the help of the LC Solution software (Shimadzu) normed and weighted to the total curve area giving the normed and weighted values according to the formula:

$$\text{normed and weighted area} = \frac{An}{\sum_{n=1}^{\infty} An} * (n-1)$$

with A being the area underneath a single peak and n the number of transfers needed to form this product. Values were plotted against the reaction time. Data points as shown in (FIG. 10C) are from a single determination. The congruence of the curves obtained in three independent experiments confirms the reliability of the assay system.

TABLE 2

Degree of synthesised polysaccharides and their corresponding retention time in minutes.

| CP NmW-135 | | CP NmY | |
|---|---|---|---|
| Retention time [min] | Degree of Polymerisation | Retention time [min] | Degree of Polymerisation |
| 2.308 | $DP_2$ | 2.381 | $DP_2$ |
| 3.54 | $DP_1$ | 3.542 | $DP_1$ |
| 4.487 | $DP_4$ | 4.469 | $DP_4$ |
| 5.223 | $DP_3$ | 5.184 | $DP_3$ |
| 6.516 | $DP_6$ | 6.4 | $DP_6$ |
| 7.174 | $DP_5$ | 7.074 | $DP_5$ |
| 8.197 | $DP_8$ | 7.990 | $DP_8$ |
| 8.85 | $DP_7$ | 8.633 | $DP_7$ |
| 9.623 | $DP_{10}$ | 9.315 | $DP_{10}$ |
| 10.257 | $DP_9$ | 9.927 | $DP_9$ |
| 10.864 | $DP_{12}$ | 10.452 | $DP_{12}$ |
| 11.47 | $DP_{11}$ | 11.047 | $DP_{11}$ |
| 11.965 | $DP_{14}$ | 11.461 | $DP_{14}$ |
| 12.544 | $DP_{13}$ | 12.026 | $DP_{13}$ |
| 12.957 | $DP_{16}$ | 12.369 | $DP_{16}$ |
| 13.508 | $DP_{15}$ | 12.836 | $DP_{15}$ |
| 13.857 | $DP_{18}$ | | |
| 14.385 | $DP_{17}$ | | |
| 14.665 | $DP_{20}$ | | |
| 15.188 | $DP_{19}$ | | |
| 15.989 | $DP_{21}$ | | |

The illustrated table represents the retention time of appropriate produced capsule polysaccharides of NmW-135 and NmY during the elution with 1 M $NaNO_3$ using an adapted curve gradient on the CarboPac PA-100 column. The elution is based on the charge of oligosaccharides and therefore all polysaccharides with sialic acid on the reducing end are represented by odd numbers and such with hexose on the reducing end are represented by even numbers.

Of note, while carbohydrate polymerases normally show a kinetic lag phase (Breyer, Protein Science 10, 1699-1711 (2001)), the progress curves obtained with $SiaD_{W-135/Y}$ represent typical enzyme reaction kinetic with an initial maximum velocity, indicating that products of progressively longer DP are not better acceptors than the starter compound 4-MU-DP3.

As separation of the two active glycosyltranferase domains was the goal of this study, it was important to reconfirm monovalence (Romanow, J Biol Chem. (2013) 26; 288(17):11718-30) of the single point mutant capsule polymerases NmW-135-(S972A)-$His_6$ and NmW-135-(E307A)-$His_6$, used as positive controls in subsequent experiments. The reaction profiles monitored in the presence of both donor sugars are shown in FIG. 11. Single transfers onto the acceptors 4-MU-DP2 and 4-MU-DP3 by NmW-135-(E307A)-$His_6$ and NmW-135-(S972A)-$His_6$, respectively, (FIG. 11A,D) could be shown. Instead, the absence of any visible transfer could be shown for reactions started with primers 4-MU-DP3 and 4-MU-DP2 with NmW-135-(E307A)-$His_6$ and NmW-135-(S972A)-$His_6$, respectively, (FIG. 11B,C) by providing unequivocal proof for the monovalent nature of these enzymes. Remarkably these pilot experiments in addition showed that Sia transfer onto 4-MU-DP2 occurred very fast. After only 15 sec >70% of the primer substrate (compare 4-MU-DP2 peak in FIG. 11C) were converted into 4-MU-DP3. However, the reaction did not proceed to completion, indicating that and equilibrium between forward and reverse reaction was reached.

Compared to the sialyltransferase reaction, transfer of Gal onto 4-MU-DP3 was slower, with only about 10% of the primer converted to 4-MU-DP4 after 15 sec reaction time. However, in contrast to the sialyl-transferase reaction this hexosyltransferase reaction proceeded to completeness within 30 min (FIG. 11D). Again, the absence of additional reaction products in FIG. 11D and the zero-activity of the control reaction (FIG. 11C) confirmed monovalence of the point mutant enzyme.

Truncation Mutagenesis to Separate Hexosyl- and Sialyl-transferase in $SiaD_{W-135}$ and $SiaD_Y$. In FIG. 12A a schematic representation of the linear sequence of $SiaD_{W-135}$ and $SiaD_Y$ is shown. The GT-B folds comprising hexosyl- and sialyl-transferase domain are shown separated by a stretch of 379 amino acids (dark bar, called linker hereafter). Since in bioinformatics analyses neither sequence homologies nor structural folds could be identified for the linker, we hypothesised that this region is not part of the catalytic domains, but maybe needed to give the GT-B folds the freedom to tertiary organize. This hypothesis was challenged when the GT-B folds (constructs CΔ639 and NΔ777 see FIG. 12A) were separately expressed and tested in the classical radioactive assay system in comparison to the monovalent enzymes. Though well expressed as soluble proteins (see FIG. 12B) activity was only detectable with the hexosyltransferase domains (NmW-135-CΔ639-$His_6$ and NmY-CΔ639-$His_6$) and not with construct NmW-135-NΔ777-$His_6$ (FIG. 12A), harboring the putative sialyltransferase of $SiaD_{W-135}$ (data not shown). Because the radioactive assay gave no activity values also with the control enzymes (as outlined in Experimental Procedures, the radioactive assay is not well suited to analyse the single transfer reactions), the assays were also carried out with the newly synthesized acceptors 4-MU-DP2 and 4-MU-DP3. Now, product profiles obtained with the hexosyltransferase domains NmW-135-CΔ639-$His_6$ and NmY-CΔ639-$His_6$ were similar to the controls (see FIG. 11), but again, no activity could be detected with the isolated sialyltransferase domains (FIG. 13). These result confirmed that the N-terminal GT-B folds, but not the C-terminal GT-B folds comprise catalytically active enzymes.

Next, we asked, if the linker (parts of the linker) may be part of the active sialyltransferase. To test this assumption, mutant NΔ398-$His_6$, which comprises the entire linker sequence (see FIG. 12A) was constructed and was tested directly from bacterial lysates in parallel to the monovalent enzyme (NmW-135-(E307A)-$His_6$) and the isolated GT-B fold (NmW-135-CΔ639-$His_6$). Addition of the linker in construct NΔ398-$His_6$ restored activity (FIG. 13).

To more precisely define the active sialyltransferase domain additional truncations as shown in FIG. 12A were carried out. In this step, attention was given to not hit predicted secondary structure elements (see FIG. 16). Constructs were expressed in E. coli BL21(DE3) bacterial cell line, protein expression monitored by western blotting and activity determined with the fluorescently labelled acceptor 4-MU-DP2 in the soluble fractions of the lysates of transformed bacteria. While the constructs NΔ562 and NΔ609 showed product profiles similar to the controls (FIG. 14) further truncation of 30 amino acids (NΔ639) completely inactivated the sialyltransferase activity. As shown in FIG. 16, the cut introduced in NΔ609 is likely to separate a β-strand from a predicted helical stretch, which is missing in NΔ639. The presence of this helical element seems of utmost importance not only for the activity but also for the stability of the truncated protein. While NΔ609 is well expressed as a soluble protein, the mutant NΔ639 was foremost found in the insoluble fraction (FIG. 12B). Further truncation as shown for construct NΔ676, NΔ729, and NΔ777 generated recombinant proteins that were well expressed in the soluble fraction, but had not functional activity. This effect on protein stability was confirmed with SiaD$_Y$ (see truncations NΔ676 and NΔ729 in FIG. 12B).

Together the mutational studies demonstrated that hexosyl- and sialyltransferase can be separated in SiaD$_{W-135}$ and SiaD$_Y$ and can be expressed as functionally active proteins. Different to the N-terminal GT-B folds, which encode classical hexosyltransferases belonging to CAZy family GT-4), the C-terminal GT-B folds comprise only parts of the functionally active sialyltransferases. The active sialyltransferases start with a predicted helical segment starting at F609 (see also FIG. 16). The sequence stretch connecting the two GT-B folds is thus not just a linking element, but part of the functional SiaTF domains in SiaD$_{W-135/Y}$. Importantly, our data indicate that the capsule polymerases of NmW-135 and Y cannot be easily regulated via the donor-acceptor ratio; see FIG. 33.

The sialyltransferase domains in SiaD$_{W-135/Y}$ define a new sialyltransferase family. As discussed previously (Romanow, J Biol Chem. (2013) 26; 288(17):11718-30) Blast search analyses carried out with the C-terminal GT-B folds of SiaD$_{W-135}$ and SiaD$_Y$ were unable to assign the sequences to one of the sialyltransferase families existing in the CAZy classification system (Coutinho (2003) J. Mol. Biol. 328, 307-317). Nevertheless, these searchers revealed weak homology to open reading frames in some bacterial proteins of unknown function. With the current knowledge that the functional sialyltransferase domains in SiaD$_{W-135/Y}$ encompass the C-terminal part of the linker region (at least F609-I778), the bioinformatics analyses was repeated and in parallel carried out with the programs BLAST and HMMER. Importantly, HMMER identified more than 30 sequences all comprising bacterial proteins of unknown function. After elimination of identical sequences further analyses by multi-sequence alignments clearly showed high conserved motifs (FIG. 15). The D/E-D/E-G motif, which is part of the catalytic centre in bacterial sialyltransferases of CAZy families GT-38, GT-52, GT-80 and in pfam 05855 (Freiberger (2007) Molecular Microbiology 65, 1258-1275), was found to be replaced by QHG (QYA in SiaD$_{W-135/Y}$ and a sequence encoding a putative sialyltransferase in *Listeria*). The known bacterial Sia-motifs HP and SS/T, that are involved in the binding of the nucleotide (sugar) (Freiberger (2007) Molecular Microbiology 65, 1258-1275; Yamamoto (2007) Biochem. Biophys. Res. Commun 365, 340-343), are highly conserved also in the newly identified sequences but seem to be part of more extended motifs. Moreover, the new alignment revealed a number of conserved positions many only present in the SiaD$_{W-135/Y}$ homologues. In summary this alignment suggests the existence of a new sialyltransferase family in which the sialyltransferase domains of the chimeric enzymes SiaD$_{W-135/Y}$ are the only functionally characterized members. No doubt, based on these data, the allocation of SiaD$_{W-135/Y}$ into CAZy family GT-4 needs new consideration.

EXAMPLE 3

Neutral Drift of a Polysialyltransferase Yields Enzymes with Processive and Distributive Mechanisms The polysialyltransferase (polyST) from *Neisseria meningitidis* serogroup B (NmB) synthesises a homopolymer of α2,8-linked sialic acid residues known as polysialic acid. The chemical and immunological identity of the bacterial polymer with polysialic acid expressed in the human brain constitutes a highly effective molecular mimicry which contributes to virulence of NmB (Muhlenhoff, Curr. Opin. Struct. Biol. 8, 558-564 (1998); Roberts, Annu. Rev. Microbiol. 50, 285-315 (1996)). Recent studies have highlighted the potential of the NmB-polyST for polysialylation of therapeutic proteins (Lindhout, Proceedings of the National Academy of Sciences (2011), doi:10.1073/pnas.1019266108), and for direct therapeutic application of polysialic acid to tissues in vivo (Maarouf, J. Biol. Chem. 287, 32770-32779 (2012)). Despite the importance of this enzyme, little is known of its structure and function.

We have recently developed two new assay systems which enable high throughput screening and detailed characterisation of polyST activity (Keys, Analytical Biochemistry 427, 107-115 (2012); Keys, Analytical Biochemistry 427, 60-68 (2012)). In this study we have used these methods to conduct a neutral drift experiment—subjecting the NmB-polyST to high mutation rates followed by purifying selection to remove inactive variants—to explore functional regions of the polyST sequence space. Detailed analysis of over 50 drifted variants (with 7.3±3.0 amino acid exchanges per sequence) revealed that some sequences had acquired new modes of chain elongation which correspond to either a processive or distributive mechanism of polymerisation. The study identifies sequence elements which control the mechanism of elongation and the dispersity of polymeric products.

The synthesis of uniform glycan structures is a necessary precursor to their evaluation as therapeutic reagents. We have explored the functional sequence space of a bacterial polysialyltransferase and identified sequence elements controlling the processive or distributive mechanism of chain elongation. The results demonstrate that these properties are independent of enzymatic activity and illuminate a pathway for the synthesis of uniform oligo- and polysaccharide structures for research and therapeutic applications.

The extracellular polysaccharides of diverse bacterial species, which have emerged from symbiotic or pathogenic coevolution with their human hosts, are a rich source of structures with important biological functions and applications as therapeutic reagents (DeAngelis, J. Glycobiology. 23, 764-777 (2013); Pollard Nat. Rev. Immunol. 9, 213-220 (2009) and Boltje, Nat. Chem. 1, 611-622 (2009)) The application of oligo- and polysaccharides will be greatly advanced by strategies to fine tune the functional properties of the polymerizing glycosyltransferases which synthesize these polysaccharides (Boltje, Nat. Chem. 1, 611-622 (2009) and Schmaltz, Chem. Rev. 111, 4259-4307 (2011)). Here we demonstrate that these enzymes can readily be engineered to produce uniform Poissonian product distributions.

Our study focused on the polysialyltransferase from *Neisseria meningitidis* serogroup B (polySTNmB), which synthesizes α2,8-linked polysialic acid (polySia), a low abundance polymer with unique biological functions and importance as a reagent for research and several emerging therapeutic applications. In mammals, polySia is a dynamically regulated posttranslational modification predominantly found on the neural cell adhesion molecule, NCAM (Mühlenhoff, Neurochem. Res. 38:1134-1143 (2013)). Due to its polyanionic nature, large size, and water binding capacity, polySia acts as a powerful anti-adhesive, globally down regulating cellular interactions and increasing cellular motility (Johnson, J. Biol. Chem. 280, 137-145 (2005)). These unique anti-adhesive properties provide plasticity in the developing and adult nervous system (Rutishauser, Nat. Rev. Neurosci. 9, 26-35 (2008)) and play a role in immune development (Drake, Proc. Natl. Acad. Sci. U.S.A. 106, 11995-12000 (2009)). PolySia is re-expressed at the cell surface by various tumors to promote invasion and metastatic potential (Hildebrandt, Adv. Exp. Med. Biol. 663, 95-109 (2010)). Moreover, some neuroinvasive bacteria produce an extracellular capsule of polySia which aids in evasion of the immune system (Corbett, Adv. Appl. Microbiol. 65, 1-26 (2008)). PolySia is currently being investigated for diverse therapeutic applications, primarily based on the ability to promote plastic processes involved in regeneration in neural tissues (El Maarouf, Adv. Exp. Med. Biol. 663, 137-147 (2010) and El Maarouf, Proc. Natl. Acad. Sci. U.S.A. 103, 16989-16994 (2006)) and its ability to improve the pharmacological profile of therapeutic proteins decorated with polySia (Constantinou, Bioconjugate Chem. 19, 643-650 (2008) and Lindhout Proc. Natl. Acad. Sci. U.S.A. 108, 7397-7402 (2011)). A major step towards these goals is the demonstration that gene therapy and chemical coupling can be avoided in these applications by using the polySTNmB to synthesize polySia directly onto therapeutic proteins (Lindhout, Proc. Natl. Acad. Sci. U.S.A. 108, 7397-7402 (2011)), cultured cells, and neural tissues in vivo (Maarouf, J. Biol. Chem. 287, 32770-32779 (2012)).

A critical feature of enzymes for use in glycoengineering applications is the ability to synthesize uniform products of defined length. The primary feature determining product length and dispersity for polymerases is the extent of their interaction with the growing polysaccharide acceptor (FIG. 17). An extended binding site confers increased affinity and an increased rate of transfer to longer chains which occupy more of the binding subsites, and may result in processive elongation (Levengood, J. Am. Chem. Soc. 133, 12758-12766 (2011) and Forsee, J. Biol. Chem. 281, 6283-6289 (2006)). This elongation-bias causes broad product distributions which are skewed towards longer chain lengths (FIG. 17*a*), and underlies the kinetic lag phase commonly observed for polymerizing glycosyltransferases Levengood, M. R., Splain, R. A. & Kiessling, L. L. J. Am. Chem. Soc. 133, 12758-12766 (2011) and Keys Anal. Biochem. 427, 107-115 (2012)). In contrast, the absence of extended interactions with the polysaccharide acceptor confers a distributive mechanism of elongation, characterized by the absence of length-bias during elongation, no kinetic lag phase, and uniform product distributions conforming to a Poisson distribution16 (FIG. 17*b*).

With very few exceptions (Jing, J. Biol. Chem. 279, 42345-42349 (2004)), the polymerizing glycosyltransferases which have been characterized to date exhibit an extended acceptor binding site and broad product distributions—properties which are not amenable to biotechnological applications. The polyST$_{NmB}$ was recently used for enzymatic polysialylation of therapeutic proteins, however, proteins were modified with a range of chain lengths from 4 to >70 residues at each site (Lindhout, Proc. Natl. Acad. Sci. U.S.A. 108, 7397-7402 (2011)). In this case, the assessment of optimal chain length is impossible, and the assessment of the desired modification is weakened due to averaging over many products. In the ideal case, enzymatic modification would be carried out by perfectly distributive enzymes, resulting in uniform chain elongation and a narrow distribution of product lengths (FIG. 17*b*). For successful application of polymerizing glycosyltransferases, strategies to engineer the product distribution are urgently needed.

Pioneering studies on ribonuclease A by delCardayré and Raines (delCardayre, Biochemistry 33, 6031-6037 (1994)) demonstrated that substrate binding could be modified independently of catalytic activity, enabling the introduction of processivity without altering activity. We proposed that this should hold true for polymerizing glycosyltransferases. As no structural data is available to identify residues interacting with the acceptor substrate, we conducted a small neutral drift to explore the polyST$_{NmB}$ sequence space. In a neutral drift, the target protein is subjected to high mutational loads under selection for the native level of catalytic activity, enabling a broad exploration of functional sequence space and facilitating the emergence of new properties (Gupta, Nat. Methods 5, 939-942 (2008)).

Our previous experiments have shown that truncation of the N-terminus of the polyST$_{NmB}$ increases soluble expression with little cost to enzymatic activity (Keys, Anal. Biochem. 427, 60-68 (2012)). The $_{\Delta 25}$polyST$_{NmB}$ was therefore used as the starting point for the neutral drift. In total, three rounds of diversity generation and screening were conducted. An initial error prone PCR library was screened using an in vivo activity assay (Keys, Anal. Biochem. 427, 60-68 (2012)) and sequencing of 122 clones revealed 163 'neutral' amino acid exchanges (FIG. 17). In two subsequent rounds these mutations were shuffled through the sequence with a high frequency of recombination within short sequence elements and high overall mutation rates (see Methods). A second tier of in vitro activity screening of a small number of clones (94 in the second round and 188 in the final screen), using a HPLC based assay (Keys, Anal. Biochem. 427, 107-115 (2012)), ensured that the polySTs maintained a level of activity comparable to the $_{\Delta 25}$polyST$_{NmB}$ reference sequence. The in vitro activity screen also proved to be a bottleneck for genetic diversity with only 21 clones passing into the third round of diversity generation. However, due to high mutagenesis rates, the diversity was sufficient to produce a broad range of elongation phenotypes. Final screening yielded a pool of 51 polymorphic sequences with 7.3±3.0 exchanges per sequence (Supplementary Data Set 1) and a range of activity between approximately 25% and 300% of the reference sequences.

To examine the functional diversity present in the final pool, the reaction time course and pattern of chain elongation was determined for all 51 enzymes. This was achieved using a recently developed fluorescent acceptor, a 1,2-diamino-4,5-methylenedioxybenzene labeled trimer of sialic acid (DMBDP3), with HPLC separation of reaction products (Keys, Anal. Biochem. 427, 107-115 (2012)) adapted to 96-well format (see Methods). In order to be able to distinguish different modes of elongation and make inferences about substrate binding, it is important that reactions are carried out with a large substrate to enzyme ratio (Levengood, J. Am. Chem. Soc. 133, 12758-12766 (2011)), therefore an approximately 100 fold molar excess of the DMB-DP3 acceptor and a 4000 fold molar excess of the donor sugar, CMP-Neu5Ac, were used. The enzymes exhibited diverse reaction kinetics and product profiles suggesting that sequences had indeed drifted in the direction of both processive and distributive mechanisms of elongation. In order to quantify the tendency of each enzyme to produce uniform or disperse product profiles, the product dispersity (Xw/Xn; where Xw is massaverage DP, and Xn is number-average DP) (Stepto, Polym. Int. 59, 23-24 (2010)) was calculated, and the mean dispersity of products over the reaction course was determined for each of the enzymes. The enzymes exhibited a range of mean dispersity values from 1.06-1.33. As a guide, analysis of the $_{\Delta 25}$polyST$_{NmB}$ in the same assay gave a mean dispersity of 1.16, and the dispersity of a uniform polymer sample with Poisson distribution of lengths approaches 1. The sequences were sorted into three categories according to high (>1.2), medium (1.1-1.2), and low (<1.1) dispersity. FIG. 18 shows examples of each category which demonstrate the diverse modes of chain elongation within the pool (results for all analyzed clones are given in Table 4).

The enzymes also exhibited different reaction kinetics which correlated broadly with the measured product dispersity. Enzymes in the high and medium dispersity categories displayed skewed product profiles and kinetic lag phases typical of polymerases with extended substrate binding sites (FIG. 18a and b). In stark contrast are the product profiles and reaction kinetics of enzymes in the low dispersity category. The majority of these enzymes have no lag phase (i.e. initial reaction rate is the maximum observed rate) and uniformly elongate acceptors giving narrow product distributions (FIG. 18c). For the low dispersity clones, the product distributions throughout the reaction closely fit a Poisson distribution, indicating that these enzymes use a distributive mechanism of elongation.

Remarkably, the Lys69Gln mutation is exclusively associated with enzymes in the low dispersity category, which display a distributive mechanism of elongation and Poissonian product distributions. The presence of numerous additional mutations in these enzymes indicates that the Lys69Gln exchange plays a dominant role in determining the mechanism of chain elongation. The molecular mechanism by which a single amino acid exchange potently affects chain elongation is of high interest for the rational engineering of related polymerases. We speculate that the mutation either alters interaction with the growing end of the polysaccharide or blocks entry of the polysaccharide to the extended binding site.

A number of single amino acid exchanges were observed to produce an elongation phenotype. The mutations Arg111His, Lys114Met, Lys143Thr and Lys412Ile increase the strength of interaction with chains of DP>10, increasing the observed lag phase and the dispersity of reaction products compared to $_{\Delta 25}$polyST$_{NmB}$ (FIG. 20). The Lys69Arg, His78Leu and Asn100Ile mutations reduce interaction with the polymer to give a more distributive elongation mechanism (FIG. 20). Interestingly, almost all of the exchanges which were observed to alter the elongation mechanism involve the replacement of large basic amino acids. Together the results indicate that basic residues in the polyST sequence contribute to an extended interaction interface for binding of the polyanionic substrate, and that mutations within this site determine the mechanism of chain elongation.

Previous neutral drift experiments demonstrated that target enzymes were able to maintain native levels of activity under high mutational loads due to the accumulation of "global suppressor mutations", which stabilized the overall protein structure (Gupta, Nat. Methods 5, 939-942 (2008)). To test if this held true in our neutral drift, despite the considerably smaller screening effort, the most highly accumulated exchanges within the pool were cloned and examined. Impressively, the majority of exchanges which were highly accumulated during the neutral drift were observed to increase the yield of activity when present alone in the $_{\Delta25}$polyST$_{NmB}$ sequence (Table 3), and had little or no effect on product distribution. Notably, the Phe460Ile exchange was the most common mutation, present in 51% of the analyzed clones, and more than tripled the yield of activity when present alone in the $_{\Delta25}$polyST$_{NmB}$ sequence. The results are consistent with previous neutral drift experiments (Gupta, Nat. Methods 5, 939-942 (2008)), and suggest that the accumulated mutations may stabilize the polyST structure.

For the biological function of polymerizing glycosyltransferases it is advantageous to have extended interaction interfaces which bind and increase the rate of synthesis of their polysaccharide products. However, for biotechnological applications, the same interface represents a distinct disadvantage, constituting a barrier to the synthesis of uniform oligo- and polysaccharide structures. The results of this study demonstrate that these interaction interfaces can be readily engineered to yield enzymes with a distributive mechanism and product profiles favorable for research and therapeutic applications.

TABLE 3

| Single mutations | | | | | |
|---|---|---|---|---|---|
| Mutation | Frequency in drifted clones | Elongation Phenotype | Mean dispersity | Initial reaction rate* (pmoles/min) | Maximum reaction rate* (pmoles/min) |
| K69R | n.p. | reduced lag | 1.143 | 60 ± 11.2 | 96.2 ± 5.4 |
| H78L | 9% | reduced lag | 1.146 | 121.5 ± 8.5 | 179.7 ± 11.2 |
| N100I | 42% | reduced lag | 1.168 | 120 ± 22.2 | 184.1 ± 14.5 |
| R111H | 32% | exacerbated lag | 1.23 | 93.2 ± 3.5 | 274.1 ± 10.5 |
| K114M | n.p. | exacerbated lag | 1.214 | 92 ± 4.3 | 256.8 ± 2 |
| K143T | n.p. | exacerbated lag | 1.242 | 56.1 ± 8.9 | 220.6 ± 10.2 |
| I151V | n.p. | none | 1.153 | 182.2 ± 11.2 | 329.7 ± 8 |
| K171T | 19% | none | 1.238 | 37.2 ± 5.7 | 150.5 ± 10.9 |
| N180I | 13% | none | 1.21 | 86.6 ± 6.7 | 209.8 ± 1.7 |
| I192V | 21% | none | 1.18 | 135.4 ± 21.7 | 274.9 ± 18.5 |
| I222V | 25% | none | 1.151 | 162.8 ± 2.3 | 278 ± 15.1 |
| I297T | 36% | none | 1.132 | 197.5 ± 3.3 | 317.9 ± 14.1 |
| I323V | 25% | none | 1.184 | 102.6 ± 7.2 | 222.8 ± 4.6 |
| E368V | 32% | none | 1.213 | 50.9 ± 3.4 | 140.4 ± 3 |
| T402S | 21% | none | 1.16 | 133.7 ± 11.2 | 249.8 ± 11.9 |
| K412I | 42% | exacerbated lag | 1.211 | 64.4 ± 2.6 | 237.7 ± 3.9 |
| F460I | 51% | none | 1.194 | 273.8 ± 20.6 | 541.1 ± 16 |
| Δ25polyST$_{NmB}$ | | | 1.181 | 79.8 ± 7 | 195.7 ± 1.9 | n.p Not present.

*Reaction rates are the average ± the standard deviation of 3 separate enzyme preparations (from different colonies) in the same experiment.

TABLE 4

PolyST clones of the neutral pool

| Category | Clone | Mean dispersity | Initial reaction rate (pmoles/min) | Maximum reaction rate (pmoles/min) | Lag phase ($Rate_{max}/Rate_{init}$) | Expression Level (% of soluble protein) |
|---|---|---|---|---|---|---|
| high dispersity | F154 | 1.201 | 57.74 | 217.11 | 3.8 | 1.34 |
| | F117 | 1.202 | 50.74 | 136.81 | 2.7 | 1.33 |
| | F139 | 1.205 | 65.38 | 248.35 | 3.8 | 1.71 |
| | F123 | 1.211 | 50.40 | 168.64 | 3.3 | 1.44 |
| | F162 | 1.212 | 36.57 | 187.99 | 5.1 | 1.33 |
| | F164 | 1.215 | 28.08 | 188.62 | 6.7 | 1.30 |
| | F072 | 1.216 | 131.50 | 650.61 | 4.9 | 1.65 |
| | F015 | 1.219 | 71.27 | 366.88 | 5.1 | 1.50 |
| | F161 | 1.221 | 49.65 | 186.94 | 3.8 | 1.45 |
| | F183 | 1.225 | 40.65 | 166.65 | 4.1 | 1.41 |
| | F126 | 1.236 | 89.80 | 233.34 | 2.6 | 1.25 |
| | F014 | 1.238 | 47.55 | 228.54 | 4.8 | 1.79 |
| | F105 | 1.239 | 37.50 | 198.49 | 5.3 | 1.18 |
| | F024 | 1.243 | 78.18 | 237.61 | 3.0 | 1.84 |
| | F180 | 1.248 | 36.75 | 191.93 | 5.2 | 1.27 |
| | F133 | 1.248 | 37.04 | 180.77 | 4.9 | 1.09 |
| | F102 | 1.280 | 69.54 | 449.11 | 6.5 | 1.65 |
| | F065 | 1.286 | 105.99 | 358.96 | 3.4 | 1.61 |
| | F093 | 1.311 | 61.08 | 261.75 | 4.3 | 2.70 |
| | F074 | 1.326 | 31.06 | 333.17 | 10.7 | 1.40 |
| medium dispersity | F119 | 1.128 | 91.88 | 142.32 | 1.5 | 1.13 |
| | F060 | 1.138 | 182.61 | 320.63 | 1.8 | 1.72 |
| | F069 | 1.148 | 105.44 | 220.62 | 2.1 | 1.48 |
| | F089 | 1.157 | 231.48 | 526.94 | 2.3 | 1.51 |
| | F146 | 1.168 | 130.02 | 258.55 | 2.0 | 1.55 |
| | F179 | 1.169 | 362.79 | 619.09 | 1.7 | 1.75 |
| | F182 | 1.170 | 37.98 | 105.10 | 2.8 | 1.21 |
| | F013 | 1.172 | 62.31 | 198.81 | 3.2 | 1.40 |
| | F043 | 1.175 | 265.16 | 419.78 | 1.6 | 2.29 |
| | F153 | 1.179 | 49.34 | 209.26 | 4.2 | 1.23 |
| | F103 | 1.182 | 119.99 | 324.98 | 2.7 | 1.31 |
| | F032 | 1.185 | 80.91 | 337.12 | 4.2 | 1.76 |
| | F175 | 1.187 | 119.34 | 348.12 | 2.9 | 1.35 |
| | F113 | 1.188 | 52.10 | 190.49 | 3.7 | 1.26 |
| | F036 | 1.188 | 53.16 | 193.45 | 3.6 | 1.26 |
| | F010 | 1.193 | 255.71 | 506.33 | 2.0 | 1.79 |
| | F159 | 1.195 | 94.80 | 214.46 | 2.3 | 1.26 |
| | F087 | 1.198 | 232.60 | 535.45 | 2.3 | 1.84 |
| | F185 | 1.198 | 113.24 | 278.22 | 2.5 | 1.37 |
| low dispersity | F184 | 1.060 | 173.76 | 173.76 | 1.0 | 1.68 |
| | F078 | 1.065 | 122.02 | 122.02 | 1.0 | 1.79 |
| | F079 | 1.067 | 205.99 | 205.99 | 1.0 | 1.53 |
| | F116 | 1.073 | 362.27 | 362.27 | 1.0 | 1.47 |
| | F034 | 1.077 | 79.31 | 79.31 | 1.0 | 1.34 |
| | F008 | 1.078 | 69.62 | 88.66 | 1.3 | 1.50 |
| | F129 | 1.080 | 111.50 | 111.50 | 1.0 | 1.39 |
| | F006 | 1.085 | 38.88 | 49.30 | 1.3 | 1.66 |
| | F138 | 1.087 | 152.25 | 172.60 | 1.1 | 1.35 |
| | F038 | 1.089 | 249.22 | 249.22 | 1.0 | 2.16 |
| | F028 | 1.092 | 76.46 | 134.30 | 1.8 | 1.33 |
| | F051 | 1.095 | 145.70 | 145.70 | 1.0 | 2.40 |
| reference sequence (repeats) | 3775_A | 1.160 | 33.80 | 134.23 | 4.0 | 1.26 |
| | 3775_B | 1.159 | 40.65 | 143.34 | 3.5 | 1.29 |
| | 3775_C | 1.160 | 41.42 | 147.61 | 3.6 | 1.32 |
| | 3775_D | 1.159 | 35.09 | 132.17 | 3.8 | 1.31 |

Discussion

Aiming to identify sequence elements contributing to the extended polysialic acid binding site in the polyST$_{NmB}$, the in vivo and the in vitro assays were combined into a throughput for exploring the polyST sequence space and identifying relationships with the mode of chain elongation. The sequence space was explored using a neutral drift experiment, where the target sequence is subjected to repeated rounds of mutagenesis and selection for the native level of activity (Bershtein, J. Mol. Biol. 379, 1029-1044 (2008) and Gupta, Nature Methods 5, 939-942 (2008)). Starting from the $_{\Delta25}$polyST$_{NmB}$, three rounds of mutagenesis and screening were used to generate a pool of 51 polymorphic sequences (7.3±3.0 amino acid exchanges per sequence) with a range of activity between approximately 25% and 300% of the original sequence. Each of these clones was then characterised in detail using the DMB-DP3 acceptor and HPLC assay. The mutated enzymes exhibited diverse modes of chain elongation. At one end of the spectrum were clones with product distributions suggestive of processive elongation. These clones were characterised by an exacerbated kinetic lag phase, a strong preference for elongated acceptor structures, and highly disperse reaction products. At the other end of the spectrum were clones with a highly distributive mechanism of chain elongation. These were characterised by the absence of a lag phase (i.e. initial reaction rate was the maximum reaction rate), no preference for elongated acceptors, and uniform product distributions.

The diverse elongation phenotypes were associated with specific amino acid exchanges. Remarkably, the Lys69Gln mutation was exclusively associated with the twelve clones exhibiting a distributive mechanism of elongation and the most uniform product distributions, indicating a dominant role for this residue in determining the mechanism of chain elongation. The Lys69Arg, His78Leu and Asn100Ile mutations also resulted in a narrowing of the product distribution, albeit less striking than that of Lys69Gln. In contrast, the mutations Arg111His, Lys114Met, Lys412Ile and Lys143Thr were demonstrated to increase activity specifically with acceptors of >10 residues in length, causing broadening of the product distributions.

The fact that most of the exchanges causing an elongation phenotype involve the replacement of basic amino acids suggests that the polyST's extended binding site is lined with basic residues which interact with the negative carboxyl groups of the polysialic acid chain. It is typical of enzymes which act on polymeric substrates to form many weak interactions with the polymer's repeating structural motifs, which prevents the formation of strong specific interactions and is thought to facilitate movement along the polymer (Breyer, Protein Science 10, 1699-1711 (2001)). However, during the initial stages of an elongation reaction, such an extended interaction interface confers an increasing affinity and increasing rate of transfer to chains which occupy more of the binding subsites (Levengood, J. Am. Chem. Soc. 133, 12758-12766 (2011)). The exact strength and extent of this interaction will sensitively affect the observed product distribution by altering the reaction rate in a chain-length dependent manner. This would explain the impressive diversity of product distributions in the neutral drift pool.

In contrast, a distributive mechanism of elongation indicates the absence of extended interactions with the polysaccharide chain and strictly nonprocessive elongation. Thus, distributive enzymes display no chain-length bias, but uniformly elongate the pool of acceptors resulting in narrow product distributions which approach a Poisson distribution (Chang, Journal of Molecular Biology 93, 219-235 (1975)), as observed for polySTs containing the Lys69Gln exchange. These considerations suggest that the Lys69Gln mutation blocks entry of the polysaccharide to the extended binding site. The proposition that residue 69 is involved in acceptor binding is supported by homology models of the polyST$_{NmB}$ structure which place this residue on a surface exposed loop in the vicinity of the proposed acceptor binding site (F. Freiberger and H. Fuchs, unpublished data).

Importantly, the rapid emergence of different mechanisms of elongation, as observed in this study, indicates that polymerising glycosyltransferases can be readily engineered to provide desired product distributions. Most promising in this respect is the introduction of a distributive mechanism with a single amino acid exchange. Distributive enzymes provide uniform (narrow) product distributions and product length is controlled simply by the ratio of donor to acceptor substrates. These are desirable properties for biotechnological applications where control of polysaccharide length is critical for the synthesis of defined structures and for the testing of optimal chain length for specific applications.

Methods

Molecular biology. Plasmids were isolated using Nucleo-Spin Plasmid™ or Extract™ kits from Machery-Nagel (Steinheim, Germany). Enzymes were purchased from New England Biolabs (Frankfurt, Germany) and all steps carried out according to the manufacturer's instructions. The DNA sequence of the Δ25polySTNmB was optimized for expression in E. coli. according to guidelines set out by Welch and colleagues24 and synthesized by Eurofins MWG Operon (Ebersberg, Germany). The gene was cloned into pET32a-Strep22 via BamHI/NotI restriction sites giving the plasmid p3775.

The first library was created by two rounds of error-prone PCR (epPCR), starting on the p3775 template. Buffer condition 3 (320 µM MnSO4; and an additional 40 µM dGTP) of the Diversify® PCR random mutagenesis kit (Clontec, California, USA) was used with 100 ng of template plasmid in a 50 µl reaction using and the T7/T7-term primer pair (Supplementary Table 2). PCR amplification was carried out with the following program:

```
30 sec at 94° C.

20 sec at 94°
30 sec at 60° C.    ⎤ 25 cycles
1 min at 68° C.     ⎦

5 min at 68° C.
```

Reaction products were separated on an agarose gel, the amplified gene purified with the NucleoSpin Extract™ kit and eluted in 50 µl. Of the eluted product, 3 µl, was used as template in a second epPCR reaction with the same buffer conditions and thermocycler program. The product of the second reaction was cloned via BamHI/NotI restriction sites into the pET32a-Strep vector22.

The protocol for the second library was designed to facilitate a high level of recombination within and between the clusters of high mutability identified from sequencing the first round clones (FIG. 19). Degenerate oligonucleotides encoding all of the diversity observed within short sequence elements were designed and ordered from Sigma-Aldrich (Steinheim, Germany) with the highest available purity (HPLC grade). The degenerate oligonucleotides were used to spike standard gene shuffling reactions with fragments (50-600 bp) of the sequenced first-round clones as template. As the optimal level of degenerate oligonucleotide incorporation could not be known, four reactions with different ratios of [oligonucleotides]:[gene fragments] were used and the reaction products pooled in the final library.

First, 122 plasmids from the first-round clones were pooled and used as template for amplification of the coding sequences using the T7/T7-term primer pair. The amplified product was purified via agarose gel electrophoresis and 1.6 µg was digested with 0.5 units of DNaseI (New England Biolabs, Frankfurt am Main, Germany) in 40 µl volume for 1 min 50 sec at 25° C. The reaction was stopped by addition of 30 mM EDTA and incubation at 75° C. for 10 min. DNaseI products were separated by agarose gel electrophoresis and fragments of 50-600 bp were extracted and purified. Four 30 µl assembly reactions contained either 130 ng, 50 ng, 25 ng or 0 ng of the 38 pooled equimolar oligonucleotides (TK229-TK266; Supplementary Table 2), 130 ng of gene fragments, 3% DMSO, 200 µM dNTPs, 0.5 units Phusion® DNA polymerase (New England Biolabs, Frankfurt am Main, Germany) and Phusion® HF buffer. The four assembly reactions were carried out with the following program:

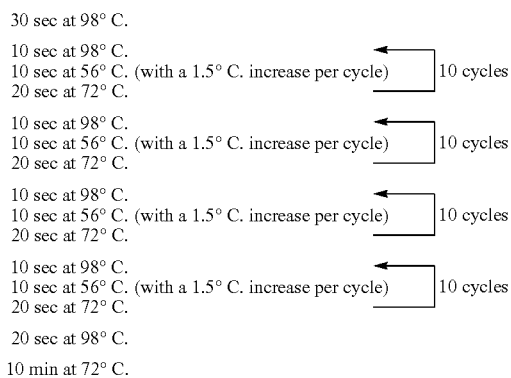

Of each assembly reaction, 5 µl was used as template to amplify full length genes in separate PCRs. Four 50 µl amplification PCRs were carried out with 0.5 units Phusion® DNA polymerase, 6% DMSO, and the TK156/TK157 primer pair (Supplementary Table 2). Reactions were thermocycled according to the following program:

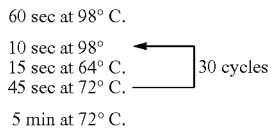

Analysis of 5 µl samples confirmed amplification of similar amounts of the full gene in all reactions. Finally all four reactions were pooled and the products cloned as described for the first library. Sequencing of the library pool ensured incorporation of the desired diversity, and sequencing of 12 random clones indicated a mutation rate of 6±5.9 amino acid exchanges per sequence.

The protocol for the third library was designed to enable fine-grade shuffling of sequences from the second round of screening with no further introduction of mutations. The 22 plasmids from the second-round clones were pooled, coding sequences were amplified and DNaseI digested as above, and gene fragments of 50-200 bp were extracted and purified. A single PCR assembly and amplification reaction was carried out as described above without the addition of synthetic oligonucleotides. The shuffled product was cloned into the expression vector as described above.

In vivo activity screening was carried out as previously described22. Briefly, library DNA was transformed into the screening strain, MB3109. Transformants were plated on Luria-Bertani (LB) agar at ~2000 colonies per 140 mm plate, and grown for 10-12 h at 37° C. until colonies had reached a diameter of 0.5-1 mm. A nitrocellulose membrane was used to copy colonies, then placed colonyside-up onto inducing plates. After incubation for 3 h at 37° C., colonies were lysed and fixed on the membrane and polySia was detected as previously described22. Positive clones were picked from the master plates and the amount of polySia synthesised by each clone was quantified with the same assay in microtiter plate format22. In each round of screening 10,000-20,000 clones were screened and those producing at least 80% of the wild type level of polySia were considered to be neutrally drifting.

Preparation of recombinant protein. Clones for analysis were transformed into BL21-gold(DE3). Colonies were picked into 150 µl LB media with appropriate antibiotics in 96-well flat bottom plates to allow for observation of optical density (OD) on a plate reader (PowerWave 340, BioTek). Dense overnight cultures were diluted 1:20 into 200 µl PowerBroth (AthenaES, Baltimore, Md., USA) and adjusted to uniform OD600. Cultures were grown at 37° C. until OD600≈1.8, then cooled on ice and supplemented with isopropyl β-D-1-thiogalactopyranoside (IPTG) to a final concentration of 0.5 mM. Protein expression was carried out at 15° C. for 20 h with shaking at 1000 rpm. Cultures typically reached an OD600 of 8.0-9.0. Expression cultures were harvested in two 100 µl aliquots, pellets were washed with PBS, and stored at −80° C. until analysis.

For cell lysis, pellets were resuspended in 100 µl lysis buffer (50 mM Tris pH 8.0, 5% glycerol, 200 µg/ml lysozyme, 10 µg/ml Dnase I, 1 mM PMSF) then subjected to two cycles of freeze-sonication (15 min on ice, snap freezing in liquid nitrogen, and thawing in sonication bath at 23° C.). Unlysed cells and debris were removed by centrifugation at 4000 g for 10 min, and cleared lysates were supplemented with 1 mM EDTA. The final cell free extracts were used directly in activity assays and protein determinations.

Polysialyltransferase assays. The in vitro activity of polySTs was determined as previously described18 except that all steps were carried out in 96-well microtiter plates using a 96-channel pipette for accuracy. The recombinant enzymes were assayed at 25° C. in 100 µl volumes containing 50 mM Tris-HCl pH 8.0, 25 mM KCl, 20 mM MgCl2, 5% glycerol, 200-1000 µM CMP-Neu5Ac, and 5.32 µM DMBDP3. Reactions were started by the addition of 25 µl of cell free extract. Reaction samples were quenched by 10-fold dilution in 100 mM Tris-HCl pH 8.0, 20 mM EDTA, followed by 10 min at 50° C. Stopped samples were centrifuged at 4000 g for 1 h prior to HPLC analysis. Separation of 10 µl samples was carried out on a CarboPac PA-100 column as previously described18. During the neutral drift experiments each plate contained two copies of the Δ25polySTNmB reference sequence and clones with at least 25% of the wild type level of activity were considered to be neutrally drifting.

Protein determinations. Total protein concentrations were determined with the BCA assay (Thermo Scientific, Rockford, Ill., USA) according to the manufacturer's instructions.

Determination of polyST expression level was carried out as previously described22. Briefly, samples of cell free extract were separated by 12% SDS-PAGE. For Western blot analysis, proteins were transferred onto PVDF (polyvinylidene fluoride) membranes (LI-COR Biosciences) and detected with 1 µg/ml mouse anti-penta-his antibody (Qiagen) and anti-mouse IR800 (1:20,000, LI-COR Biosciences) and quantified by comparison with protein standards according to the recommendations of the Odyssey infrared imaging system (LI-COR Biosciences).

EXAMPLE 4

Exploring the Capsule Biosynthesis Machinery of NmA with Regard to its Suitability for In Vitro Vaccine Production Introduction

*Neisse

Suppl 2, B71-B77). A major virulence factor of Nm is the negatively charged capsular polysaccharide (CPS). The NmA CPS (CPSA) consists of N-acetyl-mannosamine 1-phosphate units, linked by phosphodiester bonds to give the polymer $[\rightarrow 6)\text{-}\alpha\text{-D-ManpNAc-}(1\rightarrow\text{OPO}_3\rightarrow]_n$ (Liu (1971) JBC 246 (9), 2849-2858). Of note, the six most virulent Nm serogroups (NmA, -B, -C, -W, -Y and -X) wear negative CPSs. Negative charge in CPSA and CPSX is due to the phosphodiester group, while negative charge in CPSB, -C, -W, and -Y results from the incorporation of the sialic acid (Stephens (2009) Vaccine 27 Suppl 2, B71-B77).

Besides of CPSB, which is identical with polysialic acid in the human host, all CPS are immunogenic and cause the production of antibodies that are bacteriotoxic in the presence of complement (Gotschlich (1969) The Journal of experimental medicine 129 (6), 1367-1384; Stephens (2007) Lancet 369 (9580), 2196-2210). In fact, this early observation has made the use of polysaccharide-protein conjugates the gold standard in the development of vaccines against Nm strains. A number of mono- and tetravalent (the latter comprising serogroups A, C, W and Y) conjugate vaccines against Nm have been licensed (Costantino (2011) Expert opinion on drug discovery 6 (10), 1045-1066).

Crucial to the success of vaccination programs in the sub-Saharan meningitis belt is the provision of a safe and high-quality vaccine. MenAfriVac®, a conjugate vaccine with CPSA coupled to tetanus toxoid as carrier protein, has been specifically designed to address these needs (Frasch (2012) Human vaccines & immunotherapeutics 8 (6), 715-724). With under 50 cent per dose (Roberts (2010) Science 330 (6010), 1466-1467), mass vaccination campaigns were possible in Burkina Faso, Mali and Niger and installed herd immunity (Djingarey (2012) Vaccine 30, B40-B45; Caini (2013) Vaccine 31 (12), 1597-1603; LaForce (2011) Eliminating epidemic Group A meningococcal meningitis in Africa through a new vaccine. Health affairs (Project Hope) 30 (6), 1049-1057), protecting not only vaccinated but also non-vaccinated individuals and young children (Kristiansen (2013) Clinical infectious diseases 56 (3), 354-363). Recent progress made with the cloning and functional expression of capsule polymerases (CPs) (Freiberger (2007) Molecular microbiology 65 (5), 1258-1275; Romanow (2013) The Journal of biological chemistry 288 (17), 11718-11730; Peterson (2011) Journal of bacteriology 193 (7), 1576-1582) and the pioneering studies that demonstrate the suitability of the respective recombinant enzymes for the in vitro production of CPSs (McCarthy (2013) Glycoconjugate journal 30 (9), 857-870; Fiebig (2014) Glycobiology 24:150-8), have opened a new perspective for the economic and save production of conjugate vaccines. As NmA is a thread foremost in underdeveloped countries, the development of robust and economic regimes for vaccine production is of utmost relevance. Consequently, the goal of the current study was to isolate the capsular polymerase from NmA and to analyse the capability of the recombinant protein to produce CPSA in vitro. Because the sugar building block UDP-ManNAc is commercially not available, it was clear from the start of this project that a successful production chain depends on the in situ synthesis of UDP-ManNAc from cheap UDP-GlcNAc. Moreover, as CPSA is immunogenic only if O-acetylated (Berry (2002) Infection and immunity 70 (7), 3707-3713), an effective production chain needs, in addition, the O-acetyltransferase, which is able to perform this modification in a nature identical form. Based on these considerations we decided to isolate the three relevant enzymes from NmA and to explore the capacity of the recombinant proteins to work together in vitro to produce bio-identical CPSA.

The chromosomal locus (cps for capsular polysaccharide synthesis) contains the genetic information for CPS synthesis, modification and surface transport. The locus is substructured into six regions: A-D, D' and E (FIG. 21). The sequences encoded in region A are serogroup-specific and encode inter alia the polymerases responsible for CPS synthesis (Harrison (2013) Emerging infectious diseases 19 (4), 566-573). Regions B and C are highly conserved and encode the proteins necessary for export and assembly of the polysaccharide on the cell surface. In NmA, region A comprises four open reading frames (ORF) csaA, -B, -C and -D (previously designated sacA-D or mynA-D). Using insertion-mutagenesis Swartley et al. (1998, Journal of bacteriology 180 (6), 1533-1539) demonstrated that each of these genes is involved in the production of the NmA capsule. In a later study the gene product encoded in csaC was shown to be an acetyltransferase with specificity for the O-3 and O-4 positions in ManNAc (Gudlavalleti (2004) The Journal of biological chemistry 279 (41), 42765-42773). Based on their nucleotide and predicted amino acid sequence, csaA was presumed to encode an UDP-N-acetyl-$_D$-glucosamine 2-epimerase and csaB a capsule polymerase (Swartley (1998) Journal of bacteriology 180 (6), 1533-1539). Additional evidence that CsaB is in fact the NmA specific capsule polymerase arose from the demonstration that it clusters together with CsxA, the proven CP from NmX (Muindi (2014) Glycobiology 24 (2), 139-149; Fiebig Glycobiology. (2014) 24:150-8) in the so called stealth protein family, which comprises exclusively D-hexose-1-phosphoryl transferases (Sperisen (2005) PLoS computational biology 1 (6)).

Here we describe the molecular cloning of the genes csaA, csaB and csaC from NmA, the production of functional recombinant proteins and provide proof for their functional properties. Using a series of synthetic primer compounds the ManNAc-dimer linked together by phosphodiester bonds and carrying a phosphodiester at the reducing end was identified to be the minimal acceptor structure, which was preferred by CsaB if presented in non-acetylated form. Using a two-step production protocol, O-acetylated CPSA was prepared in highly pure form and was recognized by the monoclonal antibody (mAb) 935, suggesting that the in vitro produced polymer represents the bioidentical CPSA.

Results

Cloning and expression of csaA, csaB and csaC; production of recombinant proteins.

Because previous analyses carried out on these genes provided strong evidence that csaA, csaB and csaC encode the UDP-GlcNAc epimerase, the poly-ManNAc-1-phosphoryl transferase (Swartley (1998) Journal of bacteriology 180 (6), 1533-1539) and the O-acetyl transferase (Gudlavalleti (2004) The Journal of biological chemistry 279 (41), 42765-42773), respectively, primers were constructed (see Material and Methods) to amplify these ORFs. The genomic DNA isolated from Nm strain Z2491 was used as a template. Obtained PCR products were cloned into the pET22b-Strep vector (Schwarzer (2009) The Journal of biological chemistry 284 (14), 9465-9474), allowing the expression of recombinant proteins with N-terminal StrepII- and/or C-terminal $His_6$-tag. After transformation into BL21(DE3) and induction of protein expression (see Material and Methods) the distribution of recombinant proteins between the soluble (s) and insoluble (i) fractions of bacterial lysates was analyzed by western blotting against the affinity tags. The recombinant epitope tagged forms of CsaA and CsaC appeared mostly in the soluble fraction (data not shown) and could be purified directly from the bacterial lysates. CsaA was purified by IMAC (immobilized metal ion affinity chromatography) followed by a desalting step and yielded 40 mg protein/L expression culture. Though some additional faint bands were visible in Coosmassie stained SDS-PAGE (FIG. 22A), a protein fraction highly enriched in CsaA was obtained. CsaC was purified following the protocol described by Gudlavalleti (2004, The Journal of biological chemistry 279 (41), 42765-42773) and yielded 96 mg homogenously pure protein/L culture (FIG. 22A).

Similarly, the StrepII-CsaB-His$_6$, encoding the putative poly-ManNAc-1-phosphoryl transferase, was well expressed and appeared with >60% in the soluble fraction. However, the major product revealed with the anti-penta-His antibody in western blot migrated with an apparent molecular mass of 50 kDa, strongly deviating from the calculated molecular mass of 67 kDa (FIG. 22B, left lanes). Because faint signals with molecular masses >50 kDa were additionally displayed with the anti-penta-His antibody, we concluded that StrepII-CsaB-His$_6$ is either prone to N-terminal degradation or translated from an alternative start codon. Consequently, we reinvestigated the NmA genome with bioinformatics techniques. Indeed, two of the used gene prediction softwares (GeNmark and GeNmarkS) retrieved an additional ATG (starting with position 183528 of the NmA genome (NC_003116.1)). In PRODIGAL (Hyatt (2010) BMC bioinformatics 11, 119), the prediction for this second start codon was comparable to the published start codon (base No. 183321; Parkhill (2000) Nature 404 (6777), 502-506).

To investigate if translation from the alternative ATG leads to a stable protein, the corresponding truncation Δ69CsaB was cloned with (StrepII-Δ69-CsaB-His$_6$) and without (Δ69-CsaB-His$_6$) the N-terminal StrepII-tag. Test expressions in BL21(DE3) demonstrated the occurrence of proteins of the expected molecular masses, but in repeated experiments the level of expressed protein was significantly lower than for the full length construct. Moreover, to our surprise, the construct cloned with free N-terminus (Δ69-CsaB-His$_6$) was routinely higher expressed than the StrepII-tagged construct (FIG. 22B). Since rare codons that exist in the CsaB sequence may negatively impact protein expression, csaB was codon optimized (using the DNA 2.0 software and the published codon frequency tables; Welch et al. (2009)) and expression tested with the constructs StrepII-CsaB$_{co}$-His$_6$ and Δ69-CsaB$_{co}$-His$_6$. While increased degradation and concomitantly reduced expression was seen for StrepII-CsaB$_{co}$-His$_6$, Δ69-CsaB$_{co}$-His$_6$ was well expressed and no degradation was detectable in western blot with the anti-penta-His antibody (FIG. 22B).

Consecutively, enzymatic activity within the soluble fractions of the bacterial lysates was determined, with a radioactive incorporation assay previously developed for the poly-GlcNAc-1-phosphoryl transferase from NmX (Fiebig, Glycobiology (2014) 24:150-8). The fractions containing the recombinant CsaB variants were tested in the presence of CsaA and UDP-[$^{14}$C]GlcNAc. In accordance with the levels of expressed protein (FIG. 22B), StrepII-CsaB-His$_6$ and Δ69-CsaB$_{co}$-His$_6$ showed identical activity profiles (FIG. 22C). Based on these results the protein variant Δ69-CsaB$_{co}$-His$_6$ was chosen for further experiments. The protein was purified from the soluble fraction of transformed BL21 (DE3) by IMAC and SEC, yielding 60 mg of highly pure protein from 1 L bacterial culture (FIG. 22E).

Optimization of test conditions and determination of CsaB acceptors. As the donor sugar (UDP-ManNAc) used by CsaB must be produced in situ in the epimerase reaction catalyzed by CsaA, the optimization of test conditions needed the presence of both enzymes. As for CPs of other Nm strains, a hydrolysate of CPSA (CPSA$_{hyd}$) was used to prime the reaction in the presence of the CsaA substrate UDP-GlcNAc. Initial studies carried out to evaluate pH and salt conditions showed best activity values in the presence of 10-20 mM MgCl$_2$ and a pH between 8.0-8.5 (data not shown). Replacement of Mg$^{2+}$ by Ca$^{2+}$ or Mn$^{2+}$ inactivated the enzyme. While these results were similar to what we had seen with CsxA (CP of NmX), the CsaA/CsaB reaction, in contrast to the CsxA reaction, did not show sensitivity against DTT (up to 2 mM were tested).

The natural CPSA is O-acetylated in positions 3 and 4 of ManNAc (Liu (1971) The Journal of biological chemistry 246 (9), 2849-2858; Gudlavalleti et al., Carbohydr Res. 2006), we therefore interrogated if Δ69-CsaB$_{co}$-His$_6$ recognizes and elongates acetylated and non-acetylated CPSA$_{hyd}$ with the same efficiency. Therefore, the hydrolysis of CPSA was carried out before and after base treatment to obtain O-acetylated (CPSA$_{hyd(OAc)}$) and de-O-acetylated (CPSA$_{hyd(deOAc)}$) shorter saccharide chains. Knowing that CPSA hydrolysis results in a large distribution of saccharide chain lengths (ranging in size between degree of polymerization, DP, 1 and 70), anion exchange chromatography was used to separate two fractions, the averaged DP (avDP) 6 (comprising DP1-DP10) and avDP15 (comprising DP10-DP70). Both fractions were used to prime the enzyme reactions as indicated in the subsequent experimental steps.

To quantitatively assess the enzyme reactions, we adapted a spectrophotometric assay previously designed to analyse the CP from NmB (Freiberger (2007) Molecular microbiology 65 (5), 1258-1275). In the multi-enzyme assay shown in FIG. 23, the Δ69-CsaB$_{co}$-His$_6$ catalysed product formation is coupled to NADH consumption, a step, which can be continuously followed at 340 nm.

Using this assay the activity of CsaB was determined with CPSA$_{hyd}$ fractions (CPSA$_{hyd(OAc)}$ CPSA$_{hyd(deOAc)}$) of avDP6 and avDP15 (FIG. 24). Moreover, because we recently demonstrated that the hydroxyl groups at position 6 (C$_6$—OH) on the non-reducing end sugar in CPSA$_{hyd}$ is blocked by phophomonoesters (Ravenscroft (1999) Vaccine 17 (22), 2802-2816), both fractions were additionally tested after treatment with acid phosphatase (de-P) to remove this group. Independent of the size of the primers used to start the reaction, the native acetylated oligomers (CPSA$_{hyd(OAc)}$ of avDP6 and avDP15 CPSA$_{hyd(OAc)}$) were found to be poor acceptors, but activity increased steep after removal of acetyl-groups and even steeper after release of the capping phosphate residue, making CPSA$_{hyd(deOAc)}$-deP the most efficient acceptors. The size of the priming polymers was not of significance for enzymatic activity (FIG. 24; compare avDP6 and avDP15). The obtained results allowed the conclusion that the chain elongation by CsaB proceeds via the non-reducing end and by transfer of ManNAc-1P onto C$_6$—OH groups. Furthermore, since CPSA$_{hyd(deOAc)}$ was a better acceptor than CPSA$_{hyd(OAc)}$, it is likely that O-acetylation takes place on the build polymer.

Because no information on the minimal length of the priming acceptor for CsaB could be derived from the CPSA$_{hyd}$ fractions, we used well characterized synthetic compounds to interrogate this question. The compounds synthesized are shown in FIG. 25 and varied not only in length, but also with respect to O-acetylation (compounds 2, 4, 6 were 3-O-acetylated) and reducing end modifications. In compounds 1, 2, 5, 6 the reducing ends were occupied by a decyl-phosphate-ester, while a methyl group (OMe) was present in the compounds 3 and 4. The Δ69-CsaB$_{co}$-His$_6$ activity did not go beyond background (no acceptor) with compounds 1-4, but, intriguingly, steeply increased with disaccharides carrying a decyl-phosphate-ester at the reducing end (compounds 5, 6) (FIG. 25). With the non-acetylated compound 5, activity values similar to those obtained with the optimized acceptor CPSA$_{hyd(deOAc)}$-deP were measured. In line with the above data (FIG. 24), O-acetylation of compound 5 (resulting in compound 6) reduced the quality of the acceptor. Based on these data, the minimal acceptor recognized by Δ69-CsaB$_{co}$-His$_6$ could be defined as the dimer of ManNAc-1P units linked together by phosphodiester bonds. The presence of a phosphodiester at the reducing end seems obligatory, because compounds ending with OMe groups are not used.

In vitro synthesis of CPSA-chains. To analyze if long CPSA-chains can be produced with the recombinant enzymes, test reactions were carried out having the enzymes Δ69-CsaB$_{co}$-His$_6$ and StrepII-CsaA-His$_6$ at equal concentration (50 nM) and the priming oligosaccharide (CPSA$_{hyd(deOAc)}$-deP of avDP6) in 100-fold molar excess.

Reactions were started by addition of 5 mM UDP-GlcNAc. Control reactions (FIG. 26A control-1-4), in which components were omitted as indicated, were carried out in parallel. After overnight incubation, samples were loaded onto high percentage PAGE and developed by alcian blue/silver staining. CPSA$_{hyd(deOAc)}$-deP of avDP15 was loaded as size marker (FIG. 26A). In the presence of CsaA and CsaB the added oligosaccharide primers were efficiently elongated to long polymer chains (CPSA$_{iv}$, for in vitro produced CPSA). However also in control-1, in the absence of priming compounds, a faint signal indicating long CPSA was seen. In $^{31}$P NMR (FIG. 26B) the products obtained in the main reaction showed the phosphodiester signal, which is characteristic for CPSA as well as the signals that indicate the second reaction product UMP. Unexpected were the signals observed at −5.8 ppm and −9.5 ppm, which indicated the formation of UDP. As these latter signals were most prominent in control-4 (FIG. 26 B), with only StrepII-CsaA-His$_6$ and UDP-GlcNAc present, we speculated that UDP is a side product of the epimerase reaction. Support for this assumption was obtained from literature, were Sala et al (1996; Journal of the American Chemical Society 118, 3033-3034) had shown that UDP-N-acetylglucosamine 2-epimerase from E. coli, if present at high concentration, accumulates UDP and 2-acetamidoglucal, the two intermediates of the epimerization reaction.

Since all relevant $^{31}$P NMR signals were identified also in the product formed in control-1, this faint CPSA signal demonstrated that Δ69-CsaB$_{co}$-His$_6$ is capable to induce product formation de novo in the absence of a priming oligosaccharide. Importantly, this same type of de novo synthesis was shown for the CP of NmX (Fiebig, Glycobiology (2014) 24:150-8). Still, the self-priming capacity came as a surprise in the case of CsaB, were de novo formation of product was not seen if the synthetic compounds 1 or 2 where tested as primers (see FIG. 25).

To reduce UDP-ManNAc hydrolysis and simultaneously complete the incorporation of ManNAc-1P into the product, the ratio between CsaA and CsaB was varied as indicated in FIG. 26C. The reactions carried out as described above with CPSA$_{hyd(deOAc)}$-deP of avDP6 as primer. After overnight incubation, products were separated by HPLC and recorded at 214 nm (CPSA$_{iv}$) and 280 nm (UDP and UMP). As long as the concentration of CsaB was equal or higher than the concentration of CsaA, no hydrolysis of UDP-ManNAc was detectable (FIG. 26C), even not, if the enzymes were present in only 50 nM concentration and the donor sugar was not completely consumed. These data convincingly show that UDP production is a side reaction of the CsaA.

With the intention to produce purified, bio-identical CPSA in milligram amounts, the CsaA/CsaB reaction was up-scaled. The long polymers that were obtained in this reaction were purified by anion exchange chromatography (AEC) using a protocol similar to the one described (Fiebig, Glycobiology (2014) 24:150-8). CPSA$_{iv}$ eluted at NaCl clearly separated from all other reaction components (FIG. 27A). 1 mg of the purified CPSA$_{iv}$ was then used for acetylation with the recombinant CsaC. In a second AEC-step CPSA$_{iv/OAc}$ eluted as a single peak (FIG. 27B) and the obtained material was recognized by mAB 932 in dot blot analysis (FIG. 27C). $^1$H NMR spectra were recorded for CPSA$_{iv}$ and CPSA$_{iv/OAc}$ and were compared to CPSA from natural source (CPSA$_n$) treated (CPSA$_{n/deOAc}$) or not (CPSA$_n$) with alkaline. The congruence of obtained spectra confirmed the bioidentity of the synthetic products (FIG. 27D).

Finally we explored at analytical scale, if bio-identically O-acetylated CPSA can also be produced in the one pot reaction. Therefore, as described above the reaction mixture was supplemented with recombinant CsaC-His$_6$ and acetyl-CoA. Moreover, control reactions, with single compounds missing (see scheme added to FIG. 28) were carried out in parallel. After overnight incubation, products were analyzed by alcian-blue/silver stained high percentage PAGE (FIG. 28A) and immunoblotting with mAb 932 (FIG. 28B). In the presence of all components, a product recognized by mAb 932 was produced (FIG. 28B), indicating that CsaC-His$_6$ can acetylate the produced CPSA in situ. The control reactions carried out in this experiment provided clear evidence for the functional nature of CsaA and CsaC being UDP-GlcNAc/UDP-ManNAc epimerase and O-acetyl-transferase, respectively. Lastly, the similarity (size and concentration) of reaction products identified in lanes 1, 4, and 6 (FIG. 28A) strongly argue for that suitable conditions were installed for all enzymes in the one-pot reaction scheme.

Discussion

Of all pathogenic Nm serogroups, NmA has caused the most disastrous epidemics in sub-saharan Africa. The prevalence of this pathogen caused an unprecedented attempt in terms of developing a highly effective and economic vaccine, MenAfriVac® (Roberts L. Science (2010) 330:1466-7). With coasts of less than 50 cent per dose, MenAfriVac® enabled mass vaccination campaigns in Burkina Faso, Mali and Niger (LaForce (2011) Eliminating epidemic Group A meningococcal meningitis in Africa through a new vaccine. Health affairs (Project Hope) 30 (6), 1049-1057; Djingarey (2012) Vaccine 30, B40-B45; Caini (2013) From Agadez to Zinder: estimating coverage of the MenAfriVacГäö conjugate vaccine against meningococcal serogroup A in Niger, September 2010-January 2012. Vaccine 31 (12), 1597-1603), which installed herd immunity, leading to the protection not only for vaccinated but also for non-vaccinated individuals and in particular for young children (Kristiansen (2013) Clinical infectious diseases 56 (3), 354-363).

All NmA vaccines licensed today are glycoconjugate vaccines, with CPSA oligosaccharides coupled to carrier proteins. CPSA oligosaccharides are thereby hydrolysis products of CPSA isolated from large scale NmA cultures (Bardotti (2008) Vaccine 26 (18), 2284-2296). To avoid the significant coast and biohazard in association with large scale NmA cultures and the pyrogen-free production of polysaccharides, the enzyme catalyzed in vitro synthesis of CPSA would provide an attractive alternative. Towards this goal, we describe in this study, the molecular cloning and functional expression of the three enzymes (UDP-GlcNAc 2-epimerase, CsaA; NmA capsule polymerase, CsaB; O-acetyltransferase, CsaC) that are part of the capsular biosynthesis complex in NmA and represent the minimal number of enzymes needed to produce immunologically active $CPSA_{OAc}$ in vitro starting from economic precursors. Using the well characterized BL21(DE3) strain as expression host, C-terminally $His_6$-tagged versions of CsaA and CsaC could be purified in high quality and remarkable quantity (CsaA 40 mg and CsaC 96 mg per liter bacterial culture).

In CsaB a second start codon was identified starting with methionine-69 bp upstream of the first. Use of this second start codon generated a stable C-terminally $His_6$-tagged protein. However, the level of expressed protein could be significantly increased (to 60 mg/L bacterial culture) after the cDNA sequence was optimized for codon usage in BL21(DE3). If the second start codon is actually used in the natural environment cannot be answered based on the current data. However, because a multi-sequence alignment demonstrated significant similarity between the N-termini of CsaB and other capsule polymerases starting with the first methionine (data not shown), it is likely that the first and not the second start codon is used in the natural environment.

Using a two-step protocol (in test reactions even a one pot reaction; see FIG. 28) 0-acetylated CPSA ($CPSA_{iv/oAc}$) could be produced in vitro in high purity and at medium scale. $CPSA_{iv/OAc}$ was of same length as CPSA isolated from natural source ($CPSA_n$), showed $^{31}$PNMR and $^1$HNMR profiles identical with the natural polymer and was recognized by mAb 932, a standard reagent in the characterization of immunologically active CPSA. Yet it is not proven that acetylation patters exactly mirror the natural product. However, it likely that also NmA glycoconjugate vaccines in which the glycan parts ($CPSA_{hyd}$ of avDP15) are derived from natural polymers by acidic hydrolysis, show some variation in the acetylation patterns. Even though this hydrolysis is carried out under optimized conditions, the probability that acetyl-groups are released is very high.

When the CsaA/CsaB reaction was carried out under suboptimal conditions (meaning that CsaA concentrations were higher than CsaB concentrations) UDP was formed as a side product. Based on control experiments and on earlier literature data the occurrence of UDP indicates that CsaA similar to UDP-N-acetylglucosamine 2-epimerase from *E. coli*, epimerizes UDP-GlcNAc to UDP-ManNAc by forming UDP and 2-acetamidoglucal as intermediate products (Sala (1996) Journal of the American Chemical Society 118, 3033-3034). If present in access, the epimerase releases these intermediates into solution (Sala Journal of the American Chemical Society 118, 3033-3034). Logically, the side reaction was avoided by adjusting the ratio in enzyme concentrations [CsaA]<[CsaB].

O-acetyltransferases from encapsulated bacterial strains have been cloned and functionally characterized (Bergfeld (2007) The Journal of biological chemistry 282 (30), 22217-22227). In these studies addressing also structure-function-relationships the enzymes could be grouped into two families. While O-acetyltransferases of NmW-135 and NmY group into the superfamily of left-handed β-helix (LβH) proteins the O-acetyltransferases isolated from NmA (CsaA) has sequence homology to members of the α/β-hydrolase fold family, harboring a catalytic serine-tried which is part of 'nucleophilic elbow' motif (Bergfeld (2007) The Journal of biological chemistry 282 (30), 22217-22227; Bergfeld (2009) The Journal of biological chemistry 284 (1), 6-16). The α/β-hydrolase fold positions one of the catalytic serine-residues to the tip of a narrow turn. This structural motif may impact substrate recognition by the enzyme.

In the current study, we provide clear evidence that the acceptor quality of $CPSA_{hyd}$ increases significantly after release of O-acetyl-groups. Similarly, the synthetic disaccharide carrying 3-O-Ac-groups on ManNAc (compound 6) was a significantly less efficient primer than the respective compound (5) without O-acetyl-groups. These data argue for that O-acetylation takes place during or after the polymer is formed. This type of size-dependent substrate recognition has already been identified for other O-acetyltransferase that act on sugar polymers. With $CPSA_{hyd}$ a steep increase in activity was seen after dephosphorylation of the non-reducing ends. We previously demonstrated that acidic hydrolysis results (up to 70%) in fragments that are carrying phosphate at the non-reducing end. Since removal of phosphate improved the acceptor quality, it can be concluded that chain elongation proceeds by transfer of monosaccharide-phosphates to the non-reducing end.

The use of the synthetic compounds identified two other important features of CsaB: (i) the minimal efficient acceptor is the dimer and (ii) the reducing end phosphate group can be extended with rather large chemical groups (decyl-ester in the compounds tested in this study). This latter finding bears the perspective that chain elongation can be primed with reagents of very high purity and functional groups that facilitate conjugation of glycans to carrier proteins in the vaccine production chain.

Of note is the fact that CsaB is capable of self-priming. The mechanism underlying the de novo start of chain polymerisation is not understood, but was similarly observed with the CP of NmX (Fiebig, Glycobiology (2014) 24:150-8). In the case of CsaB the interpretation of the phenomenon is however further complicated by the fact that no such reaction was detectable in the presence of the artificial compounds 1-4. A possible explanation may be that these compounds compete against UDP-ManNAc in the active site pocket and thus block the initiation of the chain. However, more experimental work is needed to understand and explain this reaction.

Taken together, our study lays a new basis for the development of efficient and economic protocols with which immunologically active and highly pure $CPSA_{OAc}$ can be synthesized in vitro and used for glycoconjugate vaccine production. We provide initial evidence that $CPSA_{OAc}$ can be produced in a one pot reaction and purified to homogeneity in a single step. The used enzymes are without biohazard and provide the perspective that production chains can be established also in areas that are lacking advanced infrastructural conditions.

Material and Methods

General cloning—The genomic DNA isolated from Nm strain Z2491 was a kind gift from Dr. Heike Claus (Institute for Hygiene and Microbiology, University of Würzburg). The csaB sequence was codon optimized for use in *E. coli* BL21(DE3) using the Gene Designer software package (DNA 2.0) (Villalobos (2006) BMC bioinformatics 7, 285) and the codon frequency tables published by Welch (2009; PloS ONE 4 (9)). The mean codon frequency for each amino acid was calculated from the codon frequency tables FreqA and FreqB (Welch (2009) PloS ONE 4 (9)) and the resulting codon frequency table used as template for the in silico generation of $csaB_{co}$. $csaB_{co}$ flanked 5' by a BamHI site and 3' by a XhoI site was synthesized from Eurofins MWG Operon. All other csaA-C sequences described herein were amplified by polymerase chain reaction (PCR) using the primers shown in Table 4 and genomic DNA from Nm strain Z2491 or csaB$_{co}$ as template. PCR products were cloned via the restriction sites shown in Table 4 into the corresponding sites of the vector pET22b-Strep (Schwarzer (2009) The Journal of biological chemistry 284 (14), 9465-9474) driving the expression of recombinant proteins under the control of the T7 promoter. PCR products digested with BglII were cloned into the BamHI site of pET22b-Strep.

TABLE 4

Primers used in this study.
Restriction sites are highlighted in bold.

| Primer pair | Resulting construct |
|---|---|
| GCGGATCCAAAGTCTTAACC GTCTTTGGC CCGCTCGAGTCTATTCTTTA ATAAAGTTTCTACA | StrepII-CsaA-His$_6$ |
| GCAGATCTTTTATACTTAAT AACAGAAAATGGC CCGCTCGAGTTTCTCAAATG ATGATGGTAATG | StrepII-CsaB-His$_6$ |
| CCGCTCGAGTTTCTCAAATG ATGATGGTAATG GCAGATCTATGTTAATTCCT ATTAATTTTTTAA | StrepII-Δ69-CsaB-His$_6$ |
| CCGCTCGAGTTTCTCAAATG ATGATGGTAATG GCATCTCATATGTTAATTCC TATTAATTTTTTTAATTT | Δ69-CsaB-His$_6$ |
| GCATCTCATATGCTGATCCC GATCAATTTCTTT CCGCTCGAGTTTCTCGAAGG AGCTCGGC | Δ69-CsaB$_{Co}$-His$_6$ |
| CCGCTCGAGTATATTTTGGA TTATGGT GCGGATCCTTATCTAATTTA AAAACAGG | StrepII-CsaC-His$_6$ |

Expression and purification of recombinant CsaA, CsaB and CsaC—Freshly transformed E. coli BL21(DE3) were grown at 15° C. in PowerBroth medium for 18 h. At an optical density of OD$_{600}$=1.0 protein expression was induced by addition of 0.1 mM IPTG and allowed to proceed for a period of 20 h. In test expressions, 0.2 ml of culture-volume were pelleted with 16,000×g for 1 min. Cell pellets were lysed with 0.1 ml lysis buffer (50 mM Tris pH 8.0, 2 mM EDTA, 0.1 mg/ml lysozyme). The lysis was intensified by 3 cycles of sonication (Branson sonifier 450, 100% amplitude) interrupted by 3 min of cooling on ice. Soluble and insoluble fractions were separated by centrifugation (16,000×g, 30 min, 4° C.), the supernatant mixed (1:1) with Laemmli-buffer and used for PAGE as described below.

For protein purification, pellets from 125 mL expression culture were pelleted by centrifugation (6,000×g, 10 min, 4° C.). After a washing step with PBS, cells were re-suspended in 7.5 ml binding buffer (50 mM Tris pH 8.0, 300 mM NaCl) complemented with 40 µg/ml Bestatin (Sigma), 1 µg/ml Pepstatin (Applichem), 100 µM PMSF (Stratagene) and sonified (Branson Digital Sonifier, 50% amplitude, 8×30 s, interrupted by cooling on ice). After centrifugation at 27,000×g for 30 min, the soluble fractions were directly loaded onto a HisTrap columns (GE Healthcare) to enrich the recombinant proteins by immobilized metal ion affinity chromatography (IMAC). Columns were washed with binding buffer (50 mM Tris pH 8.0, 300 mM NaCl) and proteins eluted in step gradients using 10%, 30%, 50% and 100% elution buffer (binding buffer containing 500 mM imidazol). Fractions containing recombinant protein were pooled and the buffer exchanged to storage buffer (50 mM Tris pH 8.0, 50 mM NaCl for CsaA/CsaB; 50 mM Hepes pH 7.05, 100 mM NaCl, 5 mM MgCl2 and 1 mM EDTA for CsaC) using the HiPrep 26/10 Desalting column (GE Healthcare). Isolated proteins were concentrated using Amicon Ultra centrifugal devices (Millipore 30 MWCO). After separation into aliquots, samples were snap frozen in liquid nitrogen and stored at −80° C.

SDS-PAGE and immunoblotting—SDS-PAGE was performed under reducing conditions using 2.5% (v/v) 1-mercaptoethanol and 1.5% (w/v) SDS. Proteins were stained using Roti-Blue (Carl Roth GmbH) according to the manufacturer's guidelines. For western blot analysis samples and standard proteins were blotted onto PVDF membranes (Millipore). His-tagged proteins were detected with 0.5 µg/ml anti-penta-His antibody (Qiagen) and goat anti-mouse IR680 or goat anti-mouse IR800 antibody (LI-COR) as second antibody. Second antibodies were used in a 1:20,000 dilution.

Preparation of CPSA oligosaccharides—CPSA oligosaccharide samples with an averaged degree of polymerization (avDP) of 6 and 15, respectively, were generated by acidic hydrolysis of long CPSA chains isolated from bacterial cultures (CPSA$_n$). Therefore, solutions containing 2.5 mg CPSA/mL sodium acetate buffer (50 mM sodium acetate, pH 4.8) were incubated at 73° C. for 6 h and two pool fractions (avDP 6 and 15, respectively) were purified by anionic exchange chromatography (Q-Sepharose column, GE Healthcare) using a sodium acetate gradient. The avDP and the dispersion of saccharide chains was determined by $^{31}$P NMR and High Performance Anionic Exchange Chromatography-Pulsed Amperometric Detection (HPAEC-PAD) analysis following an established protocol (Berti (2012) Vaccine 30 (45), 6409-6415). If used in enzymatic reactions, hydrolyzed CPSA (CPSA$_{hyd}$) was dephosphorylated (CPSA$_{hyd}$-deP) using acid phosphatase (Sigma) according to the manufacturer's guidelines.

Activity testing of CsaA/CsaB by use of a radioactive assay system—CsxA/CsaB activity was analysed using an adaptation of a radioactive incorporation assay previously described for the N-acetylglucosamine-1-phosphate-transferase from NmX (Fiebig, Glycobiology (2014) 24:150-8). Briefly, assays were carried out with 5 µl of the soluble fractions of bacterial lysates expressing either recombinant CsaB or CsaA (see FIG. 22C) or with purified and epitope-tagged proteins (112 pmol StrepII-CsaA-His$_6$; 88 pmol Δ69CsaB$_{co}$-His$_6$) in a total volume of 25 µl assay buffer (50 mM Tris pH 8.0 or various pH for determination of the pH optimum). Divalent cations were added from stock solutions. The reaction was primed with 5 ng avDP15 and started by the addition of 0.05 µmol UDP-GlcNAc (Calbiochem) containing 0.05 ρCi UDP-[$^{14}$C]-GlcNAc (American Radiolabeled Chemicals). Samples were incubated at 37° C. and 5 µl aliquots spotted onto Whatman 3MM CHR paper after 0, 5, 10 and 30 min. Following descending paper chromatography, the chromatographically immobile $^{14}$C-labeled CPSA was quantified by scintillation counting.

Activity testing of CsaA/CsaB by use of a multi-enzyme spectrophotometric assay—1.2 µM of CsaA and 1 µM CsaB were assayed in the presence of 0.25 mM UDP-GlcNAc (Calbiochem), 20 mM MgCl$_2$ and 50 mM Tris pH 8.0 in a total volume of 100 µL. The consumption of UDP-GlcNAc was coupled to nicotinamide adenine dinucleotide (NADH) consumption using the following enzymes/substrates: 0.25 mM adenosine triphosphate (ATP, Roche), 1 mM phosphoenolpyruvate (PEP, ABCR), 0.3 mM (NADH, Roche), 9-15 units/ml pyruvate kinase, 13.5-21 units/ml lactic dehydrogenase (PK/LDH mix Sigma), 0.05 mg/ml nucleoside monophosphate kinase (Roche). Absorption was measured at 340 nm every 30 min using a Biotek EL 808 96-well plate reader.

Physicochemical analysis of $CPSA_{iv}$. To produce sufficient CPSA ($CPSA_{iv}$) for PAGE and NMR analyses, 0.84 nmol (1.2 µM final) of StrepII-CsaA-$His_6$ and 37.5 pmol (50 nM final) of $\Delta 69 CsaB_{co}$-$His_6$ in reaction buffer (50 mM Tris pH 8.0, 20 mM $MgCl_2$) were incubated with 5 mM UDP-GlcNAc and 6.8 µg of $CPSA_{hyd}$ of avDP6 after de-O-acetylation and dephosphorylation ($CPSA_{hyd(deOAc)}$-deP). The total reaction volume was adjusted to 750 µl. In control 1 also StrepII-CsaA-$His_6$ was used at 50 nM. Reactions as well as control samples were incubated over night at 37° C. 5 µl of each sample were then used for separation on high percentage (25%) PAGE and visualized by a combined Alcian blue/silver staining procedure (Min (1986) Analytical biochemistry 155 (2), 275-285).

The residual sample was freeze-dried, solubilized in 0.75 ml deuterium oxide ($D_2O$, 99.9% atom D; Aldrich) to give a concentration of 0.5-1 mg saccharide and used for product characterization by NMR. All the $^1H$ and $^{31}P$ NMR experiments were recorded as previously described (Fiebig, Glycobiology. (2014) 24:150-8).

HPLC-AEC was performed on a Prominence UFLC-XR (Shimadzu) equipped with a CarboPac PA-100 column (2×250 mm, Dionex). Samples were separated as described by (Keys (2012) Analytical biochemistry 427 (2), 107-115) with the minor adjustment that $H_2O$ and 1M NaCl were used as mobile phases $M_1$ and $M_2$, respectively. 5 µl of the samples were loaded for the detection of nucleotides at 280 nm and 50 µl for the detection of CPSA at 214 nm. Products were separated using an elution gradient consisting of a −2 curved gradient from 0 to 30% $M_2$ over 4 min followed by a linear gradient from 30 to 84% $M_2$ over 33 min. Enzyme concentrations were used as indicated in FIG. 6. All other reactants were used in the amounts described above.

Analysis of 2-acetamidoglucal—Assignments of 1H NMR spectrum were in agreement with those reported in literature (29). $^1H$ NMR ($D_2O$, 400 MHz): δ=6.68 (d, 1 H, $J_{1,2}$ 1.0, H-1), 4.25 (dd, H 1, $J_{3,4}$ 6.5 Hz, H-3), 3.99 (dt, 1 H, $J_{4,5}$ 8.4, $J_{5,6a}$=$J_{5,6b}$ 4.2 Hz, 6.5 Hz, H-5), 3.86 (d, 2 H, H-6), 3.77 (dd, 1 H, H-4), 2.05 (s, 3 H, $CH_3CO$). Significant signals from $^{13}C$ NMR ($D_2O$, 100 MHz): δ=141.47 (C-1), 78.70 (C-5), 68.70 (C-3), 68.36 (C-4), 59.84 (C-6), 21.84 (2×$CH_3CO$).

In vitro synthesis, purification and immunological analysis of $CPSA_{iv}$ and $CPSA_{iv(OAc)}$—To generate $CPSA_{iv}$, 10 nmol CsaA and 16 nmol CsaB were incubated over night at 37° C. in reaction buffer (50 mM Tris pH 8.0, 20 mM $MgCl_2$) complemented with 10 mM UDP-GlcNAc in a total volume of 9 ml. The reaction was primed with 1 µg of $CPSA_{hyd(deOAc)}$-deP of avDP6. Acetylation of 1 mg $CPSA_{iv}$ was performed for 4 h at 37° C. in the presence of 1.2 nmol CsaC and 14 mM acetyl-CoA (Sigma) in a total volume of 0.5 ml acetylation buffer (25 mM Tris pH 7.5, 50 mM NaCl). Both $CPSA_{iv}$ and $CPSA_{iv(OAc)}$ were purified via anion exchange chromatography (AEC) using a MonoQ HR5/5 column (Pharmacia biotech) at a flow rate of 1 ml/min and a linear sodium chloride gradient. CPS containing fractions eluting at 540 mM NaCl were pooled, dialysed (ZelluTrans, Roth, 1 kDa MWCO) against water and freeze dried for further analysis. For dot blot analyses, small aliquots of the purified $CPSA_{iv}$ and $CPSA_{iv(OAc)}$ was spotted onto nitrocellulose (Whatman) and incubated with mAb 932 specifically directed against $CPSA_{(OAc)}$ (mAb 935 was generated in the laboratory of Prof. Dr. D. Bitter-Suermann, Hannover Medical School, Institute for Medical Microbiology, and was kindly provided for this study) in a 1:10,000 dilution. Dot blots were developed with goat anti-mouse IR800 antibody (LI-COR) in 1:20,000 dilution.

EXAMPLE 5

Design and Expression of N- and C-Terminally Truncated CsxA-Constructs Carrying an N-Terminal MBP- and a C-Terminal $His_6$-Tag The materials and methods for this Example are described herein above and also shown in Fiebig, Glycobiology (2014) 24:150-8.

The secondary structure prediction software PHYRE (Kelley et al., 2009, Nat Protoc. 4, 363-371) was used to predict secondary structure elements within the CsxA amino acid sequence. Amplification of csxA using the truncation primers FF52 and FF53, annealing upstream of the conserved region (CR) 1 and downstream of CR2 in unstructured regions where no secondary structure was predicted, resulted in a dN58- or dC99-truncated CsxA, respectively.

The PCR products were cloned into a modified pET43.1 vector enabling the expression of the truncated genes as N-terminally MBP- and C-terminally $His_6$-tagged fusion constructs. After expression in BL21(DE3)Gold followed by lysis of the pelletized cells, soluble fractions were used in a radioactive incorporation assay. Following SDS-PAGE and subsequent immuno-blotting against the $His_6$-tag, the Odyssey-Software could be used to determine the amount of the respective constructs within the soluble and the insoluble fraction. The former was used to normalize the enzymatic activity obtained in the radioactive incorporation assay.

Judging from the western blot (FIG. 30. B), both full-length and truncated CsxA were expressed in good yields. The truncation of the N-terminus increased the ratio of soluble:insoluble construct from 2.4 (full-length) to 4.4, while the truncation of the C-terminus decreased the ratio to 1.2. However, the absolute amount of the ΔC99 truncation within the soluble fraction was comparable to the amount of full-length construct. The amount of ΔN58CsxA was increased by 20%. Of note, the radioactive incorporation assay showed that the activity of both the N-terminal and the C-terminal truncation was increased by 38% and 61%, respectively, if compared to the activity of the full-length construct.

With the aim of analyzing the influence of the termini towards the solubility of CsxA and furthermore defining the minimal catalytic domain of the enzyme, the truncated constructs shown in FIG. 29 were generated. It could be shown that the truncation of the N-terminus by 58 aa resulted in an increase of the ratio of the amount of protein between soluble and insoluble fraction by 80%. Moreover, the enzymatic activity was increased by 38% if compared to the full-length construct.

Group II polymerases are supposed to be part of the capsule transport complex (Steenbergen (2008) Mol. Microbiol. 68, 1252-1267). The improved solubility could indicate that hydrophobic aa within the first 58 aa of the CsxA sequence are exposed on the enzyme's surface to undergo protein-protein interactions with other components of the capsule transport complex.

The truncation of the C-terminus led to an increase of activity by 61% (compared to full-length). However, solubility was reduced by 50%. Since the C-terminus might play a role in the formation of the correct oligomerisation state of CsxA, the loss of the correct oligomerisation of ΔC99CsxA might explain the reduced solubility. However, further investigation is needed to understand these structure-function relationships.

The truncation studies showed that the minimal catalytic domain of CsxA can be reduced to a polypeptide of 329 aa, which corresponds to a reduction of 33% of the full-length sequence. Furthermore, the results indicate that the truncated termini do not contain aa of CsxA's active center.

Further Studies

In later studies, the ΔN58ΔC99 double truncation was generated and cloned, as well as all afore mentioned construct, into optimised expression vectors. The optimised expression vector is described in Fiebig (Glycobiology (2014) 24:150-8) as MBP-CsxA-His$_6$ (tac).

In accordance with the results described above, the truncation of the N-terminus led to an increase in purification yield by more than 500%, whereas the purification yield of the C-terminal truncation was comparable to the full-length construct (FIG. 31C).

Activity of the purified constructs, measured using an adaption of the multi-enzyme assay described by Freiberger et al. (2007, Molecular Microbiology 65, 1258-1275), confirmed the increased activity of both single CsxA truncations (FIG. 31D). However, the activity of the double truncation was comparable to the activity measured for the full-length construct.

Analytical size-exclusion chromatography showed that the C-terminus is not involved in oligomerisation/aggregation, since the C-terminal truncation, as well as the full-length enzyme (see Fiebig, Glycobiology. (2014) 24:150-8) forms aggregates in low salt buffer (FIG. 31A) and tri- to tetrameric assemblies in high salt buffer (FIG. 31B).

EXAMPLE 6

Regulation of ΔC99-CP-X and ΔN58ΔC99-CP-X by the Reaction Time

The materials and methods for this Example are described herein above and also shown in Fiebig, Glycobiology (2014) 24:150-8.

The C-terminally (e.g. ΔC99-CP-X) as well as the C- and N-terminally (e.g. ΔN58ΔC99-CP-X) truncated version of CP-X show a distributive polymerisation (FIG. 32). In addition, for both polypeptides the length of the produced capsular polysaccharides can be regulated via the reaction time (FIG. 32). However, if the C- and N-terminally truncated CP-X is regulated by the reaction time, the polydispersity is lower as it the C-terminally truncated version is used. Therefore, the C- and N-terminally truncated CP-X is the polypeptide which is most suitable for a regulation via the reaction time.

EXAMPLE 7

Production of Capsular Polysaccharides Using a Capsule Polymerase Coupled to a Solid Phase Preparation of the Acceptor Substrate and Determination of the Donor:Acceptor Ratio (d/a).

Oligosaccharide fractions were prepared as described in Example 1 and fractions containing DP2-10 were pooled to get a mixture of short oligosaccharides ranging from DP2-10. Using the ΔN58ΔC99 CsxA truncation, the donor to acceptor ratio was experimentally determined using 10 mM UDP-GlcNAc and variable amounts of acceptor substrate in over-night reactions to give a product distribution ranging from DP10-DP60 (FIG. 34 a). All obtained product pools were within the DP10-DP60 range and the lowest d/a was chosen for the subsequent experiment. In particular, the d/a was approximately between 100:1 and 200:1.

Expression of the Enzyme and Coupling of the Construct to the Column

ΔN58ΔC99 CsxA was expressed in a 50 mL culture volume and purified via His-Trap as described in Fiebig et al 2014a. Briefly, the cells were lysed by sonication in binding buffer (50 mM Tris pH 8.0, 1 mM DTT, 500 mM NaCl) and coupled to a 1 mL His-Trap column. The column was washed with binding buffer containing 37.5 mM imidazole to remove cell debris and non-specifically bound protein before it was equilibrated with a buffer only containing 50 mM Tris pH 8.0 and 1 mM DTT.

Production of CPSX Using ΔN58ΔC99 CsxA Coupled to a Solid Phase

Figure 34A:
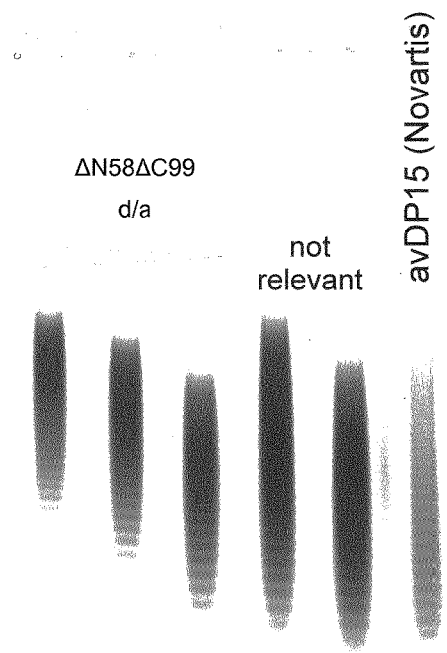

The reaction mix containing 50 mM Tris pH 8.0, 10 mM UDP-GlcNAc, 20 mM MgCl2, 1 mM DTT and the amount of acceptor determined in FIG. 34A was up-scaled to 5 mL and loaded onto the His-Trap column containing the immobilized ΔN58ΔC99 CsxA. The mix was circulated through the column using a Peristaltic P1 pump (GE Healthcare) for 2 h and aliquots were taken every 20 min. Aliquots were snap-frozen in liquid nitrogen and ΔN58ΔC99 CsxA was subsequently inactivated for 2.5 min at 98° C. The analysis was performed using the HPLC-assay described in Example 4.

Figure 34B:
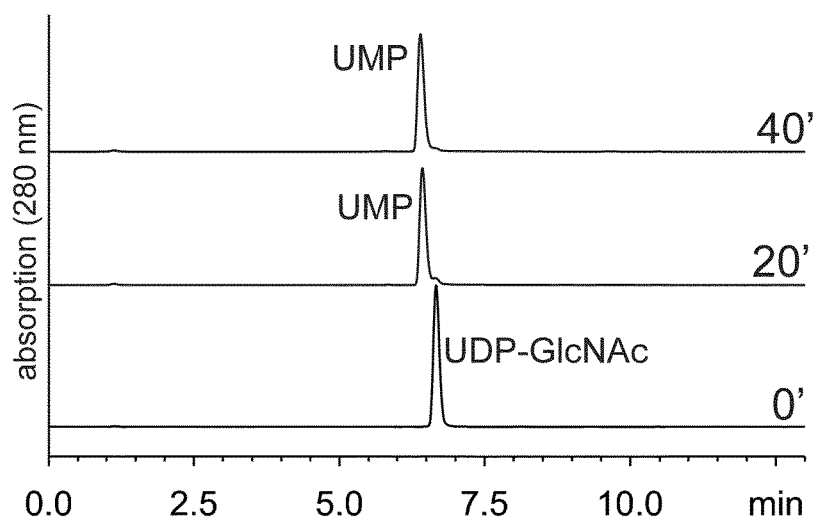
Figure 34C:
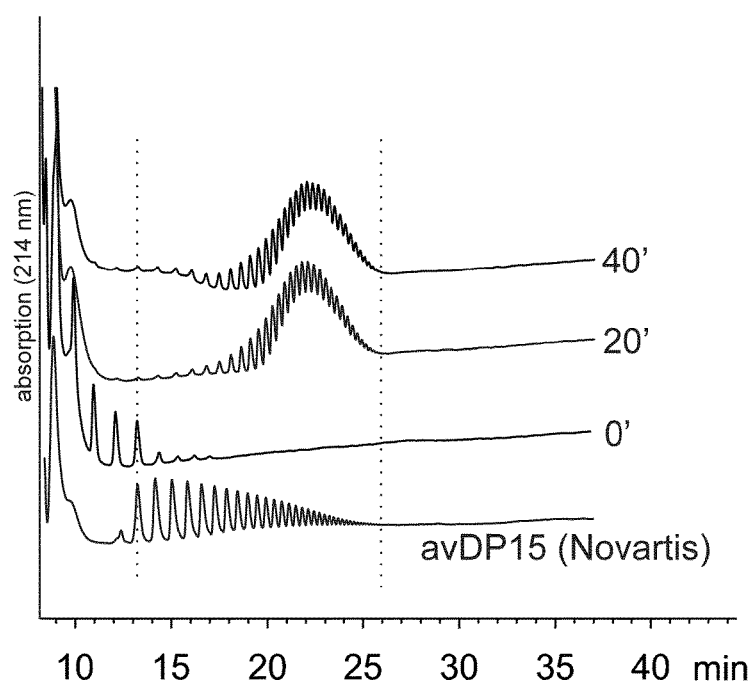
Figure 34D:
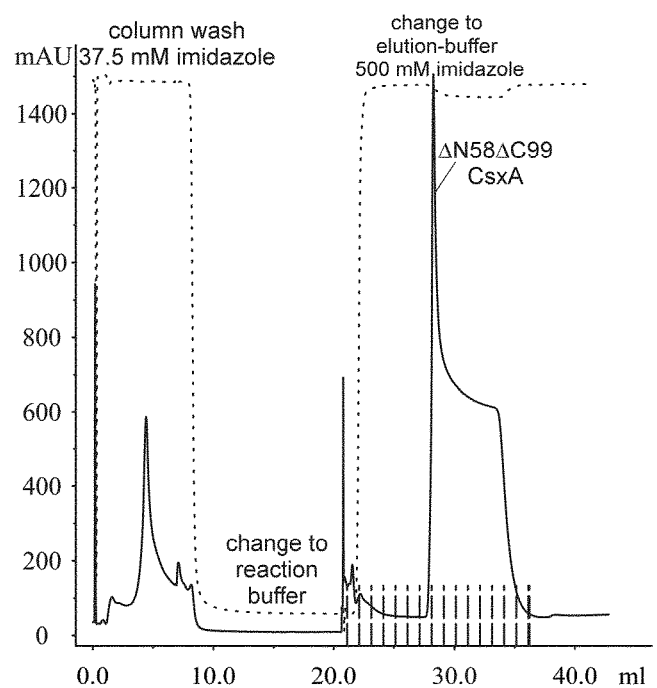

Following the consumption of the donor substrate UDP-GlcNAc and the production of the second reaction product UMP at 280 nm revealed that the reaction was finished after 20 min and shows that ΔN58ΔC99 CsxA is active even if it is bound/coupled to a solid phase (His-Trap beads) (FIG. 34B). Moreover, the HPLC-AEC (214 nm) analysis of the synthesized CPSX revealed that the ability of the distributive ΔN58ΔC99 CsxA to synthesize narrow product distribution is maintained even if the construct is coupled to a solid phase. The enzymatically produced CPSX pool is well within the range of the avDP15 pool (i.e. between DP10 and DP60) which is commonly used for vaccine manufacture (FIG. 24C). ΔN58ΔC99 CsxA was eluted after the reaction had been finished to demonstrate that it remained coupled to the column during the period of the reaction (FIG. 34D). The above presented data demonstrates that CPSX production using CsxA can be performed on a solid phase, thus omitting further purification steps to remove the enzyme from the CPSX fraction.

The present invention refers to the following nucleotide and amino acid sequences:

```
SEQ ID NO: 1:
DNA CP-A/CsaB wildtyp/full-length (1632)
atgtttatacttaataacagaaaatggcgtaaacttaaaagagaccct agcgctttctttcgagatagtaaatttaacttttaagatattttct gctaaaaatttgcaaagaattttaaaaattcatcacatatccataaa actaatataagtaaagctcaatcaaatatttcttcaaccttaaaacaa aatcggaaacaagatatgttaattcctattaatttttttaattttgaa tatatagttaaaaaacttaacaatcaaaacgcaataggtgtatatatt cttccttctaatcttactcttaagcctgcattatgtattctagaatca
``` cataaagaagacttttaaataaatttcttcttactatttcctctgaa aatttaaagcttcaatacaaatttaatggacaaataaaaaatcctaag tccgtaaatgaaatttggacagatttatttagcattgctcatgttgac atgaaactcagcacagatagaactttaagttcatctatatctcaattt tggttcagattagagttctgtaaagaagataaggattttatcttattt cctacagctaacagatattctagaaaactttggaagcactctattaaa aataatcaattatttaaagaaggcatacgaaactattcagaaatatct tcattaccctatgaagaagatcataattttgatattgatttagtattt acttgggtcaactcagaagataagaattggcaagagttatataaaaaa tataagcccgactttaatagcgatgcaaccagtacatcaagattcctt agtagagatgaattaaaattcgcattacgctcttgggaaatgaatgga tccttcattcgaaaaattttattgtctctaattgtgctcccccagca tggctagatttaaataaccctaaaattcaatgggtatatcacgaagaa attatgccacaaagtgcccttcctactttagctcacatgctattgaa accagcttgcaccatataccaggaattagtaactattttatttacagc aatgacgacttcctattaactaaaccattgaataaagacaatttcttc tattcgaatggtattgcaaagttaagattagaagcatggggaaatgtt aatggtgaatgtactgaaggagaacctgactacttaaatggtgctcgc aatgcgaacactctcttagaaaaggaatttaaaaaatttactactaaa ctacatactcactcccctcaatccatgagaactgatattttatttgag atggaaaaaaaatatccagaagagtttaatagaacactacataataaa ttccgatctttagatgatattgcagtaacgggctatctctatcatcat tatgccctactctctggacgagcactacaaagttctgacaagacggaa cttgtacagcaaaatcatgatttcaaaaagaaactaaataatgtagtg accttaactaaagaaaggaattttgacaaacttcctttgagcgtatgt atcaacgatggtgctgatagtcacttgaatgaagaatggaatgttcaa gttattaagttcttagaaactcttttcccattaccatcatcatttgag aaa SEQ ID NO: 2:
DNA CP-A/CsaB codon optimized (without)
ATGTTCATCTTGAACAACCGCAAATGGCGCAAATTGAAGCGTGACCCA

AGCGCGTTTTTTCGTGACAGCAAATTCAACTTTCTGCGCTATTTCTCC

GCGAAAAAGTTTGCGAAGAATTTCAAAAACAGCTCGCATATCCATAAA

ACCAACATTAGCAAAGCGCAGTCCAATATTTCCAGCACCTTGAAGCAG

AACCGTAAGCAGGATATGCTGATCCCGATCAATTTCTTTAATTTTGAG

TACATCGTGAAGAAACTGAATAACCAAAACGCAATCGGCGTGTACATT

CTGCCGTCTAATCTGACCCTGAAACCAGCATTGTGCATCTTGGAGTCG

CACAAAGAGGACTTCCTGAACAAATTTTTGTTGACCATTAGCAGCGAG

AACCTGAAACTGCAGTATAAGTTCAATGGTCAGATCAAAAATCCGAAA

AGCGTGAACGAAATCTGGACCGACCTGTTTAGCATTGCTCACGTCGAC

ATGAAGCTGAGCACCGACCGTACGCTGTCCTCGTCCATCAGCCAATTT

TGGTTTCGCCTGGAGTTCTGTAAAGAGGACAAGGACTTCATCCTGTTT

CCGACGGCAAATCGTTACAGCCGCAAGCTGTGGAAGCACAGCATCAAA

AATAATCAGCTGTTTAAGGAAGGTATCCGTAACTACAGCGAGATTAGC

TCGCTGCCGTACGAGGAAGACCATAACTTCGACATCGATCTGGTCTTT

ACCTGGGTCAATTCGGAAGACAAAAACTGGCAGGAACTGTACAAGAAA

TATAAGCCGGATTTTAATAGCGATGCCACCTCGACGAGCCGTTTTCTG

AGCCGTGACGAGCTGAAGTTTGCGCTGCGCTCGTGGGAAATGAACGGT

AGCTTCATCCGTAAAATCTTTATCGTCAGCAACTGCGCGCCGCCGGCC

TGGCTGGATCTGAACAATCCGAAGATCCAATGGGTGTATCACGAGGAG

ATCATGCCACAGAGCGCCCTGCCAACCTTCAGCAGCCATGCTATTGAG

ACTAGCTTGCATCACATTCCGGGCATCTCCAACTACTTCATCTACTCT

AATGACGATTTTCTGTTGACCAAACCGCTGAACAAAGACAACTTCTTT

TACTCCAACGGTATTGCTAAACTGCGTCTGGAAGCCTGGGGTAACGTT

AACGGTGAATGTACCGAAGGCGAGCCGGATTACCTGAACGGCGCGCGT

AACGCAAATACGCTGCTGGAGAAAGAGTTTAAAAAGTTTACCACCAAG

CTGCACACCCACAGCCCGCAGAGCATGCGTACCGACATCCTGTTCGAG

ATGGAGAAAAAATACCCAGAAGAGTTCAATCGCACGCTGCACAACAAG

TTCCGCAGCCTGGATGACATCGCGGTTACCGGCTACCTGTACCATCAC

TACGCATTGCTGTCTGGCCGCGCTCTGCAATCCAGCGATAAGACCGAA

CTGGTCCAGCAGAATCACGACTTTAAAAAGAAGCTGAATAATGTTGTC

ACCCTGACCAAAGAGCGTAACTTTGATAAGCTGCCGCTGAGCGTTTGT

ATTAATGACGGTGCAGACAGCCACCTGAATGAGGAGTGGAATGTGCAA

GTTATCAAATTCTTGGAGACCTTGTTCCCGTTGCCGAGCTCCTTCGAG

AAA

SEQ ID NO: 3:
DNA ΔN69-CP-A (codon optimized) (1425)
CTGATCCCGATCAATTTCTTTAATTTTGAGTACATCGTGAAGAAACTG

AATAACCAAAACGCAATCGGCGTGTACATTCTGCCGTCTAATCTGACC

CTGAAACCAGCATTGTGCATCTTGGAGTCGCACAAAGAGGACTTCCTG

AACAAATTTTTGTTGACCATTAGCAGCGAGAACCTGAAACTGCAGTAT

AAGTTCAATGGTCAGATCAAAAATCCGAAAAGCGTGAACGAAATCTGG

ACCGACCTGTTTAGCATTGCTCACGTCGACATGAAGCTGAGCACCGAC

CGTACGCTGTCCTCGTCCATCAGCCAATTTTGGTTTCGCCTGGAGTTC

TGTAAAGAGGACAAGGACTTCATCCTGTTTCCGACGGCAAATCGTTAC

AGCCGCAAGCTGTGGAAGCACAGCATCAAAAATAATCAGCTGTTTAAG

GAAGGTATCCGTAACTACAGCGAGATTAGCTCGCTGCCGTACGAGGAA

GACCATAACTTCGACATCGATCTGGTCTTTACCTGGGTCAATTCGGAA

GACAAAAACTGGCAGGAACTGTACAAGAAATATAAGCCGGATTTTAAT

AGCGATGCCACCTCGACGAGCCGTTTTCTGAGCCGTGACGAGCTGAAG

TTTGCGCTGCGCTCGTGGGAAATGAACGGTAGCTTCATCCGTAAAATC

TTTATCGTCAGCAACTGCGCGCCGCCGGCCTGGCTGGATCTGAACAAT

CCGAAGATCCAATGGGTGTATCACGAGGAGATCATGCCACAGAGCGCC

-continued

CTGCCAACCTTCAGCAGCCATGCTATTGAGACTAGCTTGCATCACATT

CCGGGCATCTCCAACTACTTCATCTACTCTAATGACGATTTTCTGTTG

ACCAAACCGCTGAACAAAGACAACTTCTTTTACTCCAACGGTATTGCT

AAACTGCGTCTGGAAGCCTGGGGTAACGTTAACGGTAATGTACCGAA

GGCGAGCCGGATTACCTGAACGGCGCGCGTAACGCAAATACGCTGCTG

GAGAAAGAGTTTAAAAAGTTTACCACCAAGCTGCACACCCACAGCCCG

CAGAGCATGCGTACCGACATCCTGTTCGAGATGGAGAAAAAATACCCA

GAAGAGTTCAATCGCACGCTGCACAACAAGTTCCGCAGCCTGGATGAC

ATCGCGGTTACCGGCTACCTGTACCATCACTACGCATTGCTGTCTGGC

CGCGCTCTGCAATCCAGCGATAAGACCGAACTGGTCCAGCAGAATCAC

GACTTTAAAAAGAAGCTGAATAATGTTGTCACCCTGACCAAAGAGCGT

AACTTTGATAAGCTGCCGCTGAGCGTTTGTATTAATGACGGTGCAGAC

AGCCACCTGAATGAGGAGTGGAATGTGCAAGTTATCAAATTCTTGGAG

ACCTTGTTCCCGTTGCCGAGCTCCTTCGAGAAA

SEQ ID NO: 4:
DNA ΔN97-CP-A (1344)
ccttctaatcttactcttaagcctgcattatgtattctagaatcacat aaagaagacttttaaataaatttcttcttactatttcctctgaaaat ttaaagcttcaatacaaatttaatggacaaataaaaaatcctaagtcc gtaaatgaaatttggacagatttatttagcattgctcatgttgacatg aaactcagcacagatagaactttaagttcatctatatctcaattttgg ttcagattagagttctgtaaagaagataaggattttatcttatttcct acagctaacagatattctagaaaactttggaagcactctattaaaaat aatcaattatttaaagaaggcatacgaaactattcagaaatatcttca ttacctatgaagaagatcataattttgatattgatttagtatttact tgggtcaactcagaagataagaattggcaagagttatataaaaaatat aagcccgactttaatagcgatgcaaccagtacatcaagattccttagt agagatgaattaaaattcgcattacgctcttgggaaatgaatggatcc ttcattcgaaaaattttattgtctctaattgtgctcccccagcatgg ctagatttaaataaccctaaaattcaatgggtatatcacgaagaaatt atgccacaaagtgcccttcctactttagctcacatgctattgaaacc agcttgcaccatataccaggaattagtaactatttatttacagcaat gacgacttcctattaactaaaccattgaataaagacaatttcttctat tcgaatggtattgcaaagttaagattagaagcatggggaaatgttaat ggtgaatgtactgaaggagaacctgactacttaaatggtgctcgcaat gcgaacactctcttagaaaaggaatttaaaaaatttactactaaacta catactcactcccctcaatccatgagaactgatattttatttgagatg gaaaaaaaatatccagaagagtttaatagaacactacataataaattc cgatctttagatgatattgcagtaacgggctatctctatcatcattat gccctactctctggacgagcactacaaagttctgacaagacggaactt gtacagcaaaatcatgatttcaaaaagaaactaaataatgtagtgacc ttaactaaagaaaggaattttgacaaacttcctttgagcgtatgtatc aacgatggtgctgatagtcacttgaatgaagaatggaatgttcaagtt attaagttcttagaaactcttttcccattaccatcatcatttgagaaa SEQ ID NO: 5:
DNA ΔN167-CP-A (1134)
Actttaagttcatctatatctcaattttggttcagattagagttctgt aaagaagataaggattttatcttatttcctacagctaacagatattct agaaaactttggaagcactctattaaaaataatcaattatttaaagaa ggcatacgaaactattcagaaatatcttcattacctatgaagaagat cataattttgatattgatttagtatttacttgggtcaactcagaagat aagaattggcaagagttatataaaaaatataagcccgactttaatagc gatgcaaccagtacatcaagattccttagtagagatgaattaaaattc gcattacgctcttgggaaatgaatggatccttcattcgaaaaattttt attgtctctaattgtgctcccccagcatggctagatttaaataaccct aaaattcaatgggtatatcacgaagaaattatgccacaaagtgccctt cctactttagctcacatgctattgaaaccagcttgcaccatatacca ggaattagtaactatttatttacagcaatgacgacttcctattaact aaaccattgaataaagacaatttcttctattcgaatggtattgcaaag ttaagattagaagcatggggaaatgttaatggtgaatgtactgaagga gaacctgactacttaaatggtgctcgcaatgcgaacactctcttagaa aaggaatttaaaaaatttactactaaactacatactcactcccctcaa tccatgagaactgatattttatttgagatggaaaaaaaatatccagaa gagtttaatagaacactacataataaattccgatctttagatgatatt gcagtaacgggctatctctatcatcattatgccctactctctggacga gcactacaaagttctgacaagacggaacttgtacagcaaaatcatgat ttcaaaaagaaactaaataatgtagtgaccttaactaaagaaaggaat tttgacaaacttcctttgagcgtatgtatcaacgatggtgctgatagt cacttgaatgaagaatggaatgttcaagttattaagttcttagaaact cttttcccattaccatcatcatttgagaaa SEQ ID NO: 6:
DNA ΔN235-CP-A (933)
gatattgatttagtatttacttgggtcaactcagaagataagaattgg caagagttatataaaaaatataagcccgactttaatagcgatgcaacc agtacatcaagattccttagtagagatgaattaaaattcgcattacgc tcttgggaaatgaatggatccttcattcgaaaaattttttattgtctct aattgtgctcccccagcatggctagatttaaataaccctaaaattcaa tgggtatatcacgaagaaattatgccacaaagtgcccttcctactttt agctcacatgctattgaaccagcttgcaccatataccaggaattagt aactatttatttacagcaatgacgacttcctattaactaaaccattg aataaagacaatttcttctattcgaatggtattgcaaagttaagatta gaagcatggggaaatgttaatggtgaatgtactgaaggagaacctgac tacttaaatggtgctcgcaatgcgaacactctcttagaaaaggaattt aaaaaatttactactaaactacatactcactcccctcaatccatgaga -continued actgatattttatttgagatggaaaaaaaatatccagaagagtttaat agaacactacataataaattccgatctttagatgatattgcagtaacg ggctatctctatcatcattatgccctactctctggacgagcactacaa agttctgacaagacggaacttgtacagcaaaatcatgatttcaaaaag aaactaaataatgtagtgaccttaactaaagaaaggaattttgacaaa cttcctttgagcgtatgtatcaacgatggtgctgatagtcacttgaat gaagaatggaatgttcaagttattaagttcttagaaactcttttcccca ttaccatcatcatttgagaaa SEQ ID NO: 7:
DNA ΔC45-CP-A (1497)
tttatacttaataacagaaaatggcgtaaacttaaaagagaccctagc gctttctttcgagatagtaaatttaactttttaagatatttttctgct aaaaaatttgcaagaattttaaaaattcatcacatatccataaaact aatataagtaaagctcaatcaaatatttcttcaaccttaaaacaaaat cggaaacaagatatgttaattcctattaattttttaatttgaatat atagttaaaaaacttaacaatcaaaacgcaataggtgtatatattctt ccttctaatcttactcttaagcctgcattatgtattctagaatcacat aaagaagacttttaaataaatttcttcttactatttcctctgaaaat ttaaagcttcaatacaaatttaatggacaaataaaaaatcctaagtcc gtaaatgaaatttggacagatttatttagcattgctcatgttgacatg aaactcagcacagatagaactttaagttcatctatatctcaattttgg ttcagattagagttctgtaaagaagataaggattttatcttatttcct acagctaacagatattctagaaaactttggaagcactctattaaaaat aatcaattatttaaagaaggcatacgaaactattcagaaatatcttca ttaccctatgaagaagatcataatttgatattgatttagtatttact tgggtcaactcagaagataagaattggcaagagttatataaaaaatat aagcccgactttaatagcgatgcaaccagtacatcaagattccttagt agagatgaattaaaattcgcattacgctcttgggaaatgaatggatcc ttcattcgaaaattttattgtctctaattgtgctcccccagcatgg ctagatttaaataaccctaaaattcaatgggtatatcacgaagaaatt atgccacaaagtgcccttcctacttttagctcacatgctattgaaacc agcttgcaccatataccaggaattagtaactatttttatttacagcaat gacgacttcctattaactaaaccattgaataaagacaatttcttctat tcgaatggtattgcaaagttaagattagaagcatggggaaatgttaat ggtgaatgtactgaaggagaacctgactacttaaatggtgctcgcaat gcgaacactctcttagaaaaggaatttaaaaaatttactactaaacta catactcactcccctcaatccatgagaactgatatttatttgagatg gaaaaaaaatatccagaagagtttaatagaacactacataataaattc cgatctttagatgatattgcagtaacgggctatctctatcatcattat gccctactctctggacgagcactacaaagttctgacaagacggaactt gtacagcaaaatcatgatttcaaaaagaaactaaataatgtagtgacc ttaactaaa SEQ ID NO: 8:
DNA ΔC25-CP-A (1557)
tttatacttaataacagaaaatggcgtaaacttaaaagagaccctagc gctttctttcgagatagtaaatttaactttttaagatatttttctgct aaaaaatttgcaagaattttaaaaattcatcacatatccataaaact aatataagtaaagctcaatcaaatatttcttcaaccttaaaacaaaat cggaaacaagatatgttaattcctattaattttttaatttgaatat atagttaaaaaacttaacaatcaaaacgcaataggtgtatatattctt ccttctaatcttactcttaagcctgcattatgtattctagaatcacat aaagaagacttttaaataaatttcttcttactatttcctctgaaaat ttaaagcttcaatacaaatttaatggacaaataaaaaatcctaagtcc gtaaatgaaatttggacagatttatttagcattgctcatgttgacatg aaactcagcacagatagaactttaagttcatctatatctcaattttgg ttcagattagagttctgtaaagaagataaggattttatcttatttcct acagctaacagatattctagaaaactttggaagcactctattaaaaat aatcaattatttaaagaaggcatacgaaactattcagaaatatcttca ttaccctatgaagaagatcataatttgatattgatttagtatttact tgggtcaactcagaagataagaattggcaagagttatataaaaaatat aagcccgactttaatagcgatgcaaccagtacatcaagattccttagt agagatgaattaaaattcgcattacgctcttgggaaatgaatggatcc ttcattcgaaaattttattgtctctaattgtgctcccccagcatgg ctagatttaaataaccctaaaattcaatgggtatatcacgaagaaatt atgccacaaagtgcccttcctacttttagctcacatgctattgaaacc agcttgcaccatataccaggaattagtaactatttttatttacagcaat gacgacttcctattaactaaaccattgaataaagacaatttcttctat tcgaatggtattgcaaagttaagattagaagcatggggaaatgttaat ggtgaatgtactgaaggagaacctgactacttaaatggtgctcgcaat gcgaacactctcttagaaaaggaatttaaaaaatttactactaaacta catactcactcccctcaatccatgagaactgatatttatttgagatg gaaaaaaaatatccagaagagtttaatagaacactacataataaattc cgatctttagatgatattgcagtaacgggctatctctatcatcattat gccctactctctggacgagcactacaaagttctgacaagacggaactt gtacagcaaaatcatgatttcaaaaagaaactaaataatgtagtgacc ttaactaaagaaaggaattttgacaaacttcctttgagcgtatgtatc aacgatggtgctgatagtcac SEQ ID NO: 9:
AS CP-A/CsaB wildtyp/full-length (544)
MFILNNRKWRKLKRDPSAFFRDSKFNFLRYFSAKKFAKNFKNSSHIHK

TNISKAQSNISSTLKQNRKQDMLIPINFFNFEYIVKKLNNQNAIGVYI

LPSNLTLKPALCILESHKEDFLNKFLLTISSENLKLQYKFNGQIKNPK

-continued

SVNEIWTDLFSIAHVDMKLSTDRTLSSSISQFWFRLEFCKEDKDFILF

PTANRYSRKLWKHSIKNNQLFKEGIRNYSEISSLPYEEDHNFDIDLVF

TWVNSEDKNWQELYKKYKPDFNSDATSTSRFLSRDELKFALRSWEMNG

SFIRKIFIVSNCAPPAWLDLNNPKIQWVYHEEIMPQSALPTFSSHAIE

TSLHHIPGISNYFIYSNDDFLLTKPLNKDNFFYSNGIAKLRLEAWGNV

NGECTEGEPDYLNGARNANTLLEKEFKKFTTKLHTHSPQSMRTDILFE

MEKKYPEEFNRTLHNKFRSLDDIAVTGYLYHHYALLSGRALQSSDKTE

LVQQNHDFKKKLNNVVTLTKERNFDKLPLSVCINDGADSHLNEEWNVQ

VIKFLETLFPLPSSFEK

SEQ ID NO: 10:
AS ΔN69-CP-A (codon optimized) (475)
LIPINFFNFEYIVKKLNNQNAIGVYILPSNLTLKPALCILESHKEDFL

NKFLLTISSENLKLQYKFNGQIKNPKSVNEIWTDLFSIAHVDMKLSTD

RTLSSSISQFWFRLEFCKEDKDFILFPTANRYSRKLWKHSIKNNQLFK

EGIRNYSEISSLPYEEDHNFDIDLVFTWVNSEDKNWQELYKKYKPDFN

SDATSTSRFLSRDELKFALRSWEMNGSFIRKIFIVSNCAPPAWLDLNN

PKIQWVYHEEIMPQSALPTFSSHAIETSLHHIPGISNYFIYSNDDFLL

TKPLNKDNFFYSNGIAKLRLEAWGNVNGECTEGEPDYLNGARNANTLL

EKEFKKFTTKLHTHSPQSMRTDILFEMEKKYPEEFNRTLHNKFRSLDD

IAVTGYLYHHYALLSGRALQSSDKTELVQQNHDFKKKLNNVVTLTKER

NFDKLPLSVCINDGADSHLNEEWNVQVIKFLETLFPLPSSFEK

SEQ ID NO: 11:
AS ΔN97-CP-A (448)
PSNLTLKPALCILESHKEDFLNKFLLTISSENLKLQYKFNGQIKNPKS

VNEIWTDLFSIAHVDMKLSTDRTLSSSISQFWFRLEFCKEDKDFILFP

TANRYSRKLWKHSIKNNQLFKEGIRNYSEISSLPYEEDHNFDIDLVFT

WVNSEDKNWQELYKKYKPDFNSDATSTSRFLSRDELKFALRSWEMNGS

FIRKIFIVSNCAPPAWLDLNNPKIQWVYHEEIMPQSALPTFSSHAIET

SLHHIPGISNYFIYSNDDFLLTKPLNKDNFFYSNGIAKLRLEAWGNVN

GECTEGEPDYLNGARNANTLLEKEFKKFTTKLHTHSPQSMRTDILFEM

EKKYPEEFNRTLHNKFRSLDDIAVTGYLYHHYALLSGRALQSSDKTEL

VQQNHDFKKKLNNVVTLTKERNFDKLPLSVCINDGADSHLNEEWNVQV

IKFLETLFPLPSSFEK

SEQ ID NO: 12:
AS ΔN167-CP-A (378)
TLSSSISQFWFRLEFCKEDKDFILFPTANRYSRKLWKHSIKNNQLFKE

GIRNYSEISSLPYEEDHNFDIDLVFTWVNSEDKNWQELYKKYKPDFNS

DATSTSRFLSRDELKFALRSWEMNGSFIRKIFIVSNCAPPAWLDLNNP

KIQWVYHEEIMPQSALPTFSSHAIETSLHHIPGISNYFIYSNDDFLLT

KPLNKDNFFYSNGIAKLRLEAWGNVNGECTEGEPDYLNGARNANTLLE

KEFKKFTTKLHTHSPQSMRTDILFEMEKKYPEEFNRTLHNKFRSLDDI

AVTGYLYHHYALLSGRALQSSDKTELVQQNHDFKKKLNNVVTLTKERN

FDKLPLSVCINDGADSHLNEEWNVQVIKFLETLFPLPSSFEK

-continued

SEQ ID NO: 13:
AS ΔN235-CP-A (311)
DIDLVFTWVNSEDKNWQELYKKYKPDFNSDATSTSRFLSRDELKFALR

SWEMNGSFIRKIFIVSNCAPPAWLDLNNPKIQWVYHEEIMPQSALPTF

SSHAIETSLHHIPGISNYFIYSNDDFLLTKPLNKDNFFYSNGIAKLRL

EAWGNVNGECTEGEPDYLNGARNANTLLEKEFKKFTTKLHTHSPQSMR

TDILFEMEKKYPEEFNRTLHNKFRSLDDIAVTGYLYHHYALLSGRALQ

SSDKTELVQQNHDFKKKLNNVVTLTKERNFDKLPLSVCINDGADSHLN

EEWNVQVIKFLETLFPLPSSFEK

SEQ ID NO: 14:
AS ΔC45-CP-A (499)
FILNNRKWRKLKRDPSAFFRDSKFNFLRYFSAKKFAKNFKNSSHIHKT

NISKAQSNISSTLKQNRKQDMLIPINFFNFEYIVKKLNNQNAIGVYIL

PSNLTLKPALCILESHKEDFLNKFLLTISSENLKLQYKFNGQIKNPKS

VNEIWTDLFSIAHVDMKLSTDRTLSSSISQFWFRLEFCKEDKDFILFP

TANRYSRKLWKHSIKNNQLFKEGIRNYSEISSLPYEEDHNFDIDLVFT

WVNSEDKNWQELYKKYKPDFNSDATSTSRFLSRDELKFALRSWEMNGS

FIRKIFIVSNCAPPAWLDLNNPKIQWVYHEEIMPQSALPTFSSHAIET

SLHHIPGISNYFIYSNDDFLLTKPLNKDNFFYSNGIAKLRLEAWGNVN

GECTEGEPDYLNGARNANTLLEKEFKKFTTKLHTHSPQSMRTDILFEM

EKKYPEEFNRTLHNKFRSLDDIAVTGYLYHHYALLSGRALQSSDKTEL

VQQNHDFKKKLNNVVTLTK

SEQ ID NO: 15:
AS ΔC25-CP-A (519)
FILNNRKWRKLKRDPSAFFRDSKFNFLRYFSAKKFAKNFKNSSHIHKT

NISKAQSNISSTLKQNRKQDMLIPINFFNFEYIVKKLNNQNAIGVYIL

PSNLTLKPALCILESHKEDFLNKFLLTISSENLKLQYKFNGQIKNPKS

VNEIWTDLFSIAHVDMKLSTDRTLSSSISQFWFRLEFCKEDKDFILFP

TANRYSRKLWKHSIKNNQLFKEGIRNYSEISSLPYEEDHNFDIDLVFT

WVNSEDKNWQELYKKYKPDFNSDATSTSRFLSRDELKFALRSWEMNGS

FIRKIFIVSNCAPPAWLDLNNPKIQWVYHEEIMPQSALPTFSSHAIET

SLHHIPGISNYFIYSNDDFLLTKPLNKDNFFYSNGIAKLRLEAWGNVN

GECTEGEPDYLNGARNANTLLEKEFKKFTTKLHTHSPQSMRTDILFEM

EKKYPEEFNRTLHNKFRSLDDIAVTGYLYHHYALLSGRALQSSDKTEL

VQQNHDFKKKLNNVVTLTKERNFDKLPLSVCINDGADSH

SEQ ID NO: 16:
DNA CP-X/CsxA full-length (1455)
ATTATGAGCAAATTAGCAAATTGGTAACCCACCCAAACCTTTTCTTT

CGAGATTATTTCTTAAAAAAAGCACCGTTAAATTATGGCGAAAATATT

AAACCTTTACCAGTCGAAACCTCTTCTCATAGCAAAAAAAATACAGCC

CATAAAACACCCGTATCATCCGACCAACCAATTGAAGATCCATACCCA

GTAACATTTCCAATTGATGTAGTTTATACTTGGGTAGATTCAGATGAT

GAAAAATTCAATGAAGAACGCCTAAAGTTTCAAAATTCAAGCACATCT

GAGACTCTACAAGGCAAAGCAGAAAGCACCGATATTGCAAGATTCCAA

TCACGCGACGAATTAAAATATTCGATTCGAAGCCTGATGAAGTATGCC

CCATGGGTAAATCATATTTACATTGTAACAAATGGTCAAATACCAAAA

TGGTTAGATACCAACAATACAAAGGTAACGATTATCCCTCACTCAACT

ATTATCGACAGTCAATTTCTCCCTACTTTTAATTCTCACGTCATTGAA

TCCTCTCTATATAAATCCCAGGATTATCAGAGCATTACATTTATTTC

AATGATGATGTCATGCTAGCTAGAGATTTAAGCCCATCTTATTTCTTT

ACAAGCAGCGGATTAGCAAAACTGTTTATTACCAACTCTCGTCTACCA

AATGGCTATAAGAATGTGAAAGACACACCAACCCAATGGGCCTCAAAA

AATTCCCGTGAGCTTTTACATGCAGAAACAGGATTTTGGGCTGAAGCC

ATGTTTGCACATACTTTTCATCCACAACGTAAAAGTGTACATGAATCT

ATTGAACACCTATGGCATGAACAATTAAATGTTTGTCGTCAAAACCGT

TTCCGTGATATTTCAGATATTAACATGGCGACATTCCTGCACCACCAT

TTTGCCATTTTGACAGGCCAAGCTCTTGCTACACGCACTAAATGTATT

TACTTTAACATTCGCTCTCCTCAAGCAGCTCAGCATTACAAAACATTA

TTAGCTCGAAAAGGAAGCGAATACAGCCCACATTCTATCTGCTTAAAT

GATCATACATCGAGCAATAAAAATATTTTATCTAATTACGAAGCCAAA

TTACAAAGCTTTTTAGAAACATACTATCCAGATGTATCAGAAGCAGAA

ATTCTCCTTCCTACTAAATCTGAAGTAGCTGAATTAGTTAAACATAAA

GATTATTTAACTGTATATACTAAATTATTACCTATTATCAATAAGCAG

CTGGTCAATAAATATAATAAACCTTATTCATATCTTTTCTATTATTTA

GGTTTATCTGCCCGGTTTTTATTTGAAGAAACGCAACAAGAACACTAC

CGGGAAACTGCTGAAGAAAATTTACAAATCTTTTGTGGCCTAAACCCA

AAACATACACTAGCCCTCAAATACTTAGCGGATGTCACCCTCACATCA

CAGCCTAGTGGACAA

SEQ ID NO: 17:
DNA ΔN58-CP-X (1284)
CCAATTGAAGATCCATACCCAGTAACATTTCCAATTGATGTAGTTTAT

ACTTGGGTAGATTCAGATGATGAAAAATTCAATGAAGAACGCCTAAAG

TTTCAAAATTCAAGCACATCTGAGACTCTACAAGGCAAAGCAGAAAGC

ACCGATATTGCAAGATTCCAATCACGCGACGAATTAAAATATTCGATT

CGAAGCCTGATGAAGTATGCCCCATGGGTAAATCATATTTACATTGTA

ACAAATGGTCAAATACCAAAATGGTTAGATACCAACAATACAAAGGTA

ACGATTATCCCTCACTCAACTATTATCGACAGTCAATTTCTCCCTACT

TTTAATTCTCACGTCATTGAATCCTCTCTATATAAATCCCAGGATTA

TCAGAGCATTACATTTATTTCAATGATGATGTCATGCTAGCTAGAGAT

TTAAGCCCATCTTATTTCTTTACAAGCAGCGGATTAGCAAAACTGTTT

ATTACCAACTCTCGTCTACCAAATGGCTATAAGAATGTGAAAGACACA

CCAACCCAATGGGCCTCAAAAAATTCCCGTGAGCTTTTACATGCAGAA

ACAGGATTTTGGGCTGAAGCCATGTTTGCACATACTTTTCATCCACAA

CGTAAAAGTGTACATGAATCTATTGAACACCTATGGCATGAACAATTA

AATGTTTGTCGTCAAAACCGTTTCCGTGATATTTCAGATATTAACATG

GCGACATTCCTGCACCACCATTTTGCCATTTTGACAGGCCAAGCTCTT

GCTACACGCACTAAATGTATTTACTTTAACATTCGCTCTCCTCAAGCA

GCTCAGCATTACAAAACATTATTAGCTCGAAAAGGAAGCGAATACAGC

CCACATTCTATCTGCTTAAATGATCATACATCGAGCAATAAAAATATT

TTATCTAATTACGAAGCCAAATTACAAAGCTTTTTAGAAACATACTAT

CCAGATGTATCAGAAGCAGAAATTCTCCTTCCTACTAAATCTGAAGTA

GCTGAATTAGTTAAACATAAAGATTATTTAACTGTATATACTAAATTA

TTACCTATTATCAATAAGCAGCTGGTCAATAAATATAATAAACCTTAT

TCATATCTTTTCTATTATTTAGGTTTATCTGCCCGGTTTTTATTTGAA

GAAACGCAACAAGAACACTACCGGGAAACTGCTGAAGAAAATTTACAA

ATCTTTTGTGGCCTAAACCCAAAACATACACTAGCCCTCAAATACTTA

GCGGATGTCACCCTCACATCACAGCCTAGTGGACAA

SEQ ID NO: 18:
DNA ΔN104-CP-X (1146)
GAAAGCACCGATATTGCAAGATTCCAATCACGCGACGAATTAAAATAT

TCGATTCGAAGCCTGATGAAGTATGCCCCATGGGTAAATCATATTTAC

ATTGTAACAAATGGTCAAATACCAAAATGGTTAGATACCAACAATACA

AAGGTAACGATTATCCCTCACTCAACTATTATCGACAGTCAATTTCTC

CCTACTTTTAATTCTCACGTCATTGAATCCTCTCTATATAAATCCCA

GGATTATCAGAGCATTACATTTATTTCAATGATGATGTCATGCTAGCT

AGAGATTTAAGCCCATCTTATTTCTTTACAAGCAGCGGATTAGCAAAA

CTGTTTATTACCAACTCTCGTCTACCAAATGGCTATAAGAATGTGAAA

GACACACCAACCCAATGGGCCTCAAAAAATTCCCGTGAGCTTTTACAT

GCAGAAACAGGATTTTGGGCTGAAGCCATGTTTGCACATACTTTTCAT

CCACAACGTAAAAGTGTACATGAATCTATTGAACACCTATGGCATGAA

CAATTAAATGTTTGTCGTCAAAACCGTTTCCGTGATATTTCAGATATT

AACATGGCGACATTCCTGCACCACCATTTTGCCATTTTGACAGGCCAA

GCTCTTGCTACACGCACTAAATGTATTTACTTTAACATTCGCTCTCCT

CAAGCAGCTCAGCATTACAAAACATTATTAGCTCGAAAAGGAAGCGAA

TACAGCCCACATTCTATCTGCTTAAATGATCATACATCGAGCAATAAA

AATATTTTATCTAATTACGAAGCCAAATTACAAAGCTTTTTAGAAACA

TACTATCCAGATGTATCAGAAGCAGAAATTCTCCTTCCTACTAAATCT

GAAGTAGCTGAATTAGTTAAACATAAAGATTATTTAACTGTATATACT

AAATTATTACCTATTATCAATAAGCAGCTGGTCAATAAATATAATAAA

CCTTATTCATATCTTTTCTATTATTTAGGTTTATCTGCCCGGTTTTA

TTTGAAGAAACGCAACAAGAACACTACCGGGAAACTGCTGAAGAAAAT

TTACAAATCTTTTGTGGCCTAAACCCAAAACATACACTAGCCCTCAAA

TACTTAGCGGATGTCACCCTCACATCACAGCCTAGTGGACAA

SEQ ID NO: 19:
DNA ΔC174-CP-X (933)
ATTATGAGCAAAATTAGCAAATTGGTAACCCACCCAAACCTTTTCTTT

CGAGATTATTCTTAAAAAAAGCACCGTTAAATTATGGCGAAAATATT

AAACCTTTACCAGTCGAAACCTCTTCTCATAGCAAAAAAAATACAGCC

CATAAAACACCCGTATCATCCGACCAACCAATTGAAGATCCATACCCA

-continued

GTAACATTTCCAATTGATGTAGTTTATACTTGGGTAGATTCAGATGAT

GAAAAATTCAATGAAGAACGCCTAAAGTTTCAAAATTCAAGCACATCT

GAGACTCTACAAGGCAAAGCAGAAAGCACCGATATTGCAAGATTCCAA

TCACGCGACGAATTAAAATATTCGATTCGAAGCCTGATGAAGTATGCC

CCATGGGTAAATCATATTTACATTGTAACAAATGGTCAAATACCAAAA

TGGTTAGATACCAACAATACAAAGGTAACGATTATCCCTCACTCAACT

ATTATCGACAGTCAATTTCTCCCTACTTTTAATTCTCACGTCATTGAA

TCCTCTCTATATAAAATCCCAGGATTATCAGAGCATTACATTTATTTC

AATGATGATGTCATGCTAGCTAGAGATTTAAGCCCATCTTATTTCTTT

ACAAGCAGCGGATTAGCAAAACTGTTTATTACCAACTCTCGTCTACCA

AATGGCTATAAGAATGTGAAAGACACACCAACCCAATGGGCCTCAAAA

AATTCCCGTGAGCTTTTACATGCAGAAACAGGATTTTGGGCTGAAGCC

ATGTTTGCACATACTTTTCATCCACAACGTAAAAGTGTACATGAATCT

ATTGAACACCTATGGCATGAACAATTAAATGTTTGTCGTCAAAACCGT

TTCCGTGATATTTCAGATATTAACATGGCGACATTCCTGCACCACCAT

TTTGCCATTTTGACAGGCCAA

SEQ ID NO: 20:
DNA ΔC99-CP-X (1158)
ATTATGAGCAAAATTAGCAAATTGGTAACCCACCCAAACCTTTTCTTT

CGAGATTATTTCTTAAAAAAAGCACCGTTAAATTATGGCGAAAATATT

AAACCTTTACCAGTCGAAACCTCTTCTCATAGCAAAAAAAATACAGCC

CATAAAACACCCGTATCATCCGACCAACCAATTGAAGATCCATACCCA

GTAACATTTCCAATTGATGTAGTTTATACTTGGGTAGATTCAGATGAT

GAAAAATTCAATGAAGAACGCCTAAAGTTTCAAAATTCAAGCACATCT

GAGACTCTACAAGGCAAAGCAGAAAGCACCGATATTGCAAGATTCCAA

TCACGCGACGAATTAAAATATTCGATTCGAAGCCTGATGAAGTATGCC

CCATGGGTAAATCATATTTACATTGTAACAAATGGTCAAATACCAAAA

TGGTTAGATACCAACAATACAAAGGTAACGATTATCCCTCACTCAACT

ATTATCGACAGTCAATTTCTCCCTACTTTTAATTCTCACGTCATTGAA

TCCTCTCTATATAAAATCCCAGGATTATCAGAGCATTACATTTATTTC

AATGATGATGTCATGCTAGCTAGAGATTTAAGCCCATCTTATTTCTTT

ACAAGCAGCGGATTAGCAAAACTGTTTATTACCAACTCTCGTCTACCA

AATGGCTATAAGAATGTGAAAGACACACCAACCCAATGGGCCTCAAAA

AATTCCCGTGAGCTTTTACATGCAGAAACAGGATTTTGGGCTGAAGCC

ATGTTTGCACATACTTTTCATCCACAACGTAAAAGTGTACATGAATCT

ATTGAACACCTATGGCATGAACAATTAAATGTTTGTCGTCAAAACCGT

TTCCGTGATATTTCAGATATTAACATGGCGACATTCCTGCACCACCAT

TTTGCCATTTTGACAGGCCAAGCTCTTGCTACACGCACTAAATGTATT

TACTTTAACATTCGCTCTCCTCAAGCAGCTCAGCATTACAAAACATTA

TTAGCTCGAAAAGGAAGCGAATACAGCCCACATTCTATCTGCTTAAAT

GATCATACATCGAGCAATAAAAATATTTTATCTAATTACGAAGCCAAA

TTACAAAGCTTTTTAGAAACATACTATCCAGATGTATCAGAAGCAGAA

ATTCTC

SEQ ID NO: 21:
DNA ΔN58ΔC99-CP-X (987)
CCAATTGAAGATCCATACCCAGTAACATTTCCAATTGATGTAGTTTAT

ACTTGGGTAGATTCAGATGATGAAAAATTCAATGAAGAACGCCTAAAG

TTTCAAAATTCAAGCACATCTGAGACTCTACAAGGCAAAGCAGAAAGC

ACCGATATTGCAAGATTCCAATCACGCGACGAATTAAAATATTCGATT

CGAAGCCTGATGAAGTATGCCCCATGGGTAAATCATATTTACATTGTA

ACAAATGGTCAAATACCAAAATGGTTAGATACCAACAATACAAAGGTA

ACGATTATCCCTCACTCAACTATTATCGACAGTCAATTTCTCCCTACT

TTTAATTCTCACGTCATTGAATCCTCTCTATATAAAATCCCAGGATTA

TCAGAGCATTACATTTATTTCAATGATGATGTCATGCTAGCTAGAGAT

TTAAGCCCATCTTATTTCTTTACAAGCAGCGGATTAGCAAAACTGTTT

ATTACCAACTCTCGTCTACCAAATGGCTATAAGAATGTGAAAGACACA

CCAACCCAATGGGCCTCAAAAAATTCCCGTGAGCTTTTACATGCAGAA

ACAGGATTTTGGGCTGAAGCCATGTTTGCACATACTTTTCATCCACAA

CGTAAAAGTGTACATGAATCTATTGAACACCTATGGCATGAACAATTA

AATGTTTGTCGTCAAAACCGTTTCCGTGATATTTCAGATATTAACATG

GCGACATTCCTGCACCACCATTTTGCCATTTTGACAGGCCAAGCTCTT

GCTACACGCACTAAATGTATTTACTTTAACATTCGCTCTCCTCAAGCA

GCTCAGCATTACAAAACATTATTAGCTCGAAAAGGAAGCGAATACAGC

CCACATTCTATCTGCTTAAATGATCATACATCGAGCAATAAAAATATT

TTATCTAATTACGAAGCCAAATTACAAAGCTTTTTAGAAACATACTAT

CCAGATGTATCAGAAGCAGAAATTCTC

SEQ ID NO: 22:
DNA ΔN65ΔC10-CP-X (1233)
GTAACATTTCCAATTGATGTAGTTTATACTTGGGTAGATTCAGATGAT

GAAAAATTCAATGAAGAACGCCTAAAGTTTCAAAATTCAAGCACATCT

GAGACTCTACAAGGCAAAGCAGAAAGCACCGATATTGCAAGATTCCAA

TCACGCGACGAATTAAAATATTCGATTCGAAGCCTGATGAAGTATGCC

CCATGGGTAAATCATATTTACATTGTAACAAATGGTCAAATACCAAAA

TGGTTAGATACCAACAATACAAAGGTAACGATTATCCCTCACTCAACT

ATTATCGACAGTCAATTTCTCCCTACTTTTAATTCTCACGTCATTGAA

TCCTCTCTATATAAAATCCCAGGATTATCAGAGCATTACATTTATTTC

AATGATGATGTCATGCTAGCTAGAGATTTAAGCCCATCTTATTTCTTT

ACAAGCAGCGGATTAGCAAAACTGTTTATTACCAACTCTCGTCTACCA

AATGGCTATAAGAATGTGAAAGACACACCAACCCAATGGGCCTCAAAA

AATTCCCGTGAGCTTTTACATGCAGAAACAGGATTTTGGGCTGAAGCC

ATGTTTGCACATACTTTTCATCCACAACGTAAAAGTGTACATGAATCT

ATTGAACACCTATGGCATGAACAATTAAATGTTTGTCGTCAAAACCGT

TTCCGTGATATTTCAGATATTAACATGGCGACATTCCTGCACCACCAT

```
TTTGCCATTTTGACAGGCCAAGCTCTTGCTACACGCACTAAATGTATT

TACTTTAACATTCGCTCTCCTCAAGCAGCTCAGCATTACAAAACATTA

TTAGCTCGAAAAGGAAGCGAATACAGCCCACATTCTATCTGCTTAAAT

GATCATACATCGAGCAATAAAAATATTTTATCTAATTACGAAGCCAAA

TTACAAAGCTTTTTAGAAACATACTATCCAGATGTATCAGAAGCAGAA

ATTCTCCTTCCTACTAAATCTGAAGTAGCTGAATTAGTTAAACATAAA

GATTATTTAACTGTATATACTAAATTATTACCTATTATCAATAAGCAG

CTGGTCAATAAATATAATAAACCTTATTCATATCTTTTCTATTATTTA

GGTTTATCTGCCCGGTTTTTATTTGAAGAAACGCAACAAGAACACTAC

CGGGAAACTGCTGAAGAAAATTTACAAATCTTTTGTGGCCTAAACCCA

AAACATACACTAGCCCTCAAATACTTAGCGGAT

SEQ ID NO: 23:
DNA ΔN67ΔC99-CP-X (960)
TTTCCAATTGATGTAGTTTATACTTGGGTAGATTCAGATGATGAAAAA

TTCAATGAAGAACGCCTAAAGTTTCAAAATTCAAGCACATCTGAGACT

CTACAAGGCAAAGCAGAAAGCACCGATATTGCAAGATTCCAATCACGC

GACGAATTAAAATATTCGATTCGAAGCCTGATGAAGTATGCCCCATGG

GTAAATCATATTTACATTGTAACAAATGGTCAAATACCAAAATGGTTA

GATACCAACAATACAAAGGTAACGATTATCCCTCACTCAACTATTATC

GACAGTCAATTTCTCCCTACTTTTAATTCTCACGTCATTGAATCCTCT

CTATATAAAATCCCAGGATTATCAGAGCATTACATTTATTTCAATGAT

GATGTCATGCTAGCTAGAGATTTAAGCCCATCTTATTTCTTTACAAGC

AGCGGATTAGCAAAACTGTTTATTACCAACTCTCGTCTACCAAATGGC

TATAAGAATGTGAAAGACACACCAACCCAATGGGCCTCAAAAAATTCC

CGTGAGCTTTTACATGCAGAAACAGGATTTTGGGCTGAAGCCATGTTT

GCACATACTTTTCATCCACAACGTAAAAGTGTACATGAATCTATTGAA

CACCTATGGCATGAACAATTAAATGTTTGTCGTCAAAACCGTTTCCGT

GATATTTCAGATATTAACATGGCGACATTCCTGCACCACCATTTTGCC

ATTTTGACAGGCCAAGCTCTTGCTACACGCACTAAATGTATTTACTTT

AACATTCGCTCTCCTCAAGCAGCTCAGCATTACAAAACATTATTAGCT

CGAAAAGGAAGCGAATACAGCCCACATTCTATCTGCTTAAATGATCAT

ACATCGAGCAATAAAAATATTTTATCTAATTACGAAGCCAAATTACAA

AGCTTTTTAGAAACATACTATCCAGATGTATCAGAAGCAGAAATTCTC

SEQ ID NO: 24:
AS CP-X/CsxA full-length (485)
IMSKISKLVTHPNLFFRDYFLKKAPLNYGENIKPLPVETSSHSKKNTA

HKTPVSSDQPIEDPYPVTFPIDVVYTWVDSDDEKFNEERLKFQNSSTS

ETLQGKAESTDIARFQSRDELKYSIRSLMKYAPWVNHIYIVTNGQIPK

WLDTNNTKVTIIPHSTIIDSQFLPTFNSHVIESSLYKIPGLSEHYIYF

NDDVMLARDLSPSYFFTSSGLAKLFITNSRLPNGYKNVKDTPTQWASK

NSRELLHAETGFWAEAMFAHTFHPQRKSVHESIEHLWHEQLNVCRQNR

FRDISDINMATFLHHHFAILTGQALATRTKCIYFNIRSPQAAQHYKTL

LARKGSEYSPHSICLNDHTSSNKNILSNYEAKLQSFLETYYPDVSEAE

ILLPTKSEVAELVKHKDYLTVYTKLLPIINKQLVNKYNKPYSYLFYYL

GLSARFLFEETQQEHYRETAEENLQIFCGLNPKHTLALKYLADVTLTS

QPSGQ

SEQ ID NO: 25:
AS ΔN58-CP-X (428)
PIEDPYPVTFPIDVVYTWVDSDDEKFNEERLKFQNSSTSETLQGKAES

TDIARFQSRDELKYSIRSLMKYAPWVNHIYIVTNGQIPKWLDTNNTKV

TIIPHSTIIDSQFLPTFNSHVIESSLYKIPGLSEHYIYFNDDVMLARD

LSPSYFFTSSGLAKLFITNSRLPNGYKNVKDTPTQWASKNSRELLHAE

TGFWAEAMFAHTFHPQRKSVHESIEHLWHEQLNVCRQNRFRDISDINM

ATFLHHHFAILTGQALATRTKCIYFNIRSPQAAQHYKTLLARKGSEYS

PHSICLNDHTSSNKNILSNYEAKLQSFLETYYPDVSEAEILLPTKSEV

AELVKHKDYLTVYTKLLPIINKQLVNKYNKPYSYLFYYLGLSARFLFE

ETQQEHYRETAEENLQIFCGLNPKHTLALKYLADVTLTSQPSGQ

SEQ ID NO: 26:
AS ΔN104-CP-X (382)
ESTDIARFQSRDELKYSIRSLMKYAPWVNHIYIVTNGQIPKWLDTNNT

KVTIIPHSTIIDSQFLPTFNSHVIESSLYKIPGLSEHYIYFNDDVMLA

RDLSPSYFFTSSGLAKLFITNSRLPNGYKNVKDTPTQWASKNSRELLH

AETGFWAEAMFAHTFHPQRKSVHESIEHLWHEQLNVCRQNRFRDISDI

NMATFLHHHFAILTGQALATRTKCIYFNIRSPQAAQHYKTLLARKGSE

YSPHSICLNDHTSSNKNILSNYEAKLQSFLETYYPDVSEAEILLPTKS

EVAELVKHKDYLTVYTKLLPIINKQLVNKYNKPYSYLFYYLGLSARFL

FEETQQEHYRETAEENLQIFCGLNPKHTLALKYLADVTLTSQPSGQ

SEQ ID NO: 27:
AS ΔC174-CP-X (311)
IMSKISKLVTHPNLFFRDYFLKKAPLNYGENIKPLPVETSSHSKKNTA

HKTPVSSDQPIEDPYPVTFPIDVVYTWVDSDDEKFNEERLKFQNSSTS

ETLQGKAESTDIARFQSRDELKYSIRSLMKYAPWVNHIYIVTNGQIPK

WLDTNNTKVTIIPHSTIIDSQFLPTFNSHVIESSLYKIPGLSEHYIYF

NDDVMLARDLSPSYFFTSSGLAKLFITNSRLPNGYKNVKDTPTQWASK

NSRELLHAETGFWAEAMFAHTFHPQRKSVHESIEHLWHEQLNVCRQNR

FRDISDINMATFLHHHFAILTGQ

SEQ ID NO: 28:
AS ΔC99-CP-X (386)
IMSKISKLVTHPNLFFRDYFLKKAPLNYGENIKPLPVETSSHSKKNTA

HKTPVSSDQPIEDPYPVTFPIDVVYTWVDSDDEKFNEERLKFQNSSTS

ETLQGKAESTDIARFQSRDELKYSIRSLMKYAPWVNHIYIVTNGQIPK

WLDTNNTKVTIIPHSTIIDSQFLPTFNSHVIESSLYKIPGLSEHYIYF

NDDVMLARDLSPSYFFTSSGLAKLFITNSRLPNGYKNVKDTPTQWASK

NSRELLHAETGFWAEAMFAHTFHPQRKSVHESIEHLWHEQLNVCRQNR

FRDISDINMATFLHHHFAILTGQALATRTKCIYFNIRSPQAAQHYKTL

LARKGSEYSPHSICLNDHTSSNKNILSNYEAKLQSFLETYYPDVSEAE

IL
```

SEQ ID NO: 29:
AS ΔN58ΔC99-CP-X (329)
PIEDPYPVTFPIDVVYTWVDSDDEKFNEERLKFQNSSTSETLQGKAES

TDIARFQSRDELKYSIRSLMKYAPWVNHIYIVTNGQIPKWLDTNNTKV

TIIPHSTIIDSQFLPTFNSHVIESSLYKIPGLSEHYIYFNDDVMLARD

LSPSYFFTSSGLAKLFITNSRLPNGYKNVKDTPTQWASKNSRELLHAE

TGFWAEAMFAHTFHPQRKSVHESIEHLWHEQLNVCRQNRFRDISDINM

ATFLHHHFAILTGQALATRTKCIYFNIRSPQAAQHYKTLLARKGSEYS

PHSICLNDHTSSNKNILSNYEAKLQSFLETYYPDVSEAEIL

SEQ ID NO: 30:
AS ΔN65ΔC10-CP-X (411)
VTFPIDVVYTWVDSDDEKFNEERLKFQNSSTSETLQGKAESTDIARFQ

SRDELKYSIRSLMKYAPWVNHIYIVTNGQIPKWLDTNNTKVTIIPHST

IIDSQFLPTFNSHVIESSLYKIPGLSEHYIYFNDDVMLARDLSPSYFF

TSSGLAKLFITNSRLPNGYKNVKDTPTQWASKNSRELLHAETGFWAEA

MFAHTFHPQRKSVHESIEHLWHEQLNVCRQNRFRDISDINMATFLHHH

FAILTGQALATRTKCIYFNIRSPQAAQHYKTLLARKGSEYSPHSICLN

DHTSSNKNILSNYEAKLQSFLETYYPDVSEAEILLPTKSEVAELVKHK

DYLTVYTKLLPIINKQLVNKYNKPYSYLFYYLGLSARFLFEETQQEHY

RETAEENLQIFCGLNPKHTLALKYLAD

SEQ ID NO: 31:
AS ΔN67ΔC99-CP-X (320)
FPIDVVYTWVDSDDEKFNEERLKFQNSSTSETLQGKAESTDIARFQSR

DELKYSIRSLMKYAPWVNHIYIVTNGQIPKWLDTNNTKVTIIPHSTII

DSQFLPTFNSHVIESSLYKIPGLSEHYIYFNDDVMLARDLSPSYFFTS

SGLAKLFITNSRLPNGYKNVKDTPTQWASKNSRELLHAETGFWAEAMF

AHTFHPQRKSVHESIEHLWHEQLNVCRQNRFRDISDINMATFLHHHFA

ILTGQALATRTKCIYFNIRSPQAAQHYKTLLARKGSEYSPHSICLNDH

TSSNKNILSNYEAKLQSFLETYYPDVSEAEIL

SEQ ID NO: 32:
UDP-GlcNAc-Epimerase (NmA) cloned from Neisseria
meningitidis serogroup A, coding sequence
>UDP-GlcNAc-Epimerase-NmA
(AF019760 REGION: 479..1597)
Atgaaagtcttaaccgtctttggcactcgccctgaagctattaaaatg gcgcctgtaattctagagttacaaaaacataacacaattacttcaaaa gtttgcattactgcacagcatcgtgaaatgctagatcaggttttgagc ctattcgaaatcaaagctgattatgatttaaatatcatgaaacccaac cagagcctacaagaaatcacaacaaatatcatctcaagccttaccgat gttcttgaagatttcaaacctgactgcgtccttgctcacggagacacc acaacaacttttgcagctagccttgctgcattctatcaaaaaatacct gttggccacattgaagcaggcctgagaacttataatttatactctcct tggccagaggaagcaaataggcgtttaacaagcgttctaagccagtgg cattttgcacctactgaagattctaaaaataacttactatctgaatca ataccttctgacaaagttattgttactggaaatactgtcatagatgca ctaatggtatctctagaaaaactaaaaataactacaattaaaaaacaa atggaacaagcttttccatttattcaggacaactctaaagtaatttta attaccgctcatagaagagaaaatcatggggaaggtattaaaaatatt ggactttctatcttagaattagctaaaaaatacccaacattctctttt gtgattccgctccatttaaatcctaacgttagaaaaccaattcaagat ttattatcctctgtgcacaatgttcatcttattgagccacaagaatac ttaccattcgtatatttaatgtctaaaagccatataatattaagtgat tcaggcggcatacaagaagaagctccatccctaggaaaaccagttctt gtattaagagatactacagaacgtcctgaagctgtagctgcaggaact gtaaaattagtaggttctgaaactcaaaatattattgagagctttaca caactaattgaataccctgaatattatgaaaaaatggctaatattgaa aacccttacgggataggtaatgcctcaaaaatcattgtagaaacttta ttaaagaatagataa SEQ ID NO: 33: UDP-GIcNAc-Epimerase (NmA) cloned from *Neisseria meningitidis* serogroup A amino acid sequence
>UDP-GIcNAc-Epimerase-NmA (AAC38285).pro
mkvltvfgtrpeaikmapvilelqkhntitskvcitaqhremldqvls lfeikadydlnimkpnqslgeittniissltdvledfkpdcvlahgdt tttfaaslaafyqkipvghieaglrtynlyspwpeeanrrltsvlsqw hfaptedsknnllsesipsdkvivtgntvidalmvsleklkittikkq megafpfiqdnskvilitahrrenhgegikniglsilelakkyptfsf yiplhlnpnvrkpiqdllssvhnvhliepqeylpfvylmskshiilsd sggiqeeapslgkpvlvlrdtterpeavaagtvklygsetqniiesft qlieypeyyekmanienpygignaskiivetllknr The sequences provided herein (e.g. the sequences corresponding to CP-A or fragments thereof) may be linked to (a) tag(s). For example, the sequences may have a StrepII-thrombin-tag at the N-terminus and/or a his-tag at the C-terminus. The constructs may be prepared by using appropriate restriction sites. For example, CP-A-constructs may be cloned by using BamHI/Bg1II and XhoI. It is mentioned that, if the N-terminus is extended (e.g. by tags), then ATG/Met1 can be omitted. Accordingly, a construct comprising the full length CP-A may comprise not 545 but 544 CP-A-amino acids. SEQ ID NOs: 34 and 37 show an example for a StrepII-thrombin-BamHI/Bg1II-CP-A-XhoI-his construct. In context of the invention, all herein disclosed sequences may be used to produce constructs as demonstrated for CP-A in SEQ ID NOs: 34 and 37.

SEQ ID NO: 34:
DNA StrepII-Thrombin-BamHI/BgIII-CsaB-XhoI-His6
atggctagctggagccacccgcagttcgaaaaaggcgccctggttccg cgtgGATCTttatacttaataacagaaaatggcgtaaacttaaaaga gaccctagcgctttctttcgagatagtaaatttaactttttaagatat ttttctgctaaaaaatttgcaaagaattttaaaaattcatcacatatc cataaaactaatataagtaaagctcaatcaaatatttcttcaacctta aaacaaaatcggaaacaagatatgttaattcctattaatttttttaat tttgaatatatagttaaaaaacttaacaatcaaaacgcaataggtgta

```
tatattcttccttctaatcttactcttaagcctgcattatgtattcta gaatcacataaagaagacttttaaataaatttcttcttactatttcc tctgaaaatttaaagcttcaatacaaatttaatggacaaataaaaat cctaagtccgtaaatgaaatttggacagatttatttagcattgctcat gttgacatgaaactcagcacagatagaactttaagttcatctatatct caattttggttcagattagagttctgtaaagaagataaggattttatc ttatttcctacagctaacagatattctagaaaactttggaagcactct attaaaaataatcaattatttaaagaaggcatacgaaactattcagaa atatcttcattaccctatgaagaagatcataattttgatattgattta gtatttacttgggtcaactcagaagataagaattggcaagagttatat aaaaaatataagcccgactttaatagcgatgcaaccagtacatcaaga ttccttagtagagatgaattaaaattcgcattacgctcttgggaaatg aatggatccttcattcgaaaattttttattgtctctaattgtgctccc ccagcatggctagatttaaataaccctaaaattcaatgggtatatcac gaagaaattatgccacaaagtgcccttcctacttttagctcacatgct attgaaaccagcttgcaccatataccaggaattagtaactattttatt tacagcaatgacgacttcctattaactaaaccattgaataaagacaat ttcttctattcgaatggtattgcaaagttaagattagaagcatgggga aatgttaatggtgaatgtactgaaggagaacctgactacttaaatggt gctcgcaatgcgaacactctcttagaaaaggaatttaaaaaatttact actaaactacatactcactcccctcaatccatgagaactgatatttta tttgagatggaaaaaaaatatccagaagagtttaatagaacactacat aataaattccgatctttagatgatattgcagtaacgggctatctctat catcattatgccctactctctggacgagcactacaaagttctgacaag acggaacttgtacagcaaaatcatgatttcaaaaagaaactaaataat gtagtgaccttaactaaagaaaggaattttgacaaacttcctttgagc gtatgtatcaacgatggtgctgatagtcacttgaatgaagaatggaat gttcaagttattaagttcttagaaactcttttcccattaccatcatca tttgagaaacTCGAGcaccaccaccaccaccac SEQ ID NO: 35:
DNA StrepII-Thrombin-BamHI/BgIII
atggctagctggagccacccgcagttcgaaaaaggcgccctggttccg cgtgGATCT SEQ ID NO: 36:
DNA XhoI-His6
cTCGAGcaccaccaccaccaccac SEQ ID NO: 37:
AS StrepII-Thrombin-BamHI/BgIII-CsaB-XhoI-His6
MASWSHPQFEKGALVPRGSFILNNRKWRKLKRDPSAFFRDSKFNFLRY

FSAKKFAKNFKNSSHIHKTNISKAQSNISSTLKQNRKQDMLIPINFFN

FEYIVKKLNNQNAIGVYILPSNLTLKPALCILESHKEDFLNKFLLTIS

SENLKLQYKFNGQIKNPKSVNEIWTDLFSIAHVDMKLSTDRTLSSSIS

QFWFRLEFCKEDKDFILFPTANRYSRKLWKHSIKNNQLFKEGIRNYSE

ISSLPYEEDHNFDIDLVFTWVNSEDKNWQELYKKYKPDFNSDATSTSR

FLSRDELKFALRSWEMNGSFIRKIFIVSNCAPPAWLDLNNPKIQWVYH

EEIMPQSALPTFSSHAIETSLHHIPGISNYFIYSNDDFLLTKPLNKDN

FFYSNGIAKLRLEAWGNVNGECTEGEPDYLNGARNANTLLEKEFKKFT

TKLHTHSPQSMRTDILFEMEKKYPEEFNRTLHNKFRSLDDIAVTGYLY

HHYALLSGRALQSSDKTELVQQNHDFKKKLNNVVTLTKERNFDKLPLS

VCINDGADSHLNEEWNVQVIKFLETLFPLPSSFEKLEHHHHHH

SEQ ID NO: 38:
AS StrepII-Thrombin-BamHI
MASWSHPQFEKGALVPRGS

SEQ ID NO: 39:
AS XhoI-His6
LEHHHHHH
```

The sequences provided herein (e.g. the sequences corresponding to Δ69-CP-A) may be cloned into the vector by using NdeI/XhoI. SEQ ID NOs: 40 and 43 show an example for a NdeI-ΔN69-CP-A-XhoI-his construct. In context of the invention, all herein disclosed sequences may be used to produce constructs as demonstrated for the codon optimized ΔN69-CP-A in SEQ ID NOs: 40 and 43.

```
SEQ ID NO: 40:
DNA NdeI-dN69CsaB(co)-XhoI-His6
catatgCTGATCCCGATCAATTTCTTTAATTTTGAGTACATCGTGAAG

AAACTGAATAACCAAAACGCAATCGGCGTGTACATTCTGCCGTCTAAT

CTGACCCTGAAACCAGCATTGTGCATCTTGGAGTCGCACAAAGAGGAC

TTCCTGAACAAATTTTTGTTGACCATTAGCAGCGAGAACCTGAAACTG

CAGTATAAGTTCAATGGTCAGATCAAAAATCCGAAAAGCGTGAACGAA

ATCTGGACCGACCTGTTTAGCATTGCTCACGTCGACATGAAGCTGAGC

ACCGACCGTACGCTGTCCTCGTCCATCAGCCAATTTTGGTTTCGCCTG

GAGTTCTGTAAAGAGGACAAGGACTTCATCCTGTTTCCGACGGCAAAT

CGTTACAGCCGCAAGCTGTGGAAGCACAGCATCAAAAATAATCAGCTG

TTTAAGGAAGGTATCCGTAACTACAGCGAGATTAGCTCGCTGCCGTAC

GAGGAAGACCATAACTTCGACATCGATCTGGTCTTTACCTGGGTCAAT

TCGGAAGACAAAAACTGGCAGGAACTGTACAAGAAATATAAGCCGGAT

TTTAATAGCGATGCCACCTCGACGAGCCGTTTTCTGAGCCGTGACGAG

CTGAAGTTTGCGCTGCGCTCGTGGGAAATGAACGGTAGCTTCATCCGT

AAAATCTTTATCGTCAGCAACTGCGCGCCGCCGGCCTGGCTGGATCTG

AACAATCCGAAGATCCAATGGGTGTATCACGAGGAGATCATGCCACAG

AGCGCCCTGCCAACCTTCAGCAGCCATGCTATTGAGACTAGCTTGCAT

CACATTCCGGGCATCTCCAACTACTTCATCTACTCTAATGACGATTTT

CTGTTGACCAAACCGCTGAACAAAGACAACTTCTTTTACTCCAACGGT

ATTGCTAAACTGCGTCTGGAAGCCTGGGGTAACGTTAACGGTGAATGT

ACCGAAGGCGAGCCGGATTACCTGAACGGCGCGCGTAACGCAAATACG

CTGCTGGAGAAAGAGTTTAAAAAGTTTACCACCAAGCTGCACACCCAC

AGCCCGCAGAGCATGCGTACCGACATCCTGTTCGAGATGGAGAAAAAA
```

-continued
TACCCAGAAGAGTTCAATCGCACGCTGCACAACAAGTTCCGCAGCCTG

GATGACATCGCGGTTACCGGCTACCTGTACCATCACTACGCATTGCTG

TCTGGCCGCGCTCTGCAATCCAGCGATAAGACCGAACTGGTCCAGCAG

AATCACGACTTTAAAAAGAAGCTGAATAATGTTGTCACCCTGACCAAA

GAGCGTAACTTTGATAAGCTGCCGCTGAGCGTTTGTATTAATGACGGT

GCAGACAGCCACCTGAATGAGGAGTGGAATGTGCAAGTTATCAAATTC

TTGGAGACCTTGTTCCCGTTGCCGAGCTCCTTCGAGAAAcTCGAGcac caccaccaccaccac

SEQ ID NO: 41:
DNA NdeI
catatg

SEQ ID NO: 42:
DNA XhoI-His6
cTCGAGcaccaccaccaccac

SEQ ID NO: 43:
AS NdeI-dN69CsaB(co)-XhoI-His6
MLIPINFFNFEYIVKKLNNQNAIGVYILPSNLTLKPALCILESHKEDF

LNKFLLTISSENLKLQYKFNGQIKNPKSVNEIWTDLFSIAHVDMKLST

DRTLSSSISQFWFRLEFCKEDKDFILFPTANRYSRKLWKHSIKNNQLF

KEGIRNYSEISSLPYEEDHNFDIDLVFTWVNSEDKNWQELYKKYKPDF

NSDATSTSRFLSRDELKFALRSWEMNGSFIRKIFIVSNCAPPAWLDLN

NPKIQWVYHEEIMPQSALPTFSSHAIETSLHHIPGISNYFIYSNDDFL

LTKPLNKDNFFYSNGIAKLRLEAWGNVNGECTEGEPDYLNGARNANTL

LEKEFKKFTTKLHTHSPQSMRTDILFEMEKKYPEEFNRTLHNKFRSLD

DIAVTGYLYHHYALLSGRALQSSDKTELVQQNHDFKKKLNNVVTLTKE

RNFDKLPLSVCINDGADSHLNEEWNVQVIKFLETLFPLPSSFEKLEHH

HHHH

SEQ ID NO: 44:
AS NdeI
M

SEQ ID NO: 45:
AS XhoI-His6
LEHHHHHH

SEQ ID NO: 46:
DNA ΔN69-CP-A(wt)(1425)
ttaattcctattaattttttaattttgaatatatagttaaaaaactt aacaatcaaaacgcaataggtgtatatattcttccttctaatcttact cttaagcctgcattatgtattctagaatcacataagaagactttta aataaatttcttcttactatttcctctgaaaatttaaagcttcaatac aaatttaatggacaaataaaaaatcctaagtccgtaaatgaaatttgg acagatttatttagcattgctcatgttgacatgaaactcagcacagat agaactttaagttcatctatatctcaattttggttcagattagagttc tgtaaagaagataaggattttatcttatttcctacagctaacagatat tctagaaaactttggaagcactctattaaaaataatcaattatttaaa gaaggcatacgaaactattcagaaatatcttcattaccctatgaagaa gatcataattttgatattgatttagtatttacttgggtcaactcagaa gataagaattggcaagagttatataaaaaatataagcccgactttaat -continued
agcgatgcaaccagtacatcaagattccttagtagagatgaattaaaa ttcgcattacgctcttgggaaatgaatggatccttcattcgaaaaatt tttattgtctctaattgtgctcccccagcatggctagatttaaataac cctaaaattcaatgggtatatcacgaagaaattatgccacaaagtgcc cttcctacttttagctcacatgctattgaaaccagcttgcaccatata ccaggaattagtaactattttatttacagcaatgacgacttcctatta actaaaccattgaataaagacaatttcttctattcgaatggtattgca aagttaagattagaagcatggggaaatgttaatggtgaatgtactgaa ggagaacctgactacttaaatggtgctcgcaatgcgaacactctctta gaaaaggaatttaaaaaatttactactaaactacatactcactcccct caatccatgagaactgatattttatttgagatggaaaaaaaatatcca gaagagtttaatgaacactacataataaattccgatctttagatgat attgcagtaacgggctatctctatcatcattatgccctactctctgga cgagcactacaaagttctgacaagacggaacttgtacagcaaaatcat gatttcaaaaagaaactaaataatgtagtgaccttaactaaagaaagg aattttgacaaacttcctttgagcgtatgtatcaacgatggtgctgat agtcacttgaatgaagaatggaatgttcaagttattaagttcttagaa actcttttcccattaccatcatcatttgagaaa The sequences provided herein (e.g. the sequences corresponding to CP-X or fragments thereof) may be linked to (a) tag(s). For example, the sequences may have an N-terminal MBP-tag followed by the protease resistant linker S3N10, and/or a C-terminal his-tag. The sequences provided herein (e.g. the sequences corresponding to CP-X or fragments thereof) may be cloned into the vector by using the restriction sites BamHI and/or XhoI. In particular in the constructs of CP-X (or fragments thereof), if the N-terminus is not truncated, then the ATG1/Met1 may not be in the construct. SEQ ID NOs: 47 and 49 show an example for a MBP-S3N10-BamHI-CP-X-XhoI-his construct. In context of the invention, all herein disclosed sequences may be used to produce constructs as demonstrated for CP-X in SEQ ID NOs: 47 and 49.

SEQ ID NO: 47:
DNA MBP-S3N10-BamHI-CsxA-Xho1-His6
atgaaaactgaagaaggtaaactggtaatctggattaacggcgataa aggctataacggtctcgctgaagtcggtaagaaattcgagaaagata ccggaattaaagtcaccgttgagcatccggataaactggaagagaaa ttcccacaggttgcggcaactggcgatggccctgacattatcttctg ggcacacgaccgctttggtggctacgctcaatctggcctgttggctg aaatcaccccggacaaagcgttccaggacaagctgtatccgtttacc tgggatgccgtacgttacaacggcaagctgattgcttacccgatcgc tgttgaagcgttatcgctgatttataacaaagatctgctgccgaacc cgccaaaaacctgggaagagatcccggcgctggataaagaactgaaa gcgaaaggtaagagcgcgctgatgttcaacctgcaagaaccgtactt cacctggccgctgattgctgctgacgggggttatgcgttcaagtatg -continued
```
aaaacggcaagtacgacattaaagacgtgggcgtggataacgctggc
gcgaaagcgggtctgaccttcctggttgacctgattaaaaacaaaca
catgaatgcagacaccgattactccatcgcagaagctgcctttaata
aaggcgaaacagcgatgaccatcaacggcccgtgggcatggtccaac
atcgacaccagcaaagtgaattatggtgtaacggtactgccgacctt
caagggtcaaccatccaaaccgttcgttggcgtgctgagcgcaggta
ttaacgccgccagtccgaacaaagagctggcgaaagagttcctcgaa
aactatctgctgactgatgaaggtctggaagcggttaataaagacaa
accgctgggtgccgtagcgctgaagtcttacgaggaagagttggcga
aagatccacgtattgccgccaccatggaaaacgcccagaaaggtgaa
atcatgccgaacatcccgcagatgtccgctttctggtatgccgtgcg
tactgcggtgatcaacgccgcagcggtcgtcagactgtcgatgaag
ccctgaaagacgcgcagactaatTCGAGCTCCAATAACAATAACAAC
AACAATAACAATAACGGATCCATTATGAGCAAAATTAGCAAATTGGT
AACCCACCCAAACCTTTTCTTTCGAGATTATTTCTTAAAAAAGCAC
CGTTAAATTATGGCGAAAATATTAAACCTTTACCAGTCGAAACCTCT
TCTCATAGCAAAAAAATACAGCCCATAAAACACCCGTATCATCCGA
CCAACCAATTGAAGATCCATACCCAGTAACATTTCCAATTGATGTAG
TTTATACTTGGGTAGATTCAGATGATGAAAAATTCAATGAAGAACGC
CTAAAGTTTCAAAATTCAAGCACATCTGAGACTCTACAAGGCAAAGC
AGAAAGCACCGATATTGCAAGATTCCAATCACGCGACGAATTAAAAT
ATTCGATTCGAAGCCTGATGAAGTATGCCCCATGGGTAAATCATATT
TACATTGTAACAAATGGTCAAATACCAAAATGGTTAGATACCAACAA
TACAAAGGTAACGATTATCCCTCACTCAACTATTATCGACAGTCAAT
TTCTCCCTACTTTTAATTCTCACGTCATTGAATCCTCTCTATATAAA
ATCCCAGGATTATCAGAGCATTACATTTATTTCAATGATGATGTCAT
GCTAGCTAGAGATTTAAGCCCATCTTATTTCTTTACAAGCAGCGGAT
TAGCAAAACTGTTTATTACCAACTCTCGTCTACCAAATGGCTATAAG
AATGTGAAAGACACACCAACCCAATGGGCCTCAAAAAATTCCCGTGA
GCTTTTACATGCAGAAACAGGATTTTGGGCTGAAGCCATGTTTGCAC
ATACTTTTCATCCACAACGTAAAAGTGTACATGAATCTATTGAACAC
CTATGGCATGAACAATTAAATGTTTGTCGTCAAAACCGTTTCCGTGA
TATTTCAGATATTAACATGGCGACATTCCTGCACCACCATTTTGCCA
TTTTGACAGGCCAAGCTCTTGCTACACGCACTAAATGTATTTACTTT
AACATTCGCTCTCCTCAAGCAGCTCAGCATTACAAAACATTATTAGC
TCGAAAAGGAAGCGAATACAGCCCACATTCTATCTGCTTAAATGATC
ATACATCGAGCAATAAAAATATTTTATCTAATTACGAAGCCAAATTA
CAAAGCTTTTTAGAAACATACTATCCAGATGTATCAGAAGCAGAAAT
TCTCCTTCCTACTAAATCTGAAGTAGCTGAATTAGTTAAACATAAAG
ATTATTTAACTGTATATACTAAATTATTACCTATTATCAATAAGCAG
```

```
CTGGTCAATAAATATAATAAACCTTATTCATATCTTTTCTATTATTT
AGGTTTATCTGCCCGGTTTTTATTTGAAGAAACGCAACAAGAACACT
ACCGGGAAACTGCTGAAGAAAATTTACAAATCTTTTGTGGCCTAAAC
CCAAAACATACACTAGCCCTCAAATACTTAGCGGATGTCACCCTCAC
ATCACAGCCTAGTGGACAACtcgagcaccaccaccaccaccac
```

SEQ ID NO: 48:
DNA MBP-S3N10-BamHI
```
atgaaaactgaagaaggtaaactggtaatctggattaacggcgataaa
ggctataacggtctcgctgaagtcggtaagaaattcgagaaagatacc
ggaattaaagtcaccgttgagcatccggataaactggaagagaaattc
ccacaggttgcggcaactggcgatggccctgacattatcttctgggca
cacgaccgctttggtggctacgctcaatctggcctgttggctgaaatc
accccggacaaagcgttccaggacaagctgtatccgtttacctgggat
gccgtacgttacaacggcaagctgattgcttacccgatcgctgttgaa
gcgttatcgctgatttataacaaagatctgctgccgaacccgccaaaa
acctgggaagagatcccgcgcgctggataaagaactgaaagcgaaggt
aagagcgcgctgatgttcaacctgcaagaaccgtacttcacctggccg
ctgattgctgctgacggggttatgcgttcaagtatgaaaacggcaag
tacgacattaaagacgtgggcgtggataacgctggcgcgaaagcgggt
ctgaccttcctggttgacctgattaaaaacaaacacatgaatgcagac
accgattactccatcgcagaagctgcctttaataaaggcgaaacagcg
atgaccatcaacgcccgtgggcatggtccaacatcgacaccagcaaa
gtgaattatggtgtaacggtactgccgaccttcaagggtcaaccatcc
aaaccgttcgttggcgtgctgagcgcaggtattaacgccgccagtccg
aacaaagagctggcgaaagagttcctcgaaaactatctgctgactgat
gaaggtctggaagcggttaataaagacaaaccgctgggtgccgtagcg
ctgaagtcttacgaggaagagttggcgaaagatccacgtattgccgcc
accatggaaaacgcccagaaaggtgaaatcatgccgaacatcccgcag
atgtccgctttctggtatgccgtgcgtactgcggtgatcaacgccgcc
agcggtcgtcagactgtcgatgaagccctgaaagacgcgcagactaat
TCGAGCTCCAATAACAATAACAACAATAACAATAACGGATCC
```

SEQ ID NO: 49:
AS MBP-S3N10-BamHI-CsxA-Xho1-His6
MKTEEGKLVIWINGDKGYNGLAEVGKKFEKDTGIKVTVEHPDKLEEKF
PQVAATGDGPDIIFWAHDRFGGYAQSGLLAEITPDKAFQDKLYPFTWD
AVRYNGKLIAYPIAVEALSLIYNKDLLPNPPKTWEEIPALDKELKAKG
KSALMFNLQEPYFTWPLIAADGGYAFKYENGKYDIKDVGVDNAGAKAG
LTFLVDLIKNKHMNADTDYSIAEAAFNKGETAMTINGPWAWSNIDTSK
VNYGVTVLPTFKGQPSKPFVGVLSAGINAASPNKELAKEFLENYLLTD
EGLEAVNKDKPLGAVALKSYEEELAKDPRIAATMENAQKGEIMPNIPQ
MSAFWYAVRTAVINAASGRQTVDEALKDAQTNSSSNNNNNNNNNGSI
MSKISKLVTHPNLFFRDYFLKKAPLNYGENIKPLPVETSSHSKKNTAH
KTPVSSDQPIEDPYPVTFPIDVVYTWVDSDDEKFNEERLKFQNSSTSE
```

```
TLQGKAESTDIARFQSRDELKYSIRSLMKYAPWVNHIYIVTNGQIPKW

LDTNNTKVTIIPHSTIIDSQFLPTFNSHVIESSLYKIPGLSEHYIYFN

DDVMLARDLSPSYFFTSSGLAKLFITNSRLPNGYKNVKDTPTQWASKN

SRELLHAETGFWAEAMFAHTFHPQRKSVHESIEHLWHEQLNVCRQNRF

RDISDINMATFLHHHFAILTGQALATRTKCIYFNIRSPQAAQHYKTLL

ARKGSEYSPHSICLNDHTSSNKNILSNYEAKLQSFLETYYPDVSEAEI

LLPTKSEVAELVKHKDYLTVYTKLLPIINKQLVNKYNKPYSYLFYYLG

LSARFLFEETQQEHYRETAEENLQIFCGLNPKHTLALKYLADVTLTSQ

PSGQLEHHHHHH

SEQ ID NO: 50:
AS MBP-S3N10-BamHI
MKTEEGKLVIWINGDKGYNGLAEVGKKFEKDTGIKVTVEHPDKLEEKF

PQVAATGDGPDIIFWAHDRFGGYAQSGLLAEITPDKAFQDKLYPFTWD

AVRYNGKLIAYPIAVEALSLIYNKDLLPNPPKTWEEIPALDKELKAKG

KSALMFNLQEPYFTWPLIAADGGYAFKYENGKYDIKDVGVDNAGAKAG

LTFLVDLIKNKHMNADTDYSIAEAAFNKGETAMTINGPWAWSNIDTSK

VNYGVTVLPTFKGQPSKPFVGVLSAGINAASPNKELAKEFLENYLLTD

EGLEAVNKDKPLGAVALKSYEEELAKDPRIAATMENAQKGEIMPNIPQ

MSAFWYAVRTAVINAASGRQTVDEALKDAQTNSSSNNNNNNNNNNGS
```

The sequences provided herein (e.g. the sequences corresponding to ΔN65ΔC10-CP-X) may have a free N-terminus. These constructs may be used, inter alia for crystallization approaches. For example, the sequences may be cloned into a vector by using NdeI and/or XhoI. SEQ ID NOs: 51 and 52 show an example for an NdeI-ΔN65ΔC10-CP-X-XhoI-his construct. In context of the invention, all herein disclosed sequences may be used to produce constructs as demonstrated for ΔN65ΔC10-CP-X in SEQ ID NOs: 51 and 52.

```
SEQ ID NO: 51:
DNA NdeI-dN65dC10-CsxA-XhoI-His6
caTATGGTAACATTTCCAATTGATGTAGTTTATACTTGGGTAGATTCA

GATGATGAAAAATTCAATGAAGAACGCCTAAAGTTTCAAAATTCAAGC

ACATCTGAGACTCTACAAGGCAAAGCAGAAAGCACCGATATTGCAAGA

TTCCAATCACGCGACGAATTAAAATATTCGATTCGAAGCCTGATGAAG

TATGCCCCATGGGTAAATCATATTTACATTGTAACAAATGGTCAAATA

CCAAAATGGTTAGATACCAACAATACAAAGGTAACGATTATCCCTCAC

TCAACTATTATCGACAGTCAATTTCTCCCTACTTTTAATTCTCACGTC

ATTGAATCCTCTCTATATAAAATCCCAGGATTATCAGAGCATTACATT

TATTTCAATGATGATGTCATGCTAGCTAGAGATTTAAGCCCATCTTAT

TTCTTTACAAGCAGCGGATTAGCAAAACTGTTTATTACCAACTCTCGT

CTACCAAATGGCTATAAGAATGTGAAAGACACACCAACCCAATGGGCC

TCAAAAAATTCCCGTGAGCTTTTACATGCAGAAACAGGATTTTGGGCT

GAAGCCATGTTTGCACATACTTTTCATCCACAACGTAAAAGTGTACAT

GAATCTATTGAACACCTATGGCATGAACAATTAAATGTTGTCGTCAA

AACCGTTTCCGTGATATTTCAGATATTAACATGGCGACATTCCTGCAC

CACCATTTTGCCATTTTGACAGGCCAAGCTCTTGCTACACGCACTAAA

TGTATTTACTTTAACATTCGCTCTCCTCAAGCAGCTCAGCATTACAAA

ACATTATTAGCTCGAAAAGGAAGCGAATACAGCCCACATTCTATCTGC

TTAAATGATCATACATCGAGCAATAAAAATATTTTATCTAATTACGAA

GCCAAATTACAAAGCTTTTTAGAAACATACTATCCAGATGTATCAGAA

GCAGAAATTCTCCTTCCTACTAAATCTGAAGTAGCTGAATTAGTTAAA

CATAAAGATTATTTAACTGTATATACTAAATTATTACCTATTATCAAT

AAGCAGCTGGTCAATAAATATAATAAACCTTATTCATATCTTTTCTAT

TATTTAGGTTTATCTGCCCGGTTTTTATTTGAAGAAACGCAACAAGAA

CACTACCGGGAAACTGCTGAAGAAAATTTACAAATCTTTTGTGGCCTA

AACCCAAAACATACACTAGCCCTCAAATACTTAGCGGATctcgagcac caccaccaccaccac

SEQ ID NO: 52:
AS NdeI-dN65dC10-CsxA-XhoI-His6
MVTFPIDVVYTWVDSDDEKFNEERLKFQNSSTSETLQGKAESTDIARF

QSRDELKYSIRSLMKYAPWVNHIYIVTNGQIPKWLDTNNTKVTIIPHS

TIIDSQFLPTFNSHVIESSLYKIPGLSEHYIYFNDDVMLARDLSPSYF

FTSSGLAKLFITNSRLPNGYKNVKDTPTQWASKNSRELLHAETGFWAE

AMFAHTFHPQRKSVHESIEHLWHEQLNVCRQNRFRDISDINMATFLHH

HFAILTGQALATRTKCIYFNIRSPQAAQHYKTLLARKGSEYSPHSICL

NDHTSSNKNILSNYEAKLQSFLETYYPDVSEAEILLPTKSEVAELVKH

KDYLTVYTKLLPIINKQLVNKYNKPYSYLFYYLGLSARFLFEETQQEH

YRETAEENLQIFCGLNPKHTLALKYLADLEHHHHHH

SEQ ID NO: 53:
DNA CsaC
Atgttatctaatttaaaaacaggaaataatatcttaggattacctgaa tttgagttgaatggctgccgattcttatataaaaaggtatagaaaaa acaattattacttttcagcatttcctcctaaagatattgctcaaaaa tataattatataaaagattttttaagttctaattatactttttagca ttcttagataccaaatatccagaagatgatgctagaggcacttattac attactaatgagttagataatggatatttacaaaccatacattgtatt attcaattattatcgaatacaaatcaagaagatacctacctttgggt tcaagtaaaggtggcgttggcgcacttctactcggtcttacatataat tatcctaatataattattaatgctcctcaagccaaattagcagattat atcaaaacacgctcgaaaaccattctttcatatatgcttggaacctct aaaagatttcaagatattaattacgattatatcaatgacttcttacta tctaaaattaagacttgcgactcctcacttaaatggaatattcatata acttgcggaaaagatgattcatatcatttaaatgaattagaaattcta aaaaatgaatttaatataaaagctattacgattaaaaccaaactaatt tctggcgggcatgataatgaagcaattgcccactatagagaatacttt aaaaccataatccaaaatata
```

SEQ ID NO: 54:
AS CsaC
MLSNLKTGNNILGLPEFELNGCRFLYKKGIEKTIITFSAFPPKDIAQK
YNYIKDFLSSNYTFLAFLDTKYPEDDARGTYYITNELDNGYLQTIHCI
IQLLSNTNQEDTYLLGSSKGGVGALLLGLTYNYPNIINAPQAKLADY
IKTRSKTILSYMLGTSKRFQDINYDYINDFLLSKIKTCDSSLKWNIHI
TCGKDDSYHLNELEILKNEFNIKAITIKTKLISGGHDNEAIAHYREYF
KTIIQNI

SEQUENCE LISTING

<160> NUMBER OF SEQ ID NOS: 135

<210> SEQ ID NO 1
<211> LENGTH: 1635
<212> TYPE: DNA
<213> ORGANISM: Neisseria meningitidis
<220> FEATURE:
<223> OTHER INFORMATION: DNA CP-A/CsaB wildtyp/full-length

<400> SEQUENCE: 1

```
atgtttatac ttaataacag aaaatggcgt aaacttaaaa gagaccctag cgctttcttt      60
cgagatagta aatttaactt tttaagatat ttttctgcta aaaaatttgc aaagaatttt     120
aaaaattcat cacatatcca taaaactaat ataagtaaag ctcaatcaaa tatttcttca     180
accttaaaac aaaatcggaa acaagatatg ttaattccta ttaattttt taattttgaa      240
tatatagtta aaaaacttaa caatcaaaac gcaataggtg tatatattct tccttctaat     300
cttactctta agcctgcatt atgtattcta gaatcacata agaagacctt tttaaataaa     360
tttcttctta ctatttcctc tgaaaattta agcttcaat acaaatttaa tggacaaata      420
aaaaatccta agtccgtaaa tgaaatttgg acagatttat ttagcattgc tcatgttgac     480
atgaaactca gcacagatag aactttaagt tcatctatat ctcaattttg gttcagatta     540
gagttctgta agaagataa ggattttatc ttatttccta cagctaacag atattctaga      600
aaactttgga agcactctat taaaaataat caattatta aagaaggcat acgaaactat       660
tcagaaatat cttcattacc ctatgaagaa gatcataatt ttgatattga tttagtattt     720
acttgggtca actcagaaga taagaattgg caagagttat ataaaaaata taagcccgac     780
tttaatagcg atgcaaccag tacatcaaga ttccttagta gagatgaatt aaaattcgca      840
ttacgctctt gggaaatgaa tggatccttc attcgaaaaa ttttattgt ctctaattgt       900
gctccccag catggctaga tttaaataac cctaaaattc aatgggtata tcacgaagaa      960
attatgccac aaagtgccct tcctacttt agctcacatg ctattgaaac cagcttgcac      1020
catataccag gaattagtaa ctattttatt tacagcaatg acgacttcct attaactaaa     1080
ccattgaata agacaattt cttctattcg aatggtattg caagttaag attagaagca      1140
tggggaaatg ttaatggtga atgtactgaa ggagaaccta ctacttaaa tggtgctcgc     1200
aatgcgaaca ctctcttaga aaaggaattt aaaaaattta ctactaaact acatactcac     1260
tccccctcaat cctatgagaac tgatatttta tttgagatgg aaaaaaaata tccagaagag     1320
tttaatagaa cactacataa taaattccga tctttagatg atattgcagt aacgggctat     1380
ctctatcatc attatgccct actctctgga cgagcactac aaagttctga caagacggaa     1440
cttgtacagc aaaatcatga tttcaaaaag aaactaaata atgtagtgac cttaactaaa     1500
gaaaggaatt ttgacaaact tcctttgagc gtatgtatca acgatggtgc tgatagtcac     1560
ttgaatgaag aatggaatgt tcaagttatt aagttcttag aaactcttt cccattacca     1620
tcatcatttg agaaa                                                     1635
```

<210> SEQ ID NO 2
<211> LENGTH: 1635
<212> TYPE: DNA
<213> ORGANISM: Neisseria meningitidis
<220> FEATURE:
<223> OTHER INFORMATION: DNA CP-A/CsaB codon optimized

<400> SEQUENCE: 2
atgttcatct tgaacaaccg caaatggcgc aaattgaagc gtgacccaag cgcgtttttt 60
cgtgacagca aattcaactt tctgcgctat ttctccgcga aaaagtttgc gaagaatttc 120
aaaaacagct cgcatatcca taaaaccaac attagcaaag cgcagtccaa tatttccagc 180
accttgaagc agaaccgtaa gcaggatatg ctgatcccga tcaatttctt taattttgag 240
tacatcgtga agaaactgaa taaccaaaac gcaatcggcg tgtacattct gccgtctaat 300
ctgaccctga aaccagcatt gtgcatcttg gagtcgcaca aagaggactt cctgaacaaa 360
tttttgttga ccattagcag cgagaacctg aaactgcagt ataagttcaa tggtcagatc 420
aaaaatccga aaagcgtgaa cgaaatctgg accgacctgt ttagcattgc tcacgtcgac 480
atgaagctga gcaccgaccg tacgctgtcc tcgtccatca gccaattttg gtttcgcctg 540
gagttctgta aagaggacaa ggacttcatc ctgtttccga cggcaaatcg ttacagccgc 600
aagctgtgga agcacagcat caaaaataat cagctgttta aggaaggtat ccgtaactac 660
agcgagatta gctcgctgcc gtacgaggaa gaccataact tcgacatcga tctggtcttt 720
acctgggtca attcggaaga caaaaactgg caggaactgt acaagaaata taagccggat 780
tttaatagcg atgccacctc gacgagccgt tttctgagcc gtgacgagct gaagtttgcg 840
ctgcgctcgt gggaaatgaa cggtagcttc atccgtaaaa tctttatcgt cagcaactgc 900
gcgccgccgg cctggctgga tctgaacaat ccgaagatcc aatgggtgta tcacgaggag 960
atcatgccac agagcgccct gccaaccttc agcagccatg ctattgagac tagcttgcat 1020
cacattccgg gcatctccaa ctacttcatc tactctaatg acgattttct gttgaccaaa 1080
ccgctgaaca aagacaactt cttttactcc aacggtattg ctaaactgcg tctggaagcc 1140
tggggtaacg ttaacggtga atgtaccgaa ggcgagccgg attacctgaa cggcgcgcgt 1200
aacgcaaata cgctgctgga gaaagagttt aaaaagttta ccaccaagct gcacacccac 1260
agcccgcaga gcatgcgtac cgacatcctg ttcgagatgg agaaaaaata cccagaagag 1320
ttcaatcgca cgctgcacaa caagttccgc agcctggatg acatcgcggt taccggctac 1380
ctgtaccatc actacgcatt gctgtctggc cgcgctctgc aatccagcga taagaccgaa 1440
ctggtccagc agaatcacga ctttaaaaag aagctgaata atgttgtcac cctgaccaaa 1500
gagcgtaact ttgataagct gccgctgagc gtttgtatta atgacggtgc agacagccac 1560
ctgaatgagg agtggaatgt gcaagttatc aaattcttgg agaccttgtt cccgttgccg 1620
agctccttcg agaaa 1635

<210> SEQ ID NO 3
<211> LENGTH: 1425
<212> TYPE: DNA
<213> ORGANISM: Neisseria meningitidis
<220> FEATURE:
<223> OTHER INFORMATION: DNA deltaN69-CP-A (codon optimized) (1425)

<400> SEQUENCE: 3
ctgatcccga tcaatttctt taattttgag tacatcgtga agaaactgaa taaccaaaac 60
gcaatcggcg tgtacattct gccgtctaat ctgaccctga aaccagcatt gtgcatcttg 120

-continued

| | |
|---|---|
| gagtcgcaca aagaggactt cctgaacaaa ttttgttga ccattagcag cgagaacctg | 180 |
| aaactgcagt ataagttcaa tggtcagatc aaaaatccga aaagcgtgaa cgaaatctgg | 240 |
| accgacctgt ttagcattgc tcacgtcgac atgaagctga gcaccgaccg tacgctgtcc | 300 |
| tcgtccatca gccaattttg gtttcgcctg gagttctgta aagaggacaa ggacttcatc | 360 |
| ctgtttccga cggcaaatcg ttacagccgc aagctgtgga agcacagcat caaaaataat | 420 |
| cagctgttta aggaaggtat ccgtaactac agcgagatta gctcgctgcc gtacgaggaa | 480 |
| gaccataact tcgacatcga tctggtcttt acctgggtca attcggaaga caaaaactgg | 540 |
| caggaactgt acaagaaata taagccggat tttaatagcg atgccacctc gacgagccgt | 600 |
| tttctgagcc gtgacgagct gaagtttgcg ctgcgctcgt gggaaatgaa cggtagcttc | 660 |
| atccgtaaaa tctttatcgt cagcaactgc gcgccgccgg cctggctgga tctgaacaat | 720 |
| ccgaagatcc aatgggtgta tcacgaggag atcatgccac agagcgccct gccaaccttc | 780 |
| agcagccatg ctattgagac tagcttgcat cacattccgg gcatctccaa ctacttcatc | 840 |
| tactctaatg acgattttct gttgaccaaa ccgctgaaca agacaacctt cttttactcc | 900 |
| aacggtattg ctaaactgcg tctggaagcc tggggtaacg ttaacggtga atgtaccgaa | 960 |
| ggcgagccgg attacctgaa cggcgcgcgt aacgcaaata cgctgctgga gaaagagttt | 1020 |
| aaaaagttta ccaccaagct gcacacccac agcccgcaga gcatgcgtac cgacatcctg | 1080 |
| ttcgagatgg agaaaaaata cccagaagag ttcaatcgca cgctgcacaa caagttccgc | 1140 |
| agcctggatg acatcgcggt taccggctac ctgtaccatc actacgcatt gctgtctggc | 1200 |
| cgcgctctgc aatccagcga taagaccgaa ctggtccagc agaatcacga ctttaaaaag | 1260 |
| aagctgaata tgttgtcac cctgaccaaa gagcgtaact ttgataagct gccgctgagc | 1320 |
| gtttgtatta atgacggtgc agacagccac ctgaatgagg agtggaatgt gcaagttatc | 1380 |
| aaattcttgg agaccttgtt cccgttgccg agctccttcg agaaa | 1425 |

<210> SEQ ID NO 4
<211> LENGTH: 1344
<212> TYPE: DNA
<213> ORGANISM: Neisseria meningitidis
<220> FEATURE:
<223> OTHER INFORMATION: DNA deltaN97-CP-A (1344)

<400> SEQUENCE: 4

| | |
|---|---|
| ccttctaatc ttactcttaa gcctgcatta tgtattctag aatcacataa agaagacttt | 60 |
| ttaaataaat ttcttcttac tatttcctct gaaaatttaa agcttcaata caaatttaat | 120 |
| ggacaaataa aaaatcctaa gtccgtaaat gaaatttgga cagatttatt tagcattgct | 180 |
| catgttgaca tgaaactcag cacagataga actttaagtt catctatatc tcaattttgg | 240 |
| ttcagattag agttctgtaa agaagataag gattttatct tatttcctac agctaacaga | 300 |
| tattctagaa aactttggaa gcactctatt aaaaataatc aattatttaa gaaggcata | 360 |
| cgaaactatt cagaaatatc ttcattaccc tatgaagaag atcataattt tgatattgat | 420 |
| ttagtattta cttgggtcaa ctcagaagat aagaattggc aagagttata taaaaaatat | 480 |
| aagcccgact ttaatagcga tgcaaccagt acatcaagat tccttagtag agatgaatta | 540 |
| aaattcgcat tacgctcttg ggaaatgaat ggatccttca ttcgaaaaat tttattgtc | 600 |
| tctaattgtg ctcccccagc atggctagat ttaaataacc ctaaaattca atgggtatat | 660 |
| cacgaagaaa ttatgccaca aagtgccctt cctacttta gctcacatgc tattgaaacc | 720 |

| agcttgcacc | atataccagg | aattagtaac | tattttattt | acagcaatga | cgacttccta | 780 |
| ttaactaaac | cattgaataa | agacaatttc | ttctattcga | atggtattgc | aaagttaaga | 840 |
| ttagaagcat | ggggaaatgt | taatggtgaa | tgtactgaag | gagaacctga | ctacttaaat | 900 |
| ggtgctcgca | atgcgaacac | tctcttagaa | aaggaattta | aaaatttac | tactaaacta | 960 |
| catactcact | cccctcaatc | catgagaact | gatattttat | ttgagatgga | aaaaaatat | 1020 |
| ccagaagagt | ttaatagaac | actacataat | aaattccgat | ctttagatga | tattgcagta | 1080 |
| acgggctatc | tctatcatca | ttatgcccta | ctctctggac | gagcactaca | aagttctgac | 1140 |
| aagacggaac | ttgtacagca | aaatcatgat | ttcaaaaaga | aactaaataa | tgtagtgacc | 1200 |
| ttaactaaag | aaaggaattt | tgacaaactt | cctttgagcg | tatgtatcaa | cgatggtgct | 1260 |
| gatagtcact | tgaatgaaga | atggaatgtt | caagttatta | agttcttaga | aactcttttc | 1320 |
| ccattaccat | catcatttga | gaaa | | | | 1344 |

<210> SEQ ID NO 5
<211> LENGTH: 1134
<212> TYPE: DNA
<213> ORGANISM: Neisseria meningitidis
<220> FEATURE:
<223> OTHER INFORMATION: DNA deltaN167-CP-A (1134)

<400> SEQUENCE: 5

| actttaagtt | catctatatc | tcaattttgg | ttcagattag | agttctgtaa | agaagataag | 60 |
| gattttatct | tatttcctac | agctaacaga | tattctagaa | aactttggaa | gcactctatt | 120 |
| aaaaataatc | aattatttaa | agaaggcata | cgaaactatt | cagaaatatc | ttcattaccc | 180 |
| tatgaagaag | atcataattt | tgatattgat | ttagtattta | cttgggtcaa | ctcagaagat | 240 |
| aagaattggc | aagagttata | taaaaaatat | aagcccgact | ttaatagcga | tgcaaccagt | 300 |
| acatcaagat | tccttagtag | agatgaatta | aaattcgcat | tacgctcttg | ggaaatgaat | 360 |
| ggatccttca | ttcgaaaaat | ttttattgtc | tctaattgtg | ctcccccagc | atggctagat | 420 |
| ttaaataacc | ctaaaattca | atgggtatat | cacgaagaaa | ttatgccaca | aagtgccctt | 480 |
| cctactttta | gctcacatgc | tattgaaacc | agcttgcacc | atataccagg | aattagtaac | 540 |
| tattttattt | acagcaatga | cgacttccta | ttaactaaac | cattgaataa | agacaatttc | 600 |
| ttctattcga | atggtattgc | aaagttaaga | ttagaagcat | ggggaaatgt | taatggtgaa | 660 |
| tgtactgaag | gagaacctga | ctacttaaat | ggtgctcgca | atgcgaacac | tctcttagaa | 720 |
| aaggaattta | aaaatttac | tactaaacta | catactcact | cccctcaatc | catgagaact | 780 |
| gatattttat | ttgagatgga | aaaaaatat | ccagaagagt | ttaatagaac | actacataat | 840 |
| aaattccgat | ctttagatga | tattgcagta | acgggctatc | tctatcatca | ttatgcccta | 900 |
| ctctctggac | gagcactaca | aagttctgac | aagacggaac | ttgtacagca | aaatcatgat | 960 |
| ttcaaaaaga | aactaaataa | tgtagtgacc | ttaactaaag | aaaggaattt | tgacaaactt | 1020 |
| cctttgagcg | tatgtatcaa | cgatggtgct | gatagtcact | tgaatgaaga | atggaatgtt | 1080 |
| caagttatta | agttcttaga | aactcttttc | ccattaccat | catcatttga | gaaa | 1134 |

<210> SEQ ID NO 6
<211> LENGTH: 933
<212> TYPE: DNA
<213> ORGANISM: Neisseria meningitidis
<220> FEATURE:
<223> OTHER INFORMATION: DNA deltaN235-CP-A (933)

<400> SEQUENCE: 6

-continued

```
gatattgatt tagtatttac ttgggtcaac tcagaagata agaattggca agagttatat      60
aaaaaatata agcccgactt taatagcgat gcaaccagta catcaagatt ccttagtaga     120
gatgaattaa aattcgcatt acgctcttgg gaaatgaatg gatccttcat tcgaaaaatt     180
tttattgtct ctaattgtgc tcccccagca tggctagatt taaataaccc taaaattcaa     240
tgggtatatc acgaagaaat tatgccacaa agtgcccttc ctactttttag ctcacatgct    300 attgaaacca gcttgcacca tataccagga attagtaact attttattta cagcaatgac    360
gacttcctat taactaaacc attgaataaa gacaatttct tctattcgaa tggtattgca    420
aagttaagat tagaagcatg gggaaatgtt aatggtgaat gtactgaagg agaacctgac    480
tacttaaatg gtgctcgcaa tgcgaacact ctcttagaaa aggaatttaa aaaatttact    540
actaaactac atactcactc ccctcaatcc atgagaactg atattttatt tgagatggaa    600
aaaaaatatc cagaagagtt taatagaaca ctacataata aattccgatc tttagatgat    660
attgcagtaa cgggctatct ctatcatcat tatgccctac tctctggacg agcactacaa    720
agttctgaca agacggaact tgtacagcaa aatcatgatt tcaaaaagaa actaaataat    780
gtagtgacct taactaaaga aaggaatttt gacaaacttc ctttgagcgt atgtatcaac    840
gatggtgctg atagtcactt gaatgaagaa tggaatgttc aagttattaa gttcttagaa    900
actcttttcc cattaccatc atcatttgag aaa                                 933
```

<210> SEQ ID NO 7
<211> LENGTH: 1497
<212> TYPE: DNA
<213> ORGANISM: Neisseria meningitidis
<220> FEATURE:
<223> OTHER INFORMATION: DNA deltaC45-CP-A (1497)

<400> SEQUENCE: 7

```
tttatactta ataacagaaa atggcgtaaa cttaaaagag accctagcgc tttctttcga      60
gatagtaaat ttaactttt aagatatttt tctgctaaaa aatttgcaaa gaattttaaa    120
aattcatcac atatccataa aactaatata agtaaagctc atcaaatat ttcttcaacc    180 ttaaaacaaa atcggaaaca agatatgtta attcctatta attttttttaa ttttgaatat    240 atagttaaaa aacttaacaa tcaaaacgca ataggtgtat atattcttcc ttctaatctt    300
actcttaagc ctgcattatg tattctagaa tcacataaag aagactttt aaataaattt    360 cttcttacta tttcctctga aaatttaaag cttcaataca aatttaatgg acaaataaaa    420
aatcctaagt ccgtaaatga aatttggaca gatttattta gcattgctca tgttgacatg    480
aaactcagca cagatagaac tttaagttca tctatatctc aattttggtt cagattagag    540
ttctgtaaag aagataagga ttttatctta tttcctacag ctaacagata ttctagaaaa    600
ctttggaagc actctattaa aaataatcaa ttatttaaag aaggcatacg aaactattca    660
gaaatatctt cattacccta tgaagaagat cataattttg atattgattt agtatttact    720
tgggtcaact cagaagataa gaattggcaa gagttatata aaaaatataa gcccgacttt    780
aatagcgatg caaccagtac atcaagattc cttagtagag atgaattaaa attcgcatta    840
cgctcttggg aaatgaatgg atccttcatt cgaaaaattt ttattgtctc taattgtgct    900
cccccagcat ggctagattt aaataaccct aaaattcaat gggtatatca cgaagaaatt    960
atgccacaaa gtgcccttcc tactttttagc tcacatgcta ttgaaccag cttgcaccat   1020 ataccaggaa ttagtaacta ttttatttac agcaatgacg acttcctatt aactaaacca   1080
```

```
ttgaataaag acaatttctt ctattcgaat ggtattgcaa agttaagatt agaagcatgg   1140
ggaaatgtta atggtgaatg tactgaagga gaacctgact acttaaatgg tgctcgcaat   1200
gcgaacactc tcttagaaaa ggaatttaaa aaatttacta ctaaactaca tactcactcc   1260
cctcaatcca tgagaactga tattttattt gagatggaaa aaaatatcc agaagagttt   1320 aatagaacac tacataataa attccgatct ttagatgata ttgcagtaac gggctatctc   1380
tatcatcatt atgccctact ctctggacga gcactacaaa gttctgacaa gacggaactt   1440
gtacagcaaa atcatgattt caaaagaaa ctaataatg tagtgacctt aactaaa      1497

<210> SEQ ID NO 8
<211> LENGTH: 1557
<212> TYPE: DNA
<213> ORGANISM: Neisseria meningitidis
<220> FEATURE:
<223> OTHER INFORMATION: DNA deltaC25-CP-A (1557)

<400> SEQUENCE: 8
tttatactta ataacagaaa atggcgtaaa cttaaaagag accctagcgc tttctttcga     60
gatagtaaat ttaactttt aagatatttt tctgctaaaa aatttgcaaa gaattttaaa   120
aattcatcac atatccataa aactaatata agtaaagctc aatcaaatat ttcttcaacc   180
ttaaaacaaa tcggaaaca agatatgtta attcctatta attttttaa ttttgaatat   240 atagttaaaa aacttaacaa tcaaaacgca ataggtgtat atattcttcc ttctaatctt   300
actcttaagc ctgcattatg tattctagaa tcacataaag aagacttttt aaataaattt   360
cttcttacta tttcctctga aaatttaaag cttcaataca aatttaatgg acaaataaaa   420
aatcctaagt ccgtaaatga aatttggaca gatttattta gcattgctca tgttgacatg   480
aaactcagca cagatagaac tttaagttca tctatatctc aattttggtt cagattagag   540
ttctgtaaag aagataagga ttttatctta tttcctacag ctaacagata ttctagaaaa   600
ctttggaagc actctattaa aaataatcaa ttatttaaag aaggcatacg aaactattca   660
gaaatatctt cattacccta tgaagaagat cataattttg atattgattt agtatttact   720
tgggtcaact cagaagataa gaattggcaa gagttatata aaaatataa gcccgacttt   780 aatagcgatg caaccagtac atcaagattc cttagtagag atgaattaaa attcgcatta   840
cgctcttggg aaatgaatgg atccttcatt cgaaaaattt ttattgtctc taattgtgct   900
cccccagcat ggctagattt aaataaccct aaaattcaat gggtatatca cgaagaaatt   960
atgccacaaa gtgcccttcc tactttagc tcacatgcta ttgaaaccag cttgcaccat   1020
ataccaggaa ttagtaacta ttttatttac agcaatgacg acttcctatt aactaaacca   1080
ttgaataaag acaatttctt ctattcgaat ggtattgcaa agttaagatt agaagcatgg   1140
ggaaatgtta atggtgaatg tactgaagga gaacctgact acttaaatgg tgctcgcaat   1200
gcgaacactc tcttagaaaa ggaatttaaa aaatttacta ctaaactaca tactcactcc   1260
cctcaatcca tgagaactga tattttattt gagatggaaa aaaatatcc agaagagttt   1320 aatagaacac tacataataa attccgatct ttagatgata ttgcagtaac gggctatctc   1380
tatcatcatt atgccctact ctctggacga gcactacaaa gttctgacaa gacggaactt   1440
gtacagcaaa atcatgattt caaaagaaa ctaataatg tagtgacctt aactaaagaa   1500
aggaattttg caaacttcc tttgagcgta tgtatcaacg atggtgctga tagtcac      1557

<210> SEQ ID NO 9
<211> LENGTH: 545
```

<212> TYPE: PRT
<213> ORGANISM: Neisseria meningitidis
<220> FEATURE:
<223> OTHER INFORMATION: AS CP-A/CsaB wildtyp/full-length (544 without M1)

<400> SEQUENCE: 9

```
Met Phe Ile Leu Asn Asn Arg Lys Trp Arg Lys Leu Lys Arg Asp Pro
1               5                   10                  15

Ser Ala Phe Phe Arg Asp Ser Lys Phe Asn Phe Leu Arg Tyr Phe Ser
            20                  25                  30

Ala Lys Lys Phe Ala Lys Asn Phe Lys Asn Ser Ser His Ile His Lys
        35                  40                  45

Thr Asn Ile Ser Lys Ala Gln Ser Asn Ile Ser Ser Thr Leu Lys Gln
    50                  55                  60

Asn Arg Lys Gln Asp Met Leu Ile Pro Ile Asn Phe Phe Asn Phe Glu
65                  70                  75                  80

Tyr Ile Val Lys Lys Leu Asn Asn Gln Asn Ala Ile Gly Val Tyr Ile
                85                  90                  95

Leu Pro Ser Asn Leu Thr Leu Lys Pro Ala Leu Cys Ile Leu Glu Ser
            100                 105                 110

His Lys Glu Asp Phe Leu Asn Lys Phe Leu Leu Thr Ile Ser Ser Glu
        115                 120                 125

Asn Leu Lys Leu Gln Tyr Lys Phe Asn Gly Gln Ile Lys Asn Pro Lys
    130                 135                 140

Ser Val Asn Glu Ile Trp Thr Asp Leu Phe Ser Ile Ala His Val Asp
145                 150                 155                 160

Met Lys Leu Ser Thr Asp Arg Thr Leu Ser Ser Ile Ser Gln Phe
                165                 170                 175

Trp Phe Arg Leu Glu Phe Cys Lys Glu Asp Lys Asp Phe Ile Leu Phe
            180                 185                 190

Pro Thr Ala Asn Arg Tyr Ser Arg Lys Leu Trp Lys His Ser Ile Lys
        195                 200                 205

Asn Asn Gln Leu Phe Lys Glu Gly Ile Arg Asn Tyr Ser Glu Ile Ser
    210                 215                 220

Ser Leu Pro Tyr Glu Glu Asp His Asn Phe Asp Ile Asp Leu Val Phe
225                 230                 235                 240

Thr Trp Val Asn Ser Glu Asp Lys Asn Trp Gln Glu Leu Tyr Lys Lys
                245                 250                 255

Tyr Lys Pro Asp Phe Asn Ser Asp Ala Thr Ser Thr Ser Arg Phe Leu
            260                 265                 270

Ser Arg Asp Glu Leu Lys Phe Ala Leu Arg Ser Trp Glu Met Asn Gly
        275                 280                 285

Ser Phe Ile Arg Lys Ile Phe Ile Val Ser Asn Cys Ala Pro Pro Ala
    290                 295                 300

Trp Leu Asp Leu Asn Asn Pro Lys Ile Gln Trp Val Tyr His Glu Glu
305                 310                 315                 320

Ile Met Pro Gln Ser Ala Leu Pro Thr Phe Ser Ser His Ala Ile Glu
                325                 330                 335

Thr Ser Leu His His Ile Pro Gly Ile Ser Asn Tyr Phe Ile Tyr Ser
            340                 345                 350

Asn Asp Asp Phe Leu Leu Thr Lys Pro Leu Asn Lys Asp Asn Phe Phe
        355                 360                 365

Tyr Ser Asn Gly Ile Ala Lys Leu Arg Leu Glu Ala Trp Gly Asn Val
    370                 375                 380
```

Asn Gly Glu Cys Thr Glu Gly Glu Pro Asp Tyr Leu Asn Gly Ala Arg
385                 390                 395                 400

Asn Ala Asn Thr Leu Leu Glu Lys Glu Phe Lys Phe Thr Thr Lys
            405                 410                 415

Leu His Thr His Ser Pro Gln Ser Met Arg Thr Asp Ile Leu Phe Glu
        420                 425                 430

Met Glu Lys Lys Tyr Pro Glu Glu Phe Asn Arg Thr Leu His Asn Lys
            435                 440                 445

Phe Arg Ser Leu Asp Asp Ile Ala Val Thr Gly Tyr Leu Tyr His His
        450                 455                 460

Tyr Ala Leu Leu Ser Gly Arg Ala Leu Gln Ser Ser Asp Lys Thr Glu
465                 470                 475                 480

Leu Val Gln Gln Asn His Asp Phe Lys Lys Lys Leu Asn Asn Val Val
            485                 490                 495

Thr Leu Thr Lys Glu Arg Asn Phe Asp Lys Leu Pro Leu Ser Val Cys
            500                 505                 510

Ile Asn Asp Gly Ala Asp Ser His Leu Asn Glu Glu Trp Asn Val Gln
        515                 520                 525

Val Ile Lys Phe Leu Glu Thr Leu Phe Pro Leu Pro Ser Ser Phe Glu
    530                 535                 540

Lys
545

<210> SEQ ID NO 10
<211> LENGTH: 475
<212> TYPE: PRT
<213> ORGANISM: Neisseria meningitidis
<220> FEATURE:
<223> OTHER INFORMATION: AS deltaN69-CP-A (codon optimized) (475)

<400> SEQUENCE: 10

Leu Ile Pro Ile Asn Phe Phe Asn Phe Glu Tyr Ile Val Lys Lys Leu
1               5                   10                  15

Asn Asn Gln Asn Ala Ile Gly Val Tyr Ile Leu Pro Ser Asn Leu Thr
            20                  25                  30

Leu Lys Pro Ala Leu Cys Ile Leu Glu Ser His Lys Glu Asp Phe Leu
        35                  40                  45

Asn Lys Phe Leu Leu Thr Ile Ser Ser Glu Asn Leu Lys Leu Gln Tyr
    50                  55                  60

Lys Phe Asn Gly Gln Ile Lys Asn Pro Lys Ser Val Asn Glu Ile Trp
65                  70                  75                  80

Thr Asp Leu Phe Ser Ile Ala His Val Asp Met Lys Leu Ser Thr Asp
                85                  90                  95

Arg Thr Leu Ser Ser Ser Ile Ser Gln Phe Trp Phe Arg Leu Glu Phe
            100                 105                 110

Cys Lys Glu Asp Lys Asp Phe Ile Leu Phe Pro Thr Ala Asn Arg Tyr
        115                 120                 125

Ser Arg Lys Leu Trp Lys His Ser Ile Lys Asn Asn Gln Leu Phe Lys
    130                 135                 140

Glu Gly Ile Arg Asn Tyr Ser Glu Ile Ser Ser Leu Pro Tyr Glu Glu
145                 150                 155                 160

Asp His Asn Phe Asp Ile Asp Leu Val Phe Thr Trp Val Asn Ser Glu
                165                 170                 175

Asp Lys Asn Trp Gln Glu Leu Tyr Lys Lys Tyr Lys Pro Asp Phe Asn
            180                 185                 190

```
Ser Asp Ala Thr Ser Thr Ser Arg Phe Leu Ser Arg Asp Glu Leu Lys
        195                 200                 205

Phe Ala Leu Arg Ser Trp Glu Met Asn Gly Ser Phe Ile Arg Lys Ile
210                 215                 220

Phe Ile Val Ser Asn Cys Ala Pro Pro Ala Trp Leu Asp Leu Asn Asn
225                 230                 235                 240

Pro Lys Ile Gln Trp Val Tyr His Glu Ile Met Pro Gln Ser Ala
        245                 250                 255

Leu Pro Thr Phe Ser Ser His Ala Ile Glu Thr Ser Leu His His Ile
        260                 265                 270

Pro Gly Ile Ser Asn Tyr Phe Ile Tyr Ser Asn Asp Phe Leu Leu
        275                 280                 285

Thr Lys Pro Leu Asn Lys Asp Asn Phe Phe Tyr Ser Asn Gly Ile Ala
        290                 295                 300

Lys Leu Arg Leu Glu Ala Trp Gly Asn Val Asn Gly Glu Cys Thr Glu
305                 310                 315                 320

Gly Glu Pro Asp Tyr Leu Asn Gly Ala Arg Asn Ala Asn Thr Leu Leu
                325                 330                 335

Glu Lys Glu Phe Lys Lys Phe Thr Thr Lys Leu His Thr His Ser Pro
        340                 345                 350

Gln Ser Met Arg Thr Asp Ile Leu Phe Glu Met Glu Lys Lys Tyr Pro
        355                 360                 365

Glu Glu Phe Asn Arg Thr Leu His Asn Lys Phe Arg Ser Leu Asp Asp
        370                 375                 380

Ile Ala Val Thr Gly Tyr Leu Tyr His His Tyr Ala Leu Leu Ser Gly
385                 390                 395                 400

Arg Ala Leu Gln Ser Ser Asp Lys Thr Glu Leu Val Gln Gln Asn His
                405                 410                 415

Asp Phe Lys Lys Lys Leu Asn Asn Val Val Thr Leu Thr Lys Glu Arg
                420                 425                 430

Asn Phe Asp Lys Leu Pro Leu Ser Val Cys Ile Asn Asp Gly Ala Asp
                435                 440                 445

Ser His Leu Asn Glu Glu Trp Asn Val Gln Val Ile Lys Phe Leu Glu
        450                 455                 460

Thr Leu Phe Pro Leu Pro Ser Ser Phe Glu Lys
465                 470                 475

<210> SEQ ID NO 11
<211> LENGTH: 448
<212> TYPE: PRT
<213> ORGANISM: Neisseria meningitidis
<220> FEATURE:
<223> OTHER INFORMATION: AS deltaN97-CP-A (448)

<400> SEQUENCE: 11

Pro Ser Asn Leu Thr Leu Lys Pro Ala Leu Cys Ile Leu Glu Ser His
1               5                   10                  15

Lys Glu Asp Phe Leu Asn Lys Phe Leu Leu Thr Ile Ser Ser Glu Asn
                20                  25                  30

Leu Lys Leu Gln Tyr Lys Phe Asn Gly Gln Ile Lys Asn Pro Lys Ser
            35                  40                  45

Val Asn Glu Ile Trp Thr Asp Leu Phe Ser Ile Ala His Val Asp Met
        50                  55                  60

Lys Leu Ser Thr Asp Arg Thr Leu Ser Ser Ser Ile Ser Gln Phe Trp
65                  70                  75                  80
```

Phe Arg Leu Glu Phe Cys Lys Glu Asp Lys Asp Phe Ile Leu Phe Pro
                85                  90                  95

Thr Ala Asn Arg Tyr Ser Arg Lys Leu Trp Lys His Ser Ile Lys Asn
            100                 105                 110

Asn Gln Leu Phe Lys Glu Gly Ile Arg Asn Tyr Ser Glu Ile Ser Ser
        115                 120                 125

Leu Pro Tyr Glu Glu Asp His Asn Phe Asp Ile Asp Leu Val Phe Thr
    130                 135                 140

Trp Val Asn Ser Glu Asp Lys Asn Trp Gln Glu Leu Tyr Lys Lys Tyr
145                 150                 155                 160

Lys Pro Asp Phe Asn Ser Asp Ala Thr Ser Thr Ser Arg Phe Leu Ser
                165                 170                 175

Arg Asp Glu Leu Lys Phe Ala Leu Arg Ser Trp Glu Met Asn Gly Ser
            180                 185                 190

Phe Ile Arg Lys Ile Phe Ile Val Ser Asn Cys Ala Pro Pro Ala Trp
        195                 200                 205

Leu Asp Leu Asn Asn Pro Lys Ile Gln Trp Val Tyr His Glu Glu Ile
    210                 215                 220

Met Pro Gln Ser Ala Leu Pro Thr Phe Ser Ser His Ala Ile Glu Thr
225                 230                 235                 240

Ser Leu His His Ile Pro Gly Ile Ser Asn Tyr Phe Ile Tyr Ser Asn
                245                 250                 255

Asp Asp Phe Leu Leu Thr Lys Pro Leu Asn Lys Asp Asn Phe Phe Tyr
            260                 265                 270

Ser Asn Gly Ile Ala Lys Leu Arg Leu Glu Ala Trp Gly Asn Val Asn
        275                 280                 285

Gly Glu Cys Thr Glu Gly Glu Pro Asp Tyr Leu Asn Gly Ala Arg Asn
    290                 295                 300

Ala Asn Thr Leu Leu Glu Lys Glu Phe Lys Lys Phe Thr Thr Lys Leu
305                 310                 315                 320

His Thr His Ser Pro Gln Ser Met Arg Thr Asp Ile Leu Phe Glu Met
                325                 330                 335

Glu Lys Lys Tyr Pro Glu Phe Asn Arg Thr Leu His Asn Lys Phe
            340                 345                 350

Arg Ser Leu Asp Asp Ile Ala Val Thr Gly Tyr Leu Tyr His His Tyr
        355                 360                 365

Ala Leu Leu Ser Gly Arg Ala Leu Gln Ser Ser Asp Lys Thr Glu Leu
    370                 375                 380

Val Gln Gln Asn His Asp Phe Lys Lys Lys Leu Asn Asn Val Val Thr
385                 390                 395                 400

Leu Thr Lys Glu Arg Asn Phe Asp Lys Leu Pro Leu Ser Val Cys Ile
                405                 410                 415

Asn Asp Gly Ala Asp Ser His Leu Asn Glu Glu Trp Asn Val Gln Val
            420                 425                 430

Ile Lys Phe Leu Glu Thr Leu Phe Pro Leu Pro Ser Ser Phe Glu Lys
        435                 440                 445

<210> SEQ ID NO 12
<211> LENGTH: 378
<212> TYPE: PRT
<213> ORGANISM: Neisseria meningitidis
<220> FEATURE:
<223> OTHER INFORMATION: AS deltaN167-CP-A (378)

<400> SEQUENCE: 12

```
Thr Leu Ser Ser Ser Ile Ser Gln Phe Trp Phe Arg Leu Glu Phe Cys
 1               5                   10                  15

Lys Glu Asp Lys Asp Phe Ile Leu Phe Pro Thr Ala Asn Arg Tyr Ser
             20                  25                  30

Arg Lys Leu Trp Lys His Ser Ile Lys Asn Asn Gln Leu Phe Lys Glu
         35                  40                  45

Gly Ile Arg Asn Tyr Ser Glu Ile Ser Ser Leu Pro Tyr Glu Glu Asp
     50                  55                  60

His Asn Phe Asp Ile Asp Leu Val Phe Thr Trp Val Asn Ser Glu Asp
 65                  70                  75                  80

Lys Asn Trp Gln Glu Leu Tyr Lys Lys Tyr Lys Pro Asp Phe Asn Ser
                 85                  90                  95

Asp Ala Thr Ser Thr Ser Arg Phe Leu Ser Arg Asp Glu Leu Lys Phe
            100                 105                 110

Ala Leu Arg Ser Trp Glu Met Asn Gly Ser Phe Ile Arg Lys Ile Phe
        115                 120                 125

Ile Val Ser Asn Cys Ala Pro Pro Ala Trp Leu Asp Leu Asn Asn Pro
    130                 135                 140

Lys Ile Gln Trp Val Tyr His Glu Glu Ile Met Pro Gln Ser Ala Leu
145                 150                 155                 160

Pro Thr Phe Ser Ser His Ala Ile Glu Thr Ser Leu His His Ile Pro
                165                 170                 175

Gly Ile Ser Asn Tyr Phe Ile Tyr Ser Asn Asp Asp Phe Leu Leu Thr
            180                 185                 190

Lys Pro Leu Asn Lys Asp Asn Phe Phe Tyr Ser Asn Gly Ile Ala Lys
        195                 200                 205

Leu Arg Leu Glu Ala Trp Gly Asn Val Asn Gly Glu Cys Thr Glu Gly
    210                 215                 220

Glu Pro Asp Tyr Leu Asn Gly Ala Arg Asn Ala Asn Thr Leu Leu Glu
225                 230                 235                 240

Lys Glu Phe Lys Lys Phe Thr Thr Lys Leu His Thr His Ser Pro Gln
                245                 250                 255

Ser Met Arg Thr Asp Ile Leu Phe Glu Met Glu Lys Lys Tyr Pro Glu
            260                 265                 270

Glu Phe Asn Arg Thr Leu His Asn Lys Phe Arg Ser Leu Asp Asp Ile
        275                 280                 285

Ala Val Thr Gly Tyr Leu Tyr His His Tyr Ala Leu Leu Ser Gly Arg
    290                 295                 300

Ala Leu Gln Ser Ser Asp Lys Thr Glu Leu Val Gln Gln Asn His Asp
305                 310                 315                 320

Phe Lys Lys Lys Leu Asn Asn Val Val Thr Leu Thr Lys Glu Arg Asn
                325                 330                 335

Phe Asp Lys Leu Pro Leu Ser Val Cys Ile Asn Asp Gly Ala Asp Ser
            340                 345                 350

His Leu Asn Glu Glu Trp Asn Val Gln Val Ile Lys Phe Leu Glu Thr
        355                 360                 365

Leu Phe Pro Leu Pro Ser Ser Phe Glu Lys
    370                 375

<210> SEQ ID NO 13
<211> LENGTH: 311
<212> TYPE: PRT
<213> ORGANISM: Neisseria meningitidis
<220> FEATURE:
```

<223> OTHER INFORMATION: AS deltaN235-CP-A (311)

<400> SEQUENCE: 13

Asp Ile Asp Leu Val Phe Thr Trp Val Asn Ser Glu Asp Lys Asn Trp
1               5                   10                  15

Gln Glu Leu Tyr Lys Lys Tyr Lys Pro Asp Phe Asn Ser Asp Ala Thr
            20                  25                  30

Ser Thr Ser Arg Phe Leu Ser Arg Asp Glu Leu Lys Phe Ala Leu Arg
        35                  40                  45

Ser Trp Glu Met Asn Gly Ser Phe Ile Arg Lys Ile Phe Ile Val Ser
50                  55                  60

Asn Cys Ala Pro Pro Ala Trp Leu Asp Leu Asn Asn Pro Lys Ile Gln
65                  70                  75                  80

Trp Val Tyr His Glu Glu Ile Met Pro Gln Ser Ala Leu Pro Thr Phe
                85                  90                  95

Ser Ser His Ala Ile Glu Thr Ser Leu His His Ile Pro Gly Ile Ser
            100                 105                 110

Asn Tyr Phe Ile Tyr Ser Asn Asp Asp Phe Leu Leu Thr Lys Pro Leu
        115                 120                 125

Asn Lys Asp Asn Phe Phe Tyr Ser Asn Gly Ile Ala Lys Leu Arg Leu
130                 135                 140

Glu Ala Trp Gly Asn Val Asn Gly Glu Cys Thr Glu Gly Pro Asp
145                 150                 155                 160

Tyr Leu Asn Gly Ala Arg Asn Ala Asn Thr Leu Leu Glu Lys Glu Phe
                165                 170                 175

Lys Lys Phe Thr Thr Lys Leu His Thr His Ser Pro Gln Ser Met Arg
            180                 185                 190

Thr Asp Ile Leu Phe Glu Met Glu Lys Lys Tyr Pro Glu Glu Phe Asn
        195                 200                 205

Arg Thr Leu His Asn Lys Phe Arg Ser Leu Asp Asp Ile Ala Val Thr
210                 215                 220

Gly Tyr Leu Tyr His His Tyr Ala Leu Leu Ser Gly Arg Ala Leu Gln
225                 230                 235                 240

Ser Ser Asp Lys Thr Glu Leu Val Gln Gln Asn His Asp Phe Lys Lys
                245                 250                 255

Lys Leu Asn Asn Val Val Thr Leu Thr Lys Glu Arg Asn Phe Asp Lys
            260                 265                 270

Leu Pro Leu Ser Val Cys Ile Asn Asp Gly Ala Asp Ser His Leu Asn
        275                 280                 285

Glu Glu Trp Asn Val Gln Val Ile Lys Phe Leu Glu Thr Leu Phe Pro
290                 295                 300

Leu Pro Ser Ser Phe Glu Lys
305                 310

<210> SEQ ID NO 14
<211> LENGTH: 499
<212> TYPE: PRT
<213> ORGANISM: Neisseria meningitidis
<220> FEATURE:
<223> OTHER INFORMATION: AS deltaC45-CP-A (499)

<400> SEQUENCE: 14

Phe Ile Leu Asn Asn Arg Lys Trp Arg Lys Leu Lys Arg Asp Pro Ser
1               5                   10                  15

Ala Phe Phe Arg Asp Ser Lys Phe Asn Phe Leu Arg Tyr Phe Ser Ala
            20                  25                  30

```
Lys Lys Phe Ala Lys Asn Phe Lys Asn Ser Ser His Ile His Lys Thr
            35                  40                  45

Asn Ile Ser Lys Ala Gln Ser Asn Ile Ser Ser Thr Leu Lys Gln Asn
 50                  55                  60

Arg Lys Gln Asp Met Leu Ile Pro Ile Asn Phe Phe Asn Phe Glu Tyr
 65                  70                  75                  80

Ile Val Lys Lys Leu Asn Asn Gln Asn Ala Ile Gly Val Tyr Ile Leu
                 85                  90                  95

Pro Ser Asn Leu Thr Leu Lys Pro Ala Leu Cys Ile Leu Glu Ser His
                100                 105                 110

Lys Glu Asp Phe Leu Asn Lys Phe Leu Leu Thr Ile Ser Ser Glu Asn
            115                 120                 125

Leu Lys Leu Gln Tyr Lys Phe Asn Gly Gln Ile Lys Asn Pro Lys Ser
        130                 135                 140

Val Asn Glu Ile Trp Thr Asp Leu Phe Ser Ile Ala His Val Asp Met
145                 150                 155                 160

Lys Leu Ser Thr Asp Arg Thr Leu Ser Ser Ser Ile Ser Gln Phe Trp
                165                 170                 175

Phe Arg Leu Glu Phe Cys Lys Glu Asp Lys Asp Phe Ile Leu Phe Pro
            180                 185                 190

Thr Ala Asn Arg Tyr Ser Arg Lys Leu Trp Lys His Ser Ile Lys Asn
        195                 200                 205

Asn Gln Leu Phe Lys Glu Gly Ile Arg Asn Tyr Ser Glu Ile Ser Ser
    210                 215                 220

Leu Pro Tyr Glu Glu Asp His Asn Phe Asp Ile Asp Leu Val Phe Thr
225                 230                 235                 240

Trp Val Asn Ser Glu Asp Lys Asn Trp Gln Glu Leu Tyr Lys Lys Tyr
                245                 250                 255

Lys Pro Asp Phe Asn Ser Asp Ala Thr Ser Thr Ser Arg Phe Leu Ser
            260                 265                 270

Arg Asp Glu Leu Lys Phe Ala Leu Arg Ser Trp Glu Met Asn Gly Ser
        275                 280                 285

Phe Ile Arg Lys Ile Phe Ile Val Ser Asn Cys Ala Pro Pro Ala Trp
    290                 295                 300

Leu Asp Leu Asn Asn Pro Lys Ile Gln Trp Val Tyr His Glu Glu Ile
305                 310                 315                 320

Met Pro Gln Ser Ala Leu Pro Thr Phe Ser Ser His Ala Ile Glu Thr
                325                 330                 335

Ser Leu His His Ile Pro Gly Ile Ser Asn Tyr Phe Ile Tyr Ser Asn
            340                 345                 350

Asp Asp Phe Leu Leu Thr Lys Pro Leu Asn Lys Asp Asn Phe Phe Tyr
        355                 360                 365

Ser Asn Gly Ile Ala Lys Leu Arg Leu Glu Ala Trp Gly Asn Val Asn
    370                 375                 380

Gly Glu Cys Thr Glu Gly Pro Asp Tyr Leu Asn Gly Ala Arg Asn
385                 390                 395                 400

Ala Asn Thr Leu Leu Glu Lys Glu Phe Lys Lys Phe Thr Thr Lys Leu
                405                 410                 415

His Thr His Ser Pro Gln Ser Met Arg Thr Asp Ile Leu Phe Glu Met
            420                 425                 430

Glu Lys Lys Tyr Pro Glu Glu Phe Asn Arg Thr Leu His Asn Lys Phe
        435                 440                 445
```

```
Arg Ser Leu Asp Asp Ile Ala Val Thr Gly Tyr Leu Tyr His His Tyr
    450                 455                 460

Ala Leu Leu Ser Gly Arg Ala Leu Gln Ser Ser Asp Lys Thr Glu Leu
465                 470                 475                 480

Val Gln Gln Asn His Asp Phe Lys Lys Leu Asn Asn Val Val Thr
                485                 490                 495

Leu Thr Lys

<210> SEQ ID NO 15
<211> LENGTH: 519
<212> TYPE: PRT
<213> ORGANISM: Neisseria meningitidis
<220> FEATURE:
<223> OTHER INFORMATION: AS deltaC25-CP-A (519)

<400> SEQUENCE: 15

Phe Ile Leu Asn Asn Arg Lys Trp Arg Lys Leu Lys Arg Asp Pro Ser
1               5                   10                  15

Ala Phe Phe Arg Asp Ser Lys Phe Asn Phe Leu Arg Tyr Phe Ser Ala
                20                  25                  30

Lys Lys Phe Ala Lys Asn Phe Lys Asn Ser Ser His Ile His Lys Thr
            35                  40                  45

Asn Ile Ser Lys Ala Gln Ser Asn Ile Ser Ser Thr Leu Lys Gln Asn
50                  55                  60

Arg Lys Gln Asp Met Leu Ile Pro Ile Asn Phe Asn Phe Glu Tyr
65                  70                  75                  80

Ile Val Lys Lys Leu Asn Asn Gln Asn Ala Ile Gly Val Tyr Ile Leu
                85                  90                  95

Pro Ser Asn Leu Thr Leu Lys Pro Ala Leu Cys Ile Leu Glu Ser His
            100                 105                 110

Lys Glu Asp Phe Leu Asn Lys Phe Leu Leu Thr Ile Ser Ser Glu Asn
        115                 120                 125

Leu Lys Leu Gln Tyr Lys Phe Asn Gly Gln Ile Lys Asn Pro Lys Ser
130                 135                 140

Val Asn Glu Ile Trp Thr Asp Leu Phe Ser Ile Ala His Val Asp Met
145                 150                 155                 160

Lys Leu Ser Thr Asp Arg Thr Leu Ser Ser Ser Ile Ser Gln Phe Trp
                165                 170                 175

Phe Arg Leu Glu Phe Cys Lys Glu Asp Lys Asp Phe Ile Leu Phe Pro
            180                 185                 190

Thr Ala Asn Arg Tyr Ser Arg Lys Leu Trp Lys His Ser Ile Lys Asn
        195                 200                 205

Asn Gln Leu Phe Lys Glu Gly Ile Arg Asn Tyr Ser Glu Ile Ser Ser
210                 215                 220

Leu Pro Tyr Glu Glu Asp His Asn Phe Asp Ile Asp Leu Val Phe Thr
225                 230                 235                 240

Trp Val Asn Ser Glu Asp Lys Asn Trp Gln Glu Leu Tyr Lys Lys Tyr
                245                 250                 255

Lys Pro Asp Phe Asn Ser Asp Ala Thr Ser Thr Ser Arg Phe Leu Ser
            260                 265                 270

Arg Asp Glu Leu Lys Phe Ala Leu Arg Ser Trp Glu Met Asn Gly Ser
        275                 280                 285

Phe Ile Arg Lys Ile Phe Ile Val Ser Asn Cys Ala Pro Pro Ala Trp
290                 295                 300

Leu Asp Leu Asn Asn Pro Lys Ile Gln Trp Val Tyr His Glu Glu Ile
```

```
                305                 310                 315                 320
Met Pro Gln Ser Ala Leu Pro Thr Phe Ser Ser His Ala Ile Glu Thr
                325                 330                 335

Ser Leu His His Ile Pro Gly Ile Ser Asn Tyr Phe Ile Tyr Ser Asn
                340                 345                 350

Asp Asp Phe Leu Leu Thr Lys Pro Leu Asn Lys Asp Asn Phe Phe Tyr
                355                 360                 365

Ser Asn Gly Ile Ala Lys Leu Arg Leu Glu Ala Trp Gly Asn Val Asn
370                 375                 380

Gly Glu Cys Thr Glu Gly Glu Pro Asp Tyr Leu Asn Gly Ala Arg Asn
385                 390                 395                 400

Ala Asn Thr Leu Leu Glu Lys Glu Phe Lys Lys Phe Thr Thr Lys Leu
                405                 410                 415

His Thr His Ser Pro Gln Ser Met Arg Thr Asp Ile Leu Phe Glu Met
                420                 425                 430

Glu Lys Lys Tyr Pro Glu Glu Phe Asn Arg Thr Leu His Asn Lys Phe
                435                 440                 445

Arg Ser Leu Asp Asp Ile Ala Val Thr Gly Tyr Leu Tyr His His Tyr
                450                 455                 460

Ala Leu Leu Ser Gly Arg Ala Leu Gln Ser Ser Asp Lys Thr Glu Leu
465                 470                 475                 480

Val Gln Gln Asn His Asp Phe Lys Lys Lys Leu Asn Asn Val Val Thr
                485                 490                 495

Leu Thr Lys Glu Arg Asn Phe Asp Lys Leu Pro Leu Ser Val Cys Ile
                500                 505                 510

Asn Asp Gly Ala Asp Ser His
                515
```

<210> SEQ ID NO 16
<211> LENGTH: 1455
<212> TYPE: DNA
<213> ORGANISM: Neisseria meningitidis
<220> FEATURE:
<223> OTHER INFORMATION: DNA CP-X/CsxA full-length (1455)

<400> SEQUENCE: 16

```
attatgagca aaattagcaa attggtaacc cacccaaacc ttttctttcg agattatttc    60
ttaaaaaaag caccgttaaa ttatggcgaa aatattaaac ctttaccagt cgaaacctct   120
tctcatagca aaaaaaatac agcccataaa acacccgtat catccgacca accaattgaa   180
gatccatacc cagtaacatt tccaattgat gtagtttata cttgggtaga ttcagatgat   240
gaaaaattca atgaagaacg cctaaagttt caaaattcaa gcacatctga gactctacaa   300
ggcaaagcag aaagcaccga tattgcaaga ttccaatcac gcgacgaatt aaaatattcg   360
attcgaagcc tgatgaagta tgccccatgg gtaaatcata tttacattgt aacaaatggt   420
caaataccaa aatggttaga taccaacaat acaaaggtaa cgattatccc tcactcaact   480
attatcgaca gtcaatttct ccctactttt aattctcacg tcattgaatc ctctctatat   540
aaaatcccag gattatcaga gcattacatt tatttcaatg atgatgtcat gctagctaga   600
gatttaagcc catcttattt ctttacaagc agcggattag caaaactgtt tattaccaac   660
tctcgtctac caaatggcta taagaatgtg aaagacacac caacccaatg ggcctcaaaa   720
aattcccgtg agcttttaca tgcagaaaca ggatttgggg ctgaagccat gtttgcacat   780
acttttcatc cacaacgtaa aagtgtacat gaatctattg aacacctatg gcatgaacaa   840
```

```
ttaaatgttt gtcgtcaaaa ccgtttccgt gatatttcag atattaacat ggcgacattc      900
ctgcaccacc attttgccat tttgacaggc caagctcttg ctacacgcac taaatgtatt      960
tactttaaca ttcgctctcc tcaagcagct cagcattaca aaacattatt agctcgaaaa     1020
ggaagcgaat acagcccaca ttctatctgc ttaaatgatc atacatcgag caataaaaat     1080
attttatcta attacgaagc caaattacaa agcttttag aaacatacta tccagatgta     1140
tcagaagcag aaattctcct tcctactaaa tctgaagtag ctgaattagt taaacataaa     1200
gattatttaa ctgtatatac taaattatta cctattatca ataagcagct ggtcaataaa     1260
tataataaac cttattcata tcttttctat tatttaggtt tatctgcccg gttttattt      1320 gaagaaacgc aacaagaaca ctaccgggaa actgctgaag aaaatttaca aatcttttgt     1380
ggcctaaacc caaaacatac actagccctc aaatacttag cggatgtcac cctcacatca     1440
cagcctagtg gacaa                                                      1455
```

<210> SEQ ID NO 17
<211> LENGTH: 1284
<212> TYPE: DNA
<213> ORGANISM: Neisseria meningitidis
<220> FEATURE:
<223> OTHER INFORMATION: DNA deltaN58-CP-X (1284)

<400> SEQUENCE: 17

```
ccaattgaag atccataccc agtaacattt ccaattgatg tagtttatac ttgggtagat       60
tcagatgatg aaaaattcaa tgaagaacgc ctaaagtttc aaaattcaag cacatctgag      120
actctacaag gcaaagcaga aagcaccgat attgcaagat ccaatcacg cgacgaatta      180 aaatattcga ttcgaagcct gatgaagtat gccccatggg taaatcatat ttacattgta      240
acaaatggtc aaataccaaa atggttagat accaacaata caaggtaac gattatccct      300 cactcaacta ttatcgacag tcaatttctc cctactttta attctcacgt cattgaatcc      360
tctctatata aaatcccagg attatcagag cattacattt atttcaatga tgatgtcatg      420
ctagctagag atttaagccc atcttatttc tttacaagca gcggattagc aaaactgttt      480
attaccaact ctcgtctacc aaatggctat aagaatgtga agacacacc aacccaatgg      540 gcctcaaaaa attcccgtga gcttttacat gcagaaacag gattttgggc tgaagccatg      600
tttgcacata cttttcatcc acaacgtaaa agtgtacatg aatctattga cacctatgg       660 catgaacaat aaatgtttg tcgtcaaaac cgtttccgtg atatttcaga tattaacatg      720
gcgacattcc tgcaccacca ttttgccatt ttgacaggcc aagctcttgc tacacgcact      780
aaatgtattt actttaacat tcgctctcct caagcagctc agcattacaa acattatta      840 gctcgaaaag gaagcgaata cagcccacat tctatctgct taaatgatca tacatcgagc      900
aataaaaata ttttatctaa ttacgaagcc aaattacaaa gcttttaga aacatactat      960 ccagatgtat cagaagcaga aattctcctt cctactaaat ctgaagtagc tgaattagtt     1020
aaacataaag attatttaac tgtatatact aaattattac ctattatcaa taagcagctg     1080
gtcaataaat ataataaacc ttattcatat cttttctatt atttaggttt atctgcccgg     1140 ttttatttg aagaaacgca acaagaacac taccgggaaa ctgctgaaga aaatttacaa     1200
atcttttgtg gcctaaaccc aaaacataca ctagccctca aatacttagc ggatgtcacc     1260
ctcacatcac agcctagtgg acaa                                            1284
```

<210> SEQ ID NO 18
<211> LENGTH: 1146

<212> TYPE: DNA
<213> ORGANISM: Neisseria meningitidis
<220> FEATURE:
<223> OTHER INFORMATION: DNA deltaN104-CP-X (1146)

<400> SEQUENCE: 18

| | | | | |
|---|---|---|---|---|
| gaaagcaccg atattgcaag attccaatca cgcgacgaat taaaatattc gattcgaagc | 60 |
| ctgatgaagt atgccccatg ggtaaatcat atttacattg taacaaatgg tcaaatacca | 120 |
| aaatggttag ataccaacaa tacaaaggta acgattatcc ctcactcaac tattatcgac | 180 |
| agtcaatttc tccctacttt taattctcac gtcattgaat cctctctata aaaatccca | 240 |
| ggattatcag agcattacat ttatttcaat gatgatgtca tgctagctag agatttaagc | 300 |
| ccatcttatt tctttacaag cagcggatta gcaaaactgt ttattaccaa ctctcgtcta | 360 |
| ccaaatggct ataagaatgt gaaagacaca ccaacccaat gggcctcaaa aaattcccgt | 420 |
| gagcttttac atgcagaaac aggattttgg gctgaagcca tgtttgcaca cttttcat | 480 |
| ccacaacgta aaagtgtaca tgaatctatt gaacacctat ggcatgaaca attaaatgtt | 540 |
| tgtcgtcaaa accgtttccg tgatatttca gatattaaca tggcgacatt cctgcaccac | 600 |
| cattttgcca ttttgacagg ccaagctctt gctacacgca ctaaatgtat ttactttaac | 660 |
| attcgctctc ctcaagcagc tcagcattac aaaacattat tagctcgaaa aggaagcgaa | 720 |
| tacagcccac attctatctg cttaaatgat catacatcga gcaataaaaa tattttatct | 780 |
| aattacgaag ccaaattaca aagcttttta gaaacatact atccagatgt atcagaagca | 840 |
| gaaattctcc ttcctactaa atctgaagta gctgaattag ttaaacataa agattattta | 900 |
| actgtatata ctaaattatt acctattatc aataagcagc tggtcaataa atataataaa | 960 |
| ccttattcat atcttttcta ttatttaggt ttatctgccc ggtttttatt tgaagaaacg | 1020 |
| caacaagaac actaccggga aactgctgaa gaaaatttac aaatcttttg tggcctaaac | 1080 |
| ccaaaacata cactagccct caaatactta gcggatgtca ccctcacatc acagcctagt | 1140 |
| ggacaa | 1146 |

<210> SEQ ID NO 19
<211> LENGTH: 933
<212> TYPE: DNA
<213> ORGANISM: Neisseria meningitidis
<220> FEATURE:
<223> OTHER INFORMATION: DNA deltaC174-CP-X (933)

<400> SEQUENCE: 19

| | | | | |
|---|---|---|---|---|
| attatgagca aaattagcaa attggtaacc cacccaaacc ttttctttcg agattatttc | 60 |
| ttaaaaaaag caccgttaaa ttatggcgaa atattaaac ctttaccagt cgaaacctct | 120 |
| tctcatagca aaaaaaatac agcccataaa acacccgtat catccgacca accaattgaa | 180 |
| gatccatacc cagtaacatt tccaattgat gtagtttata cttgggtaga ttcagatgat | 240 |
| gaaaaattca tgaagaacg cctaaagttt caaaattcaa gcacatctga gactctacaa | 300 |
| ggcaaagcag aaagcaccga tattgcaaga ttccaatcac gcgacgaatt aaaatattcg | 360 |
| attcgaagcc tgatgaagta tgccccatgg gtaaatcata tttacattgt aacaaatggt | 420 |
| caaataccaa aatggttaga taccaacaat acaaaggtaa cgattatccc tcactcaact | 480 |
| attatcgaca gtcaatttct ccctactttt aattctcacg tcattgaatc ctctctatat | 540 |
| aaaatcccag gattatcaga gcattacatt tatttcaatg atgatgtcat gctagctaga | 600 |
| gatttaagcc catcttattt ctttacaagc agcggattag caaaactgtt tattaccaac | 660 |

```
tctcgtctac caaatggcta taagaatgtg aaagacacac caacccaatg ggcctcaaaa      720
aattcccgtg agcttttaca tgcagaaaca ggattttggg ctgaagccat gtttgcacat      780
acttttcatc cacaacgtaa agtgtacat gaatctattg aacacctatg gcatgaacaa       840
ttaaatgttt gtcgtcaaaa ccgtttccgt gatatttcag atattaacat ggcgacattc      900
ctgcaccacc attttgccat tttgacaggc caa                                   933
```

<210> SEQ ID NO 20
<211> LENGTH: 1158
<212> TYPE: DNA
<213> ORGANISM: Neisseria meningitidis
<220> FEATURE:
<223> OTHER INFORMATION: DNA deltaC99-CP-X (1158)

<400> SEQUENCE: 20

```
attatgagca aaattagcaa attggtaacc cacccaaacc ttttctttcg agattatttc       60
ttaaaaaaag caccgttaaa ttatggcgaa atattaaac ctttaccagt cgaaacctct      120
tctcatagca aaaaaaatac agcccataaa acacccgtat catccgacca accaattgaa      180
gatccatacc cagtaacatt tccaattgat gtagtttata cttgggtaga ttcagatgat      240
gaaaaattca atgaagaacg cctaaagttt caaaattcaa gcacatctga gactctacaa      300
ggcaaagcag aaagcaccga tattgcaaga ttccaatcac gcgacgaatt aaaatattcg      360
attcgaagcc tgatgaagta tgccccatgg gtaaatcata tttacattgt aacaaatggt      420
caaataccaa atggttaga taccaacaat acaaaggtaa cgattatccc tcactcaact       480
attatcgaca gtcaatttct ccctactttt aattctcacg tcattgaatc ctctctatat      540
aaaatcccag gattatcaga gcattacatt tatttcaatg atgatgtcat gctagctaga      600
gatttaagcc catcttattt ctttacaagc agcggattag caaaactgtt tattaccaac      660
tctcgtctac caaatggcta taagaatgtg aaagacacac caacccaatg ggcctcaaaa      720
aattcccgtg agcttttaca tgcagaaaca ggattttggg ctgaagccat gtttgcacat      780
acttttcatc cacaacgtaa agtgtacat gaatctattg aacacctatg gcatgaacaa       840
ttaaatgttt gtcgtcaaaa ccgtttccgt gatatttcag atattaacat ggcgacattc      900
ctgcaccacc attttgccat tttgacaggc caagctcttg ctacacgcac taaatgtatt      960
tactttaaca ttcgctctcc tcaagcagct cagcattaca aaacattatt agctcgaaaa     1020
ggaagcgaat acagcccaca ttctatctgc ttaaatgatc atacatcgag caataaaaat     1080
attttatcta attacgaagc caaattacaa agcttttag aaacatacta ccagatgta      1140 tcagaagcag aaattctc                                                  1158
```

<210> SEQ ID NO 21
<211> LENGTH: 987
<212> TYPE: DNA
<213> ORGANISM: Neisseria meningitidis
<220> FEATURE:
<223> OTHER INFORMATION: DNA deltaN58 deltaC99-CP-X (987)

<400> SEQUENCE: 21

```
ccaattgaag atccataccc agtaacattt ccaattgatg tagtttatac ttgggtagat       60
tcagatgatg aaaaattcaa tgaagaacgc ctaaagtttc aaaattcaag cacatctgag      120
actctacaag gcaaagcaga aagcaccgat attgcaagat tccaatcacg cgacgaatta      180
aaatattcga ttcgaagcct gatgaagtat gccccatggg taaatcatat ttacattgta      240
acaaatggtc aaataccaaa tggttagat accaacaata caaaggtaac gattatccct       300
```

```
cactcaacta ttatcgacag tcaatttctc cctactttta attctcacgt cattgaatcc    360
tctctatata aaatcccagg attatcagag cattacattt atttcaatga tgatgtcatg    420
ctagctagag atttaagccc atcttatttc tttacaagca gcggattagc aaaactgttt    480
attaccaact ctcgtctacc aaatggctat aagaatgtga aagacacacc aacccaatgg    540
gcctcaaaaa attcccgtga gcttttacat gcagaaacag attttgggc tgaagccatg     600 tttgcacata cttttcatcc acaacgtaaa agtgtacatg aatctattga cacctatgg     660 catgaacaat taaatgtttg tcgtcaaaac cgtttccgtg atatttcaga tattaacatg    720
gcgacattcc tgcaccacca ttttgccatt ttgacaggcc aagctcttgc tacacgcact    780
aaatgtattt actttaacat tcgctctcct caagcagctc agcattacaa acattatta    840 gctcgaaaag gaagcgaata cagcccacat tctatctgct taaatgatca tacatcgagc    900
aataaaaata ttttatctaa ttacgaagcc aaattacaaa gcttttttaga aacatactat    960 ccagatgtat cagaagcaga aattctc                                        987

<210> SEQ ID NO 22
<211> LENGTH: 1233
<212> TYPE: DNA
<213> ORGANISM: Neisseria meningitidis
<220> FEATURE:
<223> OTHER INFORMATION: DNA deltaN65deltaC10-CP-X (1233)

<400> SEQUENCE: 22
gtaacatttc caattgatgt agtttatact tgggtagatt cagatgatga aaaattcaat     60
gaagaacgcc taaagtttca aaattcaagc acatctgaga ctctacaagg caaagcagaa    120
agcaccgata ttgcaagatt ccaatcacgc gacgaattaa atattcgat tcgaagcctg    180 atgaagtatg ccccatgggt aaatcatatt tacattgtaa caaatggtca aataccaaaa    240
tggttagata ccaacaatac aaaggtaacg attatccctc actcaactat tatcgacagt    300
caatttctcc ctactttttaa ttctcacgtc attgaatcct ctctatataa aatcccagga    360
ttatcagagc attacattta tttcaatgat gatgtcatgc tagctagaga tttaagccca    420
tcttatttct ttacaagcag cggattagca aaactgttta ttaccaactc tcgtctacca    480
aatggctata agaatgtgaa agacacacca acccaatggg cctcaaaaaa ttcccgtgag    540
cttttacatg cagaaacagg attttgggct gaagccatgt ttgcacatac ttttcatcca    600
caacgtaaaa gtgtacatga atctattgaa cacctatggc atgaacaatt aaatgtttgt    660
cgtcaaaacc gtttccgtga tatttcagat attaacatgg cgacattcct gcaccaccat    720
tttgccattt tgacaggcca agctcttgct acacgcacta aatgtattta ctttaacatt    780
cgctctcctc aagcagctca gcattacaaa acattattag ctcgaaaagg aagcgaatac    840
agcccacatt ctatctgctt aaatgatcat acatcgagca ataaaaatat tttatctaat    900
tacgaagcca aattacaaag cttttttagaa acatactatc cagatgtatc agaagcagaa    960
attctccttc ctactaaatc tgaagtagct gaattagtta acataaaga ttatttaact     1020 gtatatacta aattattacc tattatcaat aagcagctgg tcaataaata taataaaacct   1080 tattcatatc ttttctatta tttaggttta tctgcccggt ttttatttga agaaacgcaa    1140
caagaacact accgggaaac tgctgaagaa aatttacaaa tcttttgtgg cctaaaccca    1200
aaacatacac tagccctcaa atacttagcg gat                                1233

<210> SEQ ID NO 23
```

<211> LENGTH: 960
<212> TYPE: DNA
<213> ORGANISM: Neisseria meningitidis
<220> FEATURE:
<223> OTHER INFORMATION: DNA deltaN67deltaC99-CP-X (960)

<400> SEQUENCE: 23
tttccaattg atgtagttta tacttgggta gattcagatg atgaaaaatt caatgaagaa 60
cgcctaaagt ttcaaaattc aagcacatct gagactctac aaggcaaagc agaaagcacc 120
gatattgcaa gattccaatc acgcgacgaa ttaaaatatt cgattcgaag cctgatgaag 180
tatgccccat gggtaaatca tatttacatt gtaacaaatg gtcaaatacc aaaatggtta 240
gataccaaca atacaaaggt aacgattatc cctcactcaa ctattatcga cagtcaattt 300
ctccctactt ttaattctca cgtcattgaa tcctctctat ataaaatccc aggattatca 360
gagcattaca tttatttcaa tgatgatgtc atgctagcta gagatttaag cccatcttat 420
ttctttacaa gcagcggatt agcaaaactg tttattacca actctcgtct accaaatggc 480
tataagaatg tgaaagacac accaacccaa tgggcctcaa aaaattcccg tgagctttta 540
catgcagaaa caggattttg ggctgaagcc atgtttgcac atacttttca tccacaacgt 600
aaaagtgtac atgaatctat tgaacaccta tggcatgaac aattaaatgt ttgtcgtcaa 660
aaccgtttcc gtgatatttc agatattaac atggcgacat tcctgcacca ccattttgcc 720
attttgacag gccaagctct tgctacacgc actaaatgta tttactttaa cattcgctct 780
cctcaagcag ctcagcatta caaaacatta ttagctcgaa aaggaagcga atacagccca 840
cattctatct gcttaaatga tcatacatcg agcaataaaa atattttatc taattacgaa 900
gccaaattac aaagcttttt agaaacatac tatccagatg tatcagaagc agaaattctc 960

<210> SEQ ID NO 24
<211> LENGTH: 485
<212> TYPE: PRT
<213> ORGANISM: Neisseria meningitidis
<220> FEATURE:
<223> OTHER INFORMATION: AS CP-X/CsxA full-length (485)

<400> SEQUENCE: 24

Ile Met Ser Lys Ile Ser Lys Leu Val Thr His Pro Asn Leu Phe Phe
1 5 10 15

Arg Asp Tyr Phe Leu Lys Lys Ala Pro Leu Asn Tyr Gly Glu Asn Ile
20 25 30

Lys Pro Leu Pro Val Glu Thr Ser Ser His Ser Lys Lys Asn Thr Ala
35 40 45

His Lys Thr Pro Val Ser Ser Asp Gln Pro Ile Glu Asp Pro Tyr Pro
50 55 60

Val Thr Phe Pro Ile Asp Val Val Tyr Thr Trp Val Asp Ser Asp Asp
65 70 75 80

Glu Lys Phe Asn Glu Glu Arg Leu Lys Phe Gln Asn Ser Ser Thr Ser
85 90 95

Glu Thr Leu Gln Gly Lys Ala Glu Ser Thr Asp Ile Ala Arg Phe Gln
100 105 110

Ser Arg Asp Glu Leu Lys Tyr Ser Ile Arg Ser Leu Met Lys Tyr Ala
115 120 125

Pro Trp Val Asn His Ile Tyr Ile Val Thr Asn Gly Gln Ile Pro Lys
130 135 140

Trp Leu Asp Thr Asn Asn Thr Lys Val Thr Ile Ile Pro His Ser Thr
145 150 155 160

-continued

```
Ile Ile Asp Ser Gln Phe Leu Pro Thr Phe Asn Ser His Val Ile Glu
            165                 170                 175

Ser Ser Leu Tyr Lys Ile Pro Gly Leu Ser Glu His Tyr Ile Tyr Phe
        180                 185                 190

Asn Asp Asp Val Met Leu Ala Arg Asp Leu Ser Pro Ser Tyr Phe Phe
            195                 200                 205

Thr Ser Ser Gly Leu Ala Lys Leu Phe Ile Thr Asn Ser Arg Leu Pro
210                 215                 220

Asn Gly Tyr Lys Asn Val Lys Asp Thr Pro Thr Gln Trp Ala Ser Lys
225                 230                 235                 240

Asn Ser Arg Glu Leu Leu His Ala Glu Thr Gly Phe Trp Ala Glu Ala
            245                 250                 255

Met Phe Ala His Thr Phe His Pro Gln Arg Lys Ser Val His Glu Ser
            260                 265                 270

Ile Glu His Leu Trp His Glu Gln Leu Asn Val Cys Arg Gln Asn Arg
        275                 280                 285

Phe Arg Asp Ile Ser Asp Ile Asn Met Ala Thr Phe Leu His His His
290                 295                 300

Phe Ala Ile Leu Thr Gly Gln Ala Leu Ala Thr Arg Thr Lys Cys Ile
305                 310                 315                 320

Tyr Phe Asn Ile Arg Ser Pro Gln Ala Ala Gln His Tyr Lys Thr Leu
                325                 330                 335

Leu Ala Arg Lys Gly Ser Glu Tyr Ser Pro His Ser Ile Cys Leu Asn
            340                 345                 350

Asp His Thr Ser Ser Asn Lys Asn Ile Leu Ser Asn Tyr Glu Ala Lys
        355                 360                 365

Leu Gln Ser Phe Leu Glu Thr Tyr Tyr Pro Asp Val Ser Glu Ala Glu
    370                 375                 380

Ile Leu Leu Pro Thr Lys Ser Glu Val Ala Glu Leu Val Lys His Lys
385                 390                 395                 400

Asp Tyr Leu Thr Val Tyr Thr Lys Leu Leu Pro Ile Ile Asn Lys Gln
                405                 410                 415

Leu Val Asn Lys Tyr Asn Lys Pro Tyr Ser Tyr Leu Phe Tyr Tyr Leu
            420                 425                 430

Gly Leu Ser Ala Arg Phe Leu Phe Glu Glu Thr Gln Gln Glu His Tyr
        435                 440                 445

Arg Glu Thr Ala Glu Glu Asn Leu Gln Ile Phe Cys Gly Leu Asn Pro
    450                 455                 460

Lys His Thr Leu Ala Leu Lys Tyr Leu Ala Asp Val Thr Leu Thr Ser
465                 470                 475                 480

Gln Pro Ser Gly Gln
                485

<210> SEQ ID NO 25
<211> LENGTH: 428
<212> TYPE: PRT
<213> ORGANISM: Neisseria meningitidis
<220> FEATURE:
<223> OTHER INFORMATION: AS deltaN58-CP-X (428)

<400> SEQUENCE: 25

Pro Ile Glu Asp Pro Tyr Pro Val Thr Phe Pro Ile Asp Val Val Tyr
1               5                   10                  15

Thr Trp Val Asp Ser Asp Asp Glu Lys Phe Asn Glu Glu Arg Leu Lys
            20                  25                  30
```

Phe Gln Asn Ser Ser Thr Ser Glu Thr Leu Gln Gly Lys Ala Glu Ser
35                  40                  45

Thr Asp Ile Ala Arg Phe Gln Ser Arg Asp Glu Leu Lys Tyr Ser Ile
50                  55                  60

Arg Ser Leu Met Lys Tyr Ala Pro Trp Val Asn His Ile Tyr Ile Val
65                  70                  75                  80

Thr Asn Gly Gln Ile Pro Lys Trp Leu Asp Thr Asn Asn Thr Lys Val
                85                  90                  95

Thr Ile Ile Pro His Ser Thr Ile Ile Asp Ser Gln Phe Leu Pro Thr
                100                 105                 110

Phe Asn Ser His Val Ile Glu Ser Ser Leu Tyr Lys Ile Pro Gly Leu
                115                 120                 125

Ser Glu His Tyr Ile Tyr Phe Asn Asp Asp Val Met Leu Ala Arg Asp
130                 135                 140

Leu Ser Pro Ser Tyr Phe Phe Thr Ser Ser Gly Leu Ala Lys Leu Phe
145                 150                 155                 160

Ile Thr Asn Ser Arg Leu Pro Asn Gly Tyr Lys Asn Val Lys Asp Thr
                165                 170                 175

Pro Thr Gln Trp Ala Ser Lys Asn Ser Arg Glu Leu Leu His Ala Glu
                180                 185                 190

Thr Gly Phe Trp Ala Glu Ala Met Phe Ala His Thr Phe His Pro Gln
                195                 200                 205

Arg Lys Ser Val His Glu Ser Ile Glu His Leu Trp His Glu Gln Leu
210                 215                 220

Asn Val Cys Arg Gln Asn Arg Phe Arg Asp Ile Ser Asp Ile Asn Met
225                 230                 235                 240

Ala Thr Phe Leu His His His Phe Ala Ile Leu Thr Gly Gln Ala Leu
                245                 250                 255

Ala Thr Arg Thr Lys Cys Ile Tyr Phe Asn Ile Arg Ser Pro Gln Ala
                260                 265                 270

Ala Gln His Tyr Lys Thr Leu Leu Ala Arg Lys Gly Ser Glu Tyr Ser
                275                 280                 285

Pro His Ser Ile Cys Leu Asn Asp His Thr Ser Ser Asn Lys Asn Ile
                290                 295                 300

Leu Ser Asn Tyr Glu Ala Lys Leu Gln Ser Phe Leu Glu Thr Tyr Tyr
305                 310                 315                 320

Pro Asp Val Ser Glu Ala Glu Ile Leu Leu Pro Thr Lys Ser Glu Val
                325                 330                 335

Ala Glu Leu Val Lys His Lys Asp Tyr Leu Thr Val Tyr Thr Lys Leu
                340                 345                 350

Leu Pro Ile Ile Asn Lys Gln Leu Val Asn Lys Tyr Asn Lys Pro Tyr
                355                 360                 365

Ser Tyr Leu Phe Tyr Leu Gly Leu Ser Ala Arg Phe Leu Phe Glu
370                 375                 380

Glu Thr Gln Gln Glu His Tyr Arg Glu Thr Ala Glu Glu Asn Leu Gln
385                 390                 395                 400

Ile Phe Cys Gly Leu Asn Pro Lys His Thr Leu Ala Leu Lys Tyr Leu
                405                 410                 415

Ala Asp Val Thr Leu Thr Ser Gln Pro Ser Gly Gln
                420                 425

<210> SEQ ID NO 26
<211> LENGTH: 382

<212> TYPE: PRT
<213> ORGANISM: Neisseria meningitidis
<220> FEATURE:
<223> OTHER INFORMATION: AS deltaN104-CP-X (382)

<400> SEQUENCE: 26

Glu Ser Thr Asp Ile Ala Arg Phe Gln Ser Arg Asp Glu Leu Lys Tyr
1               5                   10                  15

Ser Ile Arg Ser Leu Met Lys Tyr Ala Pro Trp Val Asn His Ile Tyr
            20                  25                  30

Ile Val Thr Asn Gly Gln Ile Pro Lys Trp Leu Asp Thr Asn Asn Thr
        35                  40                  45

Lys Val Thr Ile Ile Pro His Ser Thr Ile Ile Asp Ser Gln Phe Leu
50                  55                  60

Pro Thr Phe Asn Ser His Val Ile Glu Ser Ser Leu Tyr Lys Ile Pro
65                  70                  75                  80

Gly Leu Ser Glu His Tyr Ile Tyr Phe Asn Asp Asp Val Met Leu Ala
                85                  90                  95

Arg Asp Leu Ser Pro Ser Tyr Phe Phe Thr Ser Ser Gly Leu Ala Lys
            100                 105                 110

Leu Phe Ile Thr Asn Ser Arg Leu Pro Asn Gly Tyr Lys Asn Val Lys
        115                 120                 125

Asp Thr Pro Thr Gln Trp Ala Ser Lys Asn Ser Arg Glu Leu Leu His
130                 135                 140

Ala Glu Thr Gly Phe Trp Ala Glu Ala Met Phe Ala His Thr Phe His
145                 150                 155                 160

Pro Gln Arg Lys Ser Val His Glu Ser Ile Glu His Leu Trp His Glu
                165                 170                 175

Gln Leu Asn Val Cys Arg Gln Asn Arg Phe Arg Asp Ile Ser Asp Ile
            180                 185                 190

Asn Met Ala Thr Phe Leu His His Phe Ala Ile Leu Thr Gly Gln
        195                 200                 205

Ala Leu Ala Thr Arg Thr Lys Cys Ile Tyr Phe Asn Ile Arg Ser Pro
210                 215                 220

Gln Ala Ala Gln His Tyr Lys Thr Leu Leu Ala Arg Lys Gly Ser Glu
225                 230                 235                 240

Tyr Ser Pro His Ser Ile Cys Leu Asn Asp His Thr Ser Ser Asn Lys
                245                 250                 255

Asn Ile Leu Ser Asn Tyr Glu Ala Lys Leu Gln Ser Phe Leu Glu Thr
            260                 265                 270

Tyr Tyr Pro Asp Val Ser Glu Ala Glu Ile Leu Leu Pro Thr Lys Ser
        275                 280                 285

Glu Val Ala Glu Leu Val Lys His Lys Asp Tyr Leu Thr Val Tyr Thr
290                 295                 300

Lys Leu Leu Pro Ile Ile Asn Lys Gln Leu Val Asn Lys Tyr Asn Lys
305                 310                 315                 320

Pro Tyr Ser Tyr Leu Phe Tyr Tyr Leu Gly Leu Ser Ala Arg Phe Leu
                325                 330                 335

Phe Glu Glu Thr Gln Gln Glu His Tyr Arg Glu Thr Ala Glu Glu Asn
            340                 345                 350

Leu Gln Ile Phe Cys Gly Leu Asn Pro Lys His Thr Leu Ala Leu Lys
        355                 360                 365

Tyr Leu Ala Asp Val Thr Leu Thr Ser Gln Pro Ser Gly Gln
370                 375                 380

<210> SEQ ID NO 27
<211> LENGTH: 311
<212> TYPE: PRT
<213> ORGANISM: Neisseria meningitidis
<220> FEATURE:
<223> OTHER INFORMATION: AS deltaC174-CP-X (311)

<400> SEQUENCE: 27

```
Ile Met Ser Lys Ile Ser Lys Leu Val Thr His Pro Asn Leu Phe Phe
1               5                   10                  15

Arg Asp Tyr Phe Leu Lys Lys Ala Pro Leu Asn Tyr Gly Glu Asn Ile
            20                  25                  30

Lys Pro Leu Pro Val Glu Thr Ser His Ser Lys Lys Asn Thr Ala
        35                  40                  45

His Lys Thr Pro Val Ser Ser Asp Gln Pro Ile Glu Asp Pro Tyr Pro
    50                  55                  60

Val Thr Phe Pro Ile Asp Val Val Tyr Thr Trp Val Asp Ser Asp Asp
65                  70                  75                  80

Glu Lys Phe Asn Glu Glu Arg Leu Lys Phe Gln Asn Ser Ser Thr Ser
                85                  90                  95

Glu Thr Leu Gln Gly Lys Ala Glu Ser Thr Asp Ile Ala Arg Phe Gln
            100                 105                 110

Ser Arg Asp Glu Leu Lys Tyr Ser Ile Arg Ser Leu Met Lys Tyr Ala
        115                 120                 125

Pro Trp Val Asn His Ile Tyr Ile Val Thr Asn Gly Gln Ile Pro Lys
    130                 135                 140

Trp Leu Asp Thr Asn Asn Thr Lys Val Thr Ile Ile Pro His Ser Thr
145                 150                 155                 160

Ile Ile Asp Ser Gln Phe Leu Pro Thr Phe Asn Ser His Val Ile Glu
                165                 170                 175

Ser Ser Leu Tyr Lys Ile Pro Gly Leu Ser Glu His Tyr Ile Tyr Phe
            180                 185                 190

Asn Asp Asp Val Met Leu Ala Arg Asp Leu Ser Pro Ser Tyr Phe Phe
        195                 200                 205

Thr Ser Ser Gly Leu Ala Lys Leu Phe Ile Thr Asn Ser Arg Leu Pro
    210                 215                 220

Asn Gly Tyr Lys Asn Val Lys Asp Thr Pro Thr Gln Trp Ala Ser Lys
225                 230                 235                 240

Asn Ser Arg Glu Leu Leu His Ala Glu Thr Gly Phe Trp Ala Glu Ala
                245                 250                 255

Met Phe Ala His Thr Phe His Pro Gln Arg Lys Ser Val His Glu Ser
            260                 265                 270

Ile Glu His Leu Trp His Glu Gln Leu Asn Val Cys Arg Gln Asn Arg
        275                 280                 285

Phe Arg Asp Ile Ser Asp Ile Asn Met Ala Thr Phe Leu His His His
    290                 295                 300

Phe Ala Ile Leu Thr Gly Gln
305                 310
```

<210> SEQ ID NO 28
<211> LENGTH: 386
<212> TYPE: PRT
<213> ORGANISM: Neisseria meningitidis
<220> FEATURE:
<223> OTHER INFORMATION: AS deltaC99-CP-X (386)

<400> SEQUENCE: 28

Ile Met Ser Lys Ile Ser Lys Leu Val Thr His Pro Asn Leu Phe Phe
1               5                   10                  15

Arg Asp Tyr Phe Leu Lys Lys Ala Pro Leu Asn Tyr Gly Glu Asn Ile
                20                  25                  30

Lys Pro Leu Pro Val Glu Thr Ser Ser His Ser Lys Lys Asn Thr Ala
            35                  40                  45

His Lys Thr Pro Val Ser Ser Asp Gln Pro Ile Glu Asp Pro Tyr Pro
        50                  55                  60

Val Thr Phe Pro Ile Asp Val Val Tyr Thr Trp Val Asp Ser Asp Asp
65                      70                  75                  80

Glu Lys Phe Asn Glu Glu Arg Leu Lys Phe Gln Asn Ser Ser Thr Ser
                    85                  90                  95

Glu Thr Leu Gln Gly Lys Ala Glu Ser Thr Asp Ile Ala Arg Phe Gln
                100                 105                 110

Ser Arg Asp Glu Leu Lys Tyr Ser Ile Arg Ser Leu Met Lys Tyr Ala
            115                 120                 125

Pro Trp Val Asn His Ile Tyr Ile Val Thr Asn Gly Gln Ile Pro Lys
            130                 135                 140

Trp Leu Asp Thr Asn Asn Thr Lys Val Thr Ile Ile Pro His Ser Thr
145                 150                 155                 160

Ile Ile Asp Ser Gln Phe Leu Pro Thr Phe Asn Ser His Val Ile Glu
                165                 170                 175

Ser Ser Leu Tyr Lys Ile Pro Gly Leu Ser Glu His Tyr Ile Tyr Phe
            180                 185                 190

Asn Asp Asp Val Met Leu Ala Arg Asp Leu Ser Pro Ser Tyr Phe Phe
            195                 200                 205

Thr Ser Ser Gly Leu Ala Lys Leu Phe Ile Thr Asn Ser Arg Leu Pro
210                 215                 220

Asn Gly Tyr Lys Asn Val Lys Asp Thr Pro Thr Gln Trp Ala Ser Lys
225                 230                 235                 240

Asn Ser Arg Glu Leu Leu His Ala Glu Thr Gly Phe Trp Ala Glu Ala
            245                 250                 255

Met Phe Ala His Thr Phe His Pro Gln Arg Lys Ser Val His Glu Ser
            260                 265                 270

Ile Glu His Leu Trp His Glu Gln Leu Asn Val Cys Arg Gln Asn Arg
            275                 280                 285

Phe Arg Asp Ile Ser Asp Ile Asn Met Ala Thr Phe Leu His His His
            290                 295                 300

Phe Ala Ile Leu Thr Gly Gln Ala Leu Ala Thr Arg Thr Lys Cys Ile
305                 310                 315                 320

Tyr Phe Asn Ile Arg Ser Pro Gln Ala Ala Gln His Tyr Lys Thr Leu
                325                 330                 335

Leu Ala Arg Lys Gly Ser Glu Tyr Ser Pro His Ser Ile Cys Leu Asn
                340                 345                 350

Asp His Thr Ser Ser Asn Lys Asn Ile Leu Ser Asn Tyr Glu Ala Lys
            355                 360                 365

Leu Gln Ser Phe Leu Glu Thr Tyr Tyr Pro Asp Val Ser Glu Ala Glu
            370                 375                 380

Ile Leu
385

<210> SEQ ID NO 29
<211> LENGTH: 329

```
<212> TYPE: PRT
<213> ORGANISM: Neisseria meningitidis
<220> FEATURE:
<223> OTHER INFORMATION: AS deltaN58deltaC99-CP-X (329)

<400> SEQUENCE: 29
```

| | | | | | | | | | | | | | | |
|---|---|---|---|---|---|---|---|---|---|---|---|---|---|---|
| Pro | Ile | Glu | Asp | Pro | Tyr | Pro | Val | Thr | Phe | Pro | Ile | Asp | Val | Val | Tyr |
| 1 | | | | 5 | | | | | 10 | | | | | 15 |
| Thr | Trp | Val | Asp | Ser | Asp | Asp | Glu | Lys | Phe | Asn | Glu | Glu | Arg | Leu | Lys |
| | | | 20 | | | | | 25 | | | | | 30 | | |
| Phe | Gln | Asn | Ser | Ser | Thr | Ser | Glu | Thr | Leu | Gln | Gly | Lys | Ala | Glu | Ser |
| | | | 35 | | | | 40 | | | | | 45 | | | |
| Thr | Asp | Ile | Ala | Arg | Phe | Gln | Ser | Arg | Asp | Glu | Leu | Lys | Tyr | Ser | Ile |
| | 50 | | | | | 55 | | | | | 60 | | | | |
| Arg | Ser | Leu | Met | Lys | Tyr | Ala | Pro | Trp | Val | Asn | His | Ile | Tyr | Ile | Val |
| 65 | | | | | 70 | | | | | 75 | | | | | 80 |
| Thr | Asn | Gly | Gln | Ile | Pro | Lys | Trp | Leu | Asp | Thr | Asn | Thr | Lys | Val |
| | | | | 85 | | | | | 90 | | | | | 95 |
| Thr | Ile | Ile | Pro | His | Ser | Thr | Ile | Ile | Asp | Ser | Gln | Phe | Leu | Pro | Thr |
| | | | | 100 | | | | | 105 | | | | | 110 | |
| Phe | Asn | Ser | His | Val | Ile | Glu | Ser | Ser | Leu | Tyr | Lys | Ile | Pro | Gly | Leu |
| | | | 115 | | | | | 120 | | | | | 125 | | |
| Ser | Glu | His | Tyr | Ile | Tyr | Phe | Asn | Asp | Asp | Val | Met | Leu | Ala | Arg | Asp |
| | 130 | | | | | 135 | | | | | 140 | | | | |
| Leu | Ser | Pro | Ser | Tyr | Phe | Phe | Thr | Ser | Ser | Gly | Leu | Ala | Lys | Leu | Phe |
| 145 | | | | | 150 | | | | | 155 | | | | | 160 |
| Ile | Thr | Asn | Ser | Arg | Leu | Pro | Asn | Gly | Tyr | Lys | Asn | Val | Lys | Asp | Thr |
| | | | | 165 | | | | | 170 | | | | | 175 | |
| Pro | Thr | Gln | Trp | Ala | Ser | Lys | Asn | Ser | Arg | Glu | Leu | Leu | His | Ala | Glu |
| | | | 180 | | | | | 185 | | | | | 190 | | |
| Thr | Gly | Phe | Trp | Ala | Glu | Ala | Met | Phe | Ala | His | Thr | Phe | His | Pro | Gln |
| | | | 195 | | | | | 200 | | | | | 205 | | |
| Arg | Lys | Ser | Val | His | Glu | Ser | Ile | Glu | His | Leu | Trp | His | Glu | Gln | Leu |
| | 210 | | | | | 215 | | | | | 220 | | | | |
| Asn | Val | Cys | Arg | Gln | Asn | Arg | Phe | Arg | Asp | Ile | Ser | Asp | Ile | Asn | Met |
| 225 | | | | | 230 | | | | | 235 | | | | | 240 |
| Ala | Thr | Phe | Leu | His | His | His | Phe | Ala | Ile | Leu | Thr | Gly | Gln | Ala | Leu |
| | | | | 245 | | | | | 250 | | | | | 255 | |
| Ala | Thr | Arg | Thr | Lys | Cys | Ile | Tyr | Phe | Asn | Ile | Arg | Ser | Pro | Gln | Ala |
| | | | 260 | | | | | 265 | | | | | 270 | | |
| Ala | Gln | His | Tyr | Lys | Thr | Leu | Leu | Ala | Arg | Lys | Gly | Ser | Glu | Tyr | Ser |
| | 275 | | | | | 280 | | | | | 285 | | | | |
| Pro | His | Ser | Ile | Cys | Leu | Asn | Asp | His | Thr | Ser | Ser | Asn | Lys | Asn | Ile |
| | 290 | | | | | 295 | | | | | 300 | | | | |
| Leu | Ser | Asn | Tyr | Glu | Ala | Lys | Leu | Gln | Ser | Phe | Leu | Glu | Thr | Tyr | Tyr |
| 305 | | | | | 310 | | | | | 315 | | | | | 320 |
| Pro | Asp | Val | Ser | Glu | Ala | Glu | Ile | Leu |
| | | | | 325 |

```
<210> SEQ ID NO 30
<211> LENGTH: 411
<212> TYPE: PRT
<213> ORGANISM: Neisseria meningitidis
<220> FEATURE:
<223> OTHER INFORMATION: AS deltaN65deltaC10-CP-X (411)

<400> SEQUENCE: 30
```

```
Val Thr Phe Pro Ile Asp Val Val Tyr Thr Trp Val Asp Ser Asp Asp
1               5                   10                  15

Glu Lys Phe Asn Glu Glu Arg Leu Lys Phe Gln Asn Ser Ser Thr Ser
                20                  25                  30

Glu Thr Leu Gln Gly Lys Ala Glu Ser Thr Asp Ile Ala Arg Phe Gln
            35                  40                  45

Ser Arg Asp Glu Leu Lys Tyr Ser Ile Arg Ser Leu Met Lys Tyr Ala
        50                  55                  60

Pro Trp Val Asn His Ile Tyr Ile Val Thr Asn Gly Gln Ile Pro Lys
65                  70                  75                  80

Trp Leu Asp Thr Asn Asn Thr Lys Val Thr Ile Ile Pro His Ser Thr
                85                  90                  95

Ile Ile Asp Ser Gln Phe Leu Pro Thr Phe Asn Ser His Val Ile Glu
                100                 105                 110

Ser Ser Leu Tyr Lys Ile Pro Gly Leu Ser Glu His Tyr Ile Tyr Phe
            115                 120                 125

Asn Asp Asp Val Met Leu Ala Arg Asp Leu Ser Pro Ser Tyr Phe Phe
130                 135                 140

Thr Ser Ser Gly Leu Ala Lys Leu Phe Ile Thr Asn Ser Arg Leu Pro
145                 150                 155                 160

Asn Gly Tyr Lys Asn Val Lys Asp Thr Pro Thr Gln Trp Ala Ser Lys
                165                 170                 175

Asn Ser Arg Glu Leu Leu His Ala Glu Thr Gly Phe Trp Ala Glu Ala
            180                 185                 190

Met Phe Ala His Thr Phe His Pro Gln Arg Lys Ser Val His Glu Ser
            195                 200                 205

Ile Glu His Leu Trp His Glu Gln Leu Asn Val Cys Arg Gln Asn Arg
            210                 215                 220

Phe Arg Asp Ile Ser Asp Ile Asn Met Ala Thr Phe Leu His His His
225                 230                 235                 240

Phe Ala Ile Leu Thr Gly Gln Ala Leu Ala Thr Arg Thr Lys Cys Ile
                245                 250                 255

Tyr Phe Asn Ile Arg Ser Pro Gln Ala Ala Gln His Tyr Lys Thr Leu
                260                 265                 270

Leu Ala Arg Lys Gly Ser Glu Tyr Ser Pro His Ser Ile Cys Leu Asn
            275                 280                 285

Asp His Thr Ser Ser Asn Lys Asn Ile Leu Ser Asn Tyr Glu Ala Lys
            290                 295                 300

Leu Gln Ser Phe Leu Glu Thr Tyr Tyr Pro Asp Val Ser Glu Ala Glu
305                 310                 315                 320

Ile Leu Leu Pro Thr Lys Ser Glu Val Ala Glu Leu Val Lys His Lys
                325                 330                 335

Asp Tyr Leu Thr Val Tyr Thr Lys Leu Leu Pro Ile Ile Asn Lys Gln
                340                 345                 350

Leu Val Asn Lys Tyr Asn Lys Pro Tyr Ser Tyr Leu Phe Tyr Tyr Leu
            355                 360                 365

Gly Leu Ser Ala Arg Phe Leu Phe Glu Glu Thr Gln Gln Glu His Tyr
370                 375                 380

Arg Glu Thr Ala Glu Glu Asn Leu Gln Ile Phe Cys Gly Leu Asn Pro
385                 390                 395                 400

Lys His Thr Leu Ala Leu Lys Tyr Leu Ala Asp
                405                 410
```

<210> SEQ ID NO 31
<211> LENGTH: 320
<212> TYPE: PRT
<213> ORGANISM: Neisseria meningitidis
<220> FEATURE:
<223> OTHER INFORMATION: AS deltaN67deltaC99-CP-X (320)

<400> SEQUENCE: 31

```
Phe Pro Ile Asp Val Val Tyr Thr Trp Val Asp Ser Asp Asp Glu Lys
1               5                   10                  15

Phe Asn Glu Glu Arg Leu Lys Phe Gln Asn Ser Ser Thr Ser Glu Thr
            20                  25                  30

Leu Gln Gly Lys Ala Glu Ser Thr Asp Ile Ala Arg Phe Gln Ser Arg
        35                  40                  45

Asp Glu Leu Lys Tyr Ser Ile Arg Ser Leu Met Lys Tyr Ala Pro Trp
    50                  55                  60

Val Asn His Ile Tyr Ile Val Thr Asn Gly Gln Ile Pro Lys Trp Leu
65                  70                  75                  80

Asp Thr Asn Asn Thr Lys Val Thr Ile Ile Pro His Ser Thr Ile Ile
                85                  90                  95

Asp Ser Gln Phe Leu Pro Thr Phe Asn Ser His Val Ile Glu Ser Ser
            100                 105                 110

Leu Tyr Lys Ile Pro Gly Leu Ser Glu His Tyr Ile Tyr Phe Asn Asp
        115                 120                 125

Asp Val Met Leu Ala Arg Asp Leu Ser Pro Ser Tyr Phe Phe Thr Ser
    130                 135                 140

Ser Gly Leu Ala Lys Leu Phe Ile Thr Asn Ser Arg Leu Pro Asn Gly
145                 150                 155                 160

Tyr Lys Asn Val Lys Asp Thr Pro Thr Gln Trp Ala Ser Lys Asn Ser
                165                 170                 175

Arg Glu Leu Leu His Ala Glu Thr Gly Phe Trp Ala Glu Ala Met Phe
            180                 185                 190

Ala His Thr Phe His Pro Gln Arg Lys Ser Val His Glu Ser Ile Glu
        195                 200                 205

His Leu Trp His Glu Gln Leu Asn Val Cys Arg Gln Asn Arg Phe Arg
    210                 215                 220

Asp Ile Ser Asp Ile Asn Met Ala Thr Phe Leu His His Phe Ala
225                 230                 235                 240

Ile Leu Thr Gly Gln Ala Leu Ala Thr Arg Thr Lys Cys Ile Tyr Phe
                245                 250                 255

Asn Ile Arg Ser Pro Gln Ala Ala Gln His Tyr Lys Thr Leu Leu Ala
            260                 265                 270

Arg Lys Gly Ser Glu Tyr Ser Pro His Ser Ile Cys Leu Asn Asp His
        275                 280                 285

Thr Ser Ser Asn Lys Asn Ile Leu Ser Asn Tyr Glu Ala Lys Leu Gln
    290                 295                 300

Ser Phe Leu Glu Thr Tyr Tyr Pro Asp Val Ser Glu Ala Glu Ile Leu
305                 310                 315                 320
```

<210> SEQ ID NO 32
<211> LENGTH: 1119
<212> TYPE: DNA
<213> ORGANISM: Neisseria meningitidis
<220> FEATURE:
<223> OTHER INFORMATION: UDP-GlcNAc-Epimerase (NmA) cloned from
    Neisseria meningitidis serogroup A, coding sequence >UDP-GlcNAc-
Epimerase-NmA (AF019760 REGION: 479..1597)

-continued

<400> SEQUENCE: 32

```
atgaaagtct taaccgtctt tggcactcgc cctgaagcta ttaaaatggc gcctgtaatt      60
ctagagttac aaaaacataa cacaattact tcaaaagttt gcattactgc acagcatcgt     120
gaaatgctag atcaggtttt gagcctattc gaaatcaaag ctgattatga tttaaatatc     180
atgaaaccca accagagcct acaagaaatc acaacaaata tcatctcaag ccttaccgat     240
gttcttgaag atttcaaacc tgactgcgtc cttgctcacg gagacaccac aacaactttt     300
gcagctagcc ttgctgcatt ctatcaaaaa atacctgttg ccacattga agcaggcctg      360
agaacttata atttatactc tccttggcca gaggaagcaa ataggcgttt aacaagcgtt     420
ctaagccagt ggcatttttgc acctactgaa gattctaaaa ataacttact atctgaatca    480
ataccttctg acaaagttat tgttactgga atactgtca tagatgcact aatggtatct      540
ctagaaaaac taaaataac tacaattaaa aaacaaatgg aacaagcttt tccatttatt      600
caggacaact ctaaagtaat tttaattacc gctcatagaa gagaaaatca tggggaaggt     660
attaaaaata ttggactttc tatcttagaa ttagctaaaa aatacccaac attctctttt     720
gtgattccgc tccatttaaa tcctaacgtt agaaaaccaa ttcaagattt attatcctct     780
gtgcacaatg ttcatcttat tgagccacaa gaatacttac cattcgtata tttaatgtct    840
aaaagccata taatattaag tgattcaggc ggcatacaag aagaagctcc atccctagga     900
aaaccagttc ttgtattaag agatactaca gaacgtcctg aagctgtagc tgcaggaact    960
gtaaaattag taggttctga aactcaaaat attattgaga gctttacaca actaattgaa    1020
taccctgaat attatgaaaa aatggctaat attgaaaacc cttacgggat aggtaatgcc    1080
tcaaaaatca ttgtagaaac tttattaaag aatagataa                           1119
```

<210> SEQ ID NO 33
<211> LENGTH: 372
<212> TYPE: PRT
<213> ORGANISM: Neisseria meningitidis
<220> FEATURE:
<223> OTHER INFORMATION: UDP-GlcNAc-Epimerase (NmA) cloned from Neisseria meningitidis serogroup A amino acid sequence >UDP-GlcNAc-Epimerase-NmA (AAC38285).pro

<400> SEQUENCE: 33

```
Met Lys Val Leu Thr Val Phe Gly Thr Arg Pro Glu Ala Ile Lys Met
1               5                   10                  15

Ala Pro Val Ile Leu Glu Leu Gln Lys His Asn Thr Ile Thr Ser Lys
            20                  25                  30

Val Cys Ile Thr Ala Gln His Arg Glu Met Leu Asp Gln Val Leu Ser
        35                  40                  45

Leu Phe Glu Ile Lys Ala Asp Tyr Asp Leu Asn Ile Met Lys Pro Asn
    50                  55                  60

Gln Ser Leu Gln Glu Ile Thr Thr Asn Ile Ile Ser Ser Leu Thr Asp
65                  70                  75                  80

Val Leu Glu Asp Phe Lys Pro Asp Cys Val Leu Ala His Gly Asp Thr
                85                  90                  95

Thr Thr Thr Phe Ala Ala Ser Leu Ala Ala Phe Tyr Gln Lys Ile Pro
            100                 105                 110

Val Gly His Ile Glu Ala Gly Leu Arg Thr Tyr Asn Leu Tyr Ser Pro
        115                 120                 125

Trp Pro Glu Glu Ala Asn Arg Arg Leu Thr Ser Val Leu Ser Gln Trp
    130                 135                 140
```

-continued

```
His Phe Ala Pro Thr Glu Asp Ser Lys Asn Asn Leu Leu Ser Glu Ser
145                 150                 155                 160

Ile Pro Ser Asp Lys Val Ile Val Thr Gly Asn Thr Val Ile Asp Ala
                165                 170                 175

Leu Met Val Ser Leu Glu Lys Leu Lys Ile Thr Thr Ile Lys Lys Gln
            180                 185                 190

Met Glu Gln Ala Phe Pro Phe Ile Gln Asp Asn Ser Lys Val Ile Leu
        195                 200                 205

Ile Thr Ala His Arg Arg Glu Asn His Gly Glu Gly Ile Lys Asn Ile
    210                 215                 220

Gly Leu Ser Ile Leu Glu Leu Ala Lys Lys Tyr Pro Thr Phe Ser Phe
225                 230                 235                 240

Val Ile Pro Leu His Leu Asn Pro Asn Val Arg Lys Pro Ile Gln Asp
                245                 250                 255

Leu Leu Ser Ser Val His Asn Val His Leu Ile Glu Pro Gln Glu Tyr
            260                 265                 270

Leu Pro Phe Val Tyr Leu Met Ser Lys Ser His Ile Ile Leu Ser Asp
        275                 280                 285

Ser Gly Gly Ile Gln Glu Glu Ala Pro Ser Leu Gly Lys Pro Val Leu
    290                 295                 300

Val Leu Arg Asp Thr Thr Glu Arg Pro Glu Ala Val Ala Ala Gly Thr
305                 310                 315                 320

Val Lys Leu Val Gly Ser Glu Thr Gln Asn Ile Ile Glu Ser Phe Thr
                325                 330                 335

Gln Leu Ile Glu Tyr Pro Glu Tyr Tyr Glu Lys Met Ala Asn Ile Glu
            340                 345                 350

Asn Pro Tyr Gly Ile Gly Asn Ala Ser Lys Ile Ile Val Glu Thr Leu
        355                 360                 365

Leu Lys Asn Arg
    370
```

```
<210> SEQ ID NO 34
<211> LENGTH: 1713
<212> TYPE: DNA
<213> ORGANISM: Neisseria meningitidis
<220> FEATURE:
<223> OTHER INFORMATION: DNA StrepII-Thrombin-BamHI/BglII-CsaB-XhoI-His6

<400> SEQUENCE: 34
atggctagct ggagccaccc gcagttcgaa aaaggcgccc tggttccgcg tggatctttt      60
atacttaata acagaaaatg gcgtaaactt aaaagagacc ctagcgcttt ctttcgagat     120
agtaaattta acttttttaag atattttttct gctaaaaaat ttgcaaagaa ttttaaaaat     180
tcatcacata tccataaaac taatataagt aaagctcaat caaatatttc ttcaaccta      240 aaacaaaatc ggaaacaaga tatgttaatt cctattaatt tttttaattt tgaatatata    300
gttaaaaaac ttaacaatca aaacgcaata ggtgtatata ttcttccttc taatcttact    360
cttaagcctg cattatgtat tctagaatca cataagaag acttttttaaa taaatttctt     420 cttactattt cctctgaaaa tttaaagctt caatacaaat ttaatggaca aataaaaaat     480
cctaagtccg taaatgaaat ttggacagat ttatttagca ttgctcatgt tgacatgaaa     540
ctcagcacag atagaacttt aagttcatct atatctcaat tttggttcag attagagttc     600
tgtaaagaag ataaggattt tatcttattt cctacagcta acagatattc tagaaaactt     660
tggaagcact ctattaaaaa taatcaatta tttaagaag gcatacgaaa ctattcagaa     720
```

```
atatcttcat tacccctatga agaagatcat aattttgata ttgatttagt atttacttgg    780
gtcaactcag aagataagaa ttggcaagag ttatataaaa aatataagcc cgactttaat    840
agcgatgcaa ccagtacatc aagattcctt agtagagatg aattaaaatt cgcattacgc    900
tcttgggaaa tgaatggatc cttcattcga aaaatttta ttgtctctaa ttgtgctccc    960
ccagcatggc tagatttaaa taaccctaaa attcaatggg tatatcacga agaaattatg    1020
ccacaaagtg cccttcctac ttttagctca catgctattg aaaccagctt gcaccatata    1080
ccaggaatta gtaactattt tatttacagc aatgacgact tcctattaac taaaccattg    1140
aataaagaca atttcttcta ttcgaatggt attgcaaagt taagattaga agcatgggga    1200
aatgttaatg gtgaatgtac tgaaggagaa cctgactact aaatggtgc tcgcaatgcg    1260 aacactctct tagaaaagga atttaaaaaa tttactacta aactacatac tcactcccct    1320
caatccatga gaactgatat tttatttgag atggaaaaaa aatatccaga gagtttaat    1380 agaacactac ataataaatt ccgatcttta gatgatattg cagtaacggg ctatctctat    1440
catcattatg ccctactctc tggacgagca ctacaaagtt ctgacaagac ggaacttgta    1500
cagcaaaatc atgatttcaa aaagaaacta aataatgtag tgaccttaac taaagaaagg    1560
aattttgaca aacttccttt gagcgtatgt atcaacgatg gtgctgatag tcacttgaat    1620
gaagaatgga atgttcaagt tattaagttc ttagaaactc ttttcccatt accatcatca    1680
tttgagaaac tcgagcacca ccaccaccac cac                                1713

<210> SEQ ID NO 35
<211> LENGTH: 57
<212> TYPE: DNA
<213> ORGANISM: Artificial Sequence
<220> FEATURE:
<223> OTHER INFORMATION: DNA StrepII-Thrombin-BamHI/BglII

<400> SEQUENCE: 35
atggctagct ggagccaccc gcagttcgaa aaaggcgccc tggttccgcg tggatct       57

<210> SEQ ID NO 36
<211> LENGTH: 24
<212> TYPE: DNA
<213> ORGANISM: Artificial Sequence
<220> FEATURE:
<223> OTHER INFORMATION: DNA XhoI-His6

<400> SEQUENCE: 36
ctcgagcacc accaccacca ccac                                           24

<210> SEQ ID NO 37
<211> LENGTH: 571
<212> TYPE: PRT
<213> ORGANISM: Neisseria meningitidis
<220> FEATURE:
<223> OTHER INFORMATION: AS StrepII-Thrombin-BamHI/BglII-CsaB-XhoI-His6

<400> SEQUENCE: 37

Met Ala Ser Trp Ser His Pro Gln Phe Glu Lys Gly Ala Leu Val Pro
1               5                   10                  15

Arg Gly Ser Phe Ile Leu Asn Asn Arg Lys Trp Arg Lys Leu Lys Arg
            20                  25                  30

Asp Pro Ser Ala Phe Phe Arg Asp Ser Lys Phe Asn Phe Leu Arg Tyr
        35                  40                  45

Phe Ser Ala Lys Lys Phe Ala Lys Asn Phe Lys Asn Ser Ser His Ile
```

-continued

```
                50                  55                  60
His Lys Thr Asn Ile Ser Lys Ala Gln Ser Asn Ile Ser Ser Thr Leu
 65                  70                  75                  80

Lys Gln Asn Arg Lys Gln Asp Met Leu Ile Pro Ile Asn Phe Phe Asn
                     85                  90                  95

Phe Glu Tyr Ile Val Lys Lys Leu Asn Gln Asn Ala Ile Gly Val
                    100                 105                 110

Tyr Ile Leu Pro Ser Asn Leu Thr Leu Lys Pro Ala Leu Cys Ile Leu
                    115                 120                 125

Glu Ser His Lys Glu Asp Phe Leu Asn Lys Phe Leu Leu Thr Ile Ser
    130                 135                 140

Ser Glu Asn Leu Lys Leu Gln Tyr Lys Phe Asn Gly Gln Ile Lys Asn
145                 150                 155                 160

Pro Lys Ser Val Asn Glu Ile Trp Thr Asp Leu Phe Ser Ile Ala His
                    165                 170                 175

Val Asp Met Lys Leu Ser Thr Asp Arg Thr Leu Ser Ser Ser Ile Ser
                180                 185                 190

Gln Phe Trp Phe Arg Leu Glu Phe Cys Lys Glu Asp Lys Asp Phe Ile
                195                 200                 205

Leu Phe Pro Thr Ala Asn Arg Tyr Ser Arg Lys Leu Trp Lys His Ser
210                 215                 220

Ile Lys Asn Asn Gln Leu Phe Lys Glu Gly Ile Arg Asn Tyr Ser Glu
225                 230                 235                 240

Ile Ser Ser Leu Pro Tyr Glu Glu Asp His Asn Phe Asp Ile Asp Leu
                    245                 250                 255

Val Phe Thr Trp Val Asn Ser Glu Asp Lys Asn Trp Gln Glu Leu Tyr
                260                 265                 270

Lys Lys Tyr Lys Pro Asp Phe Asn Ser Asp Ala Thr Ser Thr Ser Arg
                275                 280                 285

Phe Leu Ser Arg Asp Glu Leu Lys Phe Ala Leu Arg Ser Trp Glu Met
                290                 295                 300

Asn Gly Ser Phe Ile Arg Lys Ile Phe Ile Val Ser Asn Cys Ala Pro
305                 310                 315                 320

Pro Ala Trp Leu Asp Leu Asn Asn Pro Lys Ile Gln Trp Val Tyr His
                    325                 330                 335

Glu Glu Ile Met Pro Gln Ser Ala Leu Pro Thr Phe Ser Ser His Ala
                340                 345                 350

Ile Glu Thr Ser Leu His His Ile Pro Gly Ile Ser Asn Tyr Phe Ile
                355                 360                 365

Tyr Ser Asn Asp Asp Phe Leu Leu Thr Lys Pro Leu Asn Lys Asp Asn
                370                 375                 380

Phe Phe Tyr Ser Asn Gly Ile Ala Lys Leu Arg Leu Glu Ala Trp Gly
385                 390                 395                 400

Asn Val Asn Gly Glu Cys Thr Glu Gly Glu Pro Asp Tyr Leu Asn Gly
                    405                 410                 415

Ala Arg Asn Ala Asn Thr Leu Leu Glu Lys Glu Phe Lys Lys Phe Thr
                420                 425                 430

Thr Lys Leu His Thr His Ser Pro Gln Ser Met Arg Thr Asp Ile Leu
                435                 440                 445

Phe Glu Met Glu Lys Lys Tyr Pro Glu Glu Phe Asn Arg Thr Leu His
                450                 455                 460

Asn Lys Phe Arg Ser Leu Asp Asp Ile Ala Val Thr Gly Tyr Leu Tyr
465                 470                 475                 480
```

```
His His Tyr Ala Leu Leu Ser Gly Arg Ala Leu Gln Ser Ser Asp Lys
                485                 490                 495

Thr Glu Leu Val Gln Gln Asn His Asp Phe Lys Lys Lys Leu Asn Asn
            500                 505                 510

Val Val Thr Leu Thr Lys Glu Arg Asn Phe Asp Lys Leu Pro Leu Ser
        515                 520                 525

Val Cys Ile Asn Asp Gly Ala Asp Ser His Leu Asn Glu Glu Trp Asn
    530                 535                 540

Val Gln Val Ile Lys Phe Leu Glu Thr Leu Phe Pro Leu Pro Ser Ser
545                 550                 555                 560

Phe Glu Lys Leu Glu His His His His His His
                565                 570

<210> SEQ ID NO 38
<211> LENGTH: 19
<212> TYPE: PRT
<213> ORGANISM: Artificial Sequence
<220> FEATURE:
<223> OTHER INFORMATION: AS StrepII-Thrombin-BamHI

<400> SEQUENCE: 38

Met Ala Ser Trp Ser His Pro Gln Phe Glu Lys Gly Ala Leu Val Pro
1               5                   10                  15

Arg Gly Ser

<210> SEQ ID NO 39
<211> LENGTH: 8
<212> TYPE: PRT
<213> ORGANISM: Artificial Sequence
<220> FEATURE:
<223> OTHER INFORMATION: AS XhoI-His6

<400> SEQUENCE: 39

Leu Glu His His His His His His
1               5

<210> SEQ ID NO 40
<211> LENGTH: 1455
<212> TYPE: DNA
<213> ORGANISM: Neisseria meningitidis
<220> FEATURE:
<223> OTHER INFORMATION: DNA NdeI-dN69CsaB(co)-XhoI-His6

<400> SEQUENCE: 40
catatgctga tcccgatcaa tttctttaat tttgagtaca tcgtgaagaa actgaataac      60
caaaacgcaa tcggcgtgta cattctgccg tctaatctga ccctgaaacc agcattgtgc    120
atcttggagt cgcacaaaga ggacttcctg aacaaatttt tgttgaccat tagcagcgag    180
aacctgaaac tgcagtataa gttcaatggt cagatcaaaa tccgaaaag cgtgaacgaa     240 atctggaccg acctgtttag cattgctcac gtcgacatga agctgagcac cgaccgtacg    300
ctgtcctcgt ccatcagcca attttggttt cgcctggagt tctgtaaaga ggacaaggac    360
ttcatcctgt ttccgacggc aaatcgttac agccgcaagc tgtggaagca cagcatcaaa    420
aataatcagc tgtttaagga aggtatccgt aactacagcg agattagctc gctgccgtac    480
gaggaagacc ataacttcga catcgatctg gtctttacct gggtcaattc ggaagacaaa    540
aactggcagg aactgtacaa gaaatataag ccggattta atagcgatgc cacctcgacg    600
agccgttttc tgagccgtga cgagctgaag tttgcgctgc gctcgtggga aatgaacggt    660
```

-continued

```
agcttcatcc gtaaaatctt tatcgtcagc aactgcgcgc cgccggcctg gctggatctg    720
aacaatccga agatccaatg ggtgtatcac gaggagatca tgccacagag cgccctgcca    780
accttcagca gccatgctat tgagactagc ttgcatcaca ttccgggcat ctccaactac    840
ttcatctact ctaatgacga ttttctgttg accaaaccgc tgaacaaaga caacttcttt    900
tactccaacg gtattgctaa actgcgtctg gaagcctggg gtaacgttaa cggtgaatgt    960
accgaaggcg agccggatta cctgaacggc gcgcgtaacg caaatacgct gctggagaaa   1020
gagtttaaaa agtttaccac caagctgcac acccacagcc cgcagagcat gcgtaccgac   1080
atcctgttcg agatggagaa aaaatacccca gaagagttca atcgcacgct gcacaacaag   1140
ttccgcagcc tggatgacat cgcggttacc ggctacctgt accatcacta cgcattgctg   1200
tctggccgcg ctctgcaatc cagcgataag accgaactgg tccagcagaa tcacgacttt   1260
aaaaagaagc tgaataatgt tgtcaccctg accaaagagc gtaactttga taagctgccg   1320
ctgagcgttt gtattaatga cggtgcagac agccacctga atgaggagtg gaatgtgcaa   1380
gttatcaaat tcttggagac cttgttcccg ttgccgagct ccttcgagaa actcgagcac   1440
caccaccacc accac                                                   1455
```

<210> SEQ ID NO 41

<400> SEQUENCE: 41

000

<210> SEQ ID NO 42
<211> LENGTH: 24
<212> TYPE: DNA
<213> ORGANISM: Artificial Sequence
<220> FEATURE:
<223> OTHER INFORMATION: DNA XhoI-His6

<400> SEQUENCE: 42
ctcgagcacc accaccacca ccac                                           24

<210> SEQ ID NO 43
<211> LENGTH: 484
<212> TYPE: PRT
<213> ORGANISM: Neisseria meningitidis
<220> FEATURE:
<223> OTHER INFORMATION: AS NdeI-dN69CsaB(co)-XhoI-His6

<400> SEQUENCE: 43

```
Met Leu Ile Pro Ile Asn Phe Phe Asn Phe Glu Tyr Ile Val Lys Lys
1               5                   10                  15

Leu Asn Asn Gln Asn Ala Ile Gly Val Tyr Ile Leu Pro Ser Asn Leu
            20                  25                  30

Thr Leu Lys Pro Ala Leu Cys Ile Leu Glu Ser His Lys Glu Asp Phe
        35                  40                  45

Leu Asn Lys Phe Leu Leu Thr Ile Ser Ser Glu Asn Leu Lys Leu Gln
    50                  55                  60

Tyr Lys Phe Asn Gly Gln Ile Lys Asn Pro Lys Ser Val Asn Glu Ile
65                  70                  75                  80

Trp Thr Asp Leu Phe Ser Ile Ala His Val Asp Met Lys Leu Ser Thr
                85                  90                  95

Asp Arg Thr Leu Ser Ser Ser Ile Ser Gln Phe Trp Phe Arg Leu Glu
            100                 105                 110

Phe Cys Lys Glu Asp Lys Asp Phe Ile Leu Phe Pro Thr Ala Asn Arg
```

115                 120                 125
Tyr Ser Arg Lys Leu Trp Lys His Ser Ile Lys Asn Asn Gln Leu Phe
            130                 135                 140
Lys Glu Gly Ile Arg Asn Tyr Ser Glu Ile Ser Ser Leu Pro Tyr Glu
145                 150                 155                 160
Glu Asp His Asn Phe Asp Ile Asp Leu Val Phe Thr Trp Val Asn Ser
                165                 170                 175
Glu Asp Lys Asn Trp Gln Glu Leu Tyr Lys Lys Tyr Lys Pro Asp Phe
            180                 185                 190
Asn Ser Asp Ala Thr Ser Thr Ser Arg Phe Leu Ser Arg Asp Glu Leu
                195                 200                 205
Lys Phe Ala Leu Arg Ser Trp Glu Met Asn Gly Ser Phe Ile Arg Lys
            210                 215                 220
Ile Phe Ile Val Ser Asn Cys Ala Pro Pro Ala Trp Leu Asp Leu Asn
225                 230                 235                 240
Asn Pro Lys Ile Gln Trp Val Tyr His Glu Glu Ile Met Pro Gln Ser
                245                 250                 255
Ala Leu Pro Thr Phe Ser Ser His Ala Ile Glu Thr Ser Leu His His
            260                 265                 270
Ile Pro Gly Ile Ser Asn Tyr Phe Ile Tyr Ser Asn Asp Asp Phe Leu
            275                 280                 285
Leu Thr Lys Pro Leu Asn Lys Asp Asn Phe Phe Tyr Ser Asn Gly Ile
            290                 295                 300
Ala Lys Leu Arg Leu Glu Ala Trp Gly Asn Val Asn Gly Glu Cys Thr
305                 310                 315                 320
Glu Gly Glu Pro Asp Tyr Leu Asn Gly Ala Arg Asn Ala Asn Thr Leu
                325                 330                 335
Leu Glu Lys Glu Phe Lys Lys Phe Thr Thr Lys Leu His Thr His Ser
            340                 345                 350
Pro Gln Ser Met Arg Thr Asp Ile Leu Phe Glu Met Glu Lys Lys Tyr
            355                 360                 365
Pro Glu Glu Phe Asn Arg Thr Leu His Asn Lys Phe Arg Ser Leu Asp
            370                 375                 380
Asp Ile Ala Val Thr Gly Tyr Leu Tyr His His Tyr Ala Leu Leu Ser
385                 390                 395                 400
Gly Arg Ala Leu Gln Ser Ser Asp Lys Thr Glu Leu Val Gln Gln Asn
                405                 410                 415
His Asp Phe Lys Lys Lys Leu Asn Asn Val Val Thr Leu Thr Lys Glu
            420                 425                 430
Arg Asn Phe Asp Lys Leu Pro Leu Ser Val Cys Ile Asn Asp Gly Ala
            435                 440                 445
Asp Ser His Leu Asn Glu Glu Trp Asn Val Gln Val Ile Lys Phe Leu
            450                 455                 460
Glu Thr Leu Phe Pro Leu Pro Ser Ser Phe Glu Lys Leu Glu His His
465                 470                 475                 480
His His His His

<210> SEQ ID NO 44

<400> SEQUENCE: 44

000

<210> SEQ ID NO 45

```
<211> LENGTH: 8
<212> TYPE: PRT
<213> ORGANISM: Artificial Sequence
<220> FEATURE:
<223> OTHER INFORMATION: AS XhoI-His6

<400> SEQUENCE: 45

Leu Glu His His His His His His
1               5

<210> SEQ ID NO 46
<211> LENGTH: 1425
<212> TYPE: DNA
<213> ORGANISM: Neisseria meningitidis
<220> FEATURE:
<223> OTHER INFORMATION: DNA deltaN69-CP-A (wt) (1425)

<400> SEQUENCE: 46
ttaattccta ttaattttt  taattttgaa tatatagtta aaaaacttaa caatcaaaac      60
gcaataggtg tatatattct tccttctaat cttactctta agcctgcatt atgtattcta     120
gaatcacata agaagactt  tttaaataaa tttcttctta ctatttcctc tgaaaattta     180
aagcttcaat acaaatttaa tggacaaata aaaaatccta agtccgtaaa tgaaatttgg     240
acagatttat ttagcattgc tcatgttgac atgaaactca gcacagatag aactttaagt     300
tcatctatat ctcaattttg gttcagatta gagttctgta aagaagataa ggattttatc     360
ttatttccta cagctaacag atattctaga aaactttgga agcactctat taaaaataat     420
caattattta agaaggcat  acgaaactat tcagaaatat cttcattacc ctatgaagaa     480
gatcataatt ttgatattga tttagtattt acttgggtca actcagaaga taagaattgg     540
caagagttat ataaaaaata taagcccgac tttaatagcg atgcaaccag tacatcaaga     600
ttccttagta gagatgaatt aaaattcgca ttacgctctt gggaaatgaa tggatccttc     660
attcgaaaaa tttttattgt ctctaattgt gctcccccag catggctaga tttaaataac     720
cctaaaattc aatgggtata tcacgaagaa attatgccac aaagtgccct tcctactttt     780
agctcacatg ctattgaaac cagcttgcac catataccag gaattagtaa ctatttatt     840 tacagcaatg acgacttcct attaactaaa ccattgaata agacaatttt cttctattcg     900
aatggtattg caaagttaag attagaagca tggggaaatg ttaatggtga atgtactgaa     960
ggagaacctg actacttaaa tggtgctcgc aatgcgaaca ctctcttaga aaaggaattt    1020
aaaaaattta ctactaaact acatactcac tcccctcaat ccatgagaac tgatatttta    1080
tttgagatgg aaaaaaaata tccagaagag tttaatagaa cactacataa taaattccga    1140
tctttagatg atattgcagt aacgggctat ctctatcatc attatgccct actctctgga    1200
cgagcactac aaagtctga  caagacggaa cttgtacagc aaaatcatga tttcaaaaag    1260
aaactaaata atgtagtgac cttaactaaa gaaaggaatt ttgacaaact tcctttgagc    1320
gtatgtatca acgatggtgc tgatagtcac ttgaatgaag aatggaatgt tcaagttatt    1380
aagttcttag aaactctttt cccattacca tcatcatttg agaaa               1425

<210> SEQ ID NO 47
<211> LENGTH: 2628
<212> TYPE: DNA
<213> ORGANISM: Neisseria meningitidis
<220> FEATURE:
<223> OTHER INFORMATION: DNA MBP-S3N10-BamHI-CsxA-XhoI-His6

<400> SEQUENCE: 47
```

```
atgaaaactg aagaaggtaa actggtaatc tggattaacg gcgataaagg ctataacggt    60
ctcgctgaag tcggtaagaa attcgagaaa gataccggaa ttaaagtcac cgttgagcat   120
ccggataaac tggaagagaa attcccacag gttgcggcaa ctggcgatgg ccctgacatt   180
atcttctggg cacacgaccg ctttggtggc tacgctcaat ctggcctgtt ggctgaaatc   240
accccggaca aagcgttcca ggacaagctg tatccgttta cctgggatgc cgtacgttac   300
aacggcaagc tgattgctta cccgatcgct gttgaagcgt tatcgctgat ttataacaaa   360
gatctgctgc cgaacccgcc aaaaacctgg gaagagatcc cggcgctgga taagaactg    420
aaagcgaaag gtaagagcgc gctgatgttc aacctgcaag aaccgtactt cacctggccg   480
ctgattgctg ctgacggggg ttatgcgttc aagtatgaaa acggcaagta cgacattaaa   540
gacgtgggcg tggataacgc tggcgcgaaa gcgggtctga ccttcctggt tgacctgatt   600
aaaaacaaac acatgaatgc agacaccgat tactccatcg cagaagctgc ctttaataaa   660
ggcgaaacag cgatgaccat caacggcccg tgggcatggt ccaacatcga caccagcaaa   720
gtgaattatg gtgtaacggt actgccgacc ttcaagggtc aaccatccaa accgttcgtt   780
ggcgtgctga gcgcaggtat taacgccgcc agtccgaaca aagagctggc gaaagagttc   840
ctcgaaaact atctgctgac tgatgaaggt ctggaagcgg ttaataaaga caaccgctg    900
ggtgccgtag cgctgaagtc ttacgaggaa gagttggcga agatccacg tattgccgcc   960
accatggaaa cgcccagaa aggtgaaatc atgccgaaca tcccgcagat gtccgctttc  1020
tggtatgccg tgcgtactgc ggtgatcaac gccgccagcg tcgtcagac tgtcgatgaa  1080
gccctgaaag acgcgcagac taattcgagc tccaataaca ataacaacaa caataacaat  1140
aacggatcca ttatgagcaa aattagcaaa ttggtaaccc acccaaacct tttcttcga   1200
gattattct taaaaaaagc accgttaaat tatggcgaaa atattaaacc tttaccagtc  1260
gaaacctctt ctcatagcaa aaaaaataca gcccataaaa cacccgtatc atccgaccaa  1320
ccaattgaag atccataccc agtaacattt ccaattgatg tagtttatac ttgggtagat  1380
tcagatgatg aaaaattcaa tgaagaacgc ctaaagtttc aaaattcaag cacatctgag  1440
actctacaag gcaaagcaga aagcaccgat attgcaagat tccaatcacg cgacgaatta  1500
aaatattcga ttcgaagcct gatgaagtat gccccatggg taaatcatat ttacattgta  1560
acaaatggtc aaataccaaa atggttagat accaacaata caaaggtaac gattatccct  1620
cactcaacta ttatcgacag tcaatttctc cctactttta attctcacgt cattgaatcc  1680
tctctatata aaatcccagg attatcgagg cattacattt atttcaatga tgatgtcatg  1740
ctagctagag atttaagccc atcttatttc tttacaagca gcggattagc aaaactgttt  1800
attaccaact ctcgtctacc aaatggctat aagaatgtga agacacacc aacccaatgg  1860
gcctcaaaaa attcccgtga gcttttacat gcagaaacag gattttgggc tgaagccatg  1920
tttgcacata cttttcatcc acaacgtaaa agtgtacatg aatctattga acacctatgg  1980
catgaacaat taaatgtttg tcgtcaaaac cgtttccgtg atatttcaga tattaacatg  2040
gcgacattcc tgcaccacca ttttgccatt ttgacaggcc aagctcttgc tacacgcact  2100
aaatgtattt actttaacat tcgctctcct caagcagctc agcattacaa acattatta  2160
gctcgaaaag gaagcgaata cagcccacat tctatctgct aaatgatca tacatcgagc  2220
aataaaaata ttttatctaa ttacgaagcc aaattacaaa gctttttaga aacatactat  2280
ccagatgtat cagaagcaga aattctcctt cctactaaat ctgaagtagc tgaattagtt  2340
aaacataaag attatttaac tgtatatact aaattattac ctattatcaa taagcagctg  2400
```

```
gtcaataaat ataataaacc ttattcatat cttttctatt atttaggttt atctgcccgg    2460
tttttatttg aagaaacgca acaagaacac taccggaaa ctgctgaaga aaatttacaa     2520
atcttttgtg gcctaaaccc aaaacataca ctagccctca aatacttagc ggatgtcacc    2580
ctcacatcac agcctagtgg acaactcgag caccaccacc accaccac                 2628
```

<210> SEQ ID NO 48
<211> LENGTH: 1149
<212> TYPE: DNA
<213> ORGANISM: Neisseria meningitidis
<220> FEATURE:
<223> OTHER INFORMATION: DNA MBP-S3N10-BamHI

<400> SEQUENCE: 48

```
atgaaaactg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca aagcgttcca ggacaagctg tatccgttta cctgggatgc cgtacgttac     300
aacggcaagc tgattgctta cccgatcgct gttgaagcgt tatcgctgat ttataacaaa     360
gatctgctgc cgaacccgcc aaaaacctgg gaagagatcc cggcgctgga taagaactg     420 aaagcgaaag gtaagagcgc gctgatgttc aacctgcaag aaccgtactt cacctggccg     480
ctgattgctg ctgacggggg ttatgcgttc aagtatgaaa acggcaagta cgacattaaa     540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga gcgcaggtat taacgccgcc agtccgaaca aagagctggc gaaagagttc     840
ctcgaaaact atctgctgac tgatgaaggt ctggaagcgg ttaataaaga caaaccgctg     900
ggtgccgtag cgctgaagtc ttacgaggaa gagttggcga agatccacg tattgccgcc     960 accatggaaa acgcccagaa aggtgaaatc atgccgaaca tcccgcagat gtccgctttc    1020
tggtatgccg tgcgtactgc ggtgatcaac gccgccagcg tcgtcagac tgtcgatgaa     1080 gccctgaaag acgcgcagac taattcgagc tccaataaca ataacaacaa caataacaat    1140
aacggatcc                                                             1149
```

<210> SEQ ID NO 49
<211> LENGTH: 876
<212> TYPE: PRT
<213> ORGANISM: Neisseria meningitidis
<220> FEATURE:
<223> OTHER INFORMATION: AS MBP-S3N10-BamHI-CsxA-Xho1-His6

<400> SEQUENCE: 49

```
Met Lys Thr Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
```

```
                50                  55                  60
His Asp Arg Phe Gly Gly Tyr Ala Gln Ser Gly Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
                115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
                195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
                275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Ser Asn Asn Asn Asn Asn Asn Asn Asn Asn Asn Gly Ser Ile
                370                 375                 380

Met Ser Lys Ile Ser Lys Leu Val Thr His Pro Asn Leu Phe Phe Arg
385                 390                 395                 400

Asp Tyr Phe Leu Lys Lys Ala Pro Leu Asn Tyr Gly Glu Asn Ile Lys
                405                 410                 415

Pro Leu Pro Val Glu Thr Ser Ser His Ser Lys Lys Asn Thr Ala His
                420                 425                 430

Lys Thr Pro Val Ser Ser Asp Gln Pro Ile Glu Asp Pro Tyr Pro Val
                435                 440                 445

Thr Phe Pro Ile Asp Val Val Tyr Thr Trp Val Asp Ser Asp Asp Glu
                450                 455                 460

Lys Phe Asn Glu Glu Arg Leu Lys Phe Gln Asn Ser Ser Thr Ser Glu
465                 470                 475                 480
```

```
Thr Leu Gln Gly Lys Ala Glu Ser Thr Asp Ile Ala Arg Phe Gln Ser
                485                 490                 495

Arg Asp Glu Leu Lys Tyr Ser Ile Arg Ser Leu Met Lys Tyr Ala Pro
            500                 505                 510

Trp Val Asn His Ile Tyr Ile Val Thr Asn Gly Gln Ile Pro Lys Trp
        515                 520                 525

Leu Asp Thr Asn Asn Thr Lys Val Thr Ile Ile Pro His Ser Thr Ile
    530                 535                 540

Ile Asp Ser Gln Phe Leu Pro Thr Phe Asn Ser His Val Ile Glu Ser
545                 550                 555                 560

Ser Leu Tyr Lys Ile Pro Gly Leu Ser Glu His Tyr Ile Tyr Phe Asn
                565                 570                 575

Asp Asp Val Met Leu Ala Arg Asp Leu Ser Pro Ser Tyr Phe Phe Thr
            580                 585                 590

Ser Ser Gly Leu Ala Lys Leu Phe Ile Thr Asn Ser Arg Leu Pro Asn
        595                 600                 605

Gly Tyr Lys Asn Val Lys Asp Thr Pro Thr Gln Trp Ala Ser Lys Asn
    610                 615                 620

Ser Arg Glu Leu Leu His Ala Glu Thr Gly Phe Trp Ala Glu Ala Met
625                 630                 635                 640

Phe Ala His Thr Phe His Pro Gln Arg Lys Ser Val His Glu Ser Ile
                645                 650                 655

Glu His Leu Trp His Glu Gln Leu Asn Val Cys Arg Gln Asn Arg Phe
            660                 665                 670

Arg Asp Ile Ser Asp Ile Asn Met Ala Thr Phe Leu His His His Phe
        675                 680                 685

Ala Ile Leu Thr Gly Gln Ala Leu Ala Thr Arg Thr Lys Cys Ile Tyr
    690                 695                 700

Phe Asn Ile Arg Ser Pro Gln Ala Ala Gln His Tyr Lys Thr Leu Leu
705                 710                 715                 720

Ala Arg Lys Gly Ser Glu Tyr Ser Pro His Ser Ile Cys Leu Asn Asp
                725                 730                 735

His Thr Ser Ser Asn Lys Asn Ile Leu Ser Asn Tyr Glu Ala Lys Leu
            740                 745                 750

Gln Ser Phe Leu Glu Thr Tyr Tyr Pro Asp Val Ser Glu Ala Glu Ile
        755                 760                 765

Leu Leu Pro Thr Lys Ser Glu Val Ala Glu Leu Val Lys His Lys Asp
    770                 775                 780

Tyr Leu Thr Val Tyr Thr Lys Leu Leu Pro Ile Ile Asn Lys Gln Leu
785                 790                 795                 800

Val Asn Lys Tyr Asn Lys Pro Tyr Ser Tyr Leu Phe Tyr Tyr Leu Gly
                805                 810                 815

Leu Ser Ala Arg Phe Leu Phe Glu Thr Gln Gln Glu His Tyr Arg
            820                 825                 830

Glu Thr Ala Glu Glu Asn Leu Gln Ile Phe Cys Gly Leu Asn Pro Lys
        835                 840                 845

His Thr Leu Ala Leu Lys Tyr Leu Ala Asp Val Thr Leu Thr Ser Gln
    850                 855                 860

Pro Ser Gly Gln Leu Glu His His His His His
865                 870                 875

<210> SEQ ID NO 50
<211> LENGTH: 383
```

<212> TYPE: PRT
<213> ORGANISM: Neisseria meningitidis
<220> FEATURE:
<223> OTHER INFORMATION: AS MBP-S3N10-BamHI

<400> SEQUENCE: 50

| | | | | | | | | | | | | | |
|---|---|---|---|---|---|---|---|---|---|---|---|---|---|
| Met | Lys | Thr | Glu | Glu | Gly | Lys | Leu | Val | Ile | Trp | Ile | Asn | Gly | Asp | Lys |
| 1 | | | | 5 | | | | | 10 | | | | | 15 | |
| Gly | Tyr | Asn | Gly | Leu | Ala | Glu | Val | Gly | Lys | Lys | Phe | Glu | Lys | Asp | Thr |
| | | | 20 | | | | | 25 | | | | | 30 | | |
| Gly | Ile | Lys | Val | Thr | Val | Glu | His | Pro | Asp | Lys | Leu | Glu | Glu | Lys | Phe |
| | | | 35 | | | | | 40 | | | | | 45 | | |
| Pro | Gln | Val | Ala | Ala | Thr | Gly | Asp | Gly | Pro | Asp | Ile | Ile | Phe | Trp | Ala |
| | 50 | | | | | 55 | | | | | 60 | | | | |
| His | Asp | Arg | Phe | Gly | Gly | Tyr | Ala | Gln | Ser | Gly | Leu | Leu | Ala | Glu | Ile |
| 65 | | | | | 70 | | | | | 75 | | | | | 80 |
| Thr | Pro | Asp | Lys | Ala | Phe | Gln | Asp | Lys | Leu | Tyr | Pro | Phe | Thr | Trp | Asp |
| | | | | 85 | | | | | 90 | | | | | 95 | |
| Ala | Val | Arg | Tyr | Asn | Gly | Lys | Leu | Ile | Ala | Tyr | Pro | Ile | Ala | Val | Glu |
| | | | 100 | | | | | 105 | | | | | 110 | | |
| Ala | Leu | Ser | Leu | Ile | Tyr | Asn | Lys | Asp | Leu | Leu | Pro | Asn | Pro | Pro | Lys |
| | | | 115 | | | | | 120 | | | | | 125 | | |
| Thr | Trp | Glu | Glu | Ile | Pro | Ala | Leu | Asp | Lys | Glu | Leu | Lys | Ala | Lys | Gly |
| | | | 130 | | | | | 135 | | | | | 140 | | |
| Lys | Ser | Ala | Leu | Met | Phe | Asn | Leu | Gln | Glu | Pro | Tyr | Phe | Thr | Trp | Pro |
| 145 | | | | | 150 | | | | | 155 | | | | | 160 |
| Leu | Ile | Ala | Ala | Asp | Gly | Gly | Tyr | Ala | Phe | Lys | Tyr | Glu | Asn | Gly | Lys |
| | | | | 165 | | | | | 170 | | | | | 175 | |
| Tyr | Asp | Ile | Lys | Asp | Val | Gly | Val | Asp | Asn | Ala | Gly | Ala | Lys | Ala | Gly |
| | | | 180 | | | | | 185 | | | | | 190 | | |
| Leu | Thr | Phe | Leu | Val | Asp | Leu | Ile | Lys | Asn | Lys | His | Met | Asn | Ala | Asp |
| | | | 195 | | | | | 200 | | | | | 205 | | |
| Thr | Asp | Tyr | Ser | Ile | Ala | Glu | Ala | Ala | Phe | Asn | Lys | Gly | Glu | Thr | Ala |
| | | | 210 | | | | | 215 | | | | | 220 | | |
| Met | Thr | Ile | Asn | Gly | Pro | Trp | Ala | Trp | Ser | Asn | Ile | Asp | Thr | Ser | Lys |
| 225 | | | | | 230 | | | | | 235 | | | | | 240 |
| Val | Asn | Tyr | Gly | Val | Thr | Val | Leu | Pro | Thr | Phe | Lys | Gly | Gln | Pro | Ser |
| | | | | 245 | | | | | 250 | | | | | 255 | |
| Lys | Pro | Phe | Val | Gly | Val | Leu | Ser | Ala | Gly | Ile | Asn | Ala | Ala | Ser | Pro |
| | | | 260 | | | | | 265 | | | | | 270 | | |
| Asn | Lys | Glu | Leu | Ala | Lys | Glu | Phe | Leu | Glu | Asn | Tyr | Leu | Leu | Thr | Asp |
| | | | 275 | | | | | 280 | | | | | 285 | | |
| Glu | Gly | Leu | Glu | Ala | Val | Asn | Lys | Asp | Lys | Pro | Leu | Gly | Ala | Val | Ala |
| | | | 290 | | | | | 295 | | | | | 300 | | |
| Leu | Lys | Ser | Tyr | Glu | Glu | Glu | Leu | Ala | Lys | Asp | Pro | Arg | Ile | Ala | Ala |
| 305 | | | | | 310 | | | | | 315 | | | | | 320 |
| Thr | Met | Glu | Asn | Ala | Gln | Lys | Gly | Glu | Ile | Met | Pro | Asn | Ile | Pro | Gln |
| | | | | 325 | | | | | 330 | | | | | 335 | |
| Met | Ser | Ala | Phe | Trp | Tyr | Ala | Val | Arg | Thr | Ala | Val | Ile | Asn | Ala | Ala |
| | | | | 340 | | | | | 345 | | | | | 350 | |
| Ser | Gly | Arg | Gln | Thr | Val | Asp | Glu | Ala | Leu | Lys | Asp | Ala | Gln | Thr | Asn |
| | | | 355 | | | | | 360 | | | | | 365 | | |
| Ser | Ser | Ser | Asn | Asn | Asn | Asn | Asn | Asn | Asn | Asn | Asn | Gly | Ser | | |
| | | | 370 | | | | | 375 | | | | | 380 | | |

<210> SEQ ID NO 51
<211> LENGTH: 1263
<212> TYPE: DNA
<213> ORGANISM: Neisseria meningitidis
<220> FEATURE:
<223> OTHER INFORMATION: DNA NdeI-dN65dC10-CsxA-XhoI-His6

<400> SEQUENCE: 51

```
catatggtaa catttccaat tgatgtagtt tatacttggg tagattcaga tgatgaaaaa      60
ttcaatgaag aacgcctaaa gtttcaaaat tcaagcacat ctgagactct acaaggcaaa     120
gcagaaagca ccgatattgc aagattccaa tcacgcgacg aattaaaata ttcgattcga     180
agcctgatga agtatgcccc atgggtaaat catatttaca ttgtaacaaa tggtcaaata     240
ccaaaatggt tagataccaa caatacaaag gtaacgatta tccctcactc aactattatc     300
gacagtcaat ttctccctac ttttaattct cacgtcattg aatcctctct atataaaatc     360
ccaggattat cagagcatta catttatttc aatgatgatg tcatgctagc tagagattta     420
agcccatctt atttctttac aagcagcgga ttagcaaaac tgtttattac caactctcgt     480
ctaccaaatg gctataagaa tgtgaaagac acaccaaccc aatgggcctc aaaaaattcc     540
cgtgagcttt acatgcaga  acaggatttt gggctgaag  ccatgtttgc atactttt      600
catccacaac gtaaaagtgt acatgaatct attgaacacc tatggcatga acaattaaat     660
gtttgtcgtc aaaaccgttt ccgtgatatt tcagatatta acatggcgac attcctgcac     720
caccattttg ccattttgac aggccaagct cttgctacac gcactaaatg tatttacttt     780
aacattcgct ctcctcaagc agctcagcat acaaaaacat tattagctcg aaaaggaagc     840
gaatacagcc cacattctat ctgcttaaat gatcatacat cgagcaataa aaatatttta     900
tctaattacg aagccaaatt acaaagcttt ttagaaacat actatccaga tgtatcagaa     960
gcagaaattc tccttcctac taaatctgaa gtagctgaat tagttaaaca taaagattat    1020
ttaactgtat atactaaatt attacctatt atcaataagc agctggtcaa taatataat    1080
aaaccttatt catatctttt ctattatttta ggtttatctg cccggttttt atttgaagaa    1140
acgcaacaag aacactaccg ggaaactgct gaagaaaatt tacaaatctt ttgtggccta    1200
aacccaaaac atacactagc cctcaaatac ttagcggatc tcgagcacca ccaccaccac    1260
cac                                                                 1263
```

<210> SEQ ID NO 52
<211> LENGTH: 420
<212> TYPE: PRT
<213> ORGANISM: Neisseria meningitidis
<220> FEATURE:
<223> OTHER INFORMATION: AS NdeI-dN65dC10-CsxA-XhoI-His6

<400> SEQUENCE: 52

```
Met Val Thr Phe Pro Ile Asp Val Val Tyr Thr Trp Val Asp Ser Asp
1               5                   10                  15

Asp Glu Lys Phe Asn Glu Glu Arg Leu Lys Phe Gln Asn Ser Ser Thr
            20                  25                  30

Ser Glu Thr Leu Gln Gly Lys Ala Glu Ser Thr Asp Ile Ala Arg Phe
        35                  40                  45

Gln Ser Arg Asp Glu Leu Lys Tyr Ser Ile Arg Ser Leu Met Lys Tyr
    50                  55                  60

Ala Pro Trp Val Asn His Ile Tyr Ile Val Thr Asn Gly Gln Ile Pro
65                  70                  75                  80
```

```
Lys Trp Leu Asp Thr Asn Asn Thr Lys Val Thr Ile Ile Pro His Ser
                 85                  90                  95

Thr Ile Ile Asp Ser Gln Phe Leu Pro Thr Phe Asn Ser His Val Ile
            100                 105                 110

Glu Ser Ser Leu Tyr Lys Ile Pro Gly Leu Ser Glu His Tyr Ile Tyr
            115                 120                 125

Phe Asn Asp Asp Val Met Leu Ala Arg Asp Leu Ser Pro Ser Tyr Phe
            130                 135                 140

Phe Thr Ser Ser Gly Leu Ala Lys Leu Phe Ile Thr Asn Ser Arg Leu
145                 150                 155                 160

Pro Asn Gly Tyr Lys Asn Val Lys Asp Thr Pro Thr Gln Trp Ala Ser
                165                 170                 175

Lys Asn Ser Arg Glu Leu Leu His Ala Glu Thr Gly Phe Trp Ala Glu
            180                 185                 190

Ala Met Phe Ala His Thr Phe His Pro Gln Arg Lys Ser Val His Glu
            195                 200                 205

Ser Ile Glu His Leu Trp His Glu Gln Leu Asn Val Cys Arg Gln Asn
            210                 215                 220

Arg Phe Arg Asp Ile Ser Asp Ile Asn Met Ala Thr Phe Leu His His
225                 230                 235                 240

His Phe Ala Ile Leu Thr Gly Gln Ala Leu Ala Thr Arg Thr Lys Cys
                245                 250                 255

Ile Tyr Phe Asn Ile Arg Ser Pro Gln Ala Ala Gln His Tyr Lys Thr
                260                 265                 270

Leu Leu Ala Arg Lys Gly Ser Glu Tyr Ser Pro His Ser Ile Cys Leu
            275                 280                 285

Asn Asp His Thr Ser Ser Asn Lys Asn Ile Leu Ser Asn Tyr Glu Ala
            290                 295                 300

Lys Leu Gln Ser Phe Leu Glu Thr Tyr Tyr Pro Asp Val Ser Glu Ala
305                 310                 315                 320

Glu Ile Leu Leu Pro Thr Lys Ser Glu Val Ala Glu Leu Val Lys His
                325                 330                 335

Lys Asp Tyr Leu Thr Val Tyr Thr Lys Leu Leu Pro Ile Ile Asn Lys
                340                 345                 350

Gln Leu Val Asn Lys Tyr Asn Lys Pro Tyr Ser Tyr Leu Phe Tyr Tyr
            355                 360                 365

Leu Gly Leu Ser Ala Arg Phe Leu Phe Glu Glu Thr Gln Gln Glu His
            370                 375                 380

Tyr Arg Glu Thr Ala Glu Glu Asn Leu Gln Ile Phe Cys Gly Leu Asn
385                 390                 395                 400

Pro Lys His Thr Leu Ala Leu Lys Tyr Leu Ala Asp Leu Glu His His
                405                 410                 415

His His His His
        420

<210> SEQ ID NO 53
<211> LENGTH: 741
<212> TYPE: DNA
<213> ORGANISM: Neisseria meningitidis
<220> FEATURE:
<223> OTHER INFORMATION: DNA CsaC

<400> SEQUENCE: 53
atgttatcta atttaaaaac aggaaataat atcttaggat tacctgaatt tgagttgaat      60
ggctgccgat tcttatataa aaaaggtata gaaaaaacaa ttattacttt ttcagcattt     120
```

```
cctcctaaag atattgctca aaaatataat tatataaaag atttttttaag ttctaattat    180 acttttttag cattcttaga taccaaatat ccagaagatg atgctagagg cacttattac    240
attactaatg agttagataa tggatattta caaaccatac attgtattat tcaattatta    300
tcgaatacaa atcaagaaga tacctacctt ttgggttcaa gtaaaggtgg cgttggcgca    360
cttctactcg gtcttacata taattatcct aatataatta ttaatgctcc tcaagccaaa    420
ttagcagatt atatcaaaac acgctcgaaa accattcttt catatatgct tggaacctct    480
aaaagatttc aagatattaa ttacgattat atcaatgact tcttactatc taaaattaag    540
acttgcgact cctcacttaa atggaatatt catataactt gcggaaaaga tgattcatat    600
catttaaatg aattagaaat tctaaaaaat gaatttaata taaaagctat tacgattaaa    660
accaaactaa tttctggcgg gcatgataat gaagcaattg cccactatag agaatacttt    720
aaaaccataa tccaaaatat a                                              741
```

<210> SEQ ID NO 54
<211> LENGTH: 247
<212> TYPE: PRT
<213> ORGANISM: Neisseria meningitidis
<220> FEATURE:
<223> OTHER INFORMATION: AS CsaC

<400> SEQUENCE: 54

```
Met Leu Ser Asn Leu Lys Thr Gly Asn Asn Ile Leu Gly Leu Pro Glu
1               5                   10                  15

Phe Glu Leu Asn Gly Cys Arg Phe Leu Tyr Lys Lys Gly Ile Glu Lys
            20                  25                  30

Thr Ile Ile Thr Phe Ser Ala Phe Pro Pro Lys Asp Ile Ala Gln Lys
        35                  40                  45

Tyr Asn Tyr Ile Lys Asp Phe Leu Ser Ser Asn Tyr Thr Phe Leu Ala
    50                  55                  60

Phe Leu Asp Thr Lys Tyr Pro Glu Asp Ala Arg Gly Thr Tyr Tyr
65                  70                  75                  80

Ile Thr Asn Glu Leu Asp Asn Gly Tyr Leu Gln Thr Ile His Cys Ile
                85                  90                  95

Ile Gln Leu Leu Ser Asn Thr Asn Gln Glu Asp Thr Tyr Leu Leu Gly
            100                 105                 110

Ser Ser Lys Gly Gly Val Gly Ala Leu Leu Leu Gly Leu Thr Tyr Asn
        115                 120                 125

Tyr Pro Asn Ile Ile Asn Ala Pro Gln Ala Lys Leu Ala Asp Tyr
    130                 135                 140

Ile Lys Thr Arg Ser Lys Thr Ile Leu Ser Tyr Met Leu Gly Thr Ser
145                 150                 155                 160

Lys Arg Phe Gln Asp Ile Asn Tyr Asp Tyr Ile Asn Asp Phe Leu Leu
                165                 170                 175

Ser Lys Ile Lys Thr Cys Asp Ser Leu Lys Trp Asn Ile His Ile
            180                 185                 190

Thr Cys Gly Lys Asp Asp Ser Tyr His Leu Asn Glu Leu Glu Ile Leu
        195                 200                 205

Lys Asn Glu Phe Asn Ile Lys Ala Ile Thr Ile Lys Thr Lys Leu Ile
    210                 215                 220

Ser Gly Gly His Asp Asn Glu Ala Ile Ala His Tyr Arg Glu Tyr Phe
225                 230                 235                 240

Lys Thr Ile Ile Gln Asn Ile
```

<210> SEQ ID NO 55
<211> LENGTH: 34
<212> TYPE: DNA
<213> ORGANISM: Artificial Sequence
<220> FEATURE:
<223> OTHER INFORMATION: Primer KS422/KS273

<400> SEQUENCE: 55
gcatctcata tggctgttat tatatttgtt aacg                                    34

<210> SEQ ID NO 56
<211> LENGTH: 30
<212> TYPE: DNA
<213> ORGANISM: Artificial Sequence
<220> FEATURE:
<223> OTHER INFORMATION: Primer wt NmW-135

<400> SEQUENCE: 56
ccgctcgagt ttttcttggc caaaaaactg                                         30

<210> SEQ ID NO 57
<211> LENGTH: 30
<212> TYPE: DNA
<213> ORGANISM: Artificial Sequence
<220> FEATURE:
<223> OTHER INFORMATION: Primer wt NmY

<400> SEQUENCE: 57
ccgctcgagt ttttcttggc caaaaaactg                                         30

<210> SEQ ID NO 58
<211> LENGTH: 45
<212> TYPE: DNA
<213> ORGANISM: Artificial Sequence
<220> FEATURE:
<223> OTHER INFORMATION: Primer KS350/KS351

<400> SEQUENCE: 58
ctgatcatga catcagaaag tgcgggattt ccatatatat ttatg                        45

<210> SEQ ID NO 59
<211> LENGTH: 45
<212> TYPE: DNA
<213> ORGANISM: Artificial Sequence
<220> FEATURE:
<223> OTHER INFORMATION: Primer E307A

<400> SEQUENCE: 59
cataaatata tatggaaatc ccgcactttc tgatgtcatg atcag                        45

<210> SEQ ID NO 60
<211> LENGTH: 41
<212> TYPE: DNA
<213> ORGANISM: Artificial Sequence
<220> FEATURE:
<223> OTHER INFORMATION: Primer KS370/KS371

<400> SEQUENCE: 60
atctcgcgtt gctgtaggtg tttatgcaac tagcttattt g                            41

<210> SEQ ID NO 61
<211> LENGTH: 41
<212> TYPE: DNA
<213> ORGANISM: Artificial Sequence
<220> FEATURE:
<223> OTHER INFORMATION: Primer S972A

<400> SEQUENCE: 61
caaataagct agttgcataa acacctacag caacgcgaga t        41

<210> SEQ ID NO 62
<211> LENGTH: 51
<212> TYPE: DNA
<213> ORGANISM: Artificial Sequence
<220> FEATURE:
<223> OTHER INFORMATION: Primer AR11/AR12

<400> SEQUENCE: 62
atacagatat cctaatcatg acatctcaaa gcgcaggctt tggttatata t        51

<210> SEQ ID NO 63
<211> LENGTH: 51
<212> TYPE: DNA
<213> ORGANISM: Artificial Sequence
<220> FEATURE:
<223> OTHER INFORMATION: Primer E307A

<400> SEQUENCE: 63
atatataacc aaagcctgcg ctttgagatg tcatgattag gatatctgta t        51

<210> SEQ ID NO 64
<211> LENGTH: 34
<212> TYPE: DNA
<213> ORGANISM: Artificial Sequence
<220> FEATURE:
<223> OTHER INFORMATION: Primer KS422/KS421

<400> SEQUENCE: 64
gcatctcata tggctgttat tatatttgtt aacg        34

<210> SEQ ID NO 65
<211> LENGTH: 28
<212> TYPE: DNA
<213> ORGANISM: Artificial Sequence
<220> FEATURE:
<223> OTHER INFORMATION: Primer C-delta639

<400> SEQUENCE: 65
ccgctcgagg ctgcgcggaa gaatagtg        28

<210> SEQ ID NO 66
<211> LENGTH: 35
<212> TYPE: DNA
<213> ORGANISM: Artificial Sequence
<220> FEATURE:
<223> OTHER INFORMATION: Primer AR2/KS273

<400> SEQUENCE: 66
gcatctcata tgtttaataa cgtatcatta tcgtc        35

<210> SEQ ID NO 67
<211> LENGTH: 30
<212> TYPE: DNA
<213> ORGANISM: Artificial Sequence
<220> FEATURE:
<223> OTHER INFORMATION: Primer N-delta398

<400> SEQUENCE: 67
ccgctcgagt ttttcttggc caaaaaactg        30

<210> SEQ ID NO 68
<211> LENGTH: 35
<212> TYPE: DNA
<213> ORGANISM: Artificial Sequence
<220> FEATURE:
<223> OTHER INFORMATION: Primer AR1/KS273

<400> SEQUENCE: 68
gcatctcata tgactgatga taatttaata cctat    35

<210> SEQ ID NO 69
<211> LENGTH: 30
<212> TYPE: DNA
<213> ORGANISM: Artificial Sequence
<220> FEATURE:
<223> OTHER INFORMATION: Primer N-delta562

<400> SEQUENCE: 69
ccgctcgagt ttttcttggc caaaaaactg    30

<210> SEQ ID NO 70
<211> LENGTH: 35
<212> TYPE: DNA
<213> ORGANISM: Artificial Sequence
<220> FEATURE:
<223> OTHER INFORMATION: Primer AR9/AR273

<400> SEQUENCE: 70
gcatctcata tgaaatattc ttataaatat atcta    35

<210> SEQ ID NO 71
<211> LENGTH: 30
<212> TYPE: DNA
<213> ORGANISM: Artificial Sequence
<220> FEATURE:
<223> OTHER INFORMATION: Primer N-delta609

<400> SEQUENCE: 71
ccgctcgagt ttttcttggc caaaaaactg    30

<210> SEQ ID NO 72
<211> LENGTH: 35
<212> TYPE: DNA
<213> ORGANISM: Artificial Sequence
<220> FEATURE:
<223> OTHER INFORMATION: Primer AR10/KS273

<400> SEQUENCE: 72
gcatctcata tgtcttggga acttattcgt gcctc    35

<210> SEQ ID NO 73
<211> LENGTH: 30
<212> TYPE: DNA
<213> ORGANISM: Artificial Sequence
<220> FEATURE:
<223> OTHER INFORMATION: Primer N-delta639

<400> SEQUENCE: 73
ccgctcgagt ttttcttggc caaaaaactg    30

<210> SEQ ID NO 74
<211> LENGTH: 31
<212> TYPE: DNA
<213> ORGANISM: Artificial Sequence
<220> FEATURE:
<223> OTHER INFORMATION: Primer KS433/KS273

```
<400> SEQUENCE: 74
gcatctcata tgggtaagcg ttcgatggat g                                    31

<210> SEQ ID NO 75
<211> LENGTH: 30
<212> TYPE: DNA
<213> ORGANISM: Artificial Sequence
<220> FEATURE:
<223> OTHER INFORMATION: Primer N-delta676

<400> SEQUENCE: 75
ccgctcgagt ttttcttggc caaaaaactg                                      30

<210> SEQ ID NO 76
<211> LENGTH: 34
<212> TYPE: DNA
<213> ORGANISM: Artificial Sequence
<220> FEATURE:
<223> OTHER INFORMATION: Primer KS434/KS273

<400> SEQUENCE: 76
gcatctcata tgtcactgaa aagtaatgta gttg                                 34

<210> SEQ ID NO 77
<211> LENGTH: 30
<212> TYPE: DNA
<213> ORGANISM: Artificial Sequence
<220> FEATURE:
<223> OTHER INFORMATION: Primer N-delta729

<400> SEQUENCE: 77
ccgctcgagt ttttcttggc caaaaaactg                                      30

<210> SEQ ID NO 78
<211> LENGTH: 35
<212> TYPE: DNA
<213> ORGANISM: Artificial Sequence
<220> FEATURE:
<223> OTHER INFORMATION: Primer KS435/KS273

<400> SEQUENCE: 78
gcatctcata tgaatatcga agcatttcta aaacc                                35

<210> SEQ ID NO 79
<211> LENGTH: 30
<212> TYPE: DNA
<213> ORGANISM: Artificial Sequence
<220> FEATURE:
<223> OTHER INFORMATION: Primer N-delta777

<400> SEQUENCE: 79
ccgctcgagt ttttcttggc caaaaaactg                                      30

<210> SEQ ID NO 80
<211> LENGTH: 34
<212> TYPE: DNA
<213> ORGANISM: Artificial Sequence
<220> FEATURE:
<223> OTHER INFORMATION: Primer KS422/KS421

<400> SEQUENCE: 80
gcatctcata tggctgttat tatatttgtt aacg                                 34

<210> SEQ ID NO 81
```

```
<211> LENGTH: 28
<212> TYPE: DNA
<213> ORGANISM: Artificial Sequence
<220> FEATURE:
<223> OTHER INFORMATION: Primer C-delta639

<400> SEQUENCE: 81
ccgctcgagg ctgcgcggaa gaatagtg                                          28

<210> SEQ ID NO 82
<211> LENGTH: 34
<212> TYPE: DNA
<213> ORGANISM: Artificial Sequence
<220> FEATURE:
<223> OTHER INFORMATION: Primer KS422/KS374

<400> SEQUENCE: 82
gcatctcata tggctgttat tatatttgtt aacg                                   34

<210> SEQ ID NO 83
<211> LENGTH: 29
<212> TYPE: DNA
<213> ORGANISM: Artificial Sequence
<220> FEATURE:
<223> OTHER INFORMATION: Primer C-delta479

<400> SEQUENCE: 83
ccgctcgagc gtttgcatgt tgggtaaag                                         29

<210> SEQ ID NO 84
<211> LENGTH: 35
<212> TYPE: DNA
<213> ORGANISM: Artificial Sequence
<220> FEATURE:
<223> OTHER INFORMATION: Primer AR2/KS273

<400> SEQUENCE: 84
gcatctcata tgtttaataa cgtatcatta tcgtc                                  35

<210> SEQ ID NO 85
<211> LENGTH: 30
<212> TYPE: DNA
<213> ORGANISM: Artificial Sequence
<220> FEATURE:
<223> OTHER INFORMATION: Primer N-delta398

<400> SEQUENCE: 85
ccgctcgagt ttttcttggc caaaaaactg                                        30

<210> SEQ ID NO 86
<211> LENGTH: 35
<212> TYPE: DNA
<213> ORGANISM: Artificial Sequence
<220> FEATURE:
<223> OTHER INFORMATION: Primer AR1/KS273

<400> SEQUENCE: 86
gcatctcata tgactgatga taatttaata cctat                                  35

<210> SEQ ID NO 87
<211> LENGTH: 30
<212> TYPE: DNA
<213> ORGANISM: Artificial Sequence
<220> FEATURE:
<223> OTHER INFORMATION: Primer N-delta562

<400> SEQUENCE: 87
```

```
ccgctcgagt ttttcttggc caaaaaactg                              30
```

<210> SEQ ID NO 88
<211> LENGTH: 31
<212> TYPE: DNA
<213> ORGANISM: Artificial Sequence
<220> FEATURE:
<223> OTHER INFORMATION: Primer KS433/KS273

<400> SEQUENCE: 88

```
gcatctcata tgggtaagcg ttcgatggat g                            31
```

<210> SEQ ID NO 89
<211> LENGTH: 30
<212> TYPE: DNA
<213> ORGANISM: Artificial Sequence
<220> FEATURE:
<223> OTHER INFORMATION: Primer N-delta 676

<400> SEQUENCE: 89

```
ccgctcgagt ttttcttggc caaaaaactg                              30
```

<210> SEQ ID NO 90
<211> LENGTH: 34
<212> TYPE: DNA
<213> ORGANISM: Artificial Sequence
<220> FEATURE:
<223> OTHER INFORMATION: Primer KS434/KS273

<400> SEQUENCE: 90

```
gcatctcata tgtcactgaa aagtaatgta gttg                         34
```

<210> SEQ ID NO 91
<211> LENGTH: 30
<212> TYPE: DNA
<213> ORGANISM: Artificial Sequence
<220> FEATURE:
<223> OTHER INFORMATION: N-delta 729

<400> SEQUENCE: 91

```
ccgctcgagt ttttcttggc caaaaaactg                              30
```

<210> SEQ ID NO 92
<211> LENGTH: 31
<212> TYPE: DNA
<213> ORGANISM: Artificial Sequence
<220> FEATURE:
<223> OTHER INFORMATION: Recloning primer

<400> SEQUENCE: 92

```
gcatctcata tgggtaagcg ttcgatggat g                            31
```

<210> SEQ ID NO 93
<211> LENGTH: 30
<212> TYPE: DNA
<213> ORGANISM: Artificial Sequence
<220> FEATURE:
<223> OTHER INFORMATION: Recloning Primer

<400> SEQUENCE: 93

```
ccgctcgagt ttttcttggc caaaaaactg                              30
```

<210> SEQ ID NO 94
<211> LENGTH: 29
<212> TYPE: DNA

```
<213> ORGANISM: Artificial Sequence
<220> FEATURE:
<223> OTHER INFORMATION: Primer StrepII-CsaA-His6

<400> SEQUENCE: 94
gcggatccaa agtcttaacc gtctttggc                                    29

<210> SEQ ID NO 95
<211> LENGTH: 34
<212> TYPE: DNA
<213> ORGANISM: Artificial Sequence
<220> FEATURE:
<223> OTHER INFORMATION: Primer StrepII-CsaA-His6

<400> SEQUENCE: 95
ccgctcgagt ctattcttta ataaagtttc taca                              34

<210> SEQ ID NO 96
<211> LENGTH: 33
<212> TYPE: DNA
<213> ORGANISM: Artificial Sequence
<220> FEATURE:
<223> OTHER INFORMATION: Primer StrepII-CsaB-His6

<400> SEQUENCE: 96
gcagatcttt tatacttaat aacagaaaat ggc                               33

<210> SEQ ID NO 97
<211> LENGTH: 32
<212> TYPE: DNA
<213> ORGANISM: Artificial Sequence
<220> FEATURE:
<223> OTHER INFORMATION: Primer StrepII-CsaB-His6

<400> SEQUENCE: 97
ccgctcgagt ttctcaaatg atgatggtaa tg                                32

<210> SEQ ID NO 98
<211> LENGTH: 32
<212> TYPE: DNA
<213> ORGANISM: Artificial Sequence
<220> FEATURE:
<223> OTHER INFORMATION: Primer StrepII-delta69-CsaB-His6

<400> SEQUENCE: 98
ccgctcgagt ttctcaaatg atgatggtaa tg                                32

<210> SEQ ID NO 99
<211> LENGTH: 34
<212> TYPE: DNA
<213> ORGANISM: Artificial Sequence
<220> FEATURE:
<223> OTHER INFORMATION: Primer StrepII-delta69-CsaB-His6

<400> SEQUENCE: 99
gcagatctat gttaattcct attaattttt ttaa                              34

<210> SEQ ID NO 100
<211> LENGTH: 32
<212> TYPE: DNA
<213> ORGANISM: Artificial Sequence
<220> FEATURE:
<223> OTHER INFORMATION: Primer delta69-CsaB-His6

<400> SEQUENCE: 100
ccgctcgagt ttctcaaatg atgatggtaa tg                                32
```

<210> SEQ ID NO 101
<211> LENGTH: 39
<212> TYPE: DNA
<213> ORGANISM: Artificial Sequence
<220> FEATURE:
<223> OTHER INFORMATION: Primer delta69-CsaB-His6

<400> SEQUENCE: 101
gcatctcata tgttaattcc tattaatttt ttttaattt                              39

<210> SEQ ID NO 102
<211> LENGTH: 33
<212> TYPE: DNA
<213> ORGANISM: Artificial Sequence
<220> FEATURE:
<223> OTHER INFORMATION: Primer delta69-CsaBCo-His6

<400> SEQUENCE: 102
gcatctcata tgctgatccc gatcaatttc ttt                                    33

<210> SEQ ID NO 103
<211> LENGTH: 28
<212> TYPE: DNA
<213> ORGANISM: Artificial Sequence
<220> FEATURE:
<223> OTHER INFORMATION: Primer delta69-CsaBCo-His6

<400> SEQUENCE: 103
ccgctcgagt ttctcgaagg agctcggc                                          28

<210> SEQ ID NO 104
<211> LENGTH: 27
<212> TYPE: DNA
<213> ORGANISM: Artificial Sequence
<220> FEATURE:
<223> OTHER INFORMATION: Primer StrepII-CsaC-His6

<400> SEQUENCE: 104
ccgctcgagt atattttgga ttatggt                                           27

<210> SEQ ID NO 105
<211> LENGTH: 28
<212> TYPE: DNA
<213> ORGANISM: Artificial Sequence
<220> FEATURE:
<223> OTHER INFORMATION: Primer StrepII-CsaC-His6

<400> SEQUENCE: 105
gcggatcctt atctaattta aaaacagg                                          28

<210> SEQ ID NO 106
<211> LENGTH: 366
<212> TYPE: PRT
<213> ORGANISM: Neisseria meningitidis
<220> FEATURE:
<223> OTHER INFORMATION: NmL (CsIA); Homologue of CsxA/CsaB

<400> SEQUENCE: 106

Met Lys Arg Leu Lys Lys Leu Thr Arg Glu Pro Gly Val Phe Phe Arg
1               5                   10                  15

Asp Tyr Phe Asn Lys Lys Tyr Pro Val Arg Asn Ile Glu Gln Arg Ile
                20                  25                  30

Asn Glu Ile Glu Glu Pro Ala Ile Ala Asn Ser Leu His Leu Ala
            35                  40                  45

```
Ala Val Glu Ser Ala Ile His Leu Ser Pro Phe Lys Ile Asp Val Val
         50                  55                  60

Phe Thr Trp Val Asp Asn Ser Asp Thr Gln Trp Gln Gln Arg His Gln
 65                  70                  75                  80

Gln Tyr Cys His Ala Ala Ser Pro Asn Asn Leu Tyr Ser Asn Asp Glu
                 85                  90                  95

Thr Arg Phe Ala Asn His Asn Glu Leu Tyr Tyr Ser Leu His Ser Val
                100                 105                 110

Arg Ser Phe Leu Pro Trp Val Asn His Ile Tyr Ile Ile Thr Asp Ser
            115                 120                 125

Gln Thr Pro Lys Trp Phe Lys Ser Ala Glu Tyr Pro Asn Val Ser Ile
        130                 135                 140

Ile Asp His Ser Glu Ile Ile Asp Lys Gln Tyr Leu Pro Thr Phe Asn
145                 150                 155                 160

Ser His Val Ile Glu Ala His Leu His Asn Ile Pro Asn Leu Ser Glu
                165                 170                 175

His Phe Ile Tyr Phe Asn Asp Asp Val Phe Val Ala Arg Pro Leu His
                180                 185                 190

Arg Glu His Phe Phe His Ala Asn Gly Ile Ala Ser Leu Phe Ile Ala
            195                 200                 205

Asp Lys Ser Leu Gln Lys Met Ala Thr Lys Gly Thr Ile Thr Pro Thr
        210                 215                 220

Leu Ser Ala Ser Gln Asn Cys Ile Arg Leu Leu Asn Gln Arg Tyr Asp
225                 230                 235                 240

Cys Asn Leu Asp His Pro Leu Val His Thr Tyr Val Pro Leu Arg Lys
                245                 250                 255

Ser Gly Phe Gln Thr Ala Trp Gln Tyr Tyr Arg Glu Glu Ile Lys Ala
                260                 265                 270

Phe Leu Pro Asn Lys Phe Arg Thr Asn Gln Asp Leu Asn Leu Ala Thr
            275                 280                 285

Phe Leu Val Pro Trp Leu Met Tyr Leu Asp Gly Lys Ser Ile Pro Asn
        290                 295                 300

Asn Asp Ile Cys Tyr Tyr Phe Asn Ile Arg Ser Asn Lys Ala Pro Thr
305                 310                 315                 320

Gln Tyr Leu Lys Leu Leu Gln Lys Asn Glu Asp Asn Gln Gln Pro His
                325                 330                 335

Ser Phe Cys Ala Asn Asp Phe His Ser Glu Gln Gln Leu Tyr Asp Tyr
                340                 345                 350

His Ala Lys Leu Ile Ala Met Leu Lys Asp Tyr Phe Lys Ile
            355                 360                 365

<210> SEQ ID NO 107
<211> LENGTH: 1037
<212> TYPE: PRT
<213> ORGANISM: Neisseria meningitidis
<220> FEATURE:
<223> OTHER INFORMATION: polymerase of serogroup Y

<400> SEQUENCE: 107

Met Ala Val Ile Ile Phe Val Asn Gly Ile Arg Ala Val Asn Gly Leu
 1               5                  10                  15

Val Lys Ser Ser Ile Asn

```
Leu Ser Pro Pro Phe His Leu His Pro Asn Val Lys Thr Ser Ser Ile
    50                  55                  60

Ile Asp Leu Phe Asn Asp Ile Pro Glu Asn Val Ser Cys Arg Asn Ile
65                  70                  75                  80

Pro Phe Tyr Ser Ile His Gln Gln Phe Phe Lys Ala Glu Tyr Ser Ala
                85                  90                  95

His Tyr Lys His Val Leu Met Lys Ile Glu Ser Leu Leu Ser Glu Glu
                100                 105                 110

Asp Ser Ile Ile Phe Thr His Pro Leu Gln Leu Glu Met Tyr Arg Leu
            115                 120                 125

Ala Asn Asn Asn Ile Lys Ser Lys Ala Lys Leu Ile Val Gln Ile His
    130                 135                 140

Gly Asn Tyr Met Glu Glu Ile His Asn Tyr Glu Ile Trp Ala Arg Asn
145                 150                 155                 160

Ile Asp Tyr Val Asp Tyr Leu Gln Thr Val Ser Asp Glu Met Leu Glu
                165                 170                 175

Glu Met His Ser His Phe Lys Ile Lys Lys Asp Lys Leu Val Phe Ile
            180                 185                 190

Pro Asn Ile Thr Tyr Pro Ile Ser Leu Glu Lys Lys Glu Ala Asp Phe
            195                 200                 205

Phe Ile Lys Asp Asn Glu Asp Ile Asp Asn Ala Gln Lys Phe Lys Arg
    210                 215                 220

Ile Ser Ile Val Gly Ser Ile Gln Pro Arg Lys Asn Gln Leu Asp Ala
225                 230                 235                 240

Ile Lys Ile Ile Asn Lys Ile Lys Asn Glu Asn Tyr Ile Leu Gln Ile
                245                 250                 255

Tyr Gly Lys Ser Ile Asn Lys Asp Tyr Phe Glu Leu Ile Lys Lys Tyr
            260                 265                 270

Ile Lys Asp Asn Lys Leu Gln Asn Arg Ile Leu Phe Lys Gly Glu Ser
    275                 280                 285

Ser Glu Gln Glu Ile Tyr Glu Asn Thr Asp Ile Leu Ile Met Thr Ser
    290                 295                 300

Gln Ser Glu Gly Phe Gly Tyr Ile Phe Leu Glu Gly Met Val Tyr Asp
305                 310                 315                 320

Ile Pro Ile Leu Ala Tyr Asn Phe Lys Tyr Gly Ala Asn Asp Phe Ser
                325                 330                 335

Asn Tyr Asn Glu Asn Ala Ser Val Phe Lys Thr Gly Asp Ile Ser Gly
            340                 345                 350

Met Ala Lys Lys Ile Ile Glu Leu Leu Asn Asn Pro Glu Lys Tyr Lys
        355                 360                 365

Glu Leu Val Gln Tyr Asn His Asn Arg Phe Leu Lys Gly Tyr Ala Lys
    370                 375                 380

Asp Val Val Met Ala Lys Tyr Phe Thr Ile Leu Pro Arg Ser Phe Asn
385                 390                 395                 400

Asn Val Ser Leu Ser Ser Ala Phe Ser Arg Lys Glu Leu Asp Glu Phe
                405                 410                 415

Gln Asn Ile Thr Phe Ser Ile Glu Asp Ser Asn Asp Leu Ala His Ile
            420                 425                 430

Trp Asn Phe Glu Leu Thr Asn Pro Ala Gln Asn Met Asn Phe Phe Ala
        435                 440                 445

Leu Val Gly Lys Arg Lys Phe Pro Met Asp Ala His Ile Gln Gly Thr
    450                 455                 460
```

```
Gln Cys Thr Ile Lys Ile Ala His Lys Lys Thr Gly Asn Leu Leu Ser
465                 470                 475                 480

Leu Leu Leu Lys Lys Arg Asn Gln Leu Asn Leu Ser Arg Gly Tyr Thr
            485                 490                 495

Leu Ile Ala Glu Asp Asn Ser Tyr Glu Lys Tyr Ile Gly Ala Ile Ser
        500                 505                 510

Asn Lys Gly Asn Phe Glu Ile Ile Ala Asn Lys Lys Asn Ser Leu Val
        515                 520                 525

Thr Ile Asn Lys Ser Thr Leu Glu Leu His Gly Ile Pro His Glu Leu
        530                 535                 540

His Gln Asn Lys Leu Leu Ile Ala Leu Pro Asn Met Gln Thr Pro Leu
545                 550                 555                 560

Lys Ile Thr Asp Asp Asn Leu Ile Pro Ile Gln Ala Ser Ile Lys Leu
            565                 570                 575

Glu Lys Ile Gly Asn Thr Tyr Tyr Pro Cys Phe Leu Pro Ser Gly Ile
            580                 585                 590

Phe Asn Asn Ile Cys Leu Asp Tyr Gly Glu Ser Lys Ile Ile Asn
595                 600                 605

Phe Ser Lys Tyr Ser Tyr Lys Tyr Ile Tyr Asp Ser Ile Arg His Ile
    610                 615                 620

Glu Gln His Thr Asp Ile Ser Asp Ile Ile Val Cys Asn Val Tyr Ser
625                 630                 635                 640

Trp Glu Leu Ile Arg Ala Ser Val Ile Glu Ser Leu Met Glu Phe Thr
                645                 650                 655

Gly Lys Trp Glu Lys His Phe Gln Thr Ser Pro Lys Ile Asp Tyr Arg
            660                 665                 670

Phe Asp His Glu Gly Lys Arg Ser Met Asp Asp Val Phe Ser Glu Glu
        675                 680                 685

Thr Phe Ile Met Glu Phe Pro Arg Lys Asn Gly Ile Asp Lys Lys Thr
        690                 695                 700

Ala Ala Phe Gln Asn Ile Pro Asn Ser Ile Val Met Glu Tyr Pro Gln
705                 710                 715                 720

Thr Asn Gly Tyr Ser Met Arg Ser His Ser Leu Lys Ser Asn Val Val
            725                 730                 735

Ala Ala Lys His Phe Leu Glu Lys Leu Asn Lys Ile Lys Val Asp Ile
            740                 745                 750

Lys Phe Lys Lys His Asp Leu Ala Asn Ile Lys Lys Met Asn Arg Ile
        755                 760                 765

Ile Tyr Glu His Leu Gly Ile Asn Ile Asn Ile Glu Ala Phe Leu Lys
        770                 775                 780

Pro Arg Leu Glu Lys Phe Lys Arg Glu Glu Lys Tyr Phe His Asp Phe
785                 790                 795                 800

Phe Lys Arg Asn Asn Phe Lys Glu Val Ile Phe Pro Ser Thr Tyr Trp
                805                 810                 815

Asn Pro Gly Ile Ile Cys Ala Ala His Lys Gln Gly Ile Lys Val Ser
            820                 825                 830

Asp Ile Gln Tyr Ala Ala Ile Thr Pro Tyr His Pro Ala Tyr Phe Lys
        835                 840                 845

Ser Pro Lys Ser His Tyr Val Ala Asp Lys Leu Phe Leu Trp Ser Glu
        850                 855                 860

Tyr Trp Asn His Glu Leu Leu Pro Asn Pro Thr Arg Glu Ile Gly Ser
865                 870                 875                 880

Gly Ala Ala Tyr Trp Tyr Ala Leu Asp Asp Val Arg Phe Ser Glu Lys
```

```
                        885                 890                 895
Leu Asn Tyr Asp Tyr Ile Phe Leu Ser Gln Ser Arg Ile Ser Ser Arg
                900                 905                 910

Leu Leu Ser Phe Ala Ile Glu Phe Ala Leu Lys Asn Pro Gln Leu Gln
            915                 920                 925

Leu Leu Phe Ser Lys His Leu Asp Glu Asn Ile Asp Leu Lys Asn Arg
        930                 935                 940

Ile Ile Pro Asp Asn Leu Ile Ile Ser Thr Glu Ser Ser Ile Gln Gly
945                 950                 955                 960

Ile Asn Glu Ser Arg Val Ala Val Gly Val Tyr Ser Thr Ser Leu Phe
                965                 970                 975

Glu Ala Leu Ala Cys Gly Lys Gln Thr Phe Val Val Lys Tyr Pro Gly
            980                 985                 990

Tyr Glu Ile Met Ser Asn Glu Ile Asp Ser Gly Leu Phe Phe Ala Val
        995                 1000                1005

Glu Thr Pro Glu Glu Met Leu Glu Lys Thr Ser Pro Asn Trp Val Ala
    1010                1015                1020

Val Ala Asp Ile Glu Asn Gln Phe Phe Gly Gln Glu Lys
1025                1030                1035

<210> SEQ ID NO 108
<211> LENGTH: 1037
<212> TYPE: PRT
<213> ORGANISM: Neisseria meningitidis
<220> FEATURE:
<223> OTHER INFORMATION: polymerase of serogroup W-135

<400> SEQUENCE: 108

Met Ala Val Ile Ile Phe Val Asn Gly Ile Arg Ala Val Asn Gly Leu
1               5                   10                  15

Val Lys Ser Ser Ile Asn Thr Ala Asn Ala Phe Ala Glu Glu Gly Leu
            20                  25                  30

Asp Val His Leu Ile Asn Phe Val Gly Asn Ile Th

```
            210                 215                 220
Ile Ser Ile Val Gly Ser Ile Gln Pro Arg Lys Asn Gln Leu Asp Ala
225                 230                 235                 240

Ile Lys Ile Ile Asn Lys Ile Lys Asn Glu Asn Tyr Ile Leu Gln Ile
                245                 250                 255

Tyr Gly Lys Ser Ile Asn Lys Asp Tyr Phe Glu Leu Ile Lys Lys Tyr
                260                 265                 270

Ile Lys Asp Asn Lys Leu Gln Asn Arg Ile Leu Phe Lys Gly Glu Ser
            275                 280                 285

Ser Glu Gln Glu Ile Tyr Glu Asn Thr Asp Ile Leu Ile Met Thr Ser
            290                 295                 300

Glu Ser Glu Gly Phe Pro Tyr Ile Phe Met Glu Gly Met Val Tyr Asp
305                 310                 315                 320

Ile Pro Ile Val Val Tyr Asp Phe Lys Tyr Gly Ala Asn Asp Tyr Ser
                325                 330                 335

Asn Tyr Asn Glu Asn Gly Cys Val Phe Lys Thr Gly Asp Ile Ser Gly
                340                 345                 350

Met Ala Lys Lys Ile Ile Glu Leu Leu Asn Asn Pro Glu Lys Tyr Lys
            355                 360                 365

Glu Leu Val Gln Tyr Asn His Asn Arg Phe Leu Lys Glu Tyr Ala Lys
            370                 375                 380

Asp Val Val Met Ala Lys Tyr Phe Thr Ile Leu Pro Arg Ser Phe Asn
385                 390                 395                 400

Asn Val Ser Leu Ser Ser Ala Phe Ser Arg Lys Glu Leu Asp Glu Phe
                405                 410                 415

Gln Asn Ile Thr Phe Ser Ile Glu Asp Ser Asn Asp Leu Ala His Ile
            420                 425                 430

Trp Asn Phe Glu Leu Thr Asn Pro Ala Gln Asn Met Asn Phe Phe Ala
            435                 440                 445

Leu Val Gly Lys Arg Lys Phe Pro Met Asp Ala His Ile Gln Gly Thr
450                 455                 460

Gln Cys Thr Ile Lys Ile Ala His Lys Lys Thr Gly Asn Leu Leu Ser
465                 470                 475                 480

Leu Leu Leu Lys Lys Arg Asn Gln Leu Asn Leu Ser Arg Gly Tyr Thr
                485                 490                 495

Leu Ile Ala Glu Asp Asn Ser Tyr Glu Lys Tyr Ile Gly Ala Ile Ser
                500                 505                 510

Asn Lys Gly Asn Phe Glu Ile Ile Ala Asn Lys Lys Ser Ser Leu Val
            515                 520                 525

Thr Ile Asn Lys Ser Thr Leu Glu Leu His Glu Ile Pro His Glu Leu
            530                 535                 540

His Gln Asn Lys Leu Leu Ile Ala Leu Pro Asn Met Gln Thr Pro Leu
545                 550                 555                 560

Lys Ile Thr Asp Asp Asn Leu Ile Pro Ile Gln Ala Ser Ile Lys Leu
                565                 570                 575

Glu Lys Ile Gly Asn Thr Tyr Tyr Pro Cys Phe Leu Pro Ser Gly Ile
            580                 585                 590

Phe Asn Asn Ile Cys Leu Asp Tyr Gly Glu Glu Ser Lys Ile Ile Asn
            595                 600                 605

Phe Ser Lys Tyr Ser Tyr Lys Tyr Ile Tyr Asp Ser Ile Arg His Ile
            610                 615                 620

Glu Gln His Thr Asp Ile Ser Asp Ile Ile Val Cys Asn Val Tyr Ser
625                 630                 635                 640
```

-continued

Trp Glu Leu Ile Arg Ala Ser Val Ile Glu Ser Leu Met Glu Phe Thr
                645                 650                 655
Gly Lys Trp Glu Lys His Phe Gln Thr Ser Pro Lys Ile Asp Tyr Arg
            660                 665                 670
Phe Asp His Glu Gly Lys Arg Ser Met Asp Asp Val Phe Ser Glu Glu
        675                 680                 685
Thr Phe Ile Met Glu Phe Pro Arg Lys Asn Gly Ile Asp Lys Lys Thr
    690                 695                 700
Ala Ala Phe Gln Asn Ile Pro Asn Ser Ile Val Met Glu Tyr Pro Gln
705                 710                 715                 720
Thr Asn Gly Tyr Ser Met Arg Ser His Ser Leu Lys Ser Asn Val Val
                725                 730                 735
Ala Ala Lys His Phe Leu Glu Lys Leu Asn Lys Ile Lys Val Asp Ile
            740                 745                 750
Lys Phe Lys Lys His Asp Leu Ala Asn Ile Lys Lys Met Asn Arg Ile
        755                 760                 765
Ile Tyr Glu His Leu Gly Ile Asn Ile Asn Ile Glu Ala Phe Leu Lys
    770                 775                 780
Pro Arg Leu Glu Lys Phe Lys Arg Glu Lys Tyr Phe His Asp Phe
785                 790                 795                 800
Phe Lys Arg Asn Asn Phe Lys Glu Val Ile Phe Pro Ser Thr Tyr Trp
                805                 810                 815
Asn Pro Gly Ile Ile Cys Ala Ala His Lys Gln Gly Ile Lys Val Ser
            820                 825                 830
Asp Ile Gln Tyr Ala Ala Ile Thr Pro Tyr His Pro Ala Tyr Phe Lys
        835                 840                 845
Ser Pro Lys Ser His Tyr Val Ala Asp Lys Leu Phe Leu Trp Ser Glu
    850                 855                 860
Tyr Trp Asn His Glu Leu Leu Pro Asn Pro Thr Arg Glu Ile Gly Ser
865                 870                 875                 880
Gly Ala Ala Tyr Trp Tyr Ala Leu Asp Asp Val Arg Phe Ser Glu Lys
                885                 890                 895
Leu Asn Tyr Asp Tyr Ile Phe Leu Ser Gln Ser Arg Ile Ser Ser Arg
        900                 905                 910
Leu Leu Ser Phe Ala Ile Glu Phe Ala Leu Lys Asn Pro Gln Leu Gln
    915                 920                 925
Leu Leu Phe Ser Lys His Pro Asp Glu Asn Ile Asp Leu Lys Asn Arg
930                 935                 940
Ile Ile Pro Asp Asn Leu Ile Ile Ser Thr Glu Ser Ser Ile Gln Gly
945                 950                 955                 960
Ile Asn Glu Ser Arg Val Ala Val Gly Val Tyr Ser Thr Ser Leu Phe
                965                 970                 975
Glu Ala Leu Ala Cys Gly Lys Gln Thr Phe Val Val Lys Tyr Pro Gly
            980                 985                 990
Tyr Glu Ile Met Ser Asn Glu Ile Asp Ser Gly Leu Phe Phe Ala Val
        995                 1000                1005
Glu Thr Pro Glu Glu Met Leu Glu Lys Thr Ser Pro Asn Trp Val Ala
    1010                1015                1020
Val Ala Asp Ile Glu Asn Gln Phe Phe Gly Gln Glu Lys
1025                1030                1035

<210> SEQ ID NO 109
<211> LENGTH: 495

<212> TYPE: PRT
<213> ORGANISM: Neisseria meningitidis
<220> FEATURE:
<223> OTHER INFORMATION: Polysialyltransferase of NmB

<400> SEQUENCE: 109

```
Met Leu Lys Lys Ile Lys Lys Ala Leu Phe Gln Pro Lys Lys Phe Phe
1               5                   10                  15

Gln Asp Ser Met Trp Leu Thr Thr Ser Pro Phe Tyr Leu Thr Pro Pro
            20                  25                  30

Arg Asn Asn Leu Phe Val Ile Ser Asn Leu Gly Gln Leu Asn Gln Val
        35                  40                  45

Gln Ser Leu Ile Lys Ile Gln Lys Leu Thr Asn Asn Leu Leu Val Ile
    50                  55                  60

Leu Tyr Thr Ser Lys Asn Leu Lys Met Pro Lys Leu Val His Gln Ser
65                  70                  75                  80

Ala Asn Lys Asn Leu Phe Glu Ser Ile Tyr Leu Phe Glu Leu Pro Arg
                85                  90                  95

Ser Pro Asn Asn Ile Thr Pro Lys Lys Leu Leu Tyr Ile Tyr Arg Ser
            100                 105                 110

Tyr Lys Lys Ile Leu Asn Ile Ile Gln Pro Ala His Leu Tyr Met Leu
        115                 120                 125

Ser Phe Thr Gly His Tyr Ser Tyr Leu Ile Ser Ile Ala Lys Lys Lys
    130                 135                 140

Asn Ile Thr Thr His Leu Ile Asp Glu Gly Thr Gly Thr Tyr Ala Pro
145                 150                 155                 160

Leu Leu Glu Ser Phe Ser Tyr His Pro Thr Lys Leu Glu Arg Tyr Leu
                165                 170                 175

Ile Gly Asn Asn Leu Asn Ile Lys Gly Tyr Ile Asp His Phe Asp Ile
            180                 185                 190

Leu His Val Pro Phe Pro Glu Tyr Ala Lys Lys Ile Phe Asn Ala Lys
        195                 200                 205

Lys Tyr Asn Arg Phe Phe Ala His Ala Gly Gly Ile Ser Ile Asn Asn
    210                 215                 220

Asn Ile Ala Asn Leu Gln Lys Lys Tyr Gln Ile Ser Lys Asn Asp Tyr
225                 230                 235                 240

Ile Phe Val Ser Gln Arg Tyr Pro Ile Ser Asp Asp Leu Tyr Tyr Lys
                245                 250                 255

Ser Ile Val Glu Ile Leu Asn Ser Ile Ser Leu Gln Ile Lys Gly Lys
            260                 265                 270

Ile Phe Ile Lys Leu His Pro Lys Glu Met Gly Asn Asn Tyr Val Met
        275                 280                 285

Ser Leu Phe Leu Asn Met Val Glu Ile Asn Pro Arg Leu Val Val Ile
    290                 295                 300

Asn Glu Pro Pro Phe Leu Ile Glu Pro Leu Ile Tyr Leu Thr Asn Pro
305                 310                 315                 320

Lys Gly Ile Ile Gly Leu Ala Ser Ser Ser Leu Ile Tyr Thr Pro Leu
                325                 330                 335

Leu Ser Pro Ser Thr Gln Cys Leu Ser Ile Gly Glu Leu Ile Ile Asn
            340                 345                 350

Leu Ile Gln Lys Tyr Ser Met Val Glu Asn Thr Glu Met Ile Gln Glu
        355                 360                 365

His Leu Glu Ile Ile Lys Lys Phe Asn Phe Ile Asn Ile Leu Asn Asp
    370                 375                 380
```

```
Leu Asn Gly Val Ile Ser Asn Pro Leu Phe Lys Thr Glu Glu Thr Phe
385                 390                 395                 400

Glu Thr Leu Leu Lys Ser Ala Glu Phe Ala Tyr Lys Ser Lys Asn Tyr
                405                 410                 415

Phe Gln Ala Ile Phe Tyr Trp Gln Leu Ala Ser Lys Asn Asn Ile Thr
                420                 425                 430

Leu Leu Gly His Lys Ala Leu Trp Tyr Tyr Asn Ala Leu Tyr Asn Val
                435                 440                 445

Lys Gln Ile Tyr Lys Met Glu Tyr Ser Asp Ile Phe Tyr Ile Asp Asn
            450                 455                 460

Ile Ser Val Asp Phe His Ser Lys Asp Lys Leu Thr Trp Glu Lys Ile
465                 470                 475                 480

Lys His Tyr Tyr Tyr Ser Ala Asp Asn Arg Ile Gly Arg Asp Arg
                485                 490                 495

<210> SEQ ID NO 110
<211> LENGTH: 492
<212> TYPE: PRT
<213> ORGANISM: Neisseria meningitidis
<220> FEATURE:
<223> OTHER INFORMATION: Polysialyltransferase of NmC

<400> SEQUENCE: 110

Met Leu Gln Lys Ile Arg Lys Ala Leu Phe His Pro Lys Lys Phe Phe
1               5                   10                  15

Gln Asp Ser Gln Trp Phe Ala Thr Pro Leu Phe Ser Ser Phe Ala Pro
                20                  25                  30

Lys Ser Asn Leu Phe Ile Ile Ser Thr Phe Ala Gln Leu Asn Gln Ala
            35                  40                  45

His Ser Leu Thr Lys Met Gln Lys Leu Lys Asn Asn Leu Leu Val Ile
50                  55                  60

Leu Tyr Thr Thr Gln Asn Met Lys Met Pro Lys Leu Ile Gln Lys Ser
65                  70                  75                  80

Val Asp Lys Glu Leu Phe Ser Val Thr Tyr Met Phe Glu Leu Pro Arg
                85                  90                  95

Lys Pro Gly Ile Val Ser Pro Lys Lys Phe Leu Tyr Ile Gln Arg Gly
                100                 105                 110

Tyr Lys Lys Leu Leu Lys Thr Ile Gln Pro Ala His Leu Tyr Val Met
            115                 120                 125

Ser Phe Ala Gly His Tyr Ser Ser Leu Leu Ser Leu Ala Lys Lys Met
            130                 135                 140

Asn Ile Thr Thr His Leu Val Glu Glu Gly Thr Ala Thr Tyr Ala Pro
145                 150                 155                 160

Leu Leu Glu Ser Phe Thr Tyr Lys Pro Thr Lys Phe Glu Gln Arg Phe
                165                 170                 175

Val Gly Asn Asn Leu His Gln Lys Gly Tyr Phe Asp Lys Phe Asp Ile
                180                 185                 190

Leu His Val Ala Phe Pro Glu Tyr Ala Lys Lys Ile Phe Asn Ala Asn
            195                 200                 205

Glu Tyr His Arg Phe Phe Ala His Ser Gly Gly Ile Ser Thr Ser Gln
            210                 215                 220

Ser Ile Ala Lys Ile Gln Asp Lys Tyr Arg Ile Ser Gln Asn Asp Tyr
225                 230                 235                 240

Ile Phe Val Ser Gln Arg Tyr Pro Val Ser Asp Glu Val Tyr Tyr Lys
                245                 250                 255
```

```
Thr Ile Val Glu Thr Leu Asn Gln Met Ser Leu Arg Ile Glu Gly Lys
                260                 265                 270

Ile Phe Ile Lys Leu His Pro Lys Glu Met Glu Asn Lys Asn Ile Met
            275                 280                 285

Ser Leu Phe Leu Asn Met Val Thr Ile Asn Pro Arg Leu Val Val Ile
        290                 295                 300

Asn Glu Pro Pro Phe Leu Ile Asp Pro Leu Ile Tyr Leu Thr Thr Pro
305                 310                 315                 320

Lys Gly Ile Ile Gly Leu Thr Ser Thr Ser Ile Val Tyr Thr Pro Leu
                325                 330                 335

Leu Ser Pro Thr Thr Gln Cys Leu Ser Ile Gly Gln Ile Val Ile Asp
            340                 345                 350

Ser Ile His His Thr Ala Gln Gln Glu Asn Thr Ala Leu Ile Glu Glu
        355                 360                 365

His Leu Glu Ile Val Lys Gln Phe Asp Phe Ile Lys Ile Leu Ser Ser
    370                 375                 380

Ile Glu Asp Gly Ile Asp Thr Asn Ser Phe Lys Thr Glu Glu Thr Leu
385                 390                 395                 400

Glu Met Leu Leu Lys Ser Ala Glu Tyr Ala Tyr Lys Asn Lys Asn Phe
                405                 410                 415

Tyr Gln Ala Ile Phe Tyr Trp Gln Leu Ala Ser Asn Asn Asp Leu Ser
            420                 425                 430

Val Leu Gly Tyr Lys Ser Leu Trp Tyr Tyr Asn Ala Leu Asn Lys Val
        435                 440                 445

Lys Gln Asn Tyr Lys Met Lys Tyr Leu Glu Ile Asn Tyr Ile Glu Arg
    450                 455                 460

Ile Ser Leu Tyr Phe Asn Asp Lys Asp Lys Met Ile Trp Gln Asn Ile
465                 470                 475                 480

Lys Asn Asp Phe Phe Lys Tyr Ser Leu Cys Asn Gln
                485                 490

<210> SEQ ID NO 111
<211> LENGTH: 409
<212> TYPE: PRT
<213> ORGANISM: Escherichia coli
<220> FEATURE:
<223> OTHER INFORMATION: Escherichia coli K1

<400> SEQUENCE: 111

Met Ile Phe Asp Ala Ser Leu Lys Lys Leu Arg Lys Leu Phe Val Asn
1               5                   10                  15

Pro Ile Gly Phe Phe Arg Asp Ser Trp Phe Phe Asn Ser Lys Asn Lys
                20                  25                  30

Ala Glu Glu Leu Leu Ser Pro Leu Lys Ile Lys Ser Lys Asn Ile Phe
            35                  40                  45

Ile Ile Ser Asn Leu Gly Gln Leu Lys Lys Ala Glu Ser Phe Val Gln
        50                  55                  60

Lys Phe Ser Lys Arg Ser Asn Tyr Leu Ile Val Leu Ala Thr Glu Lys
65                  70                  75                  80

Asn Thr Glu Met Pro Lys Ile Ile Val Glu Gln Ile Asn Asn Lys Leu
                85                  90                  95

Phe Ser Ser Tyr Lys Val Leu Phe Ile Pro Thr Phe Pro Asn Val Phe
            100                 105                 110

Ser Leu Lys Lys Val Ile Trp Phe Tyr Asn Val Tyr Asn Tyr Leu Val
        115                 120                 125
```

-continued

Leu Asn Ser Lys Ala Lys Asp Ala Tyr Phe Met Ser Tyr Ala Gln His
130                 135                 140

Tyr Ala Ile Phe Val Tyr Leu Phe Lys Lys Asn Asn Ile Arg Cys Ser
145                 150                 155                 160

Leu Ile Glu Glu Gly Thr Gly Thr Tyr Lys Thr Glu Lys Glu Asn Pro
            165                 170                 175

Val Val Asn Ile Asn Phe Tyr Ser Glu Ile Ile Asn Ser Ile Ile Leu
            180                 185                 190

Phe His Tyr Pro Asp Leu Lys Phe Glu Asn Val Tyr Gly Thr Tyr Pro
        195                 200                 205

Ile Leu Leu Lys Lys Phe Asn Ala Gln Lys Phe Val Glu Phe Lys
210                 215                 220

Gly Ala Pro Ser Val Lys Ser Ser Thr Arg Ile Asp Asn Val Ile His
225                 230                 235                 240

Lys Tyr Ser Ile Thr Arg Asp Asp Ile Ile Tyr Ala Asn Gln Lys Tyr
                245                 250                 255

Leu Ile Glu His Thr Leu Phe Ala Asp Ser Leu Ile Ser Ile Leu Leu
            260                 265                 270

Arg Ile Asp Lys Pro Asp Asn Ala Arg Ile Phe Ile Lys Pro His Pro
            275                 280                 285

Lys Glu Pro Lys Lys Asn Ile Asn Ala Ile Gln Lys Ala Ile Lys Lys
290                 295                 300

Ala Lys Cys Arg Asp Ile Ile Leu Ile Thr Glu Pro Asp Phe Leu Ile
305                 310                 315                 320

Glu Pro Val Ile Lys Lys Ala Lys Ile Lys His Leu Ile Gly Leu Thr
                325                 330                 335

Ser Ser Ser Leu Val Tyr Ala Pro Leu Val Ser Lys Arg Cys Gln Ser
            340                 345                 350

Tyr Ser Ile Ala Pro Leu Met Ile Lys Leu Cys Asp Asn Asp Lys Ser
        355                 360                 365

Gln Lys Gly Ile Asn Thr Leu Arg Leu His Phe Asp Ile Leu Lys Asn
370                 375                 380

Phe Asp Asn Val Lys Ile Leu Ser Asp Asp Ile Thr Ser Pro Ser Leu
385                 390                 395                 400

His Asp Lys Arg Ile Phe Leu Gly Glu
            405

<210> SEQ ID NO 112
<211> LENGTH: 409
<212> TYPE: PRT
<213> ORGANISM: Escherichia coli
<220> FEATURE:
<223> OTHER INFORMATION: Escherichia coli K92

<400> SEQUENCE: 112

Met Ile Phe Asp Ala Ser Leu Lys Lys Leu Arg Lys Leu Phe Val Asn
1               5                   10                  15

Pro Ile Gly Phe Phe Arg Asp Ser Trp Phe Phe Asn Ser Lys Asn Lys
            20                  25                  30

Ala Glu Glu Leu Leu Ser Pro Leu Lys Ile Lys Ser Lys Asn Ile Phe
        35                  40                  45

Ile Val Ala His Leu Gly Gln Leu Lys Lys Ala Glu Leu Phe Ile Gln
    50                  55                  60

Lys Phe Ser Arg Arg Ser Asn Phe Leu Ile Val Leu Ala Thr Lys Lys
65                  70                  75                  80

Asn Thr Glu Met Pro Arg Leu Ile Leu Glu Gln Met Asn Lys Lys Leu
            85                  90                  95

Phe Ser Ser Tyr Lys Leu Leu Phe Ile Pro Thr Glu Pro Asn Thr Phe
            100                 105                 110

Ser Leu Lys Lys Val Ile Trp Phe Tyr Asn Val Tyr Lys Tyr Ile Val
            115                 120                 125

Leu Asn Ser Lys Ala Lys Asp Ala Tyr Phe Met Ser Tyr Ala Gln His
130                 135                 140

Tyr Ala Ile Phe Ile Trp Leu Phe Lys Lys Asn Asn Ile Arg Cys Ser
145                 150                 155                 160

Leu Ile Glu Glu Gly Thr Gly Thr Tyr Lys Thr Glu Lys Lys Pro
            165                 170                 175

Leu Val Asn Ile Asn Phe Tyr Ser Trp Ile Ile Asn Ser Ile Ile Leu
            180                 185                 190

Phe His Tyr Pro Asp Leu Lys Phe Glu Asn Val Tyr Gly Thr Phe Pro
            195                 200                 205

Asn Leu Leu Lys Glu Lys Phe Asp Ala Lys Lys Ile Phe Glu Phe Lys
            210                 215                 220

Thr Ile Pro Leu Val Lys Ser Ser Thr Arg Met Asp Asn Leu Ile His
225                 230                 235                 240

Lys Tyr Arg Ile Thr Arg Asp Asp Ile Ile Tyr Val Ser Gln Arg Tyr
            245                 250                 255

Trp Ile Asp Asn Glu Leu Tyr Ala His Leu Leu Ile Ser Thr Leu Met
            260                 265                 270

Arg Ile Asp Lys Ser Asp Asn Ala Arg Val Phe Ile Lys Pro His Pro
            275                 280                 285

Lys Glu Thr Lys Lys Tyr Ile Asn Ala Ile Gln Gly Ala Ile Asn Lys
            290                 295                 300

Ala Lys Arg Arg Asp Ile Ile Ile Val Glu Lys Asp Phe Leu Ile
305                 310                 315                 320

Glu Ser Ile Ile Lys Lys Cys Lys Ile Lys His Leu Ile Gly Leu Ala
            325                 330                 335

Ser Ser Ser Leu Val Tyr Ala Pro Leu Val Tyr Lys Glu Cys Lys Thr
            340                 345                 350

Tyr Ser Ile Ala Pro Ile Ile Ile Lys Leu Cys Asn Asn Glu Lys Ser
            355                 360                 365

Gln Lys Gly Ile Asn Thr Leu Arg Leu His Phe Asp Ile Leu Lys Asn
            370                 375                 380

Phe Asp Asn Val Lys Ile Leu Ser Asp Asp Ile Thr Ser Pro Ser Leu
385                 390                 395                 400

His Asp Lys Arg Ile Phe Leu Gly Glu
            405

<210> SEQ ID NO 113
<211> LENGTH: 29
<212> TYPE: DNA
<213> ORGANISM: Artificial Sequence
<220> FEATURE:
<223> OTHER INFORMATION: Primer StrepII-deltaN235-CsaB-His6

<400> SEQUENCE: 113
gcagatctat tgatttagta tttacttgg                                    29

<210> SEQ ID NO 114
<211> LENGTH: 32
<212> TYPE: DNA

<213> ORGANISM: Artificial Sequence
<220> FEATURE:
<223> OTHER INFORMATION: Primer StrepII-deltaN235-CsaB-His6

<400> SEQUENCE: 114
ccgctcgagt ttctcaaatg atgatggtaa tg                                 32

<210> SEQ ID NO 115
<211> LENGTH: 29
<212> TYPE: DNA
<213> ORGANISM: Artificial Sequence
<220> FEATURE:
<223> OTHER INFORMATION: Primer StrepII-deltaN167-CsaB-His6

<400> SEQUENCE: 115
gcagatctac tttaagttca tctatatct                                     29

<210> SEQ ID NO 116
<211> LENGTH: 32
<212> TYPE: DNA
<213> ORGANISM: Artificial Sequence
<220> FEATURE:
<223> OTHER INFORMATION: Primer StrepII-deltaN167-CsaB-His6

<400> SEQUENCE: 116
ccgctcgagt ttctcaaatg atgatggtaa tg                                 32

<210> SEQ ID NO 117
<211> LENGTH: 30
<212> TYPE: DNA
<213> ORGANISM: Artificial Sequence
<220> FEATURE:
<223> OTHER INFORMATION: Primer StrepII-deltaN97-CsaB-His6

<400> SEQUENCE: 117
gcagatctcc ttctaatctt actcttaagc                                    30

<210> SEQ ID NO 118
<211> LENGTH: 32
<212> TYPE: DNA
<213> ORGANISM: Artificial Sequence
<220> FEATURE:
<223> OTHER INFORMATION: Primer StrepII-deltaN97-CsaB-His6

<400> SEQUENCE: 118
ccgctcgagt ttctcaaatg atgatggtaa tg                                 32

<210> SEQ ID NO 119
<211> LENGTH: 33
<212> TYPE: DNA
<213> ORGANISM: Artificial Sequence
<220> FEATURE:
<223> OTHER INFORMATION: Primer StrepII-deltaC41-CsaB-His6

<400> SEQUENCE: 119
gcagatcttt tatacttaat aacagaaaat ggc                                33

<210> SEQ ID NO 120
<211> LENGTH: 32
<212> TYPE: DNA
<213> ORGANISM: Artificial Sequence
<220> FEATURE:
<223> OTHER INFORMATION: Primer StrepII-deltaC41-CsaB-His6

<400> SEQUENCE: 120
cgcctcgaga aaattccttt ctttagttaa gg                                 32

<210> SEQ ID NO 121
<211> LENGTH: 33
<212> TYPE: DNA
<213> ORGANISM: Artificial Sequence
<220> FEATURE:
<223> OTHER INFORMATION: Primer StrepII-deltaC25-CsaB-His6

<400> SEQUENCE: 121
gcagatcttt tatacttaat aacagaaaat ggc                    33

<210> SEQ ID NO 122
<211> LENGTH: 28
<212> TYPE: DNA
<213> ORGANISM: Artificial Sequence
<220> FEATURE:
<223> OTHER INFORMATION: Primer StrepII-deltaC25-CsaB-His6

<400> SEQUENCE: 122
cgcctcgagg tgactatcag caccatcg                          28

<210> SEQ ID NO 123
<211> LENGTH: 32
<212> TYPE: DNA
<213> ORGANISM: Artificial Sequence
<220> FEATURE:
<223> OTHER INFORMATION: Primer MBP-deltaN58-CsxA-His6

<400> SEQUENCE: 123
cgggatcccc aattgaagat ccatacccag ta                     32

<210> SEQ ID NO 124
<211> LENGTH: 29
<212> TYPE: DNA
<213> ORGANISM: Artificial Sequence
<220> FEATURE:
<223> OTHER INFORMATION: Primer MBP-deltaN58-CsxA-His6

<400> SEQUENCE: 124
ccgctcgagt tgtccactag gctgtgatg                         29

<210> SEQ ID NO 125
<211> LENGTH: 32
<212> TYPE: DNA
<213> ORGANISM: Artificial Sequence
<220> FEATURE:
<223> OTHER INFORMATION: Primer MBP-deltaC99-CsxA-His6

<400> SEQUENCE: 125
gcggatccat tatgagcaaa attagcaaat tg                     32

<210> SEQ ID NO 126
<211> LENGTH: 33
<212> TYPE: DNA
<213> ORGANISM: Artificial Sequence
<220> FEATURE:
<223> OTHER INFORMATION: Primer MBP-deltaC99-CsxA-His6

<400> SEQUENCE: 126
ccgctcgagg agaatttctg cttctgatac atc                    33

<210> SEQ ID NO 127
<211> LENGTH: 32
<212> TYPE: DNA
<213> ORGANISM: Artificial Sequence
<220> FEATURE:

<223> OTHER INFORMATION: Primer MBP-deltaN58deltaC99-CsxA-His6

<400> SEQUENCE: 127
cgggatcccc aattgaagat ccatacccag ta                32

<210> SEQ ID NO 128
<211> LENGTH: 33
<212> TYPE: DNA
<213> ORGANISM: Artificial Sequence
<220> FEATURE:
<223> OTHER INFORMATION: Primer MBP-deltaN58deltaC99-CsxA-His6

<400> SEQUENCE: 128
ccgctcgagg agaatttctg cttctgatac atc                33

<210> SEQ ID NO 129
<211> LENGTH: 33
<212> TYPE: DNA
<213> ORGANISM: Artificial Sequence
<220> FEATURE:
<223> OTHER INFORMATION: Primer MBP-deltaN104-CsxA-His6

<400> SEQUENCE: 129
cgggatccga aagcaccgat attgcaagat tcc                33

<210> SEQ ID NO 130
<211> LENGTH: 33
<212> TYPE: DNA
<213> ORGANISM: Artificial Sequence
<220> FEATURE:
<223> OTHER INFORMATION: Primer MBP-deltaN104-CsxA-His6

<400> SEQUENCE: 130
ccgctcgagg agaatttctg cttctgatac atc                33

<210> SEQ ID NO 131
<211> LENGTH: 32
<212> TYPE: DNA
<213> ORGANISM: Artificial Sequence
<220> FEATURE:
<223> OTHER INFORMATION: Primer MBP-deltaC174-CsxA-His6

<400> SEQUENCE: 131
gcggatccat tatgagcaaa attagcaaat tg                 32

<210> SEQ ID NO 132
<211> LENGTH: 37
<212> TYPE: DNA
<213> ORGANISM: Artificial Sequence
<220> FEATURE:
<223> OTHER INFORMATION: Primer MBP-deltaC174-CsxA-His6

<400> SEQUENCE: 132
ccgctcgagt tggcctgtca aaatggcaaa atggtgg            37

<210> SEQ ID NO 133
<211> LENGTH: 58
<212> TYPE: PRT
<213> ORGANISM: Neisseria meningitidis
<220> FEATURE:
<223> OTHER INFORMATION: Fragment Figure 7 CslA

<400> SEQUENCE: 133

Thr Phe Leu Val Pro Trp Leu Met Tyr Leu Asp Gly Lys Ser Ile Pro
1               5                   10                  15

```
Asn Asn Asp Ile Cys Tyr Tyr Phe Asn Ile Arg Ser Asn Lys Ala Pro
            20                  25                  30

Thr Gln Tyr Leu Lys Leu Leu Gln Lys Asn Glu Asp Asn Gln Gln Pro
        35                  40                  45

His Ser Phe Cys Ala Asn Asp Phe His Ser
    50                  55

<210> SEQ ID NO 134
<211> LENGTH: 60
<212> TYPE: PRT
<213> ORGANISM: Neisseria meningitidis
<220> FEATURE:
<223> OTHER INFORMATION: Fragment Figure 7 CsaB

<400> SEQUENCE: 134

Gly Tyr Leu Tyr His His Tyr Ala Leu Leu Ser Gly Arg Ala Leu Gln
1               5                   10                  15

Ser Ser Asp Lys Thr Glu Leu Val Gln Gln Asn His Asp Phe Lys Lys
            20                  25                  30

Lys Leu Asn Asn Val Val Thr Leu Thr Lys Glu Arg Asn Phe Asp Lys
        35                  40                  45

Leu Pro Leu Ser Val Cys Ile Asn Asp Gly Ala Asp
    50                  55                  60

<210> SEQ ID NO 135
<211> LENGTH: 58
<212> TYPE: PRT
<213> ORGANISM: Neisseria meningitidis
<220> FEATURE:
<223> OTHER INFORMATION: Fragment Figure 7 CsxA

<400> SEQUENCE: 135

Thr Phe Leu His His His Phe Ala Ile Leu Thr Gly Gln Ala Leu Ala
1               5                   10                  15

Thr Arg Thr Lys Cys Ile Tyr Phe Asn Ile Arg Ser Pro Gln Ala Ala
            20                  25                  30

Gln His Tyr Lys Thr Leu Leu Ala Arg Lys Gly Ser Glu Tyr Ser Pro
        35                  40                  45

His Ser Ile Cys Leu Asn Asp His Thr Ser
    50                  55
```

The invention claimed is:

1. In vitro method for producing *Neisseria meningitidis* capsular polysaccharides which have a defined length, wherein said method comprises the steps of:

(I) (a) incubating at least one capsule polymerase with at least one donor carbohydrate and at least one acceptor carbohydrate; wherein the ratio of donor carbohydrate to acceptor carbohydrate is a ratio from 10:1 to 400:1; and (b) isolating the resulting capsular polysaccharides, wherein the capsule polymerase comprises a) the amino acid sequence of SEQ ID NO: 28, 29 or 31, said polymerase having a length that is 95% or less than that of the wild-type polymerase; or b) the polymerase of a) that comprises an amino acid sequence having at least 80% identity to SEQ ID NO: 28, 29 or 31, and being functional, wherein being functional comprises the ability to transfer GlcNAc-1P or a derivative thereof from UDP-GlcNAc or a derivative thereof onto an acceptor carbohydrate; or (II) (a) incubating at least one capsule polymerase with at least one donor carbohydrate and at least one acceptor carbohydrate; wherein the incubation time ranges from 3 to 45 minutes; and (b) isolating the resulting capsular polysaccharides, wherein the capsule polymerase comprises a) the amino acid sequence of SEQ ID NO: 28, 29 or 31, said polymerase having a length that is 95% or less than that of the wild-type polymerase; or b) the polymerase of a) that comprises an amino acid sequence having at least 80 % identity to SEQ ID NO: 28, 29 or 31, and being functional, wherein being functional comprises the ability to transfer GlcNAc-1P or a derivative thereof from UDP-GlcNAc or a derivative thereof onto an acceptor carbohydrate; or (III) (a) incubating at least one capsule polymerase with at least one donor carbohydrate and at least one acceptor carbohydrate; wherein (i) the ratio of donor carbohydrate to acceptor carbohydrate is a ratio from 10:1 to 10000:1, and (ii) the incubation time ranges from 3 to 45 minutes; and (b) isolating the resulting capsular polysaccharides, wherein the capsule polymerase comprises a) the amino acid sequence of SEQ ID NO: 28, 29 or 31, said polymerase having a length that is 95% or less than that of the wild-type polymerase; or b) the polymerase of a) that comprises an amino acid sequence having at least 80% identity to SEQ ID NO: 28, 29 or 31, and being functional, wherein being functional comprises the ability to transfer GlcNAc-1P or a derivative thereof from UDP-GlcNAc or a derivative thereof onto an acceptor carbohydrate.

2. The method of claim 1, wherein the capsule polymerase of Neisseria meningitidis serogroup A is the polypeptide of any one of (a) to (f):

(a) a polypeptide comprising an amino acid sequence encoded by a nucleic acid molecule having the nucleic acid sequence of any one of SEQ ID NO: 1 to 3;

(b) a polypeptide comprising the amino acid sequence of SEQ ID NO: 9 or 10;

(c) a polypeptide encoded by a nucleic acid molecule encoding a polypeptide comprising the amino acid sequence of SEQ ID NO: 9 or 10, wherein the function comprises the ability to transfer ManNAc-1P or a derivative thereof from UDP-ManNAc or a derivative thereof onto an acceptor carbohydrate;

(d) a polypeptide having at least 80% identity to the polypeptide of any one of (a) to (d), whereby said polypeptide is functional; wherein the function comprises the ability to transfer ManNAc-1P or a derivative thereof from UDP-ManNAc or a derivative thereof onto an acceptor carbohydrate; and (e) a polypeptide as defined in (a), (c) and (d) comprising an amino acid sequence encoded by a nucleic acid molecule being degenerate as a result of the genetic code to the nucleotide sequence of the nucleic acid molecule.

3. The method of claim 1, wherein at least 60% of the produced capsular polysaccharides have a degree of polymerization (DP) of 10 to 60 or an average degree of polymerization (avDP) of 15 to 20.

4. The method of claim 1, wherein (i) the ratio of donor carbohydrate to acceptor carbohydrate is a ratio from 10:1 to 80:1; and the capsule polymerase is a polypeptide comprising maximal 80% of the amino acid sequence of SEQ ID NO: 24 and comprising the amino acid sequence of SEQ ID NO: 28; or (ii) the ratio of donor carbohydrate to acceptor carbohydrate is a ratio from 100:1 to 400:1; and the capsule polymerase is a polypeptide comprising maximal 68% of the amino acid sequence of SEQ ID NO: 24 and comprising the amino acid sequence of SEQ ID NO: 29.

5. The method of claim 1, wherein said donor carbohydrate is activated or wherein said donor carbohydrate is activated during step (a).

6. The method of claim 5, wherein said donor carbohydrate is activated during step (a) by contacting said donor carbohydrate with an activating enzyme; and wherein in step (a) said donor carbohydrate may be further contacted with phosphoenolpyruvate (PEP) and/or at least one activating nucleotide.

7. The method of claim 5, wherein said donor carbohydrate is activated by linkage to an activating nucleotide; wherein said activating nucleotide is cytosine monophosphate, cytosine diphosphate, cytosine triphosphate, uracil monophosphate, uracil diphosphate, thymidine diphosphate, adenosine monophosphate, or uracil triphosphate.

8. The method of claim 1, wherein:

(i) wherein at least one donor carbohydrate is UDP-GlcNAc;

(ii) at least one donor carbohydrate is GlcNAc-1-P.

9. The method of claim 8, wherein the capsule polymerase is the capsule polymerase of Neisseria meningitidis serogroup A and wherein at least one donor carbohydrate is UDP-GlcNAc and wherein in step (a) the capsule polymerase is further incubated with the UDP-GlcNAc-epimerase.

10. The method of claim 1, wherein at least 80% of the acceptor carbohydrates are polysaccharides with a degree of polymerization of (DP) of ≥4.

11. The method of claim 1, wherein (i) the acceptor carbohydrate is non-acetylated and/or dephosphorylated;

(ii) the acceptor carbohydrate carries one or more additional functional groups at its reducing end;

(iii) the acceptor carbohydrate is a dimer or trimer of GlcNAc1P carrying a phosphodiester at the reducing end, wherein the phosphate group at the reducing end may be extended with alkyl-azides, alkyl-amines or sulfhydryl-groups.

12. The method of claim 11, wherein the acceptor carbohydrate is a dimer or trimer of GlcNAc-1P carrying a phosphodiester at the reducing end, wherein the phosphate group at the reducing end may be extended with alkyl-azides, alkyl-amindes or sulfhydryl-groups and wherein the acceptor carbohydrate is a disaccharide carrying a decyl-phosphate-ester at the reducing end.

13. The method of claim 1, wherein said acceptor carbohydrate is purified.

14. The method of claim 1, further comprising O-acetylation of the produced capsule polysaccharides; wherein the O-acetylation is performed by contacting the produced capsule polysaccharides with an O-acetyltransferase.

15. The method of claim 14, wherein the O-acetyltransferase is the polypeptide of any one of (a) to (f):

(a) a polypeptide comprising an amino acid sequence encoded by a nucleic acid molecule having the nucleic acid sequence of SEQ ID NO: 53;

(b) a polypeptide comprising the amino acid sequence of SEQ ID NO: 54;

(c) a polypeptide encoded by a nucleic acid molecule encoding a polypeptide comprising the amino acid sequence of SEQ ID NO: 54 having a function that comprises the ability to transfer Acetyl-groups from the donor Acetyl-Coenzyme A onto hydroxyl-groups of UDP-ManNAc or oligo- and polymeric structures consisting of ManNAc-1-phosphate units linked together by phosphodiester linkages;

(d) a polypeptide having at least 80% identity to the polypeptide of any one of (a) to (c), whereby said polypeptide is functional; wherein the function comprises the ability to transfer Acetyl-groups from the donor Acetyl-Coenzyme A onto hydroxyl-groups of UDP-ManNAc or oligo- and polymeric structures consisting of ManNAc-1-phosphate units linked together by phosphodiester linkages; and (e) a polypeptide as defined in (a), (c) and (d) comprising an amino acid sequence encoded by a nucleic acid molecule being degenerate as a result of the genetic code to the nucleotide sequence of the nucleic acid molecule.

16. The method of claim 14, wherein the capsule polymerase is the capsule polymerase of *Neisseria meningitidis* serogroup A; and wherein the produced capsule polysaccharides may be O-acetylated in positions 3 and 4 of ManNAc.

17. The method of claim 1, further comprising covalently attaching the produced capsular polysaccharides to a carrier molecule; wherein the carrier molecule may be tetanus toxoid and/or $CRM_{197}$.

18. The method of claim 1, wherein the capsule polymerase is immobilized on a solid phase.

19. A capsular polysaccharide which has been produced by the method of claim 1.

20. The capsular polysaccharide of claim 19, wherein said capsular polysaccharide is comprised in a vaccine that further comprises a pharmaceutically acceptable carrier.

21. The method of claim 1, wherein the ratio of donor carbohydrate to acceptor carbohydrate is a ratio of from 10:1 to 400:1.

22. The method of claim 1 (III), wherein the ratio of donor carbohydrate to acceptor carbohydrate is a ratio of from 200:1 to 1000:1.

23. The method of claim 11, wherein the acceptor carbohydrate is non-acetylated and dephosphorylated.

24. The method of claim 1 wherein the polymerase consists of the amino acid sequence of SEQ ID NO:28, 29 or 31.

* * * * *